(12) United States Patent
Mun et al.

(10) Patent No.: US 11,299,459 B2
(45) Date of Patent: Apr. 12, 2022

(54) COMPOUND FOR ORGANIC ELECTRIC ELEMENT, ORGANIC ELECTRIC ELEMENT COMPRISING THE SAME AND ELECTRONIC DEVICE THEREOF

(71) Applicant: DUK SAN NEOLUX CO., LTD., Cheonan-si (KR)

(72) Inventors: Soung Yun Mun, Cheonan-si (KR); Seul-gi Kim, Daejeon (KR); Sun-Hee Lee, Hwaseong-si (KR); Yeon Hee Choi, Cheonan-si (KR); Jung Wook Lee, Gunsan-si (KR)

(73) Assignee: DUK SAN NEOLUX CO., LTD., Cheonan-si (KR)

( * ) Notice: Subject to any disclaimer, the term of this patent is extended or adjusted under 35 U.S.C. 154(b) by 251 days.

(21) Appl. No.: 15/753,803

(22) PCT Filed: Aug. 4, 2016

(86) PCT No.: PCT/KR2016/008597
§ 371 (c)(1),
(2) Date: Feb. 20, 2018

(87) PCT Pub. No.: WO2017/030307
PCT Pub. Date: Feb. 23, 2017

(65) Prior Publication Data
US 2018/0282276 A1    Oct. 4, 2018

(30) Foreign Application Priority Data

Aug. 20, 2015    (KR) ........................ 10-2015-0117582

(51) Int. Cl.

| | | |
|---|---|---|
| *C07D 209/82* | (2006.01) | |
| *C07D 495/04* | (2006.01) | |
| *C09K 11/06* | (2006.01) | |
| *C07D 405/12* | (2006.01) | |
| *C07F 7/00* | (2006.01) | |
| *C07D 403/10* | (2006.01) | |
| *C07D 403/12* | (2006.01) | |
| *C07D 409/04* | (2006.01) | |
| *C07D 409/12* | (2006.01) | |
| *C07D 519/00* | (2006.01) | |
| *C07D 209/94* | (2006.01) | |

(Continued)

(52) U.S. Cl.
CPC ......... *C07D 209/82* (2013.01); *C07D 209/94* (2013.01); *C07D 307/91* (2013.01); *C07D 333/76* (2013.01); *C07D 403/04* (2013.01); *C07D 403/10* (2013.01); *C07D 403/12* (2013.01); *C07D 405/12* (2013.01); *C07D 405/14* (2013.01); *C07D 409/04* (2013.01); *C07D 409/12* (2013.01); *C07D 409/14* (2013.01); *C07D 417/04* (2013.01); *C07D 491/048* (2013.01); *C07D 495/04* (2013.01); *C07D 519/00* (2013.01); *C07F 7/00* (2013.01); *C07F 7/0816* (2013.01); *C09K 11/06* (2013.01); *H01L 51/0032* (2013.01); *H01L 51/0071* (2013.01); *H01L 51/50* (2013.01); *H01L 51/5012* (2013.01); *C09K 2211/1029* (2013.01); *C09K 2211/1088* (2013.01); *H01L 51/0056* (2013.01); *H01L 51/5056* (2013.01)

(58) Field of Classification Search
CPC .. C07D 209/82; C07D 209/94; C07D 307/91; C07D 333/76; C07D 403/04; C07D 403/10; C07D 403/12; C07D 405/12; C07D 405/14; C07D 409/04; C07D 409/12; C07D 409/14; C07D 417/04; C07D 491/048; C07D 495/04; C07D 519/00; C07F 7/00; C07F 7/0816; C09K 11/06; C09K 2211/1029; C09K 2211/1088; H01L 51/0032; H01L 51/0056; H01L 51/0071; H01L 51/50; H01L 51/5012; H01L 51/5056
See application file for complete search history.

(56) References Cited

U.S. PATENT DOCUMENTS

| | | | | |
|---|---|---|---|---|
| 2004/0124766 A1* | 7/2004 | Nakagawa | .......... | H01L 51/0064 313/504 |
| 2013/0069049 A1* | 3/2013 | Park | ..................... | C07D 487/04 257/40 |

(Continued)

FOREIGN PATENT DOCUMENTS

| | | |
|---|---|---|
| KR | 10-2011-0021487 A | 3/2011 |
| KR | 10-2014-0097936 A | 8/2014 |

(Continued)

OTHER PUBLICATIONS

Shi et al., "Synthesis, Structure, Properties, and Application of a Carbazole-Based Diaza[7]helicene in a Deep-Blue-Emitting OLED", Chem. Eur. J., 2012, vol. 18, pp. 8092-8099.

*Primary Examiner* — Dawn L Garrett
(74) *Attorney, Agent, or Firm* — Vorys, Sater, Seymour & Pease LLP; Mih Suhn Koh

(57) ABSTRACT

The present invention provides the compound represented by Formula 1, and an organic electric element comprising a first electrode, a second electrode, and an organic material layer formed between the first electrode and the second electrode, wherein the organic material layer comprises the compound represented by Formula 1. The driving voltage of an organic electronic device can be lowered, and the luminous efficiency, color purity and life time of an organic electronic device can be improved by comprising the compound represented by Formula 1 in the organic material layer.

16 Claims, 1 Drawing Sheet

(51) Int. Cl.
*C07D 405/14* (2006.01)
*C07D 403/04* (2006.01)
*C07D 491/048* (2006.01)
*C07D 409/14* (2006.01)
*C07F 7/08* (2006.01)
*H01L 51/00* (2006.01)
*H01L 51/50* (2006.01)
*C07D 333/76* (2006.01)
*C07D 417/04* (2006.01)
*C07D 307/91* (2006.01)

(56) References Cited

U.S. PATENT DOCUMENTS

| 2015/0171334 A1* | 6/2015 | Kato | H01L 51/0055 |
| | | | 257/40 |
| 2016/0093812 A1* | 3/2016 | Stoessel | C09K 11/06 |
| | | | 257/40 |
| 2016/0225992 A1* | 8/2016 | Ito | C09B 23/148 |

FOREIGN PATENT DOCUMENTS

| KR | 10-2014-0130089 A | 11/2014 |
| KR | 10-2016-0089033 A | 7/2016 |
| WO | WO 2011/000455 A1 * | 1/2011 |
| WO | WO 2011/057701 A1 * | 5/2011 |

* cited by examiner

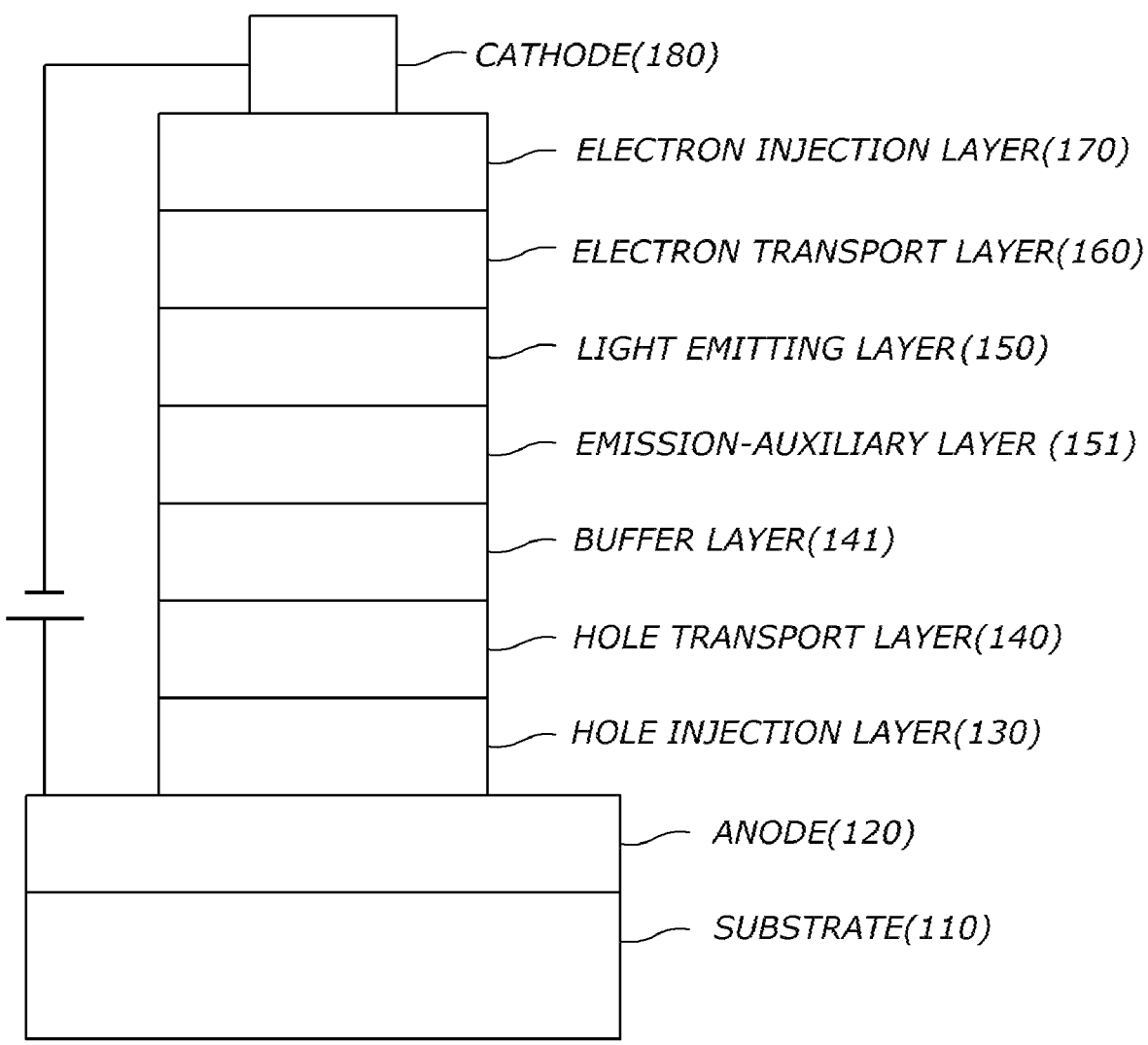

COMPOUND FOR ORGANIC ELECTRIC ELEMENT, ORGANIC ELECTRIC ELEMENT COMPRISING THE SAME AND ELECTRONIC DEVICE THEREOF

CROSS-REFERENCE TO RELATED APPLICATIONS

This patent application claims priority from and the benefit under 35 U.S.C. 119(a) of Korean Patent Application No. 10-2015-0117582, filed on Aug. 20, 2015, and International Patent Application No. PCT/KR2016/008597, filed on Aug. 4, 2016, the disclosure of which is incorporated herein by reference in its entirety.

BACKGROUND

Technical Field

The present invention relates to compounds for organic electric elements, organic electric elements comprising the same, and electronic devices thereof.

Background Art

Polycyclic ring compound containing heteroatoms has very different characteristics depending on the material structure, and thus it is being applied as material of various layers of OLED.

In particular, the heterocyclic compound is characterized in that the band gap (HOMO, LUMO), electrical characteristics, chemical properties, and physical properties are different depending on the number of rings and fused positions, the kind and arrangement of heteroatoms. Therefore, it has been developed and applied to various OLED layers (HTL or phosphorescent host: U.S. Pat. No. 8,334,058, KR 1108398; applied as ETL: KR 0813385, KR 0765078).

Recently, OLED materials have been actively developed for the kind, number; and positions of heteroatoms in the 5-membered ring compound (KR 1418146, KR 0938796, KR 2011-0043439, KR 20112-0140557, KR 2013-0071547, JP 2010-230312, etc.).

Object, Technical Solution and Effects of the Invention

An object of the present invention is to provide a compound allowing a driving voltage to lower, luminous efficiency to improve and lifetime to optimize by using the characteristics of polycyclic ring compound, an organic electric element employing the same, and an electric device thereof.

In accordance with an aspect of the present invention, the present invention provides the compound represented by the following Formula.

[Formula 1]

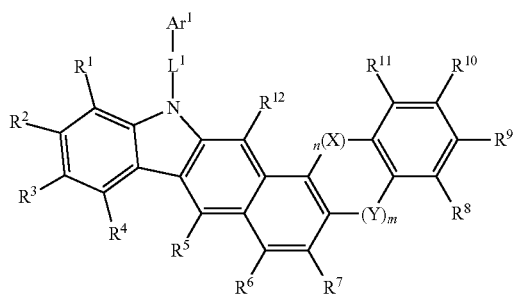

In another aspect of the present invention, organic electric elements comprising the compound represented by the formula 1 above and electronic devices including the organic electric element are provided.

By using the compound according to embodiments of the present invention, driving voltage of the element can be lowered, and luminous efficiency, color purity and life span of the element can be remarkably improved.

BRIEF DESCRIPTION OF THE DRAWINGS

The FIGURE illustrates an example of an organic light emitting diode according to an embodiment of the present invention: 100 is organic electric element, 110 is substrate, 120 is first electrode, 130 is hole injection layer, 140 is hole transport layer, 141 is buffer layer, 150 is light emitting layer, 151 is emission-auxiliary layer, 160 is electron transport layer, 170 is electron injection layer, and 180 is second electrode.

DETAILED DESCRIPTION

Hereinafter, some embodiments of the present invention will be described in detail with reference to the accompanying illustrative drawings.

In designation of reference numerals to components in respective drawings, it should be noted that the same elements will be designated by the same reference numerals although they are shown in different drawings. Further, in the following description of the present invention, a detailed description of known functions and configurations incorporated herein will be omitted when it may make the subject matter of the present invention rather unclear.

In addition, terms, such as first, second, A, B, (a), (b) or the like may be used herein when describing components of the present invention. Each of these terminologies is not used for defining an essence, order or sequence of a corresponding component but used merely to distinguish the corresponding component from other component(s). It should be noted that if it is described in the specification that one component is "connected," "coupled" or "joined" to another component, a third component may be "connected," "coupled," and "joined" between the first and second components, although the first component may be directly connected, coupled or joined to the second component.

In addition, it will be understood that when an element such as a layer, film, region or substrate is referred to as being "on" or "over" another element, it can be directly on the other element or intervening elements may also be present. In contrast, when an element is referred to as being "directly on" another element, there are no intervening elements present.

As used in the specification and the accompanying claims, unless otherwise stated, the following is the meaning of the term as follows.

Unless otherwise stated, the term "halo" or "halogen" as used herein includes fluorine (F), chlorine (Cl), bromine (Br), or iodine (I).

Unless otherwise stated, the term "alkyl" or "alkyl group" as used herein has a single bond of 1 to 60 carbon atoms, and means aliphatic functional radicals including a linear alkyl group, a branched chain alkyl group, a cycloalkyl group (alicyclic), or an alkyl group substituted with a cycloalkyl.

Unless otherwise stated, the term "halo alkyl" or "halogen alkyl" as used herein includes an alkyl group substituted with a halogen.

Unless otherwise stated, the term "alkenyl" or "alkynyl" as used herein has, but not limited to, double or triple bonds of 2 to 60 carbon atoms, and includes a linear alkyl group, or a branched chain alkyl group.

Unless otherwise stated, the term "cycloalkyl" as used herein means, but not limited to, alkyl forming a ring having 3 to 60 carbon atoms.

The term "alkoxyl group", "alkoxy group" or "alkyloxy group" as used herein means an oxygen radical attached to an alkyl group, but not limited to, and has 1 to 60 carbon atoms.

The term "aryloxyl group" or "aryloxy group" as used herein means an oxygen radical attached to an aryl group, but not limited to, and has 6 to 60 carbon atoms.

Unless otherwise stated, the term "fluorenyl group" or "fluorenylene group" as used herein means, univalent or bivalent functional group which R, R' and R" are all hydrogen in the structural formula below, "substituted fluorenyl group" or "substituted fluorenylene group" means, functional group which at least any one of R, R' and R" is a functional group other than hydrogen, and fluorenyl group" or "fluorenylene group" comprises spiro compound which is formed by linking R and R' together with the carbon bonded to them.

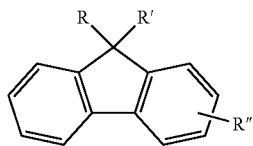

Unless otherwise stated, the term "aryl group" or "arylene group" as used herein has, but not limited to, 6 to 60 carbon atoms. The aryl group or arylene group include a monocyclic rings, ring assemblies, fused polycyclic system or spiro compounds.

Unless otherwise stated, the term "heterocyclic group" as used herein means, but not limited to, a non-aromatic ring as well as an aromatic ring like "heteroaryl group" or "heteroarylene group". The heterocyclic group as used herein means, but not limited to, a ring containing one or more heteroatoms, and having 2 to 60 carbon atoms. Unless otherwise stated, the term "heteroatom" as used herein represents N, O, S, P or Si. The heterocyclic group means a monocyclic, ring assemblies, fused polycyclic system or spiro compound containing one or more heteroatoms.

Also, the term "heterocyclic group" may include $SO_2$ instead of carbon consisting of cycle. For example, "heterocyclic group" includes the following compound.

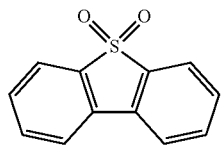 [SMILES: O=S1(=O)c2ccccc2-c2ccccc21]

Unless otherwise stated, the term "ring" as used herein means, a monocyclic and polycyclic, an aliphatic ring and heterocyclic group containing at least one heteroatom, and an aromatic ring and a non-aromatic ring.

Unless otherwise stated, the term "polycyclic" as used herein means, ring assemblies like biphenyl and terphenyl, fused polycyclic system and spiro compound, an aromatic ring and a non-aromatic ring, and an aliphatic ring and heterocyclic group containing at least one heteroatom.

Unless otherwise stated, the term "ring assemblies" as used herein means, two or more cyclic systems (single rings or fused systems) which are directly joined to each other by double or single bonds are named ring assemblies when the number of such direct ring junctions is one less than the number of cyclic systems involved. The ring assemblies also mean, same or different ring systems are directly joined to each other by double or single bonds.

Unless otherwise stated, the term "fused polycyclic system" as used herein means, fused ring type which has at least two atoms as the common members, fused two or more aliphatic ring systems and a fused hetero ring system containing at least one heteroatom. Fused polycyclic system is an aromatic ring, a hetero aromatic ring, an aliphatic ring, or the combination of these.

Unless otherwise stated, the term "spiro compound" as used herein has, a spiro union which means union having one atom as the only common member of two rings. The common atom is designated as 'spiro atom'. The compounds are defined as 'monospiro-', 'dispiro-' or 'trispiro-' depending on the number of spiro atoms in one compound.

Also, when prefixes are named subsequently, it means that substituents are listed in the order described first. For example, an arylalkoxy means an alkoxy substituted with an aryl, an alkoxylcarbonyl means a carbonyl substituted with an alkoxyl, and an arylcarbonylalkenyl also means an alkenyl substitutes with an arylcarbonyl, wherein the arylcarbonyl may be a carbonyl substituted with an aryl.

Unless otherwise stated, the term "substituted or unsubstituted" as used herein means that substitution is carried out by at least one substituent selected from the group consisting of, but not limited to, deuterium, halogen, an amino group, a nitrile group, a nitro group, a $C_1$-$C_{20}$ alkyl group, a $C_1$-$C_{20}$ alkoxy group, a $C_1$-$C_{20}$ alkylamine group, a $C_1$-$C_{20}$ alkylthio group, a $C_6$-$C_{20}$ arylthio group, a $C_2$-$C_{20}$ alkenyl group, a $C_2$-$C_{20}$ alkynyl group, a $C_3$-$C_{20}$ cycloalkyl group, a $C_6$-$C_{60}$ aryl group, a $C_6$-$C_{20}$ aryl group substituted by deuterium, a $C_8$-$C_{20}$ arylalkenyl group, a silane group, a boron group, a germanium group, and a $C_2$-$C_{20}$ heterocyclic group containing at least one heteroatom selected from the group consisting of O, N, S, Si, and P.

In the present description, a 'group name' corresponding to an aryl group, an arylene group, a heterocyclic group, and the like exemplified for each symbol and its substituent may be written in the name of functional group reflecting the valence, and may also be described under the name of a parent compound. For example, in the case of phenanthrene which is a kind of aryl group, it may be described by distinguishing valence such as 'phenanthryl (group)' when it is 'monovalent group', and as 'phenanthrylene (group)' when it is 'divalent group', and it may also be described as a parent compound name, 'phenanthrene', regardless of its valence. Similarly, in the case of pyrimidine, it may be described as 'pyrimidine' regardless of its valence, and it may also be described as the name of corresponding functional group such as pyrimidinyl (group) when it is 'monovalent group', and as 'pyrimidylene (group)' when it is 'divalent group'.

Otherwise specified, the formulas used in the present invention are as defined in the index definition of the substituent of the following formula.

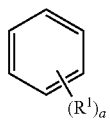

Wherein, when a is an integer of zero, the substituent R¹ is absent, when a is an integer of 1, the sole R¹ is linked to any one of the carbon atoms constituting the benzene ring, when a is an integer of 2 or 3, the substituent R¹s may be the same and different, and are linked to the benzene ring as follows. when a is an integer of 4 to 6, the substituents R¹s may be the same and different, and are linked to the benzene ring in a similar manner to that when a is an integer of 2 or 3, hydrogen atoms linked to carbon constituents of the benzene ring being not represented as usual.

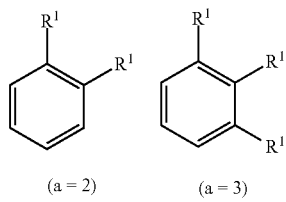

The FIGURE illustrates an organic electric element according to an embodiment of the present invention.

Referring to the FIGURE, an organic electric element 100 according to an embodiment of the present invention includes a first electrode 120 formed on a substrate 110, a second electrode 180, and an organic material layer between the first electrode 110 and the second electrode 180, which contains the inventive compound. Here, the first electrode 120 may be an anode (positive electrode), and the second electrode 180 may be a cathode (negative electrode). In the case of an inverted organic electric element, the first electrode may be a cathode, and the second electrode may be an anode.

The organic material layer may include a hole injection layer 130, a hole transport layer 140, a light emitting layer 150, an electron transport layer 160, and an electron injection layer 170 formed in sequence on the first electrode 120. Here, at least one layer of the organic material layer may be omitted, the organic material layer may further include a hole blocking layer, an electron blocking layer, an emission-auxiliary layer 151, an electron transport auxiliary layer, a buffer layer 141, etc., and the electron transport layer 160 or the like may serve as the hole blocking layer.

Although not shown, the organic electric element according to an embodiment of the present invention may further include at least one protective layer or one capping layer formed on at least one of the sides the first and second electrodes, which is a side opposite to the organic material layer.

The inventive compound employed in the organic material layer may be used as a material of a hole injection layer 130, a hole transport layer 140, an electron transport layer 160, an electron transport auxiliary layer, as a host or a dopant material of a light emitting layer 150, or as a material of a capping layer. For example, the inventive compound may be used as material of the light emitting layer 150, the hole transport layer 140, and/or the emission-auxiliary layer 151, preferably, as the hole transport layer 140, and/or the emission-auxiliary layer 151.

On the other hand, even if the core is the same core, the band gap, the electrical characteristics, the interface characteristics, and the like may be different depending on which substituent is bonded at which position. Therefore, it is necessary to study the selection of the core and the combination of the sub-substituent. Specially, long life span and high efficiency can be simultaneously achieved when the optimal combination of energy levels and T1 values, inherent material properties (mobility, interfacial properties, etc.), and the like among the respective layers of an organic material layer is achieved.

According to the present invention, energy levels and $T_1$ values between organic material layers, inherent material properties (mobility, interfacial properties, etc.), and the like can be optimized by forming a hole transport layer 140 and/or a light emitting layer 150 which comprise the compound represented by the Formula 1, and thus it is possible to simultaneously improve the life span and efficiency of the organic electronic element.

The organic electric element according to an embodiment of the present invention may be manufactured using various deposition methods. The organic electric element according to an embodiment of the present invention may be manufactured using a PVD (physical vapor deposition) method or CVD (chemical vapor deposition) method. For example, the organic electric element may be manufactured by depositing a metal, a conductive metal oxide, or a mixture thereof on the substrate to form the anode 120, forming the organic material layer including the hole injection layer 130, the hole transport layer 140, the light emitting layer 150, the electron transport layer 160, and the electron injection layer 170 thereon, and then depositing a material, which can be used as the cathode 180, thereon. Also, an emission-auxiliary layer 151 may be formed between a hole transport layer 140 and a light emitting layer 150, and an electron transport auxiliary layer may be formed between a light emitting layer 150 and an electron transport layer 160.

Also, the organic material layer may be manufactured in such a manner that a smaller number of layers are formed using various polymer materials by a soluble process or solvent process, for example, spin coating, nozzle printing, inkjet printing, slot coating, dip coating, roll-to-roll, doctor blading, screen printing, or thermal transfer, instead of deposition. Since the organic material layer according to the present invention may be formed in various ways, the scope of protection of the present invention is not limited by a method of forming the organic material layer.

The organic electric element according to an embodiment of the present invention may be of a top emission type, a bottom emission type, or a dual emission type depending on the material used.

WOLED (White Organic Light Emitting Device) has advantages of high resolution realization, an excellent processability, and being produced by using conventional color filter technologies for LCDs. Various structures for WOLED which mainly used as back light units have been suggested and patented. WOLED may employ various arrangement methods, representatively, a parallel side-by-side arrangement method of R (Red), G (Green), B (Blue) light-emitting units, a vertical stack arrangement method of RGB light-emitting units, and a CCM (color conversion material) method in which electroluminescence from a blue (B) organic light emitting layer, and the present invention may be applied to such WOLED.

Also, the organic electric element according to an embodiment of the present invention may be any one of an organic light emitting diode, an organic solar cell, an organic photo conductor, an organic transistor, and an element for monochromatic or white illumination.

Another embodiment of the present invention provides an electronic device including a display device which includes the above described organic electric element, and a control unit for controlling the display device. Here, the electronic device may be a wired/wireless communication terminal which is currently used or will be used in the future, and covers all kinds of electronic devices including a mobile communication terminal such as a cellular phone, a personal digital assistant (PDA), an electronic dictionary, a point-to-multipoint (PMP), a remote controller, a navigation unit, a game player, various kinds of TVs, and various kinds of computers.

Hereinafter, an organic electric element according to an aspect of the present invention will be described.

The compound according to an aspect of the present invention is represented by the following Formula 1.

[Formula 1]

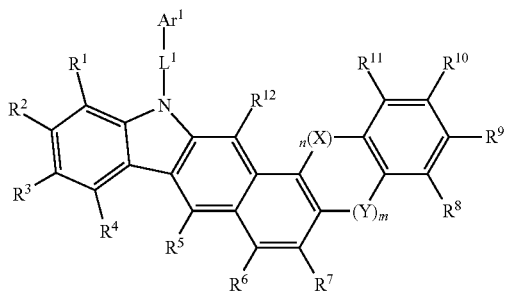

In Formula 1 above, each of symbols may be defined as follows.

X and Y are each independently O, S, $C(R^{13})(R^{14})$ or $Si(R^{13})(R^{14})$. m and n are each an integer of 0 or 1, and m+n is an integer of 1 or more, when m and n are each 0, each bridge Y and X mean single bonds. At this time, in $C(R^{13})(R^{14})$ or $Si(R^{13})(R^{14})$, $R^{13}$ and $R^{14}$ are each independently selected from the group consisting of hydrogen, deuterium, a $C_1$-$C_{50}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxyl group, a $C_1$-$C_{30}$ Silyl group, a $C_6$-$C_{60}$ aryl group, a $C_2$-$C_{60}$ heterocyclic group containing at least one heteroatom selected from the group consisting of O, N, S, Si, and P, a fluorenyl group, a fused ring group of a $C_6$-$C_{60}$ aromatic ring and a $C_3$-$C_{60}$ aliphatic ring, and a group consisting of -L'-N($R^a$)($R^b$). $R^{13}$ and $R^{14}$ may be linked to each other to form a spiro-compound together with C or Si to which they are bonded.

When $R^{13}$ and $R^{14}$ are an alkyl group, preferably, they may be a $C_1$-$C_{10}$ alkyl group, for example, methyl group. When $R^{13}$ and $R^{14}$ are an aryl group, preferably, they may be a $C_6$-$C_{18}$ aryl group, for example, phenyl and the like.

$R^1$ to $R^{12}$ are each independently selected from the group consisting of hydrogen, deuterium, halogen, a $C_6$-$C_{60}$ aryl group, a fluorenyl group, a $C_2$-$C_{60}$ heterocyclic group containing at least one heteroatom selected from the group consisting of O, N, S, Si and P, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_1$-$C_{50}$ alkynyl group, a $C_1$-$C_{30}$ alkoxyl group, a $C_6$-$C_{30}$ aryloxyl group and -L'-N($R^a$)($R^b$).

In addition to, neighboring groups of $R^1$ to $R^{12}$ may be linked to each other to form a ring. For example, neighboring $R^1$ and $R^2$, neighboring $R^2$ and $R^3$, neighboring $R^3$ and $R^4$, neighboring $R^6$ and $R^7$, neighboring $R^8$ and $R^9$, neighboring $R^9$ and $R^{10}$, or neighboring $R^{10}$ and $R^{11}$ may be linked to each other to form a ring.

The ring formed by linking between neighboring groups of $R^1$ to $R^{12}$ may be a $C_6$-$C_{60}$ aromatic ring, a fluorene, a $C_2$-$C_{60}$ heterocyclic group containing at least one heteroatom selected from the group consisting of O, N, S, Si, and P, or a fused ring group of a $C_6$-$C_{60}$ aromatic ring and a $C_3$-$C_{60}$ aliphatic ring. For example, the ring formed by linking between neighboring groups of $R^1$ to $R^{12}$ may be benzene, and the like, and thus, naphthalene, phenanthrene and the like may be formed together with benzene ring to which they are bonded.

When $R^1$ to $R^{12}$ are an aryl group, they may be preferably a $C_6$-$C_{30}$ aryl group, more preferably a $C_6$-$C_{18}$ aryl group, for example, phenyl, naphthyl, biphenyl, terphenyl and the like. When $R^1$ to $R^{12}$ are a heterocyclic group, they may be preferably a $C_2$-$C_{30}$ heterocyclic group, more preferably a $C_2$-$C_{25}$ heterocyclic group, for example, pyridyl, carbazol, dibenzothienocarbazole, dibenzofurocarbazole, 9,9-dimethyl-9H-fluorenocarbazole and the like. When $R^1$ to $R^{12}$ are a fluorenyl group, they may be 9,9-dimethyl-9H-fluorene and the like.

$L^1$ may be selected from the group consisting of a single bond; a $C_6$-$C_{60}$ arylene group; a fluorenylene group; a $C_2$-$C_{60}$ heterocyclic group containing at least one heteroatom selected from the group consisting of O, N, S, Si, and P; a fused ring of a $C_6$-$C_{60}$ aromatic ring and a $C_3$-$C_{60}$ aliphatic ring.

When $L^1$ is an arylene group, $L^1$ may be a $C_6$-$C_{30}$ arylene group, preferably a $C_6$-$C_{18}$ arylene group, for example, phenylene; when $L^1$ is a heterocyclic group, $L^1$ may be preferably a $C_2$-$C_{30}$ heterocyclic group, more preferably a $C_2$-$C_{25}$ heterocyclic group, for example, pyrimidine, triazine, quinazoline, carbazole, dibenzothiophene, dibenzofuran, benzoquinazoline, dibenzoquinazoline, benzothienopyrimidine, benzofuropyrimidine, naphthothienopyrimindine, naphthofuropyrinmidine, phenanthrothienopyrimidine, phenanthrofurfuropyrimidine, dibenzothienocarbazole, dibenzofurocarbazole, 9,9-dimethyl-9H-fluorenocarbazole, and the like. When $L^1$ is a fluorenylene group, $L^1$ may be 9,9-dimethyl-9H-fluorene.

$Ar^1$ is selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group containing at least one heteroatom selected from the group consisting of O, N, S, Si, and P, -L'-N($R^a$)($R^b$).

When $Ar^1$ is an aryl group, $Ar^1$ may be preferably a $C_6$-$C_{30}$ aryl group, more preferably a $C_6$-$C_{18}$ aryl group, for example, phenyl, biphenyl, terphenyl, naphthalene, pyrene and the like. When $Ar^1$ is a heterocyclic group, $Ar^1$ may be preferably a $C_2$-$C_{30}$ heterocyclic group, more preferably a $C_2$-$C_{26}$ heterocyclic group, for example, pyridine, pyrimidine, quinazoline, carbazole, thianthrene, dibenzothiophene, dibenzofuran, benzoquinazoline, dibenzoquinazoline, benzothienopyrimidine, benzofuropyrimidine, naphthothienopyrimidine, naphthofuropyrimidine, phenanthrothienopyrimidine, phenanthrofuropyrimidine, dibenzothihenocarbazole, dibenzofurocarbazole, 9,9-dimethyl-9H-fluorenocarbazole, dibydrobenzo[b]benzosilobenzocarbazole, diphenyl-di hydrobenzo[b]benzosilobenzocarbazole and the like. When $Ar^1$ is a fluorenylene group, $Ar^1$ may be 9,9-dimethyl-9H-fluorene.

In -L'-N($R^a$)($R^b$) above, L' may be selected from the group consisting of a single bond; a $C_6$-$C_{60}$ arylene group;

a fluorenylene group; a $C_2$-$C_{60}$ heterocyclic group containing at least one heteroatom selected from the group consisting of O, N, S, Si, and P; a fused ring of a $C_3$-$C_{60}$ aliphatic ring and a $C_6$-$C_{60}$ aromatic ring, and L' may be further substituted with substituent. For example, L' may be further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group and —N($R^a$)($R^b$).

When L' is an arylene group, L' may be a $C_6$-$C_{30}$ arylene group, preferably a $C_6$-$C_{18}$ arylene group, for example, phenylene, biphenyl, terphenyl, and the like; when L' is a heterocyclic group, L' may be preferably a $C_6$-$C_{30}$ heterocyclic group, more preferably a $C_6$-$C_{12}$ heterocyclic group, for example, dibenzothiophene; when L' is a fluorenylene group, L' may be 9,9-dimethyl-9H-fluorene.

In -L'-N($R^a$)($R^b$) and —N($R^a$)($R^b$) above, $R^a$ and $R^b$ may be each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; a fused ring of a $C_3$-$C_{60}$ aliphatic ring and a $C_6$-$C_{60}$ aromatic ring.

When $R^a$ and $R^b$ are a $C_6$-$C_{60}$ aryl group, $R^a$ and $R^b$ may be preferably a $C_6$-$C_{30}$ aryl group, more preferably a $C_6$-$C_{14}$ aryl group, for example, phenyl, biphenyl, naphthyl, phenanthrene and the like. When $R^a$ and $R^b$ are a heterocyclic group, $R^a$ and $R^b$ may be preferably $C_2$-$C_{30}$ heterocyclic group, more preferably $C_2$-$C_{26}$ heterocyclic group, for example, dibenzothiophene, dibenzofuran, carbazole, benzocarbazole and the like. When $R^a$ and $R^b$ are a fluorenyl group, $R^a$ and $R^b$ may be 9,9-dimethyl-9H-fluorene, 9,9'-spirobifluorene and the like.

Preferably, in -L'-N($R^a$)($R^b$), L' may be any one selected from the group consisting of the following Formulas.

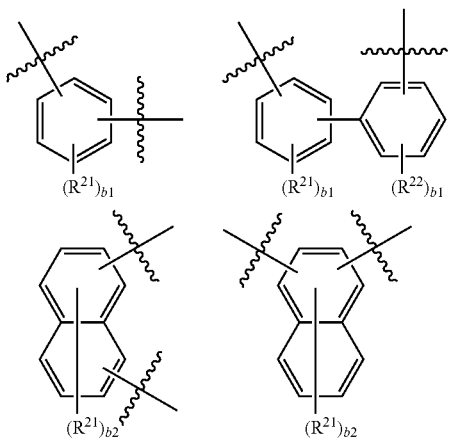

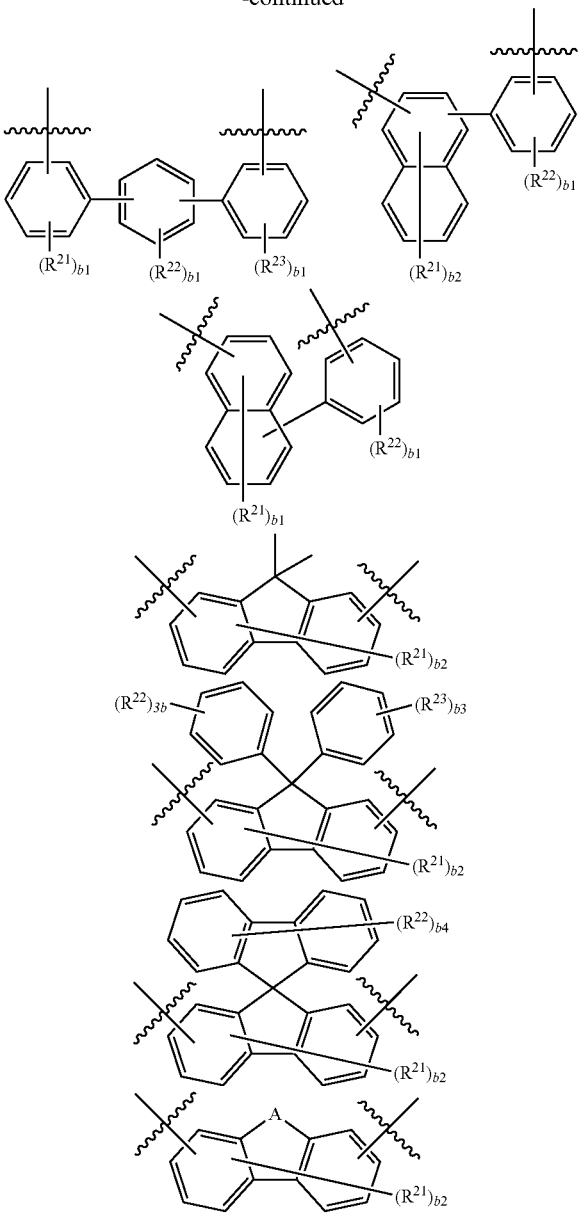

In group of the above formulas, $R^{21}$ to $R^{23}$ are each independently selected from the group consisting of hydrogen, deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group, and —N($R^a$)($R^b$). In N($R^a$)($R^b$), R and $R^b$ are the same as defined above.

b1 is an integer of 0 to 4, b2 is an integer of 0 to 6, b3 is an integer of 0 to 5, and b4 is an integer of 0 to 8. When b1 to b4 are each an integer of 2 or more, neighboring groups of $R^{21}$ to $R^{23}$ may be linked to each other to form a ring. Here, the formed ring may be a $C_6$-$C_{60}$ aromatic ring, a fluorene, a $C_2$-$C_{60}$ heterocyclic group containing at least one heteroatom selected from the group consisting of O, N, S, Si, and P, or a fused ring of a $C_6$-$C_{60}$ aromatic ring and a $C_3$-$C_{60}$ aliphatic ring.

In group of the above formulas group, A is an $N(Ar^2)$, O, S, $C(R^{13})(R^{14})$ or $Si(R^{13})(R^{14})$, wherein $Ar^2$ is the same as $Ar^1$ defined in formula 1 and $R^3$ and $R^4$ are the same as defined in formula 1.

In formula 1, when each symbol is an aryl group, a fluorenyl group, a heterocyclic group, a fused ring group, an arylene group, an alkyl group, an alkenyl group, an alkynyl group, an alkynyl group, an alkoxyl group, an aryloxy group or fluorenylene group, they may be each optionally further substituted with deuterium, halogen, a silane group, a siloxane group, a boron group, a germanium group, a cyano group, a nitro group, a $C_1$-$C_{20}$ alkylthio group, a $C_1$-$C_{20}$ alkoxyl group, $C_1$-$C_{20}$ alkyl group, $C_2$-$C_{20}$ alkenyl group, $C_2$-$C_{20}$ alkynyl group, a $C_6$-$C_{20}$ aryl group, a $C_6$-$C_{20}$ aryl group substituted with deuterium, a $C_3$-$C_{20}$ cycloalkyl group, a $C_7$-$C_{20}$ arylalkyl group, and a $C_8$-$C_{20}$ arylalkenyl group.

When m is 0 and n is 1 in the above formula 1, formula 1 may be represented by the following formula 2, and when m is 1 and n is 0 in the above formula 1, formula 1 may be represented by the following formula 3.

<Formula 2>

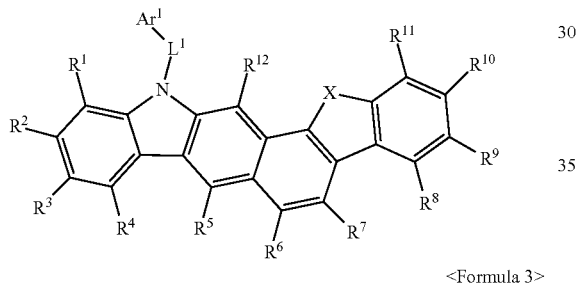

<Formula 3>

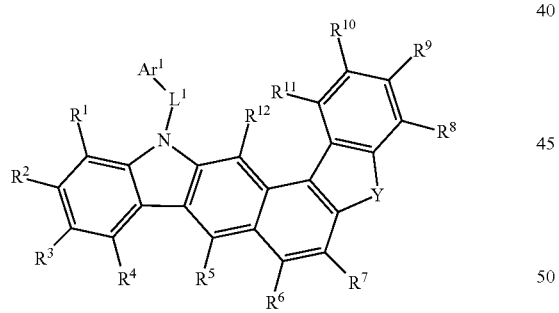

In formulas 2 and 3 above, each of $R^1$ to $R^{12}$, $Ar^1$, $L^1$, X, Y and the like is the same as defined in formula 1 above.

Preferably, in formulas 1 to 3 above, $Ar^1$ may be a $C_6$-$C_{20}$ aryl group represented by

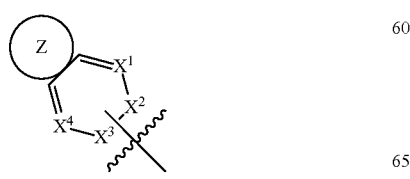

or a $C_2$-$C_{60}$ heterocyclic group containing at least one heteroatom selected from the group consisting of O, N, S, Si, and P, for example, any one of the following formulas Z-10 to Z-22.

<FormulaZ-1>

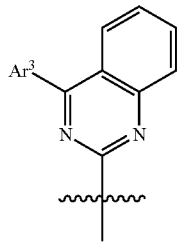

<FormulaZ-2>

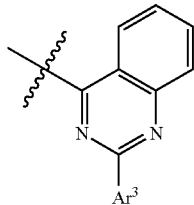

<FormulaZ-3>

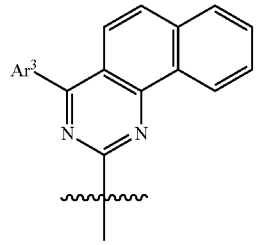

<FormulaZ-4>

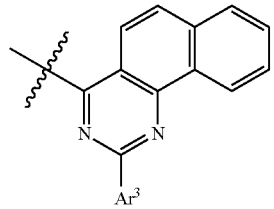

<FormulaZ-5>

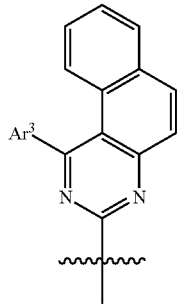

<FormulaZ-6>
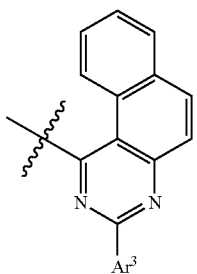
<FormulaZ-6>
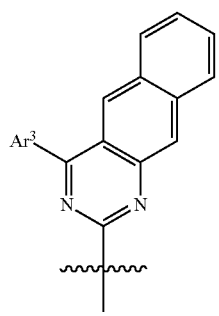
<FormulaZ-8>
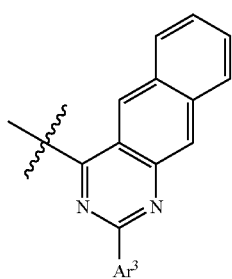
<FormulaZ-9>
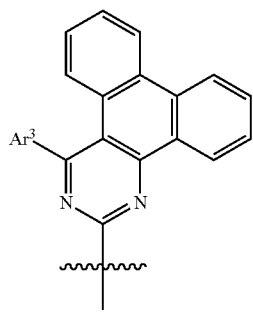
<FormulaZ-10>
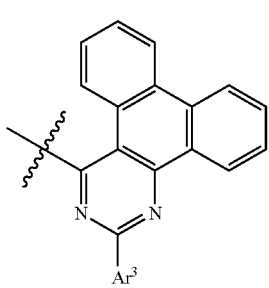
<FormulaZ-11>
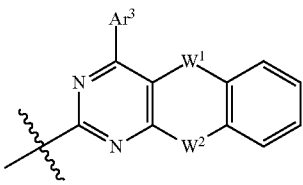
<FormulaZ-12>
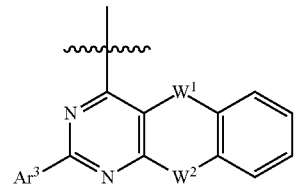
<FormulaZ-13>
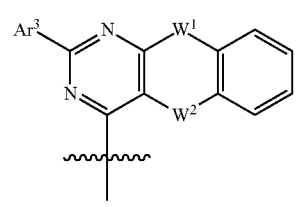
<FormulaZ-14>
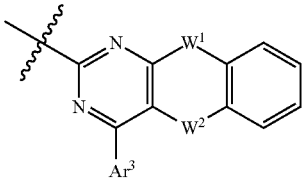
<FormulaZ-15>
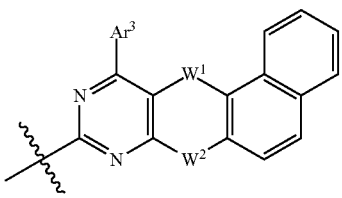
<FormulaZ-16>
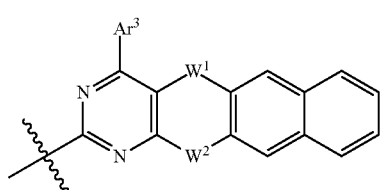
<FormulaZ-17>
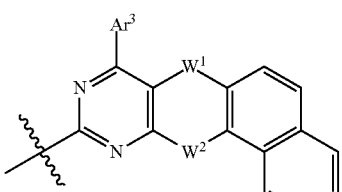
<FormulaZ-18>
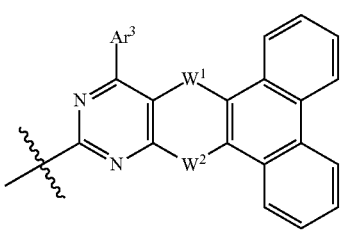

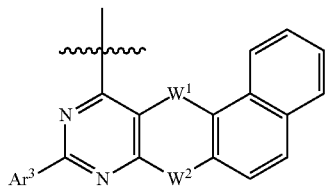
<Formula Z-19>

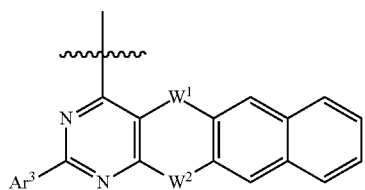
<Formula Z-20>

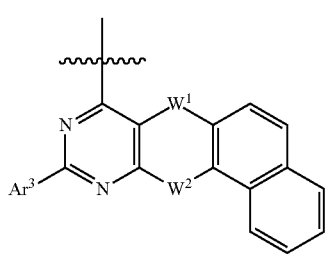
<Formula Z-21>

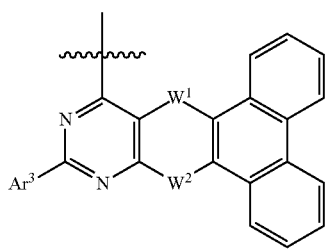
<Formula Z-22>

In formulas Z-1 to Z-22 above, $Ar^3$ is the same as $Ar^1$ defined in formula 1, and $W^1$ and $W^2$ are each independently a single bond, $C(R^{13})(R^{14})$, $N(Ar^2)$, O, S, or $Si(R^{13})(R^{14})$. Here, $Ar^2$ is the same as $Ar^1$ defined in formula 1, and $R^{13}$ and $R^{14}$ are the same as in defined in formula 1.

When $Ar^1$ is

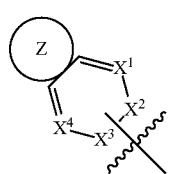

in formulas 2 and 3 above, the above formula 2 may be represented by the following formula 4 and the above formula 3 may be represented by the following formula 5.

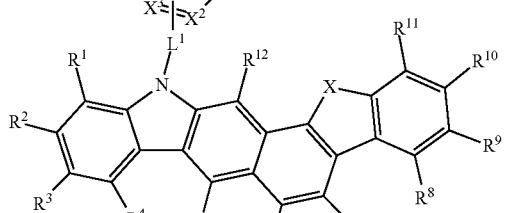
<Formula 4>

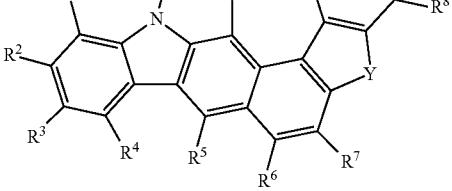
<Formula 5>

In formulas 4 and 5 above, each of $R^1$ to $R^{12}$, $L^1$, X, Y and the like is the same as defined in formula 1, and $X^1$ to $X^4$ are each independently N, C or $C(R^{13})$.

Preferably, at least one of $X^1$ to $X^4$ is N and at least one of $X^1$ to $X^4$ is C boned to L, wherein $R^{13}$ is the same as defined in formula 1. Z ring is a substituted or unsubstituted $C_6$-$C_{60}$ aromatic ring or a substituted or unsubstituted $C_2$-$C_{60}$ heterocyclic group containing at least one heteroatom of O, N, S, Si, and P. Z ring may be preferably a $C_6$-$C_{18}$ aromatic ring or a $C_2$-$C_{17}$ heterocyclic group, for example, benzene, naphthalene, phenanthrene, quinoline, quinoxaline, benzoquinoline, benzoquinoxaline, benzothiophene, dibenzothiophene, benzofuran, dibenzofuran, benzophenanthrothiophene, benzophenanthrofuran, and the like.

Preferably, in formulas 4 and 5, Z ring may be represented by any one of the following formulas Z'-1 to Z'-9.

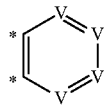
<Formula Z'-1>

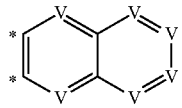
<Formula Z'-2>

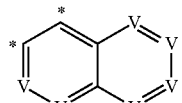
<Formula Z'-3>

-continued

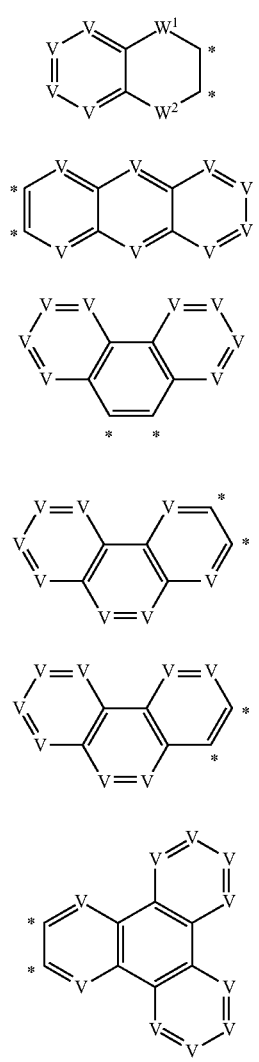

<FormulaZ'-4>

<FormulaZ'-5>

<FormulaZ'-6>

<FormulaZ'-7>

<FormulaZ'-8>

<FormulaZ'-9>

In formulas Z'-1 to Z'-9, "*" indicates the position fused with ring containing $X^1$ to $X^4$, V is independently $C(R^{13})$ or N, and $W^1$ and $W^2$ are each independently a single bond, $C(R^{13})(R^{14})$, $N(Ar^2)$, O, S, or $Si(R^{13})(R^{14})$, wherein $R^{13}$ and $R^{14}$ are the same as defined in formula 1, and $Ar^2$ is the same as $Ar^1$ defined in formula 1.

Specifically, the compound represented by Formula 1 above may be one of the following compounds.

-continued

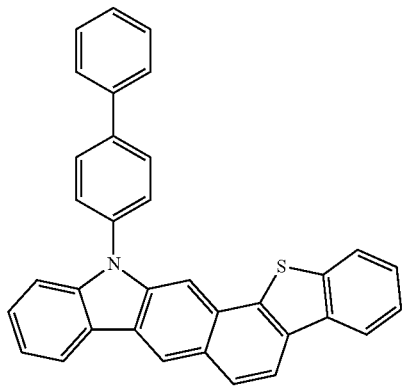

1-1-2

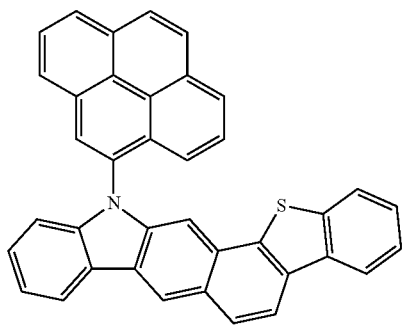

1-1-3

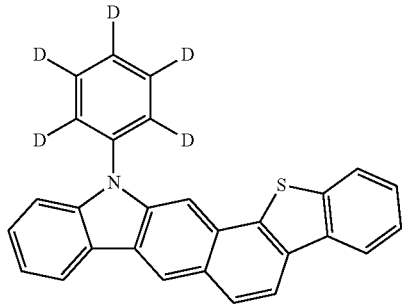

1-1-4

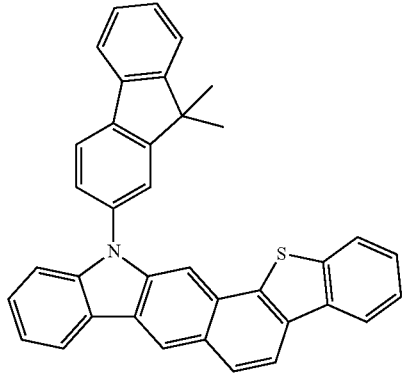

1-1-5

1-1-6
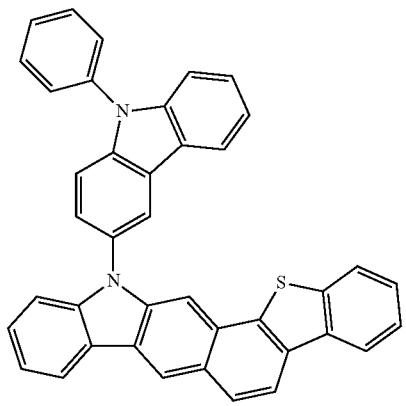
1-1-7
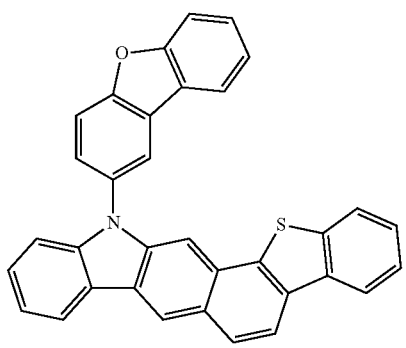
1-1-8
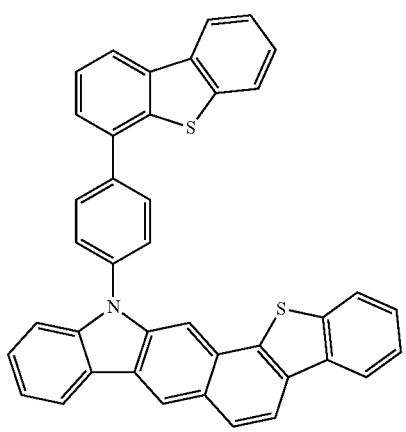
1-1-9
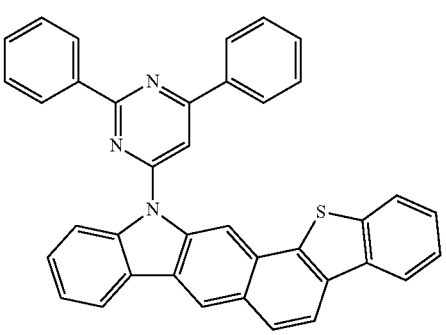
1-1-10
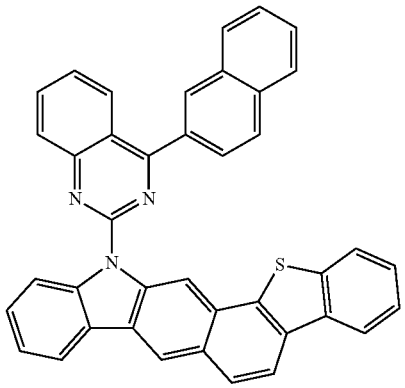
1-1-11
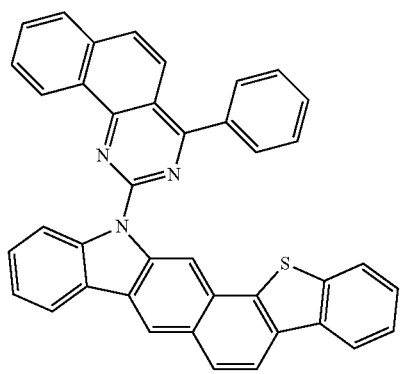
1-1-12
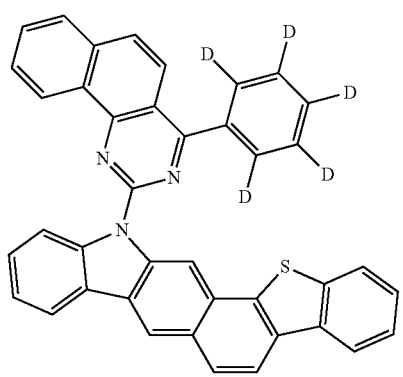
1-1-13
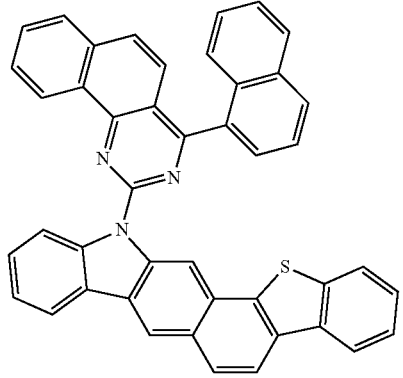

1-1-14
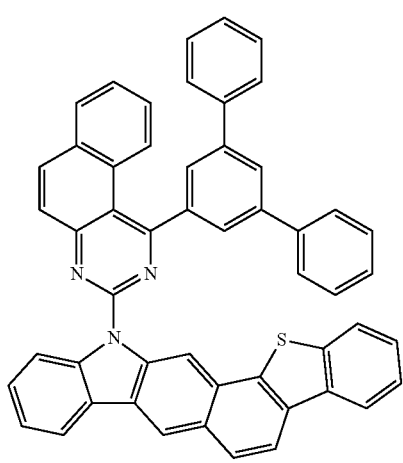
1-1-15
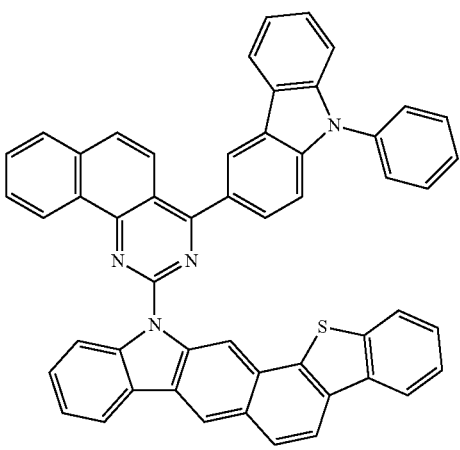
1-1-16
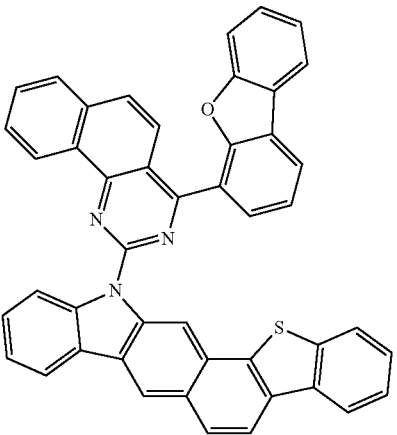
1-1-17
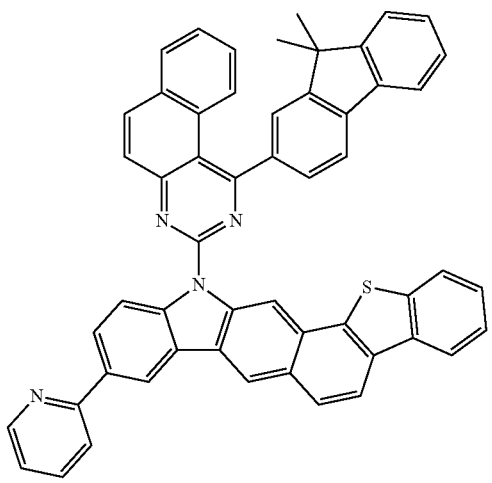
1-1-18
1-1-19

1-1-20
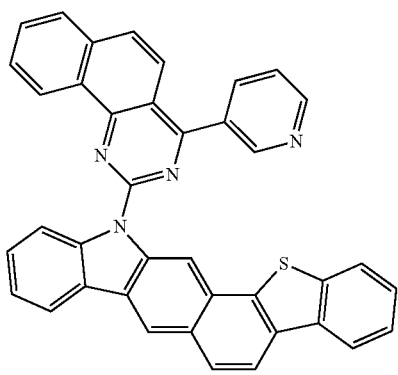
1-1-21
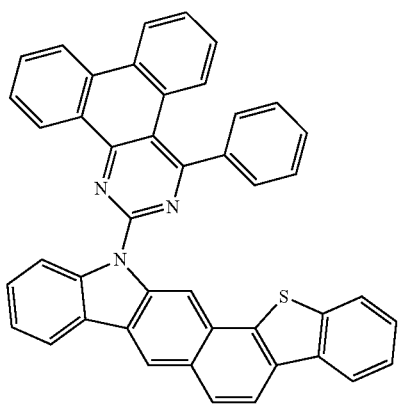
1-1-22
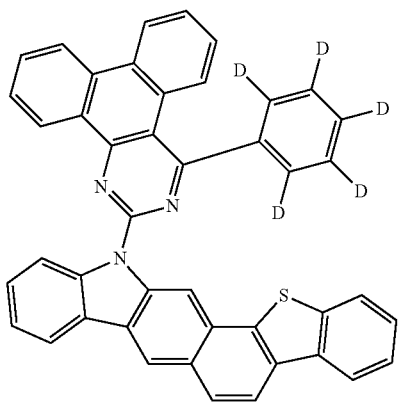
1-1-23
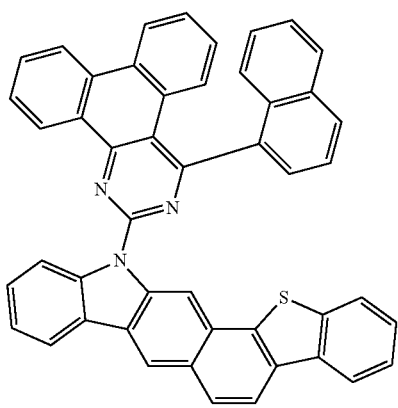
1-1-24
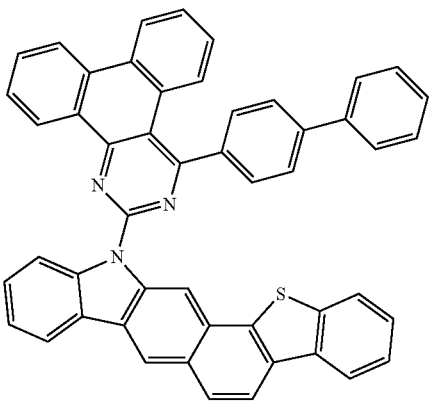
1-1-25
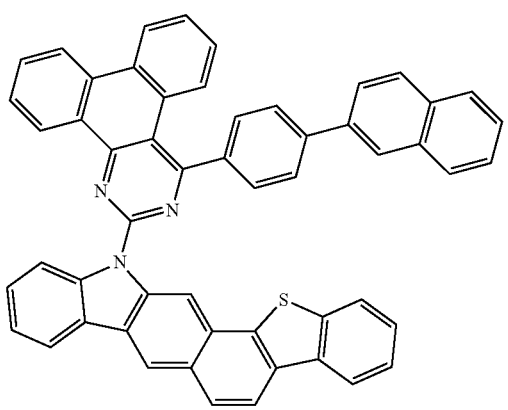
1-1-26
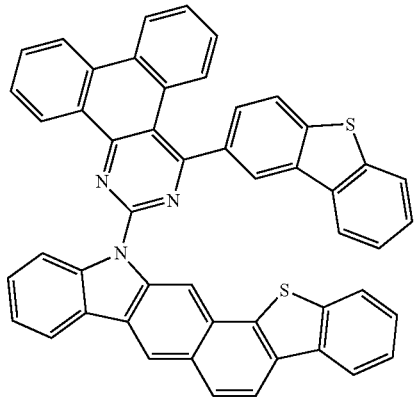
1-1-27
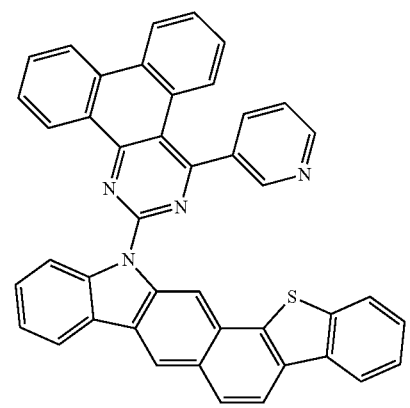

25
-continued
1-1-28
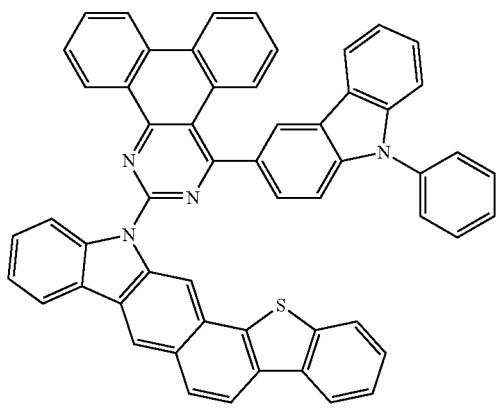
1-1-29
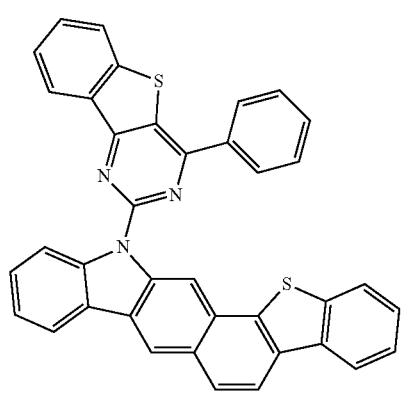
1-1-30
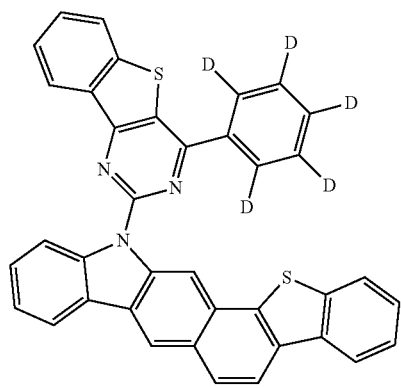
1-1-31
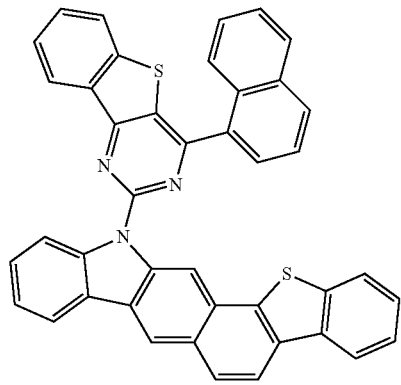
26
-continued
1-1-32
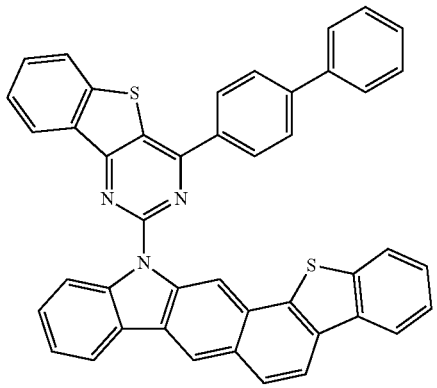
1-1-33
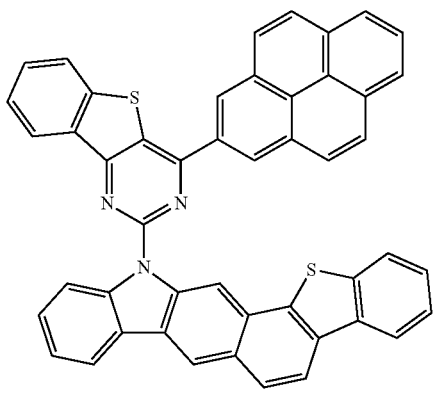
1-1-34
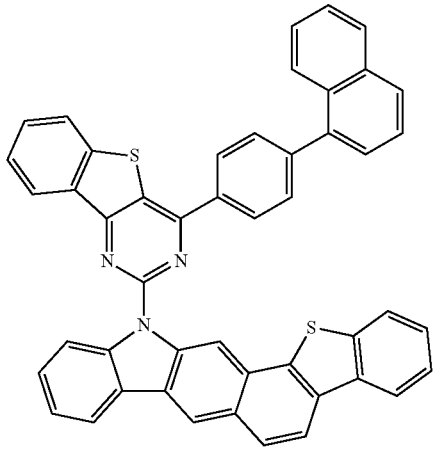
1-1-35
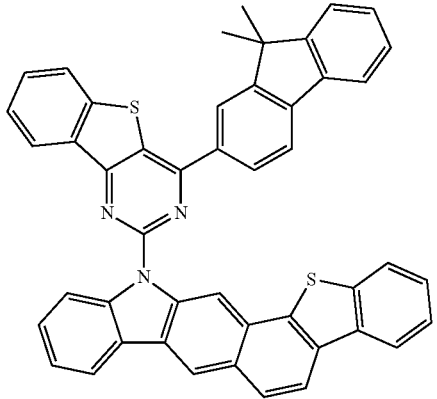

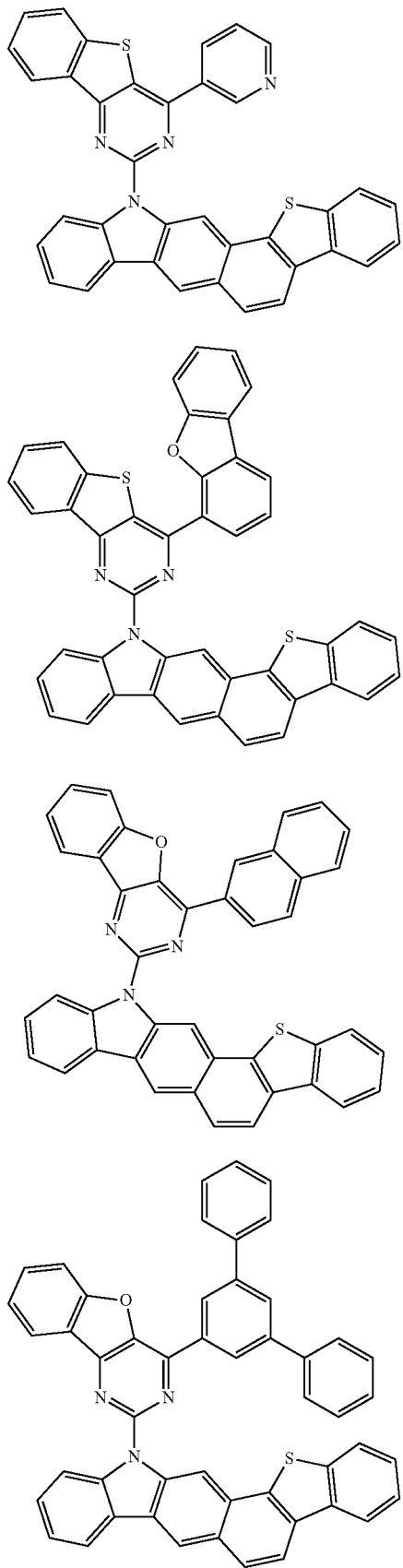
1-1-36
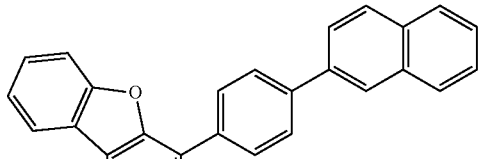
1-1-37
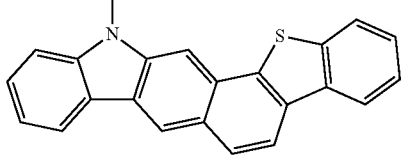
1-1-38
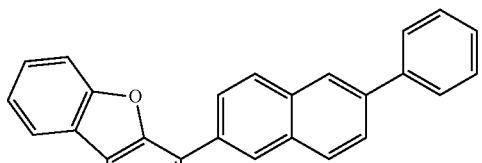
1-1-39
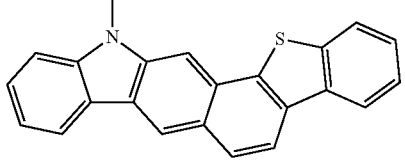
1-1-40
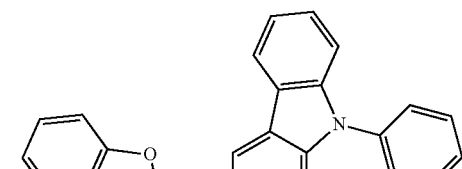
1-1-41
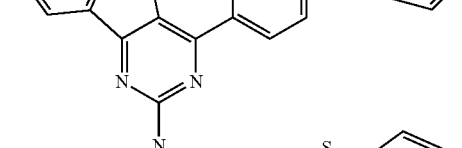
1-1-42
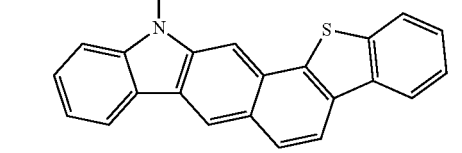
1-1-43
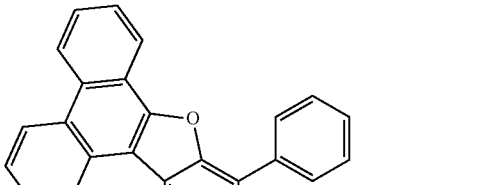
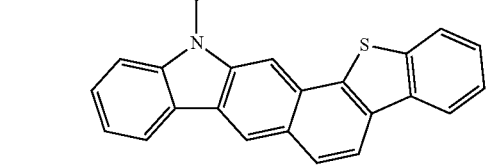

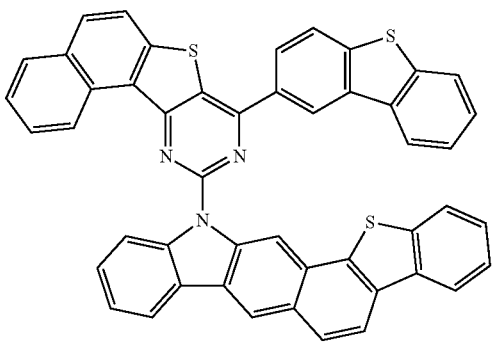
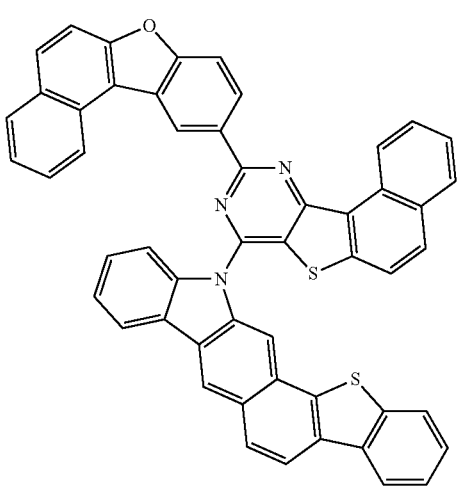

-continued
1-1-51
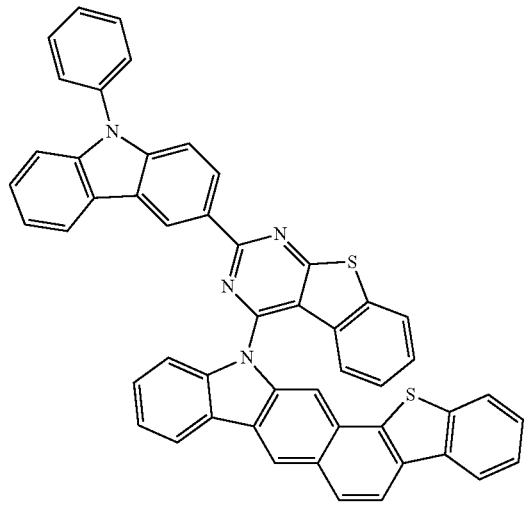
1-1-52
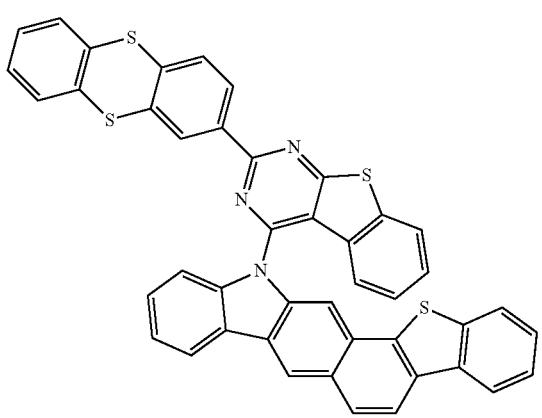
1-1-53
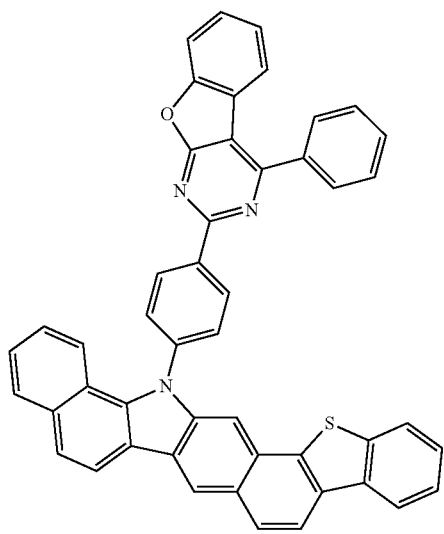
-continued
1-1-54
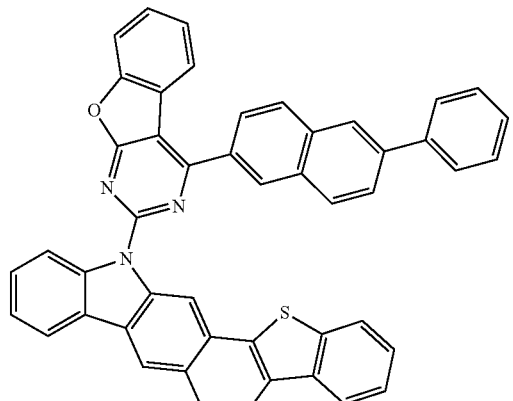
1-1-55
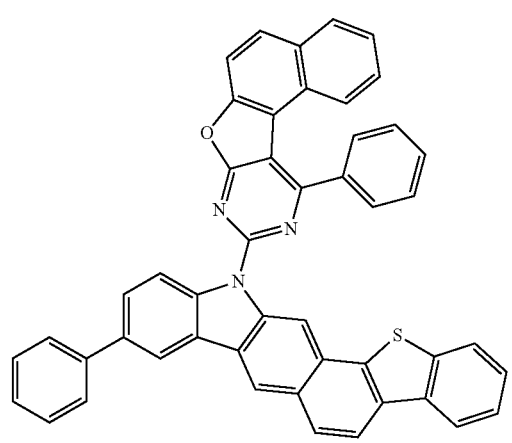
1-1-56
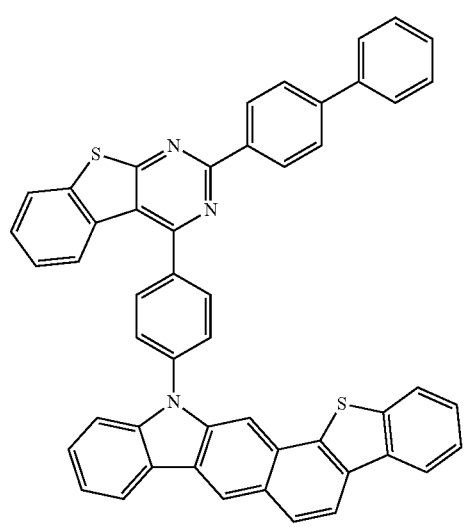

1-1-57
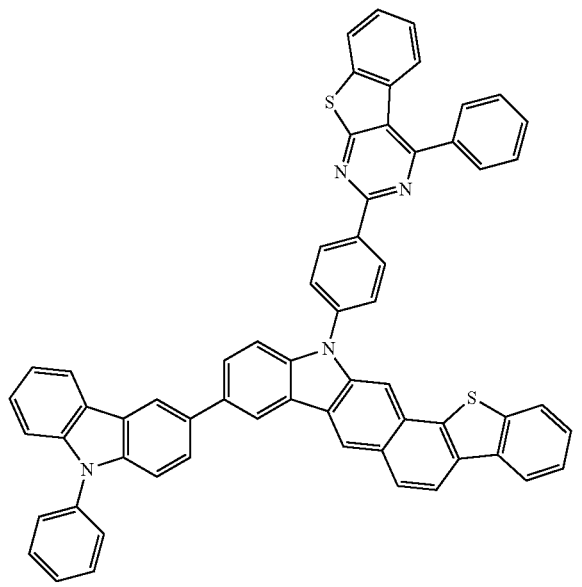
1-1-58
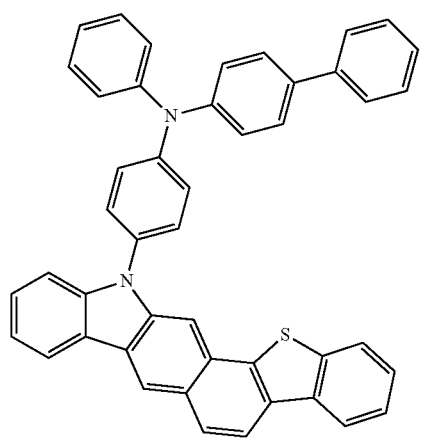
1-1-59
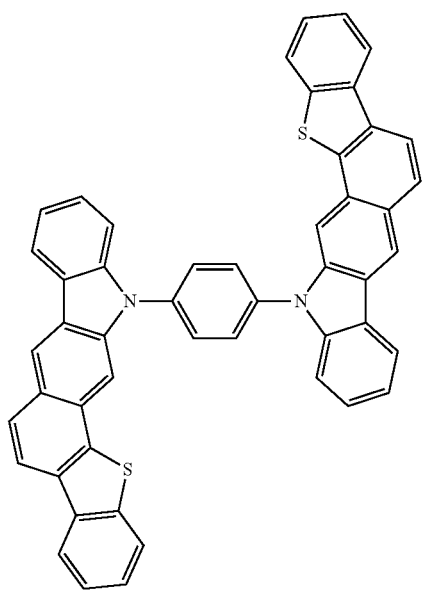
1-1-60
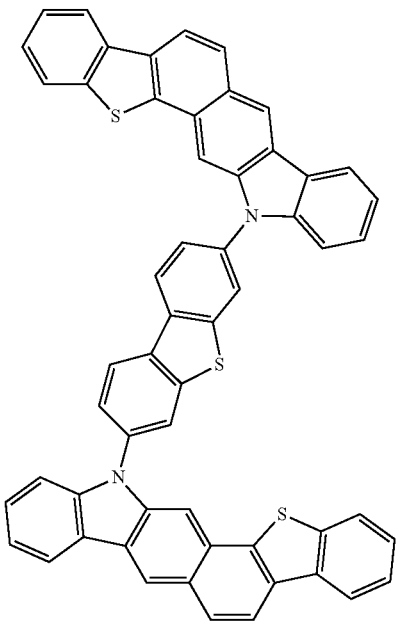
1-1-61
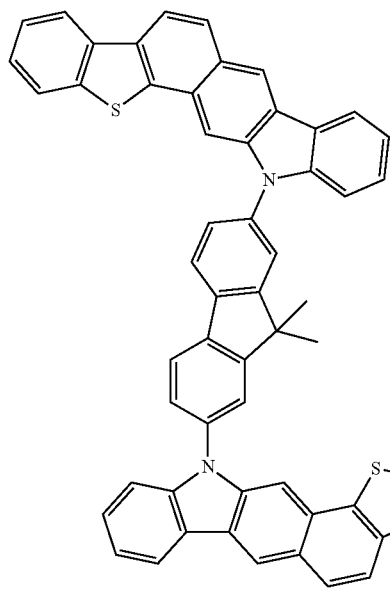
1-1-62
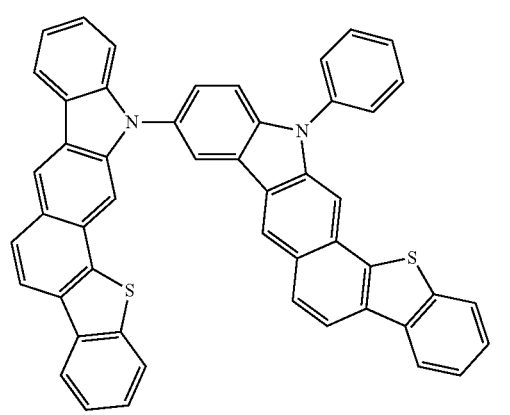

1-1-63
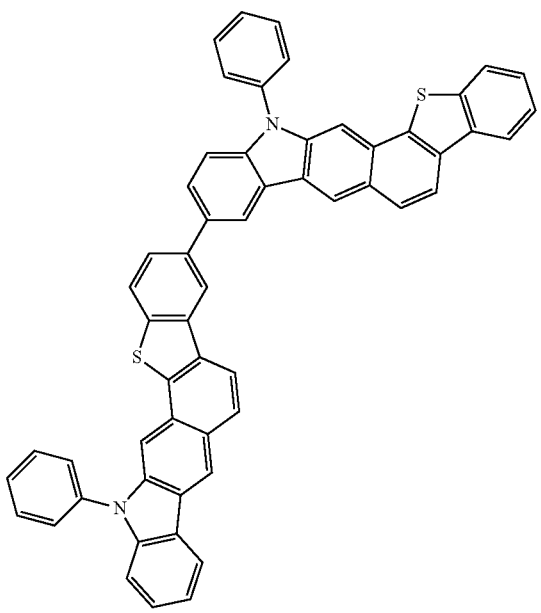
1-2-1
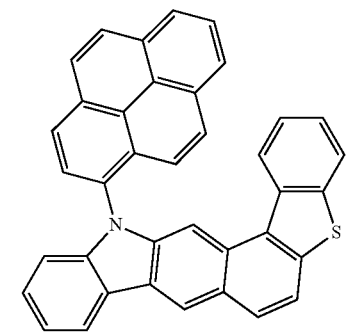
1-2-2
1-2-3
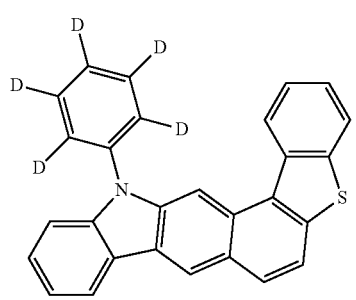
1-2-4
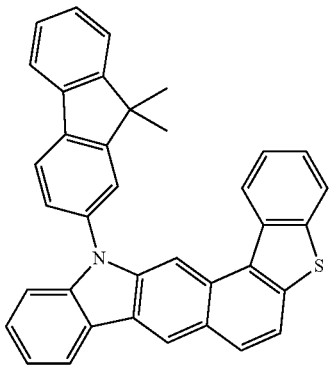
1-2-5
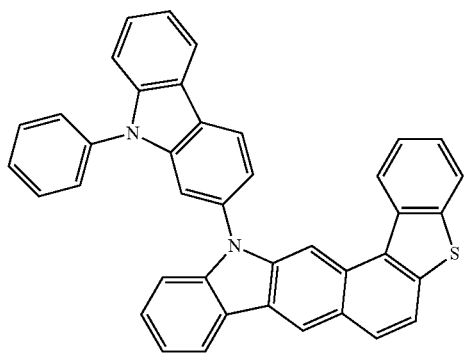
1-2-6
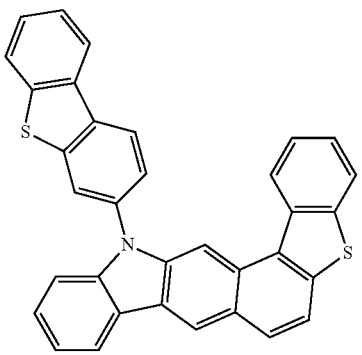
1-2-7
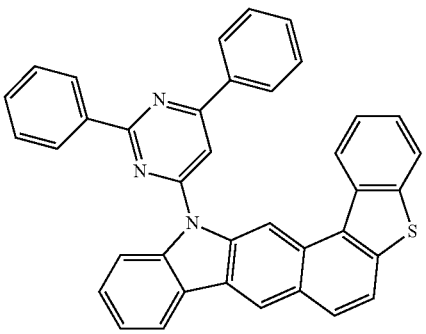

1-2-8
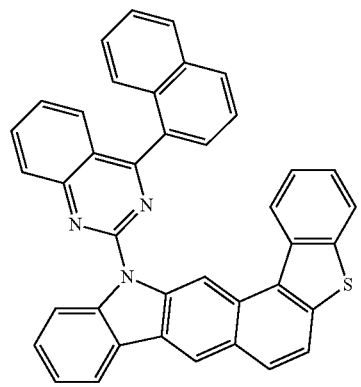
1-2-12
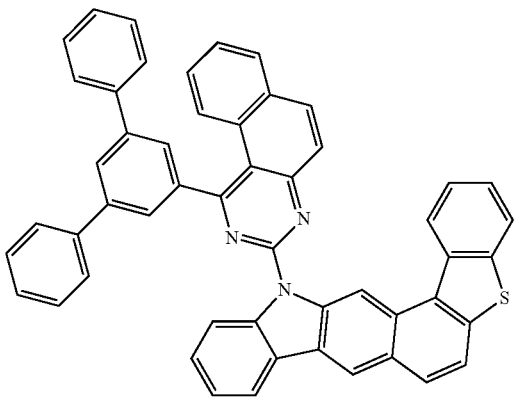
1-2-9
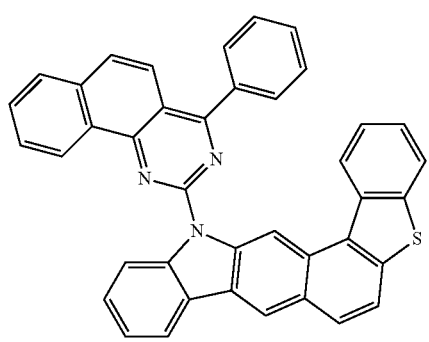
1-2-13
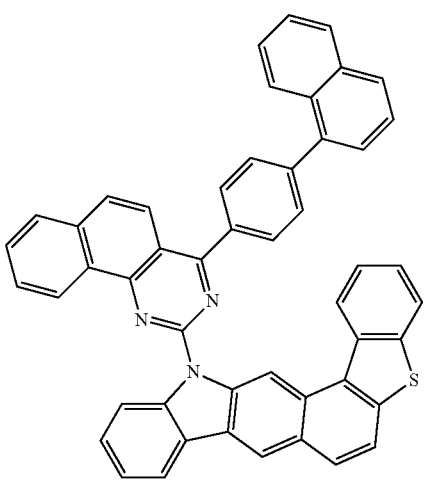
1-2-10
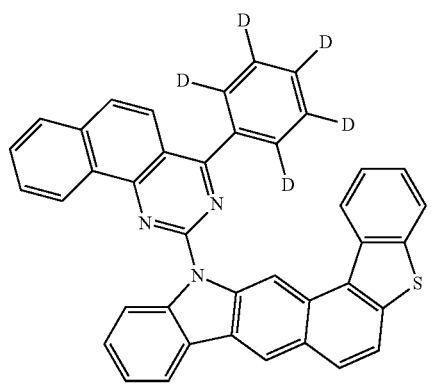
1-2-11
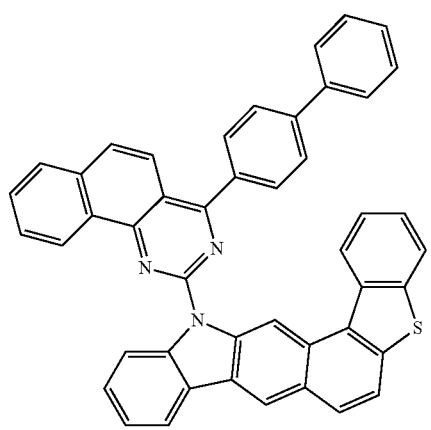
1-2-14
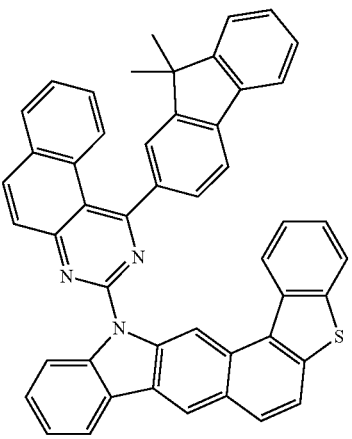

1-2-15
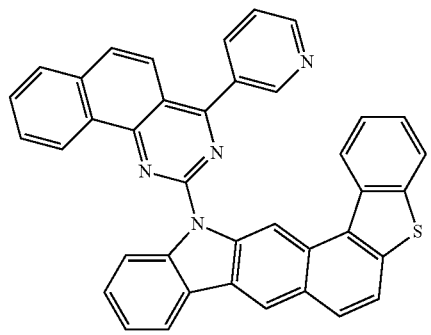
1-2-16
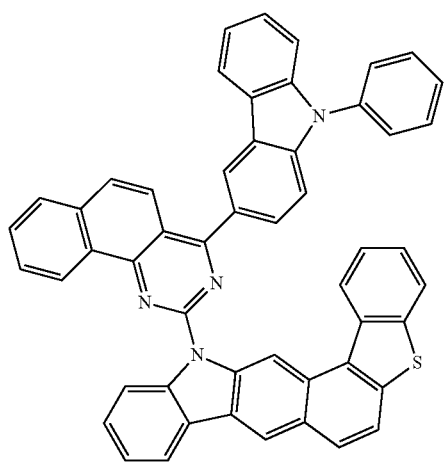
1-2-17
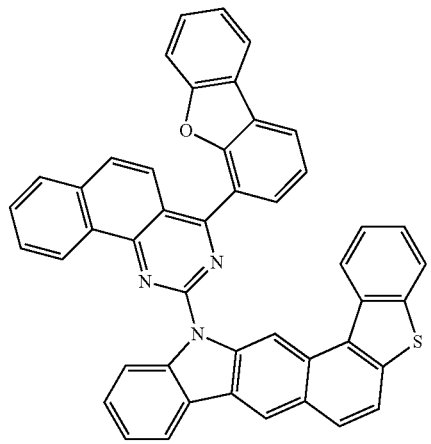
1-2-18
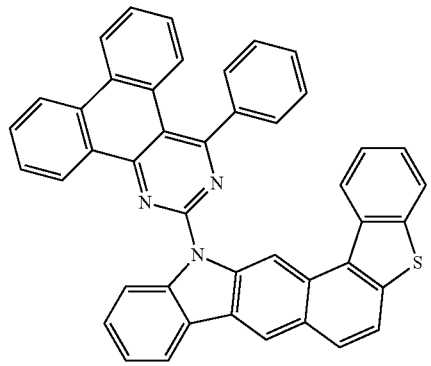
1-2-19
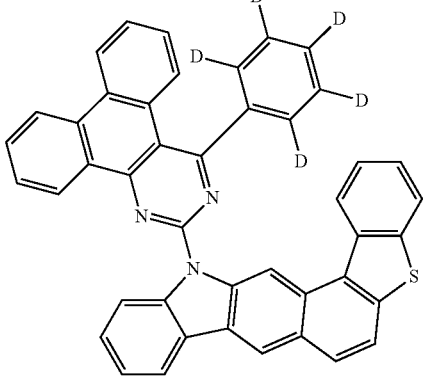
1-2-20
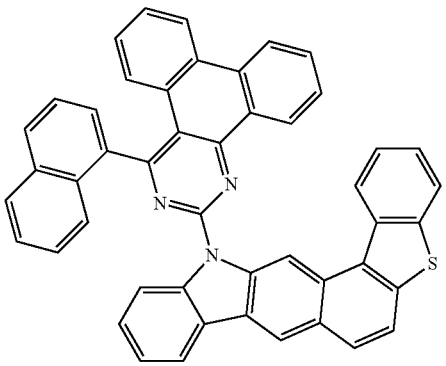
1-2-21
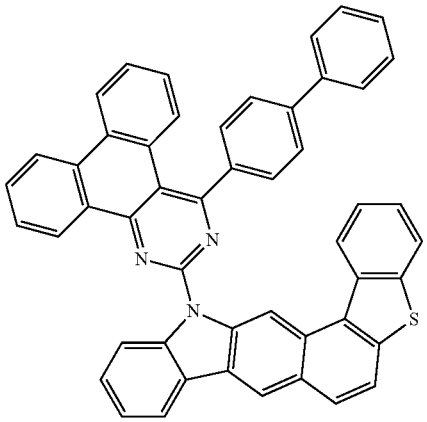
1-2-22
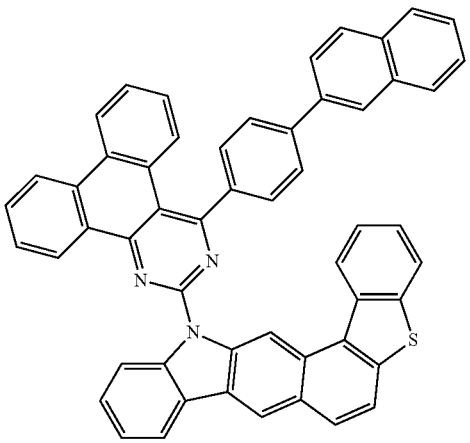

1-2-23
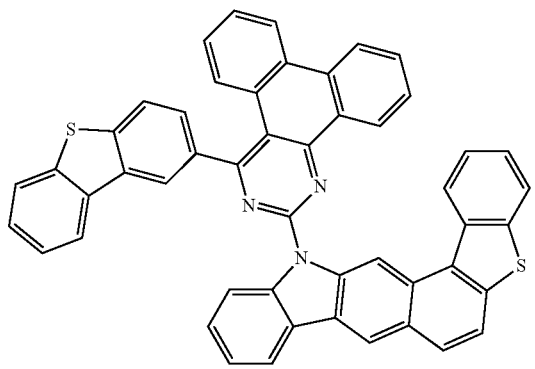
1-2-24
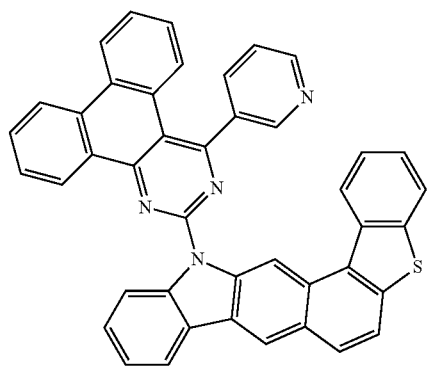
1-2-25
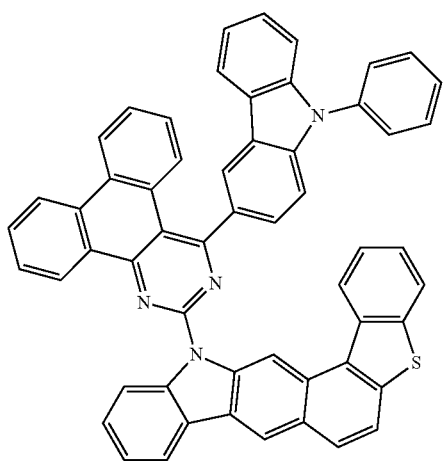
1-2-26
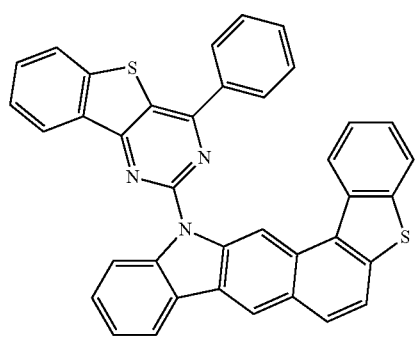
1-2-27
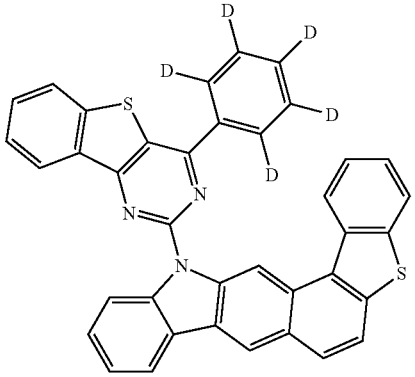
1-2-28
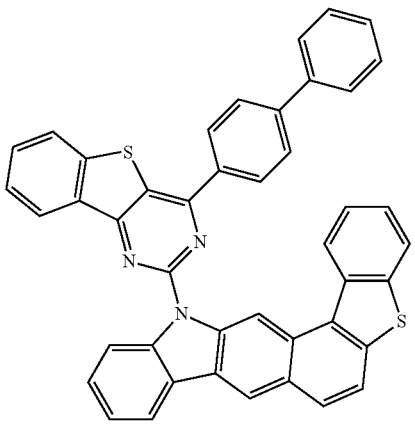
1-2-29
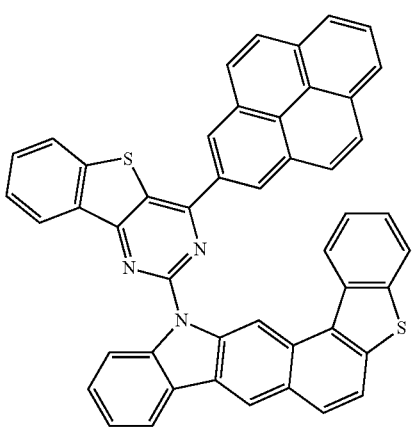
1-2-30
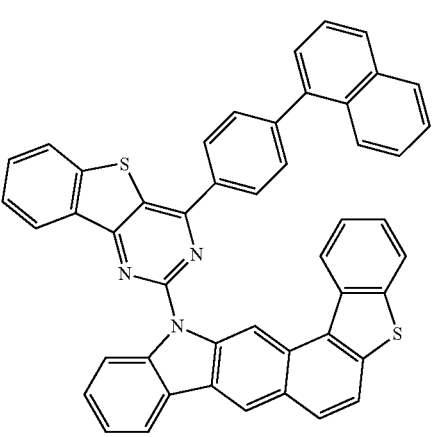

1-2-31
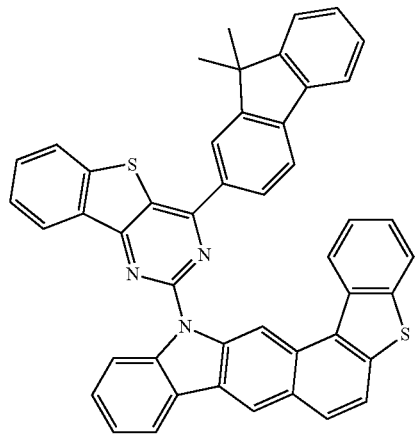
1-2-34
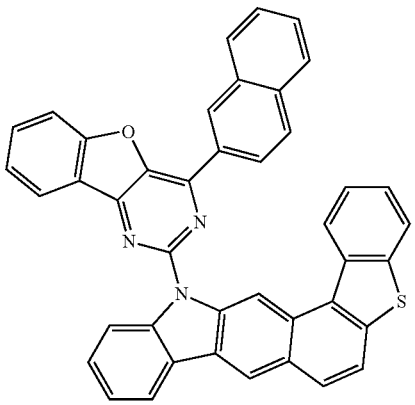
1-2-32
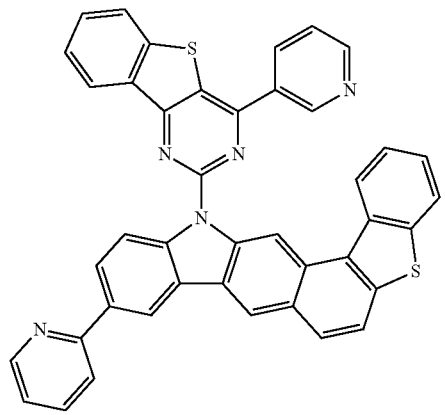
1-2-35
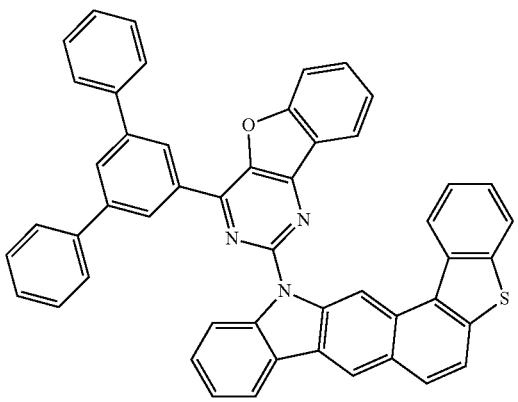
1-2-33
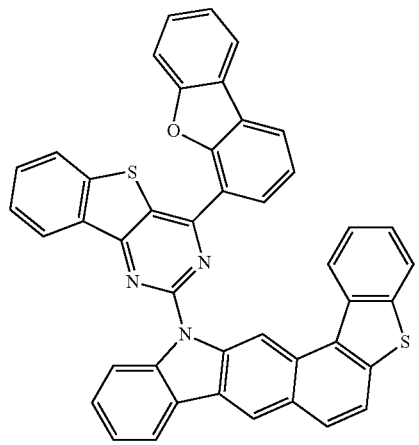
1-2-36
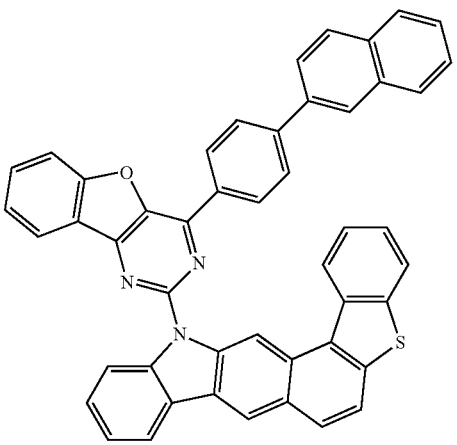

-continued
1-2-37
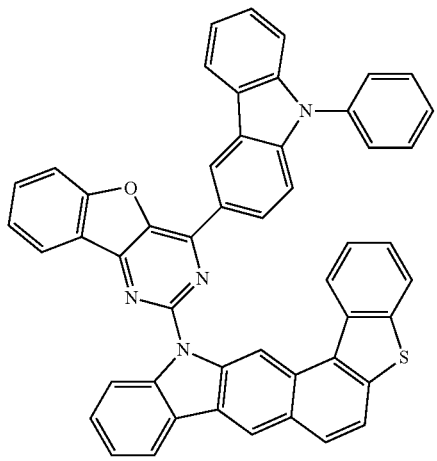
1-2-38
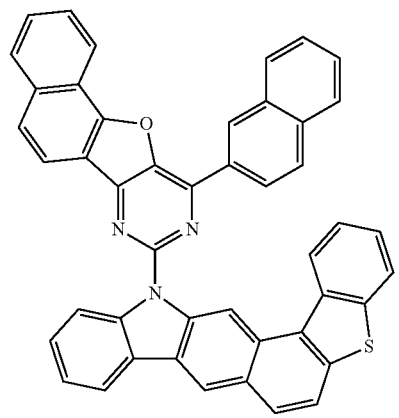
1-2-39
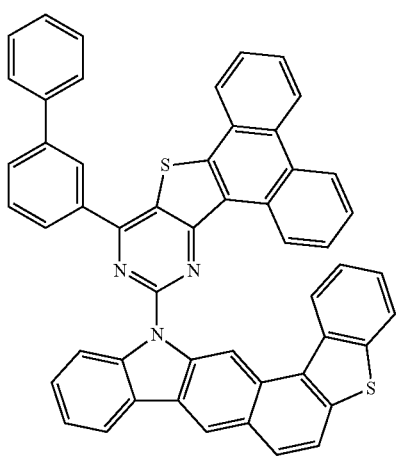
1-2-40
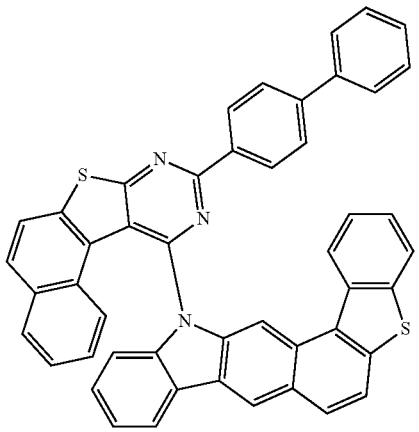
1-2-41
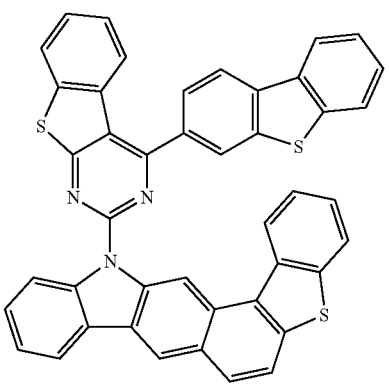
1-2-42
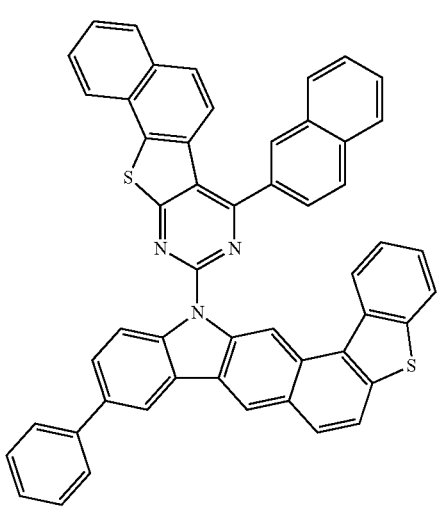

1-2-43
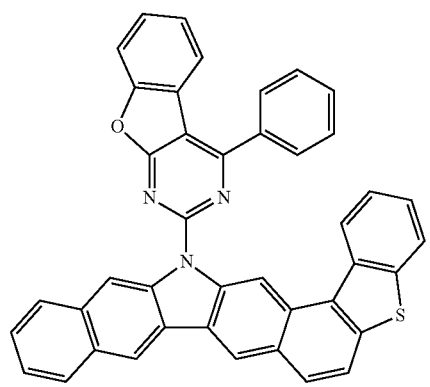
1-2-46
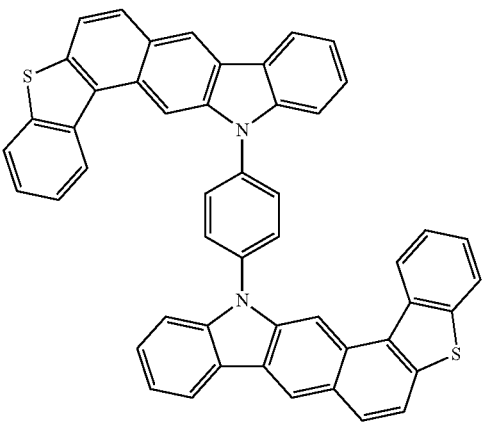
1-2-44
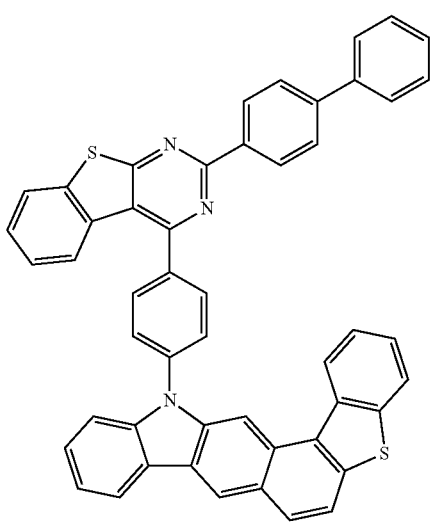
1-2-47
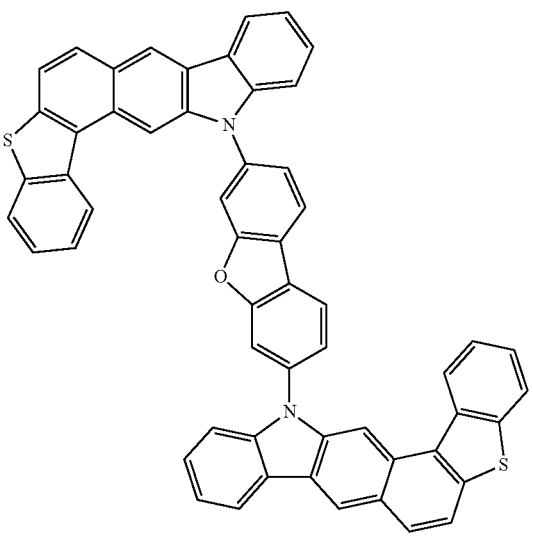
1-2-45
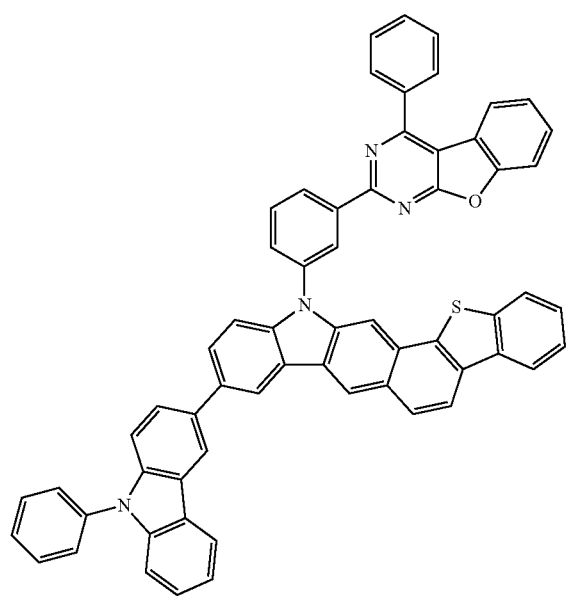
1-2-48
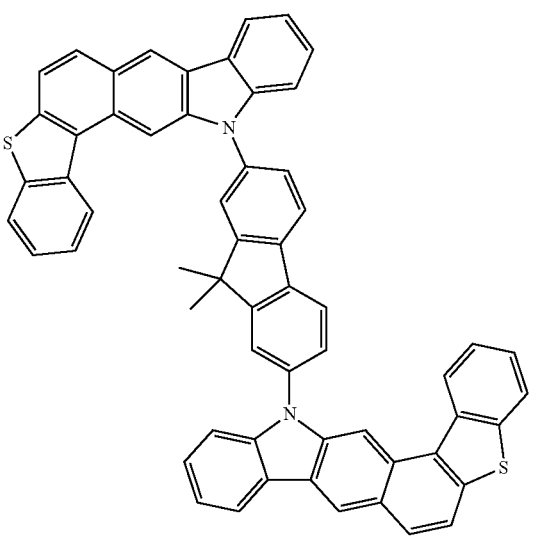

1-2-49
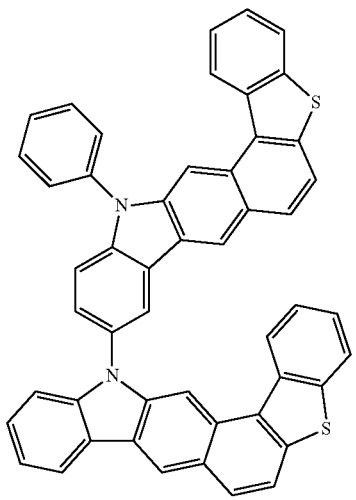
1-2-50
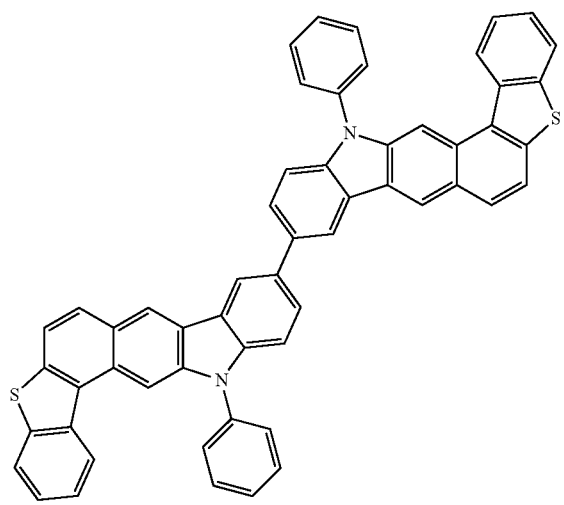
2-1-1
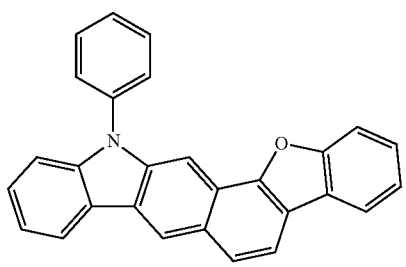
2-1-2
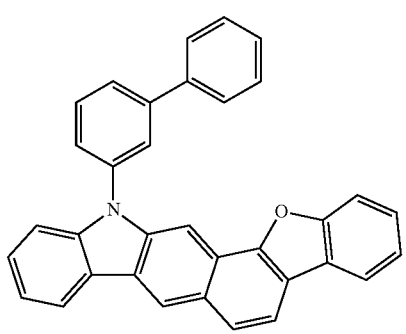
2-1-3
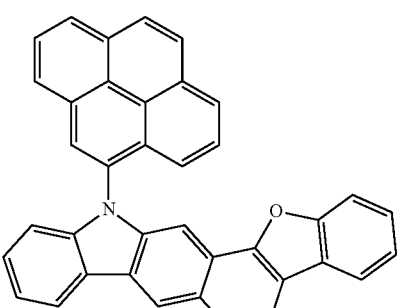
2-1-4
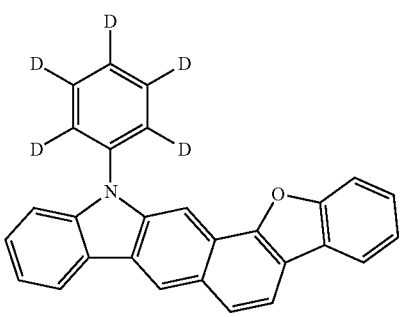
2-1-5
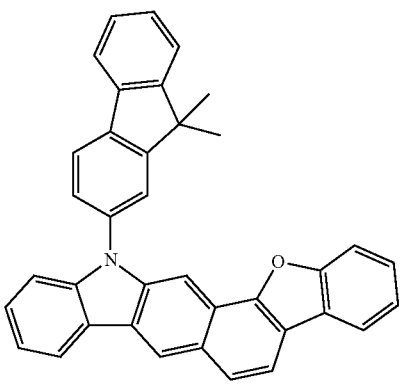
2-1-6
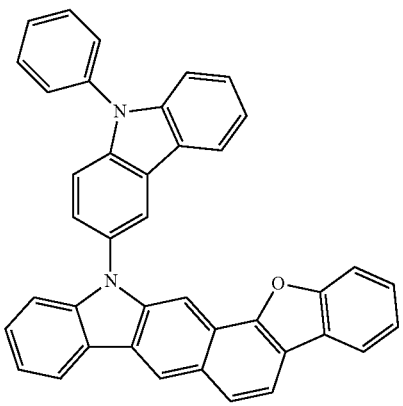

2-1-7
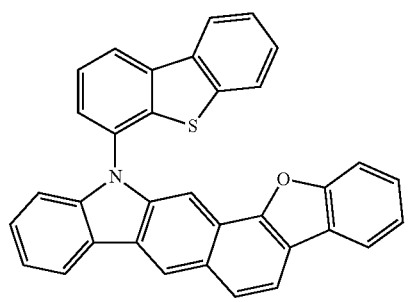
2-1-8
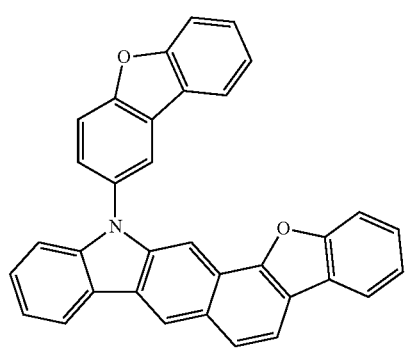
2-1-9
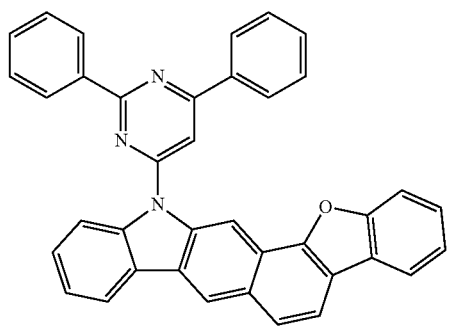
2-1-10
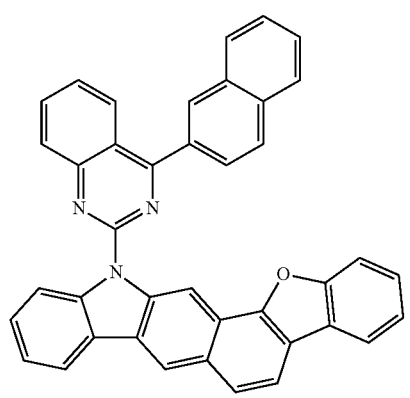
2-1-11
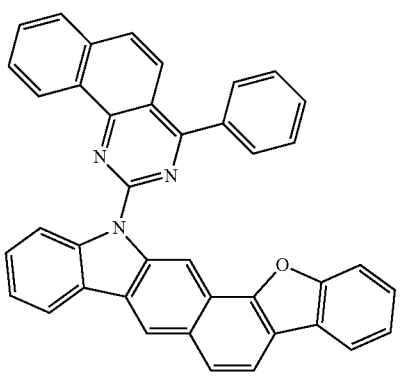
2-1-12
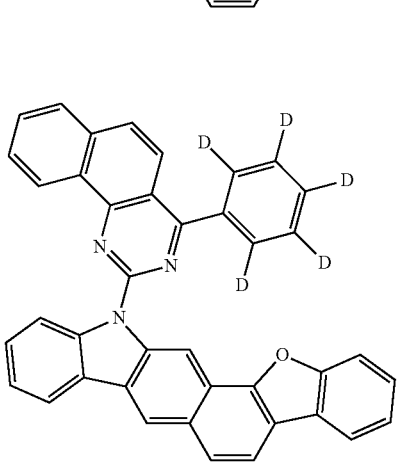
2-1-13
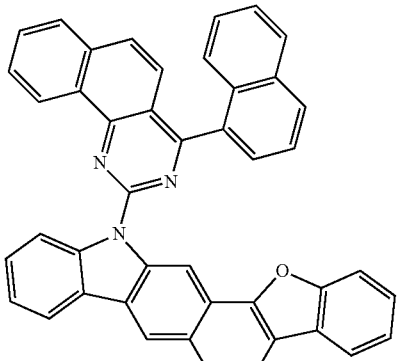
2-1-14
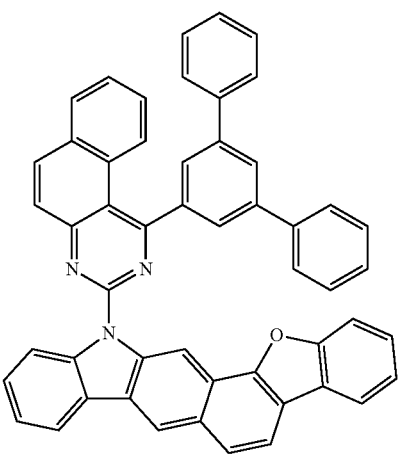

2-1-15
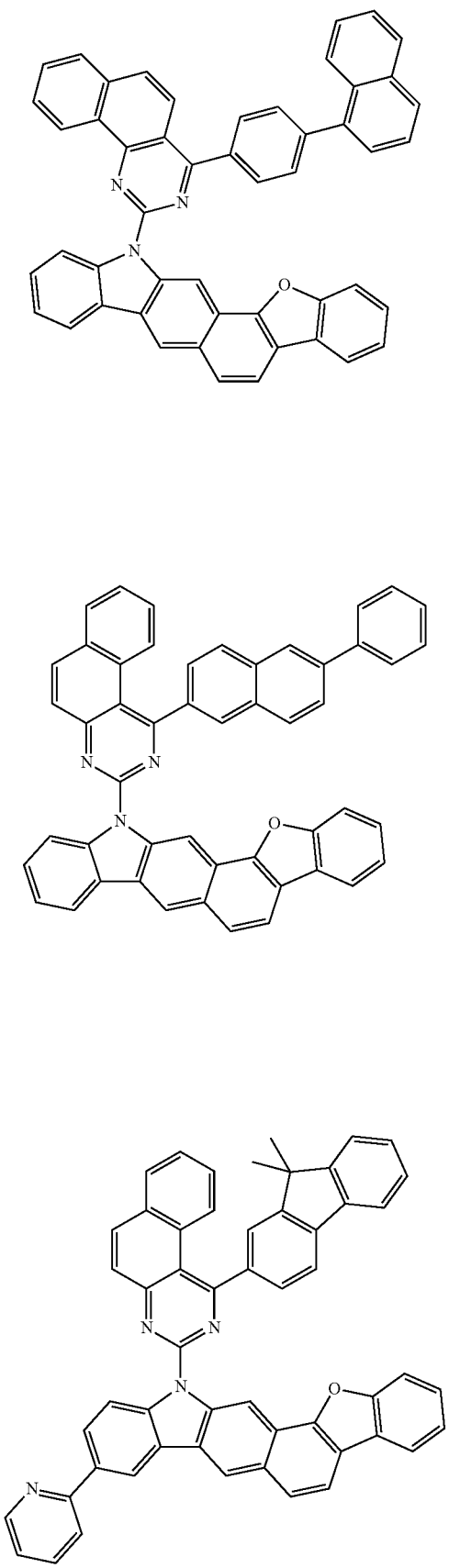
2-1-16
2-1-17
2-1-18
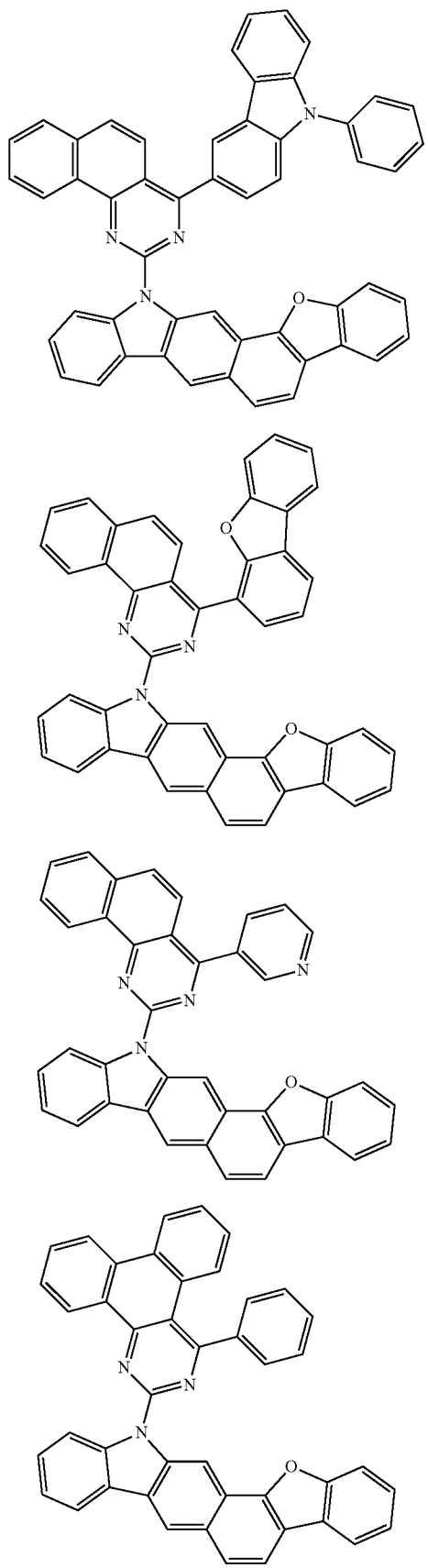
2-1-19
2-1-20
2-1-21

2-1-22
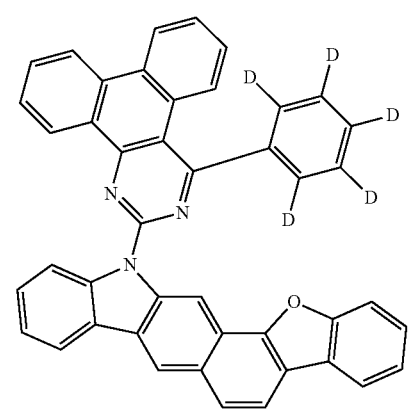
2-1-23
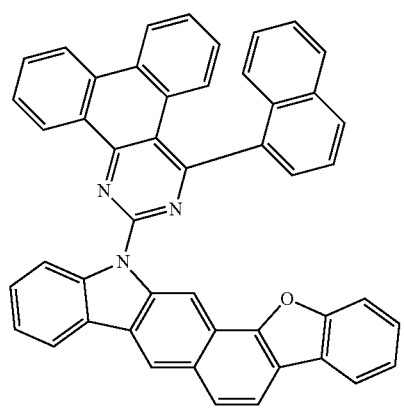
2-1-24
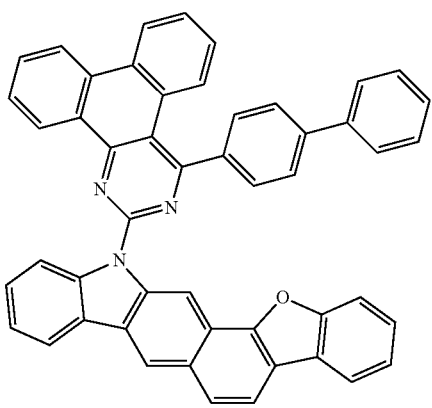
2-1-25
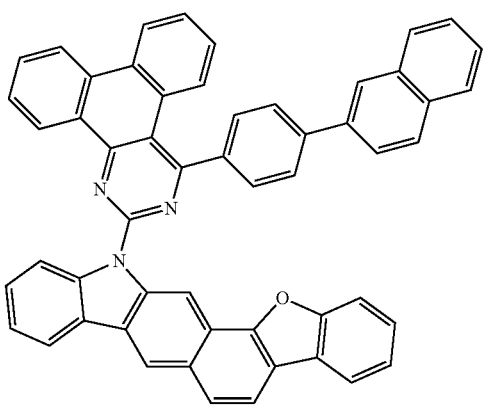
2-1-26
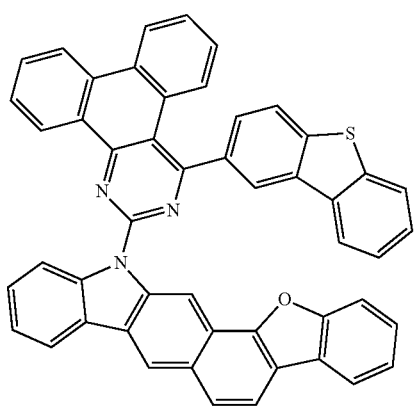
2-1-27
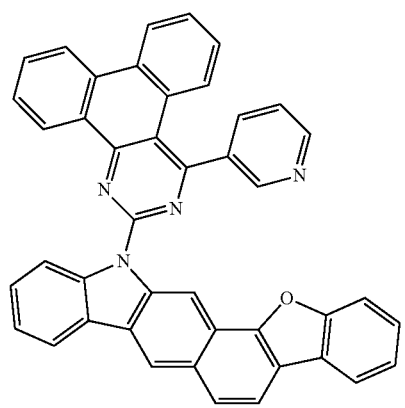
2-1-28
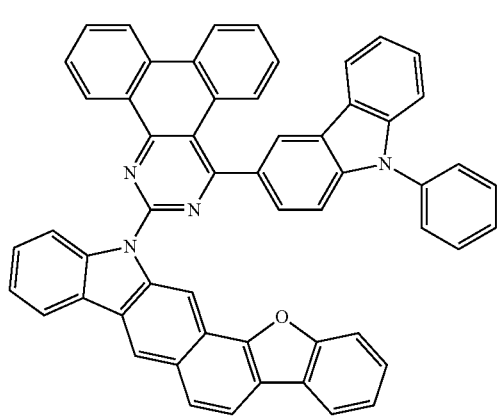
2-1-29
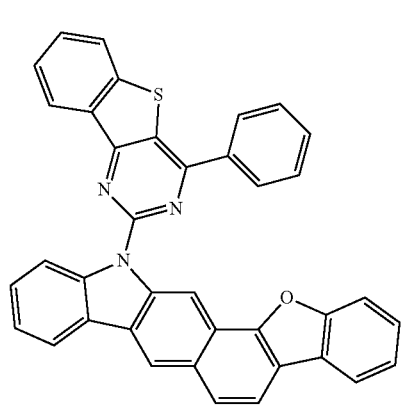

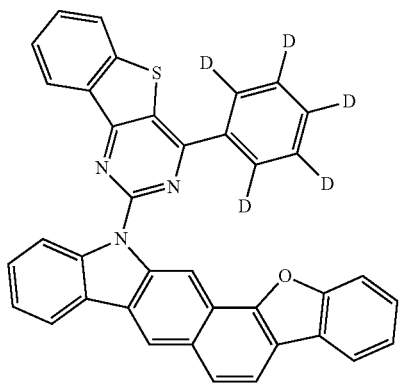
2-1-30
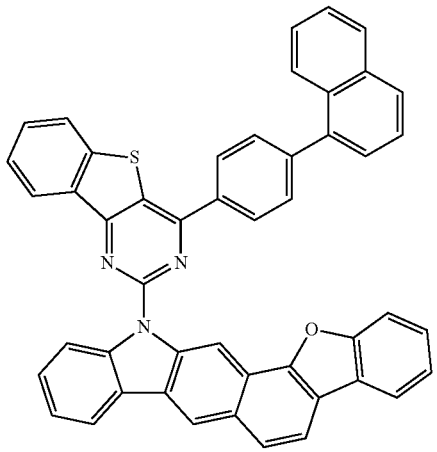
2-1-34
2-1-31
2-1-35
2-1-32
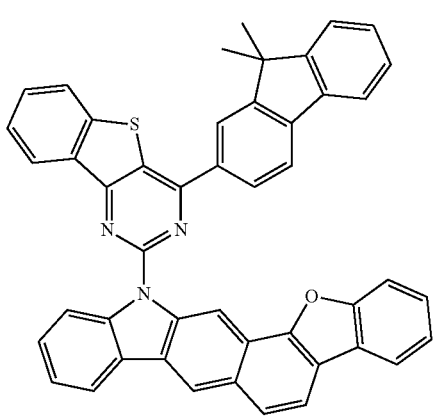
2-1-36
2-1-33
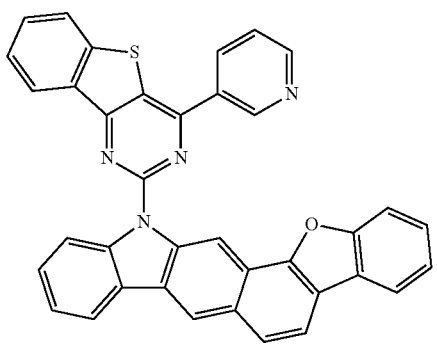
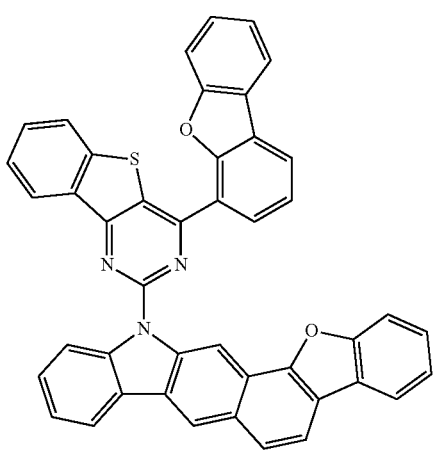
2-1-37

2-1-38
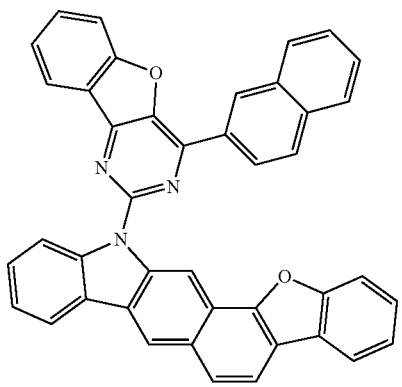
2-1-39
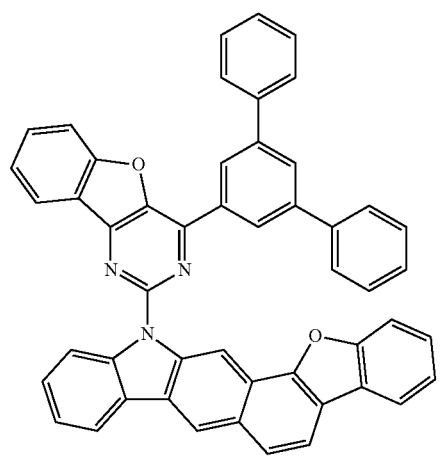
2-1-40
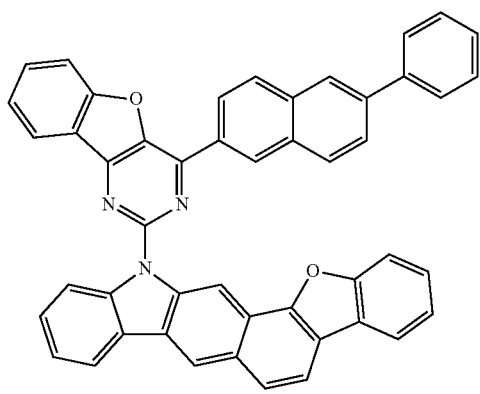
2-1-41
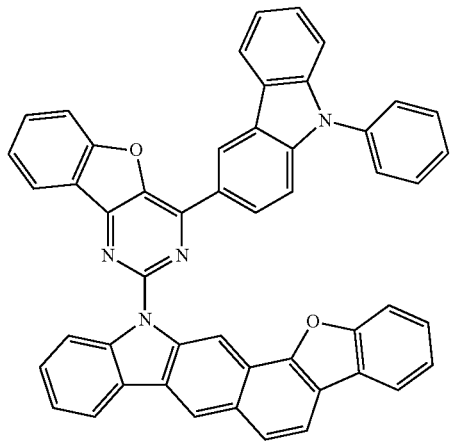
2-1-42
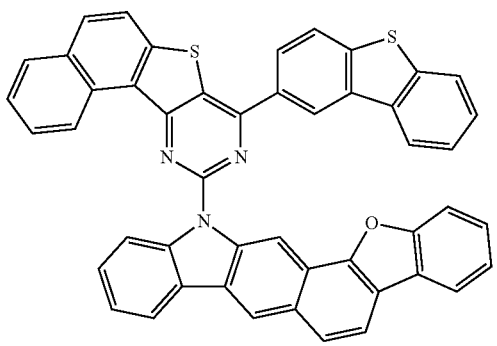
2-1-43
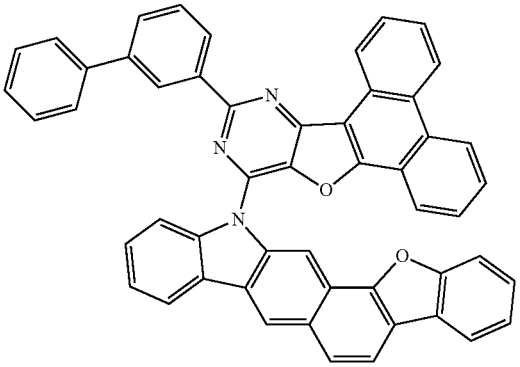

2-1-44
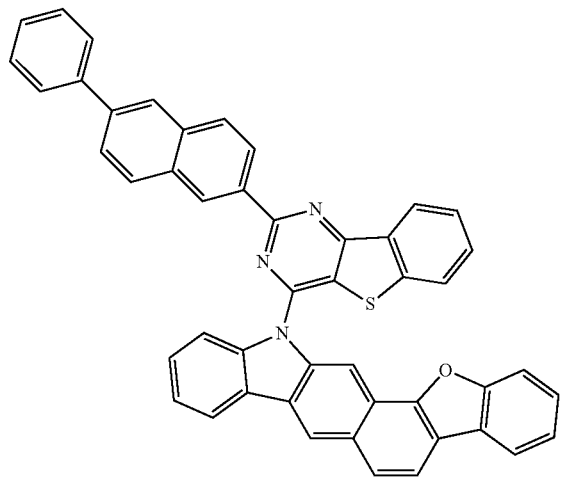
2-1-45
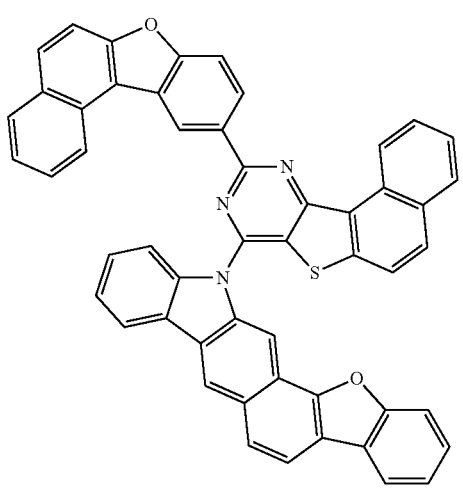
2-1-46
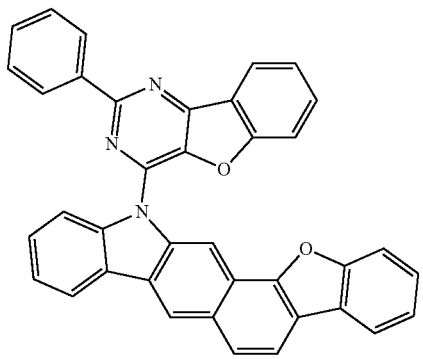
2-1-47
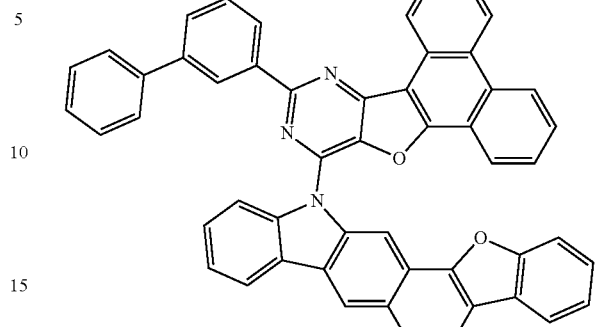
2-1-48
2-1-49
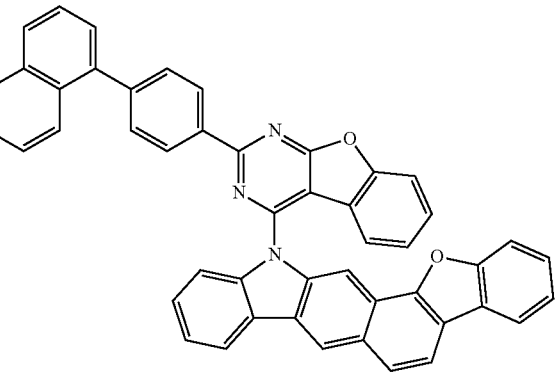

2-1-50
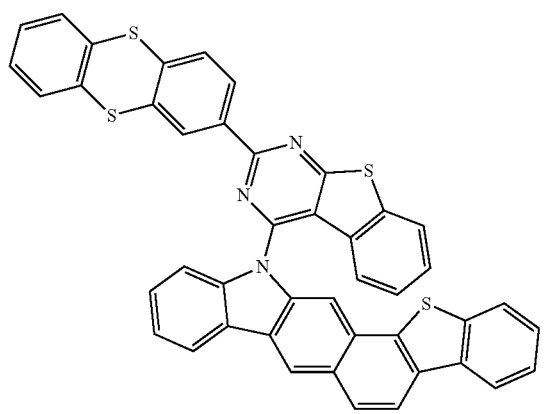
2-1-53
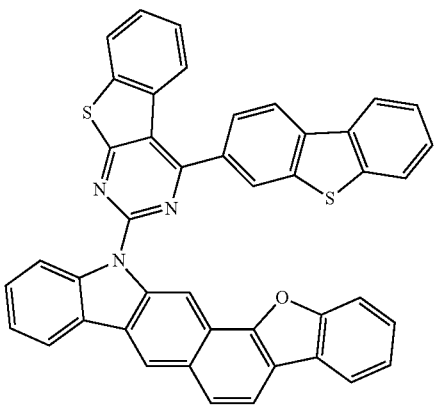
2-1-51
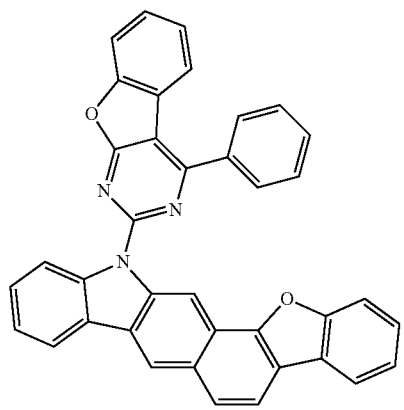
2-1-54
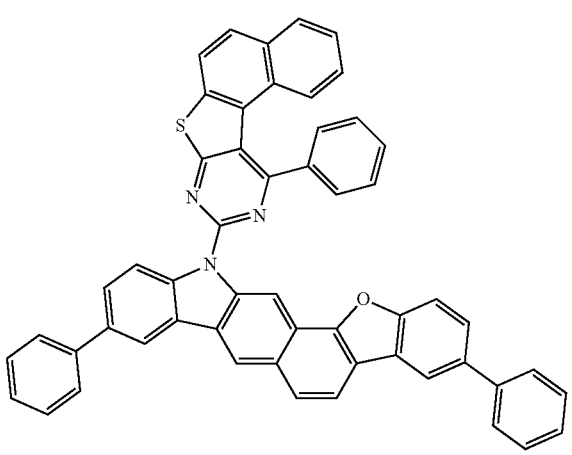
2-1-52
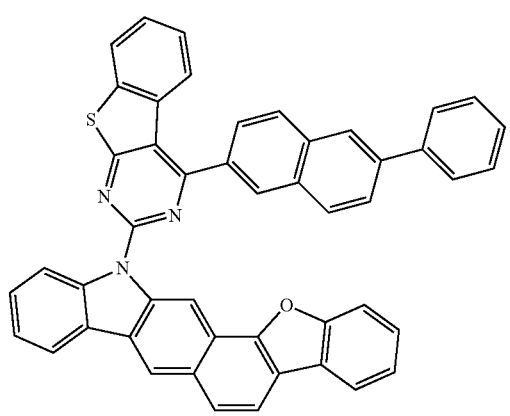
2-1-55
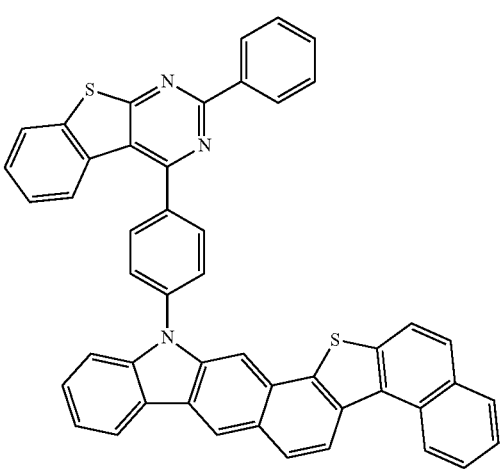

-continued
2-1-56
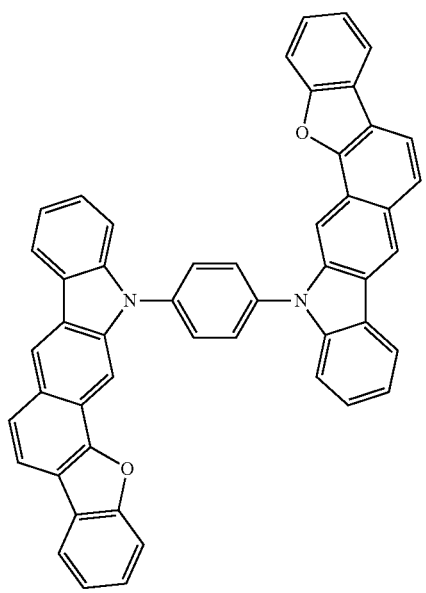
2-1-57
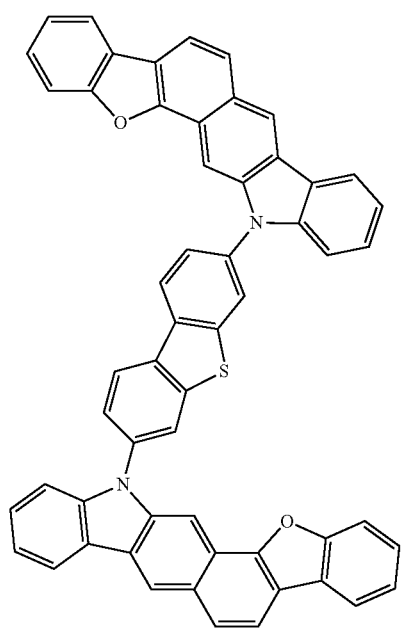
-continued
2-1-58
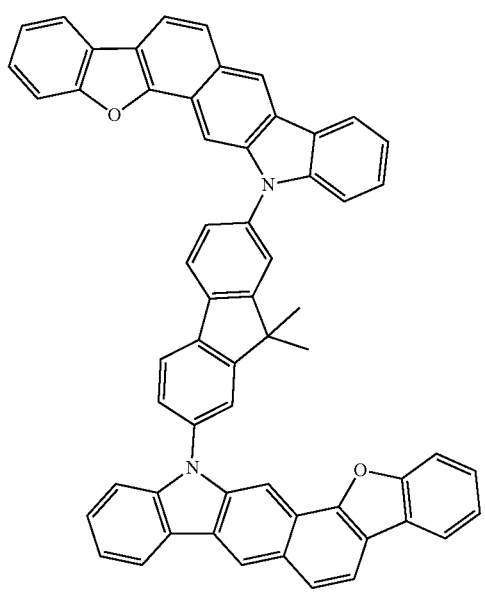
2-1-59
2-1-60
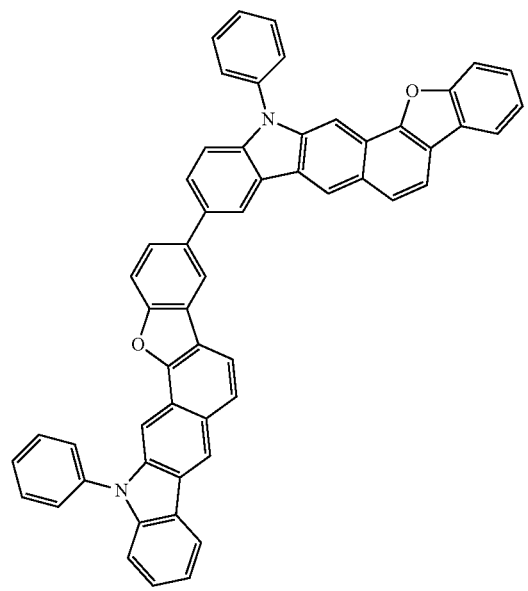

2-2-1
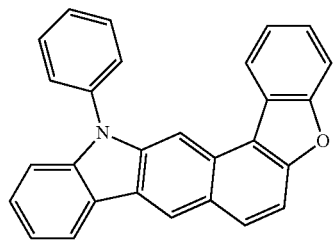
2-2-2
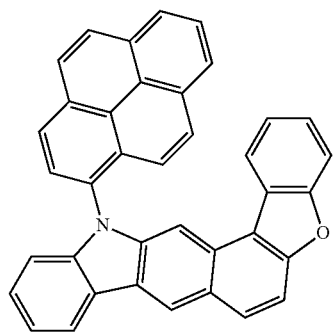
2-2-3
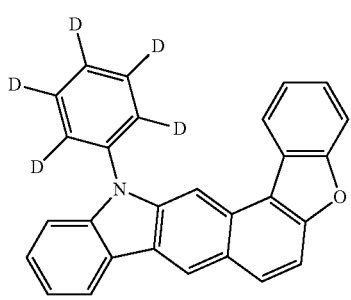
2-2-4
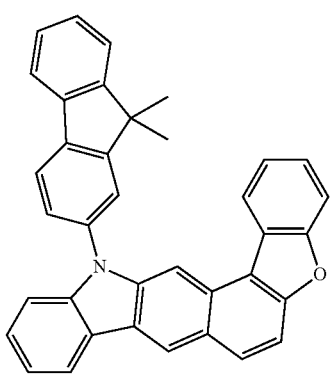
2-2-5
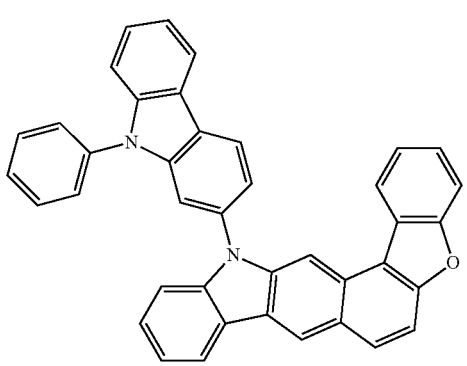
2-2-6
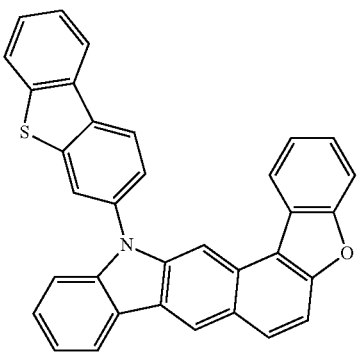
2-2-7
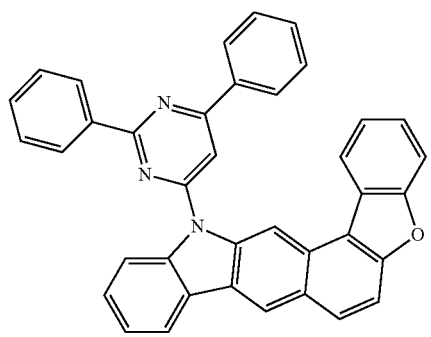
2-2-8
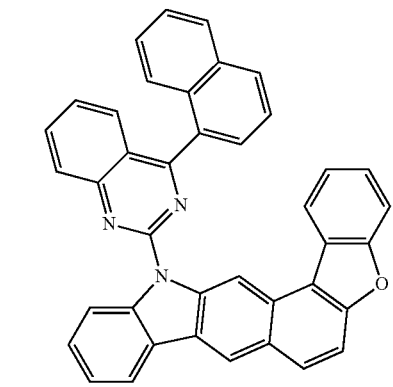
2-2-9
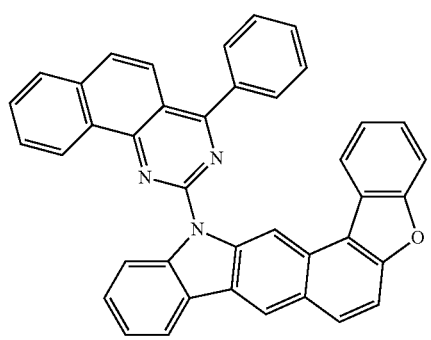

2-2-10
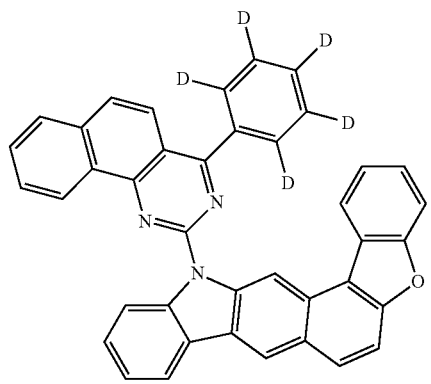
2-2-11
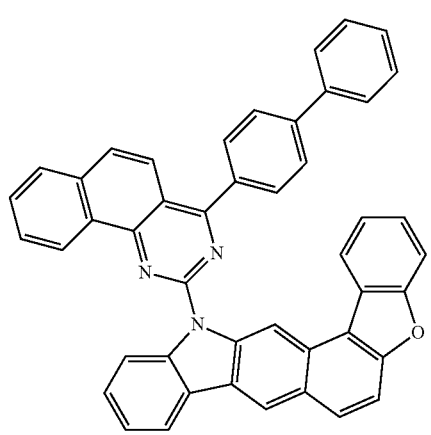
2-2-12
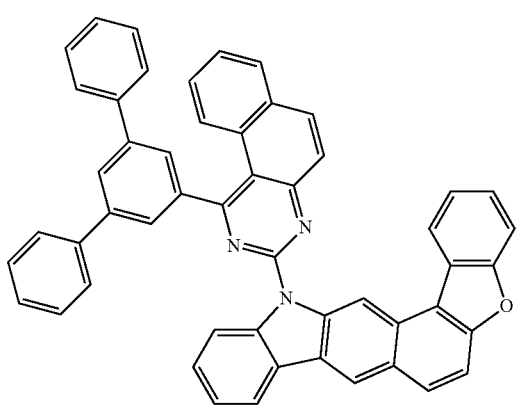
2-2-13
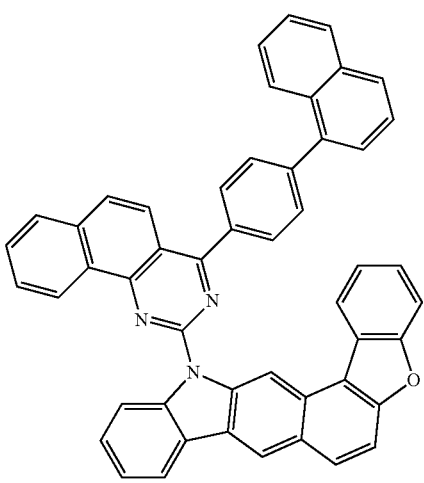
2-2-14
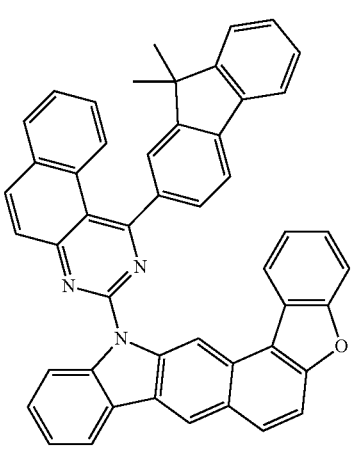
2-2-15
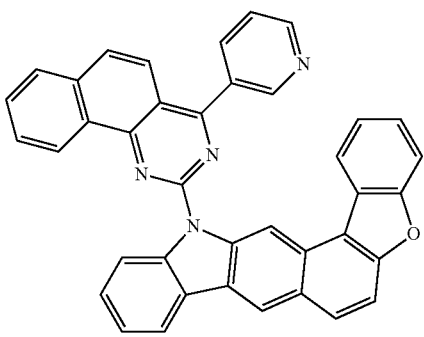

2-2-16
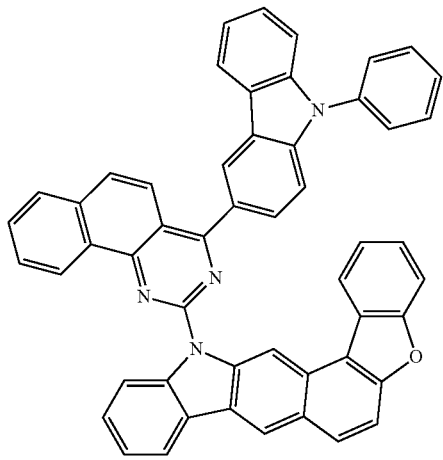
2-2-17
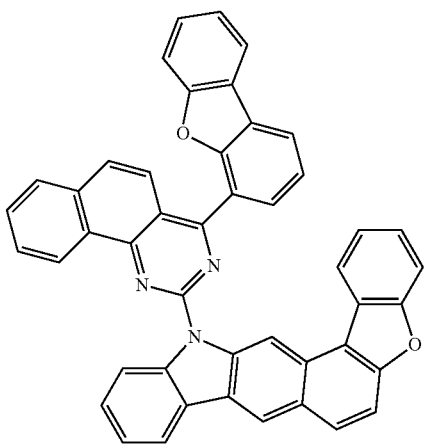
2-2-18
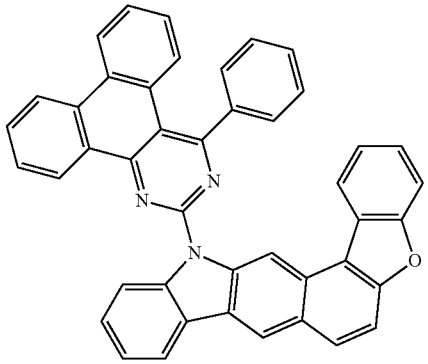
2-2-19
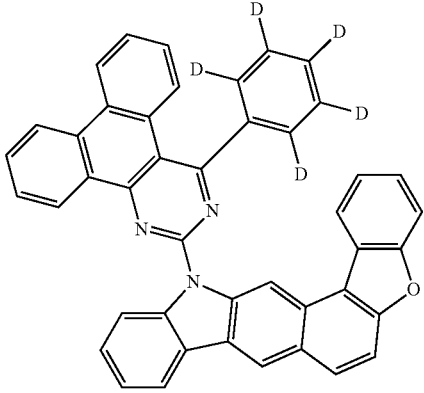
2-2-20
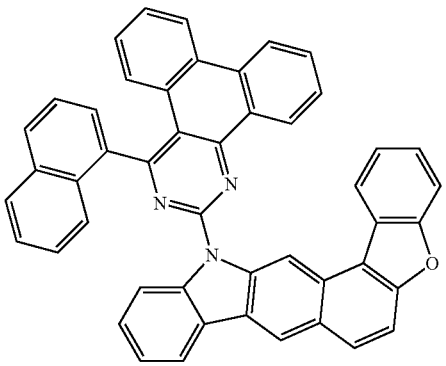
2-2-21
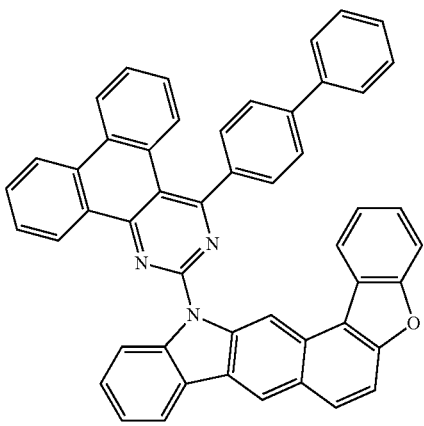
2-2-22
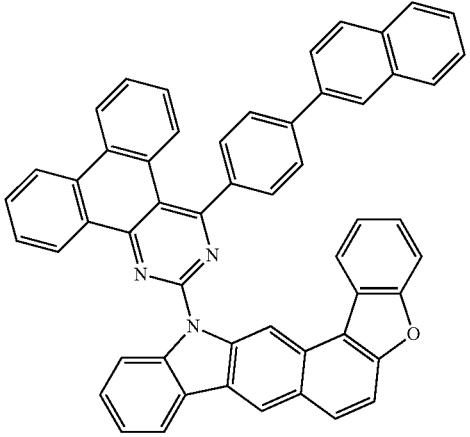

2-2-23
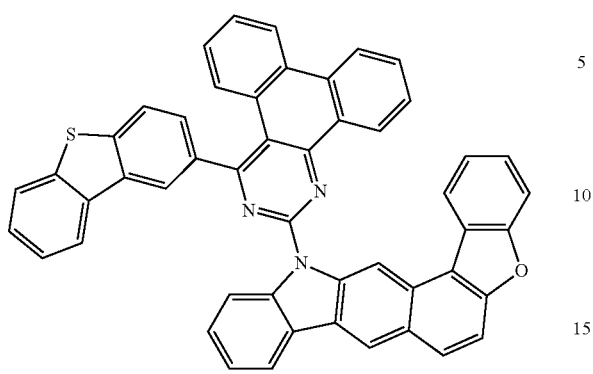
2-2-24
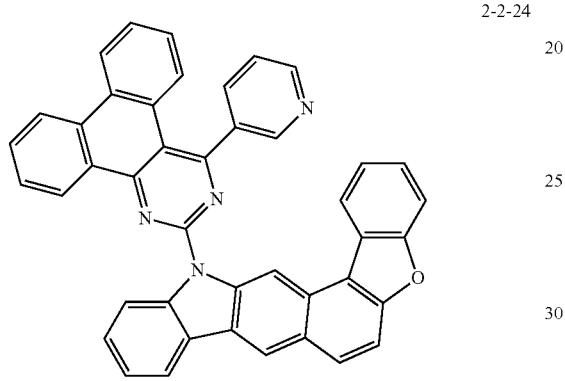
2-2-25
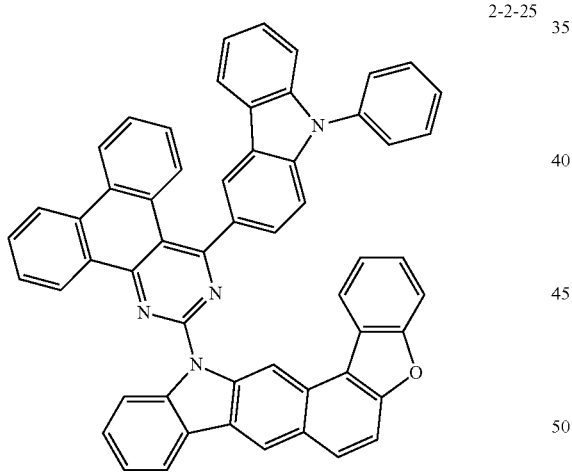
2-2-26
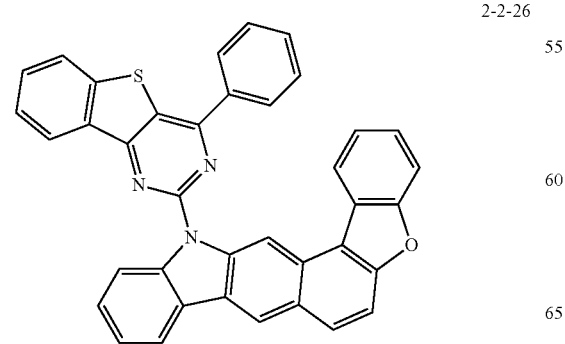
2-2-27
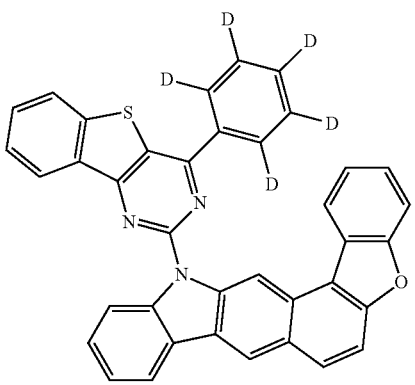
2-2-28
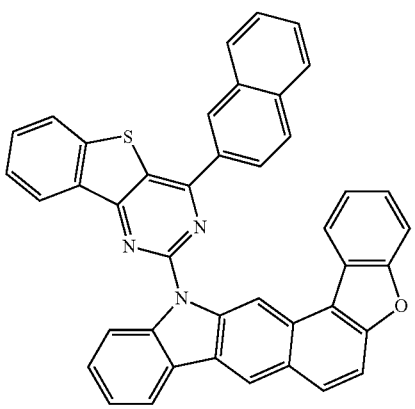
2-2-29
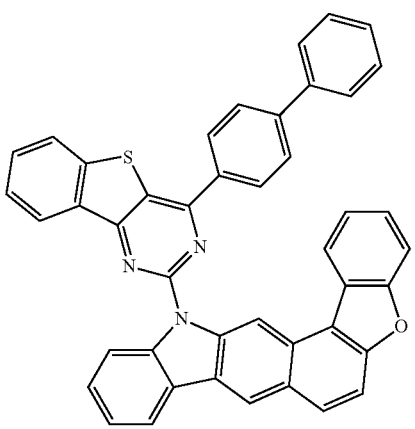
2-2-30
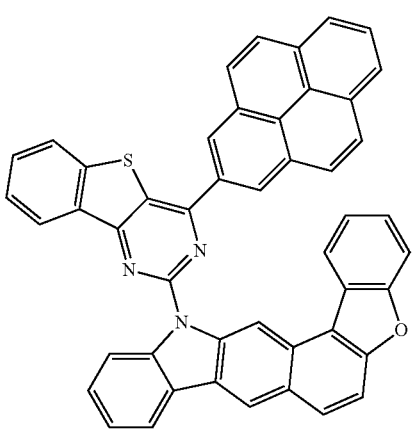

-continued
2-2-31
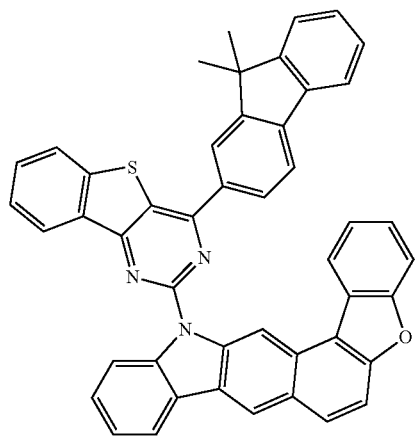
2-2-32
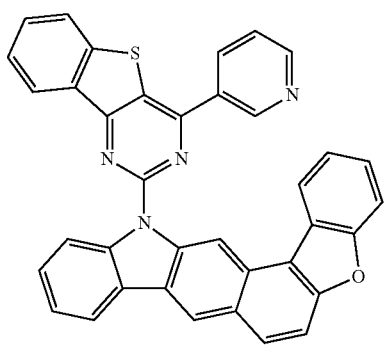
2-2-33
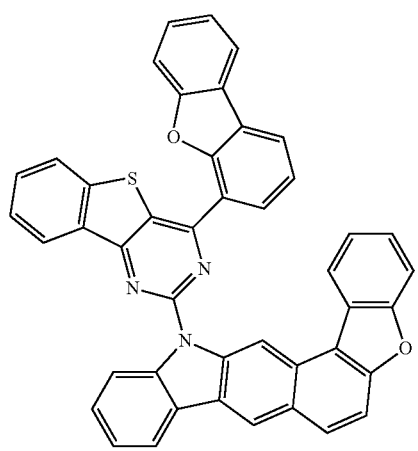
2-2-34
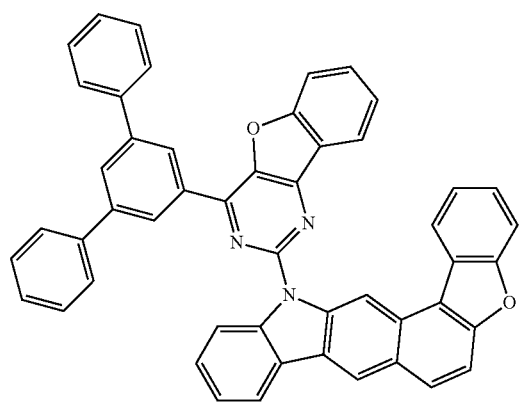
-continued
2-2-35
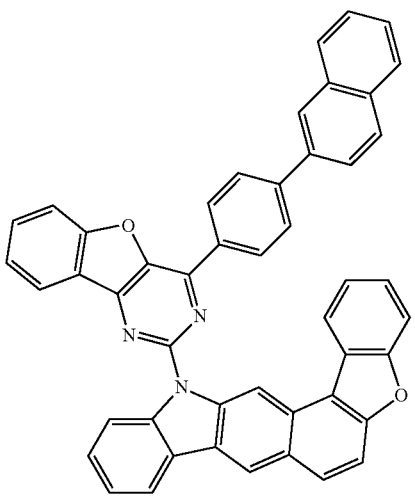
2-2-36
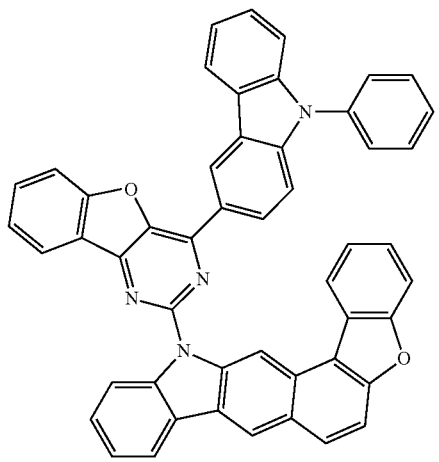
2-2-37
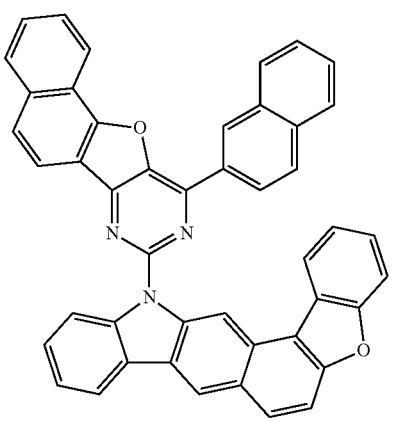

2-2-38
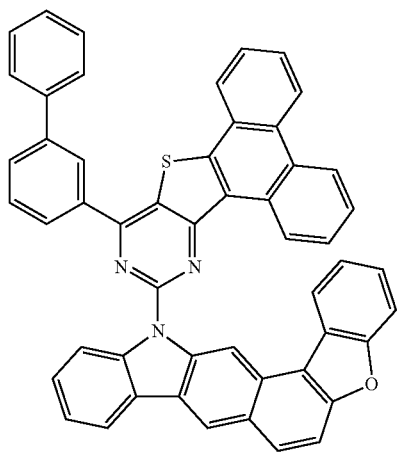
2-2-39
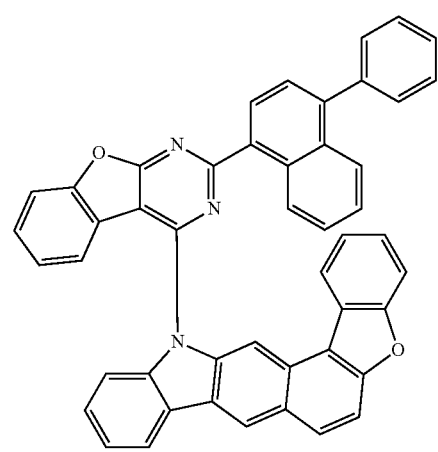
2-2-40
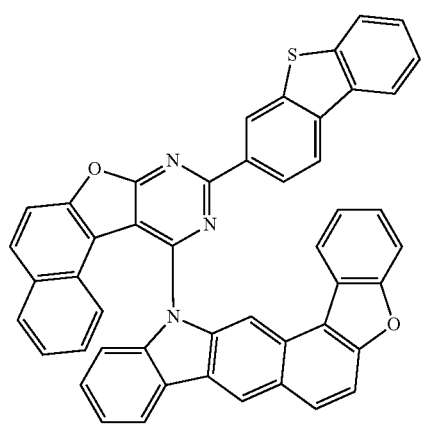
2-2-41
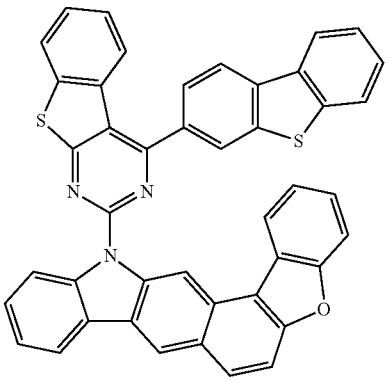
2-2-42
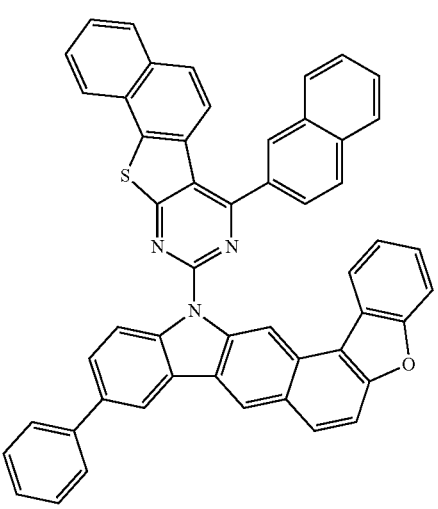
2-2-43
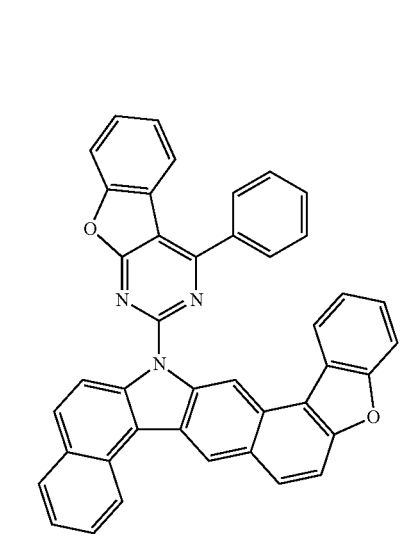

2-2-44
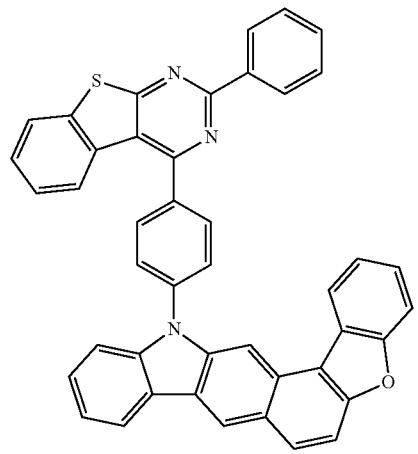
2-2-45
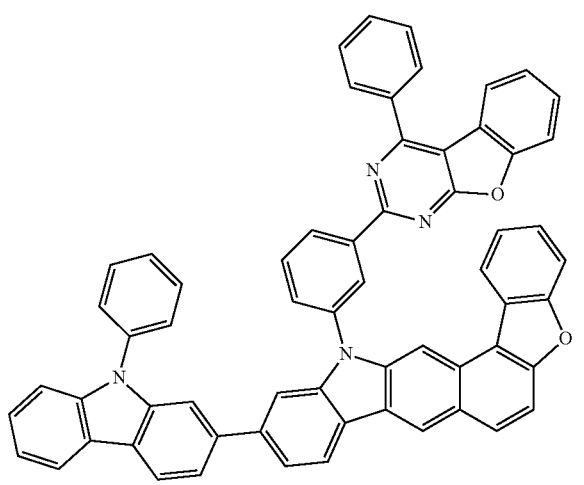
2-2-46
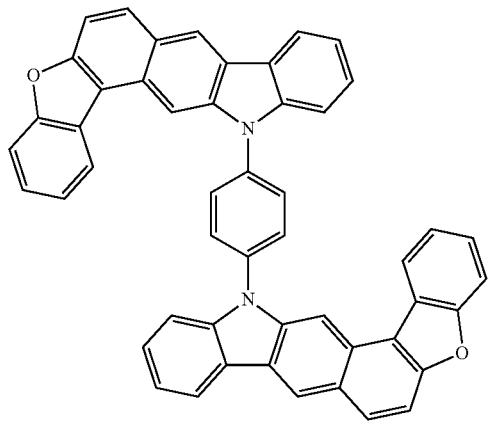
2-2-47
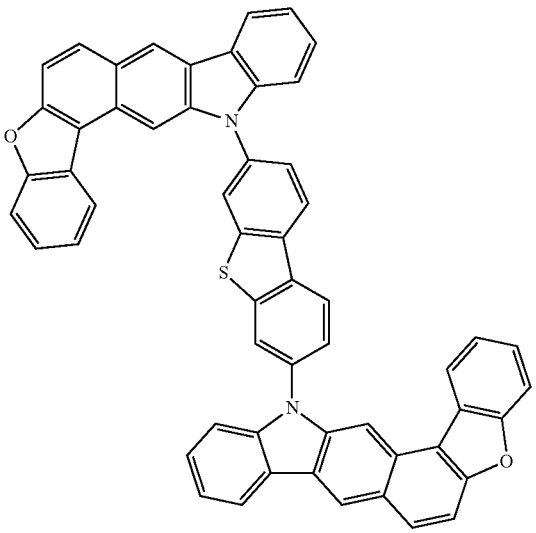
2-2-48
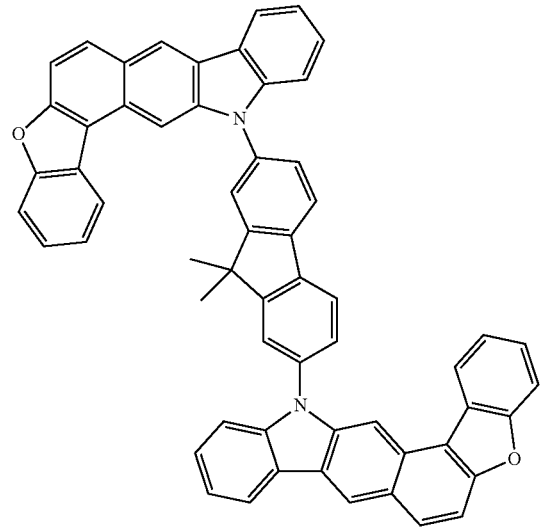
2-2-49
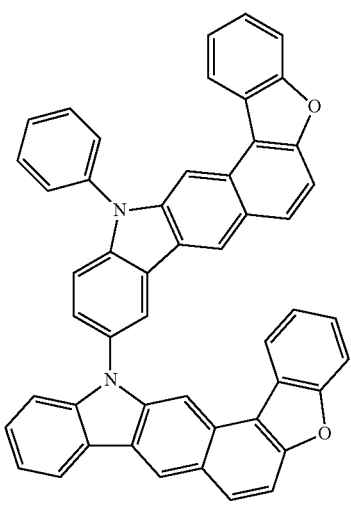

2-2-50
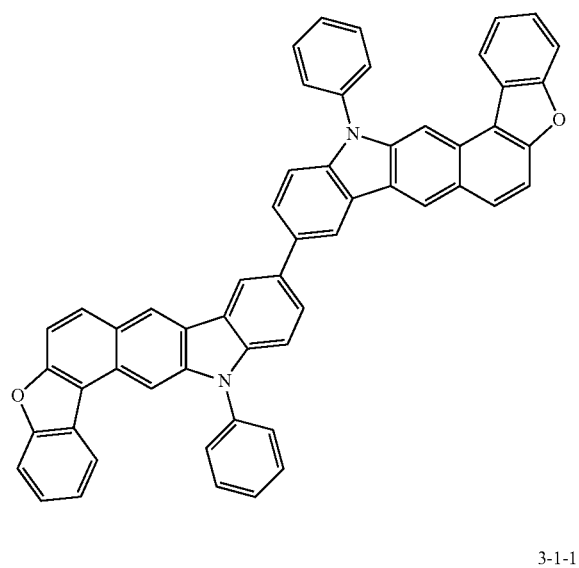
3-1-1
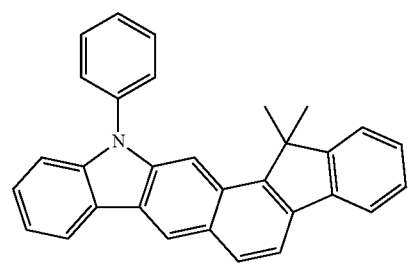
3-1-2
3-1-3
3-1-4
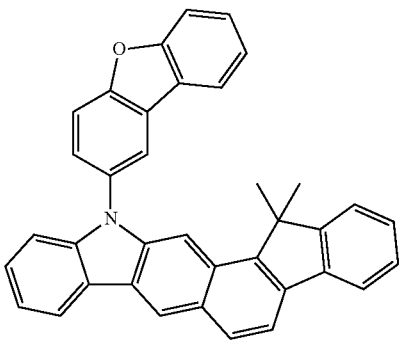
3-1-5
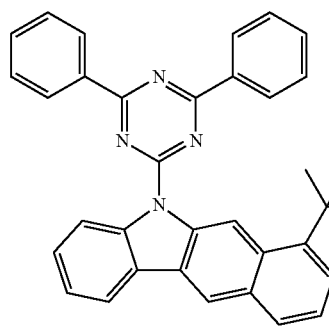
3-1-6
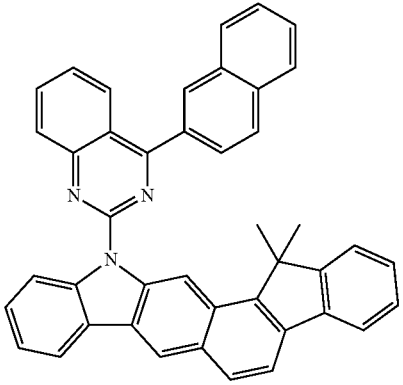
3-1-7
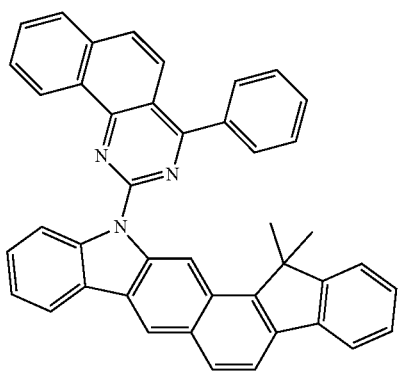

3-1-8
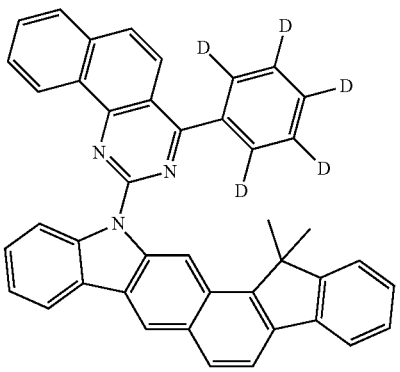
3-1-9
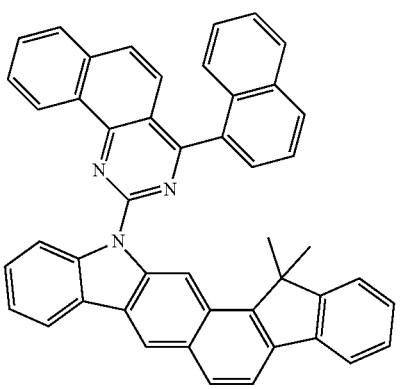
3-1-10
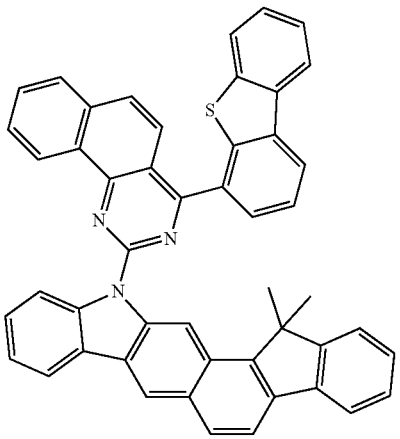
3-1-11
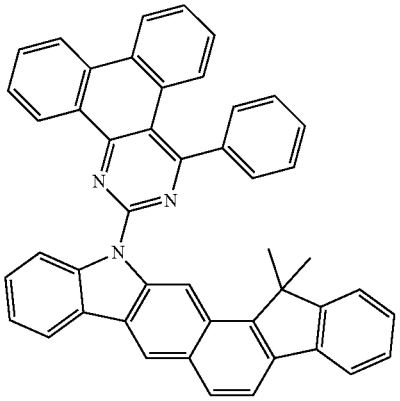
3-1-12
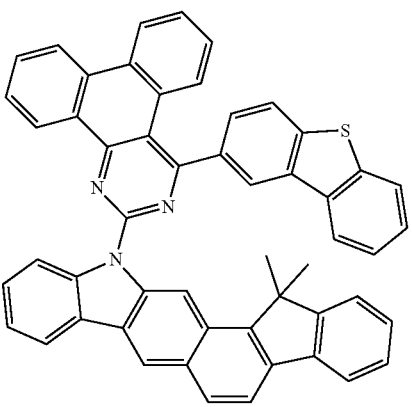
3-1-13
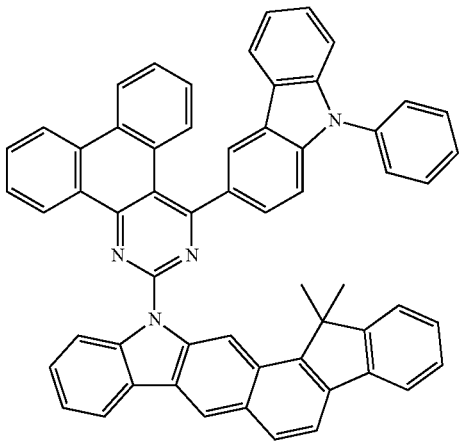
3-1-14
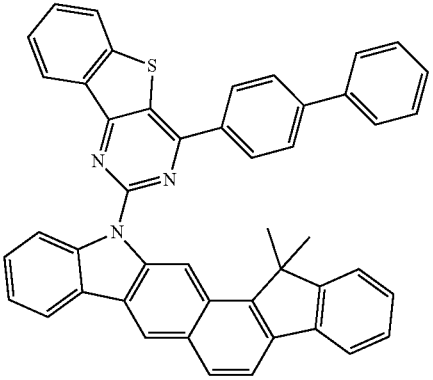

3-1-15
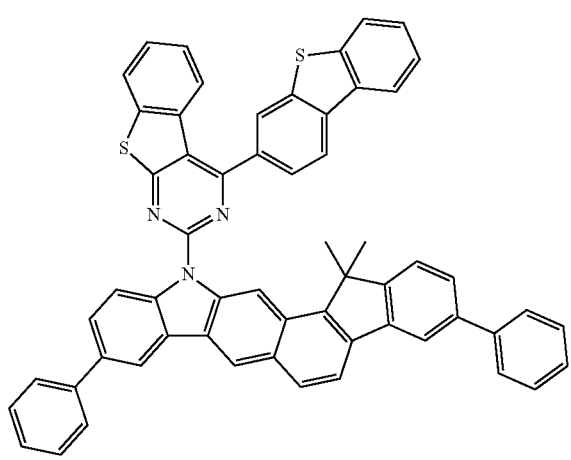
3-1-16
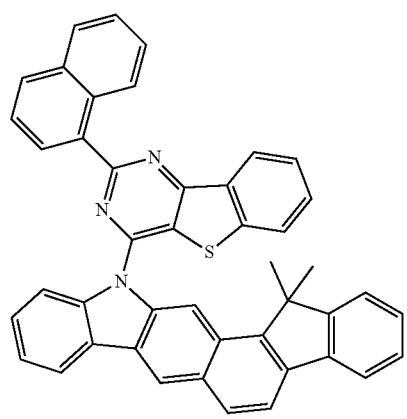
3-1-17
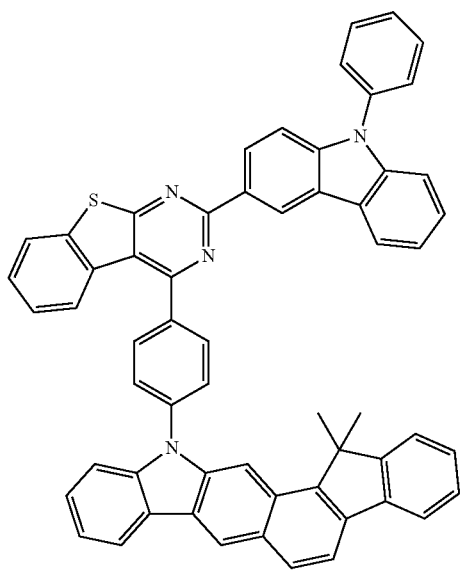
3-1-18
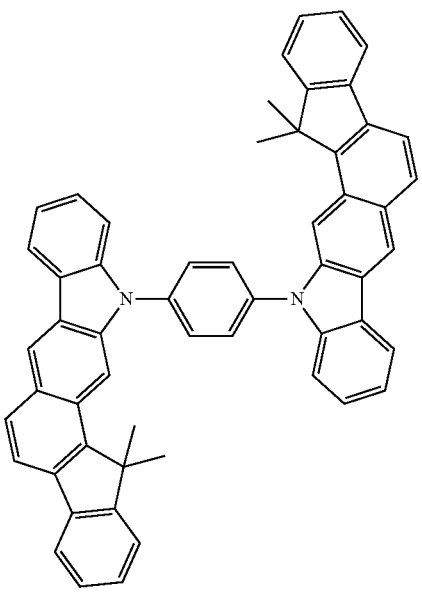
3-1-19
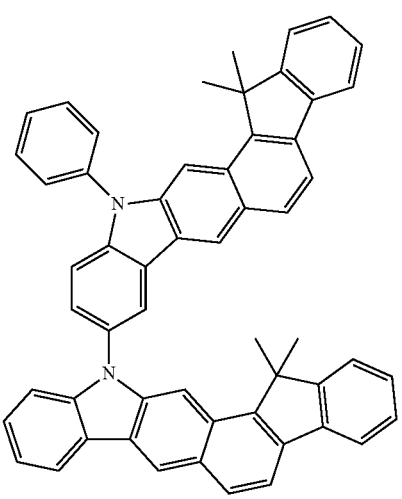

3-1-20
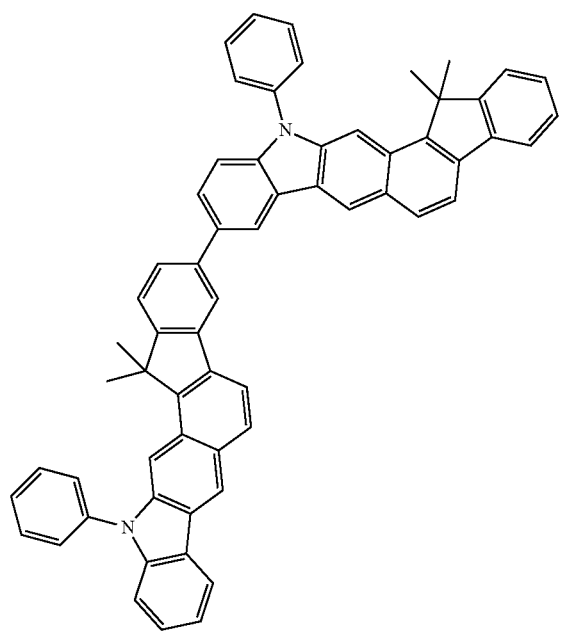
3-2-1
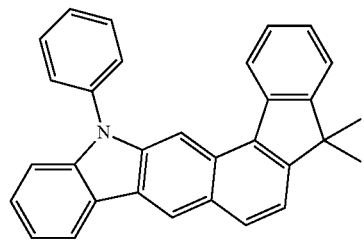
3-2-2
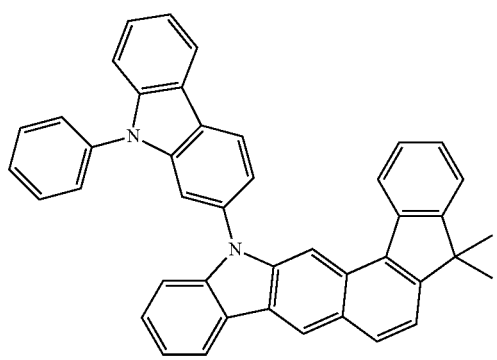
3-2-3
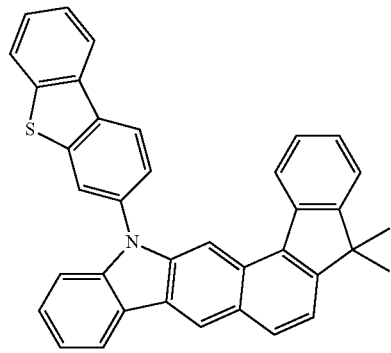
3-2-4
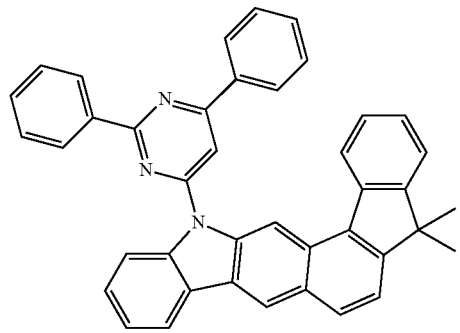
3-2-5
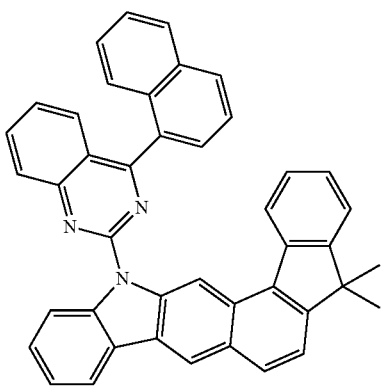
3-2-6
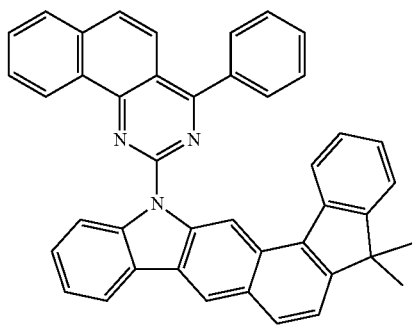
3-2-7
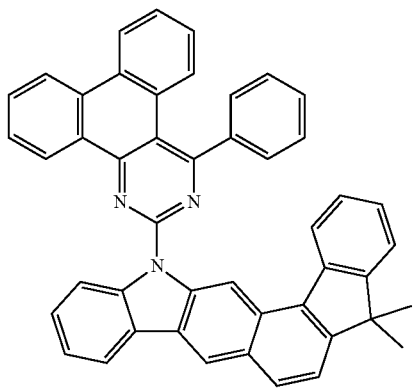

3-2-8
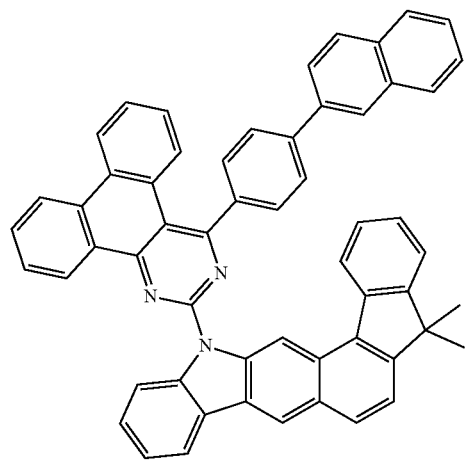
3-2-9
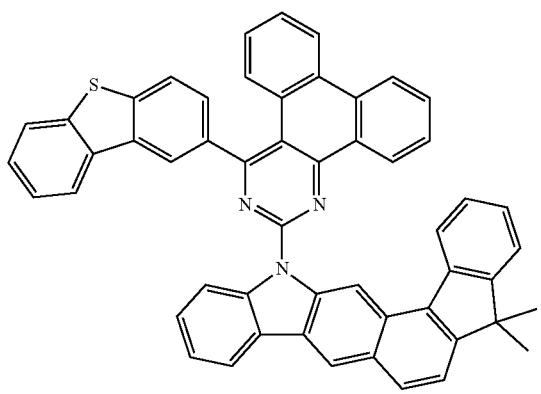
3-2-10
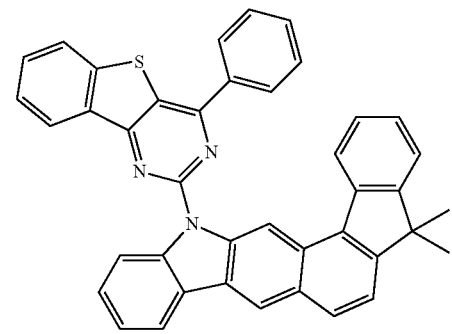
3-2-11
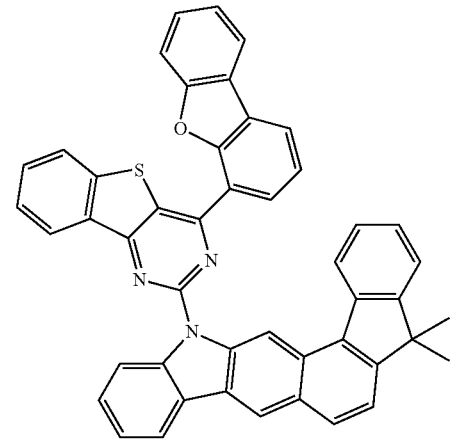
3-2-12
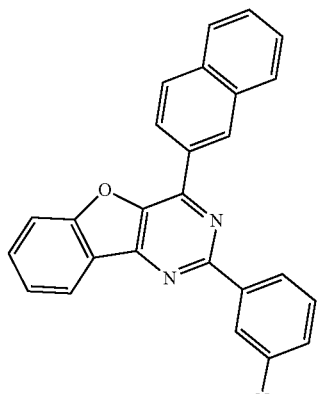
3-2-13
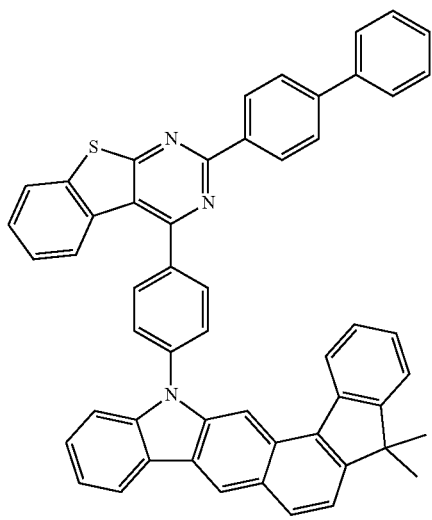
3-2-14
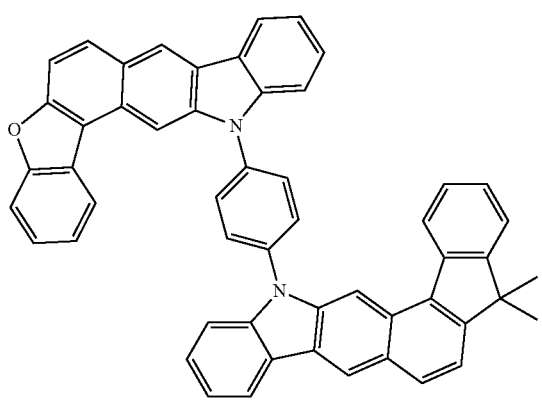

-continued
3-2-15
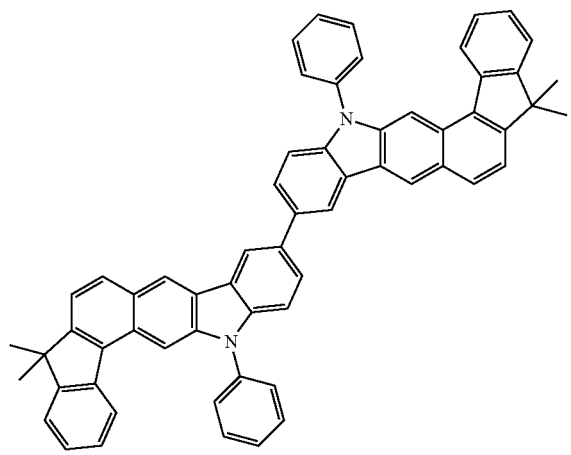
4-1-4
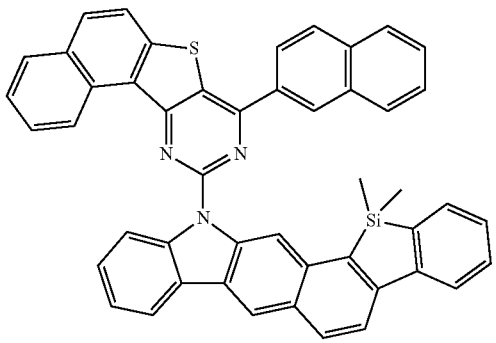
4-1-1
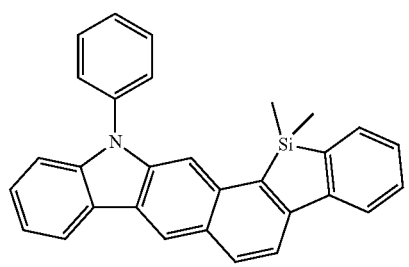
4-2-1
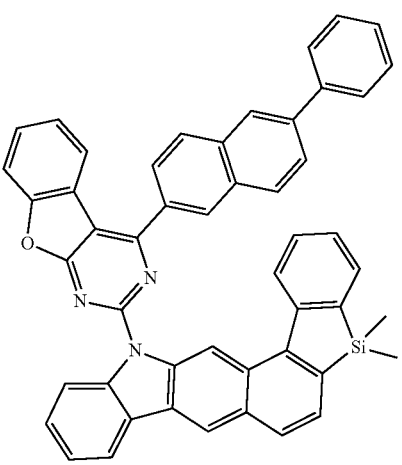
4-1-2
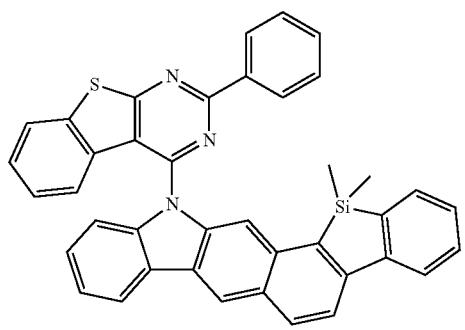
4-1-3
4-2-2
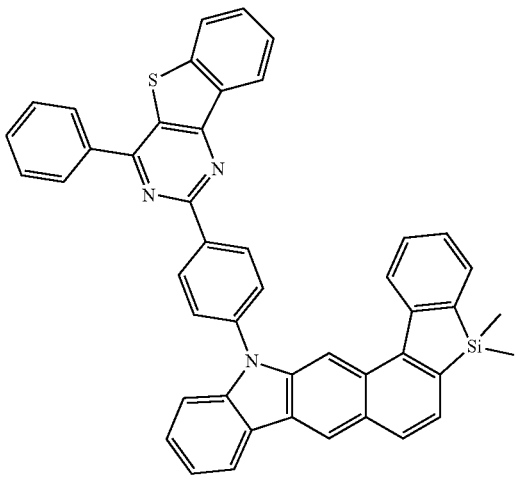

-continued 4-2-3

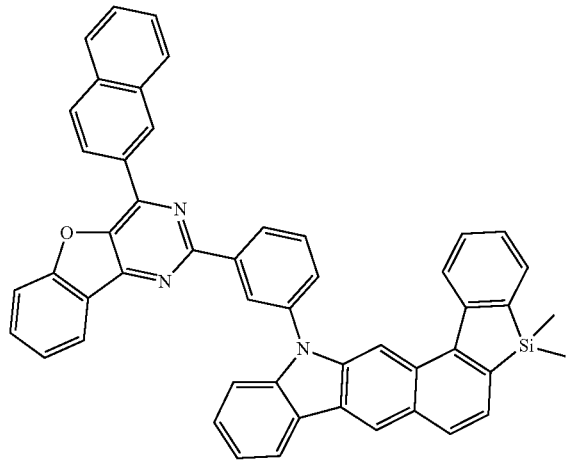

4-2-4

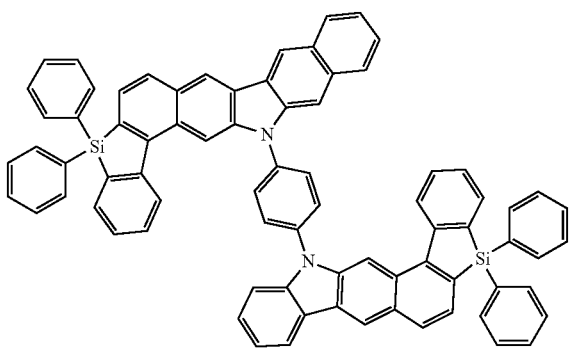

Preferably, at least one of $R^1$ to $R^{12}$ in formula 1 is -L'-N($R^a$)($R^b$), and formula 1 may be represented by the following formula 6.

[Formula 6]

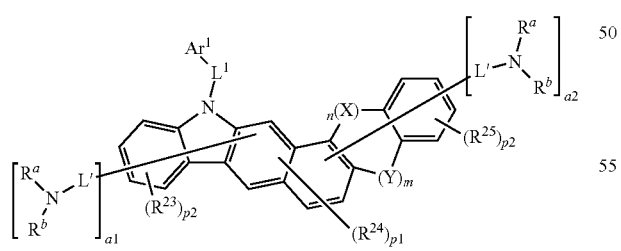

In the above formula 6, each symbol of $Ar^1$, $L^1$, L' X, Y, m, n, $R^a$ and $R^b$ and the like is the same as defined in formula 1, $R^{23}$ to $R^{25}$ are the same as $R^1$ to $R^{12}$ defined in formula 1. p1 and p2 are each an integer of 0 to 4, and a1 and a2 are each an integer of 0 to 4.

Preferably, in the above formula 6, a1 and a2 are each an integer of 0 or 1, and a1+a2 is 1. That is, preferably, any one of $R^1$ to $R^{12}$ is -L'-N($R^a$)($R^b$) and thus the above formula 6 may be represented by any one of the following formulas 6-1 to 6-4.

<Formula 6-1>

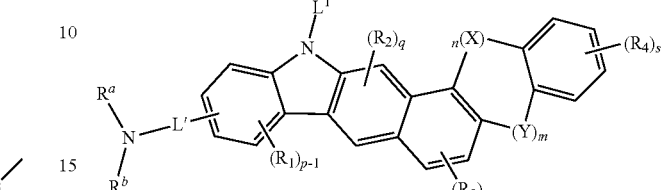

<Formula 6-2>

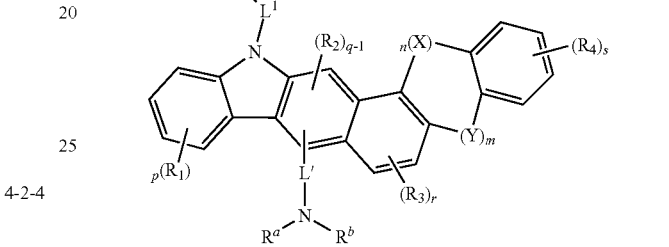

<Formula 6-3>

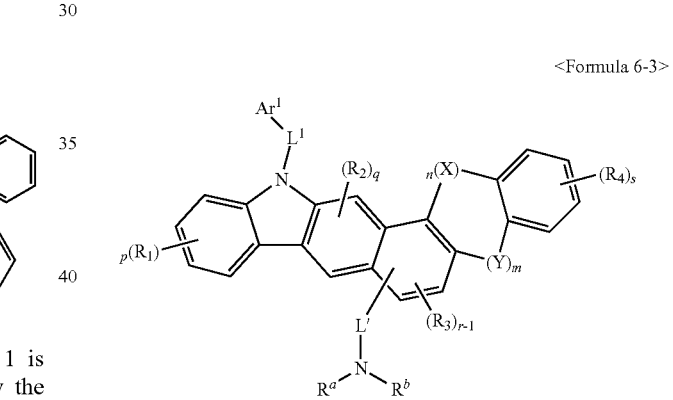

<Formula 6-4>

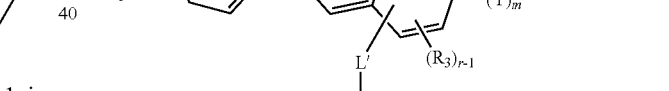

In formulas 6-1 to 6-4 above, $R_1$, $R_2$, $R_3$ and $R_4$ are each corresponding to $R^{23}$, $R^{24}$, $R^{24}$, $R^{25}$ of the above formula 6 and thus they are each the same as $R^1$-$R^{12}$ defined in formula 1, p and s are each an integer of 0 to 4 and q and r are each an integer of 0 to 2.

Specifically, the compound represented by the above Formula 6 may be any one of the following compounds.

A 1-1-1
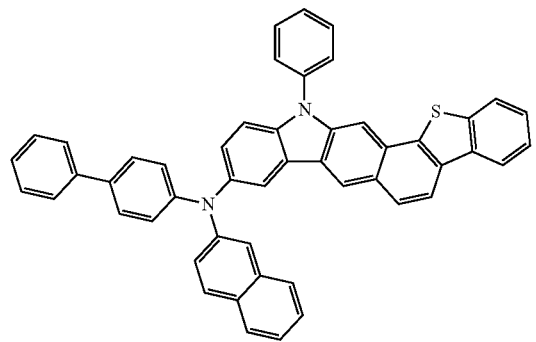
A 1-1-2
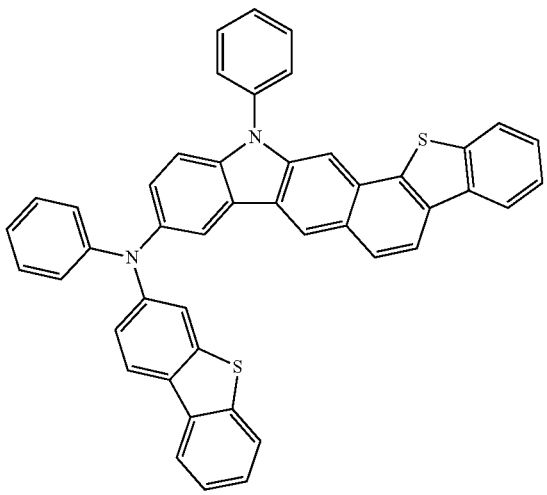
A 1-1-3
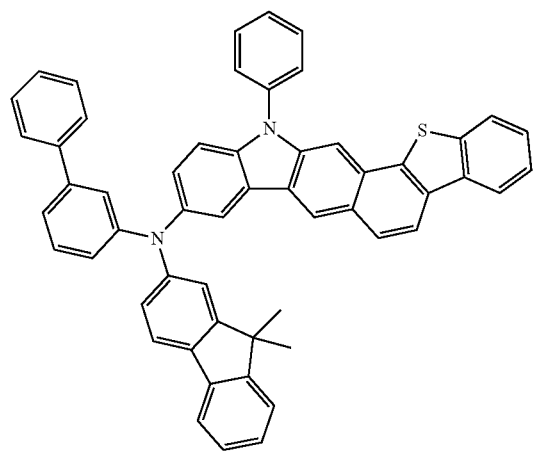
A 1-1-4
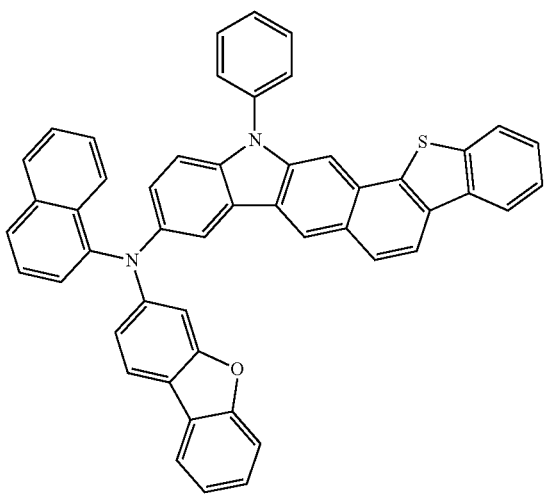
A 1-1-5
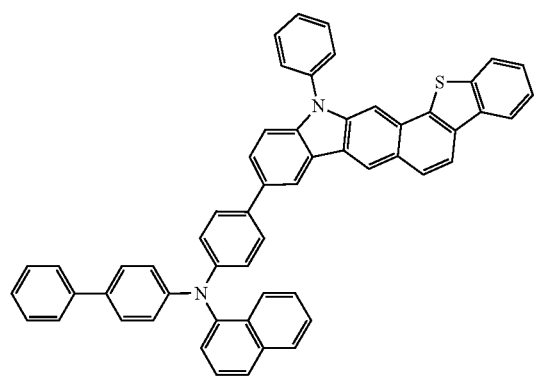
A 1-1-6
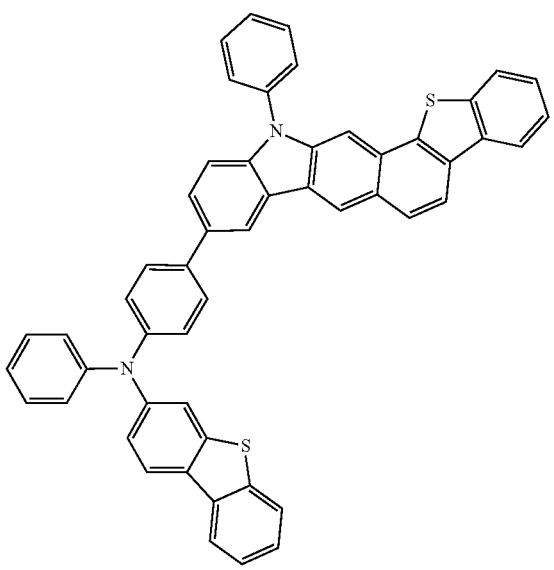

A 1-1-7
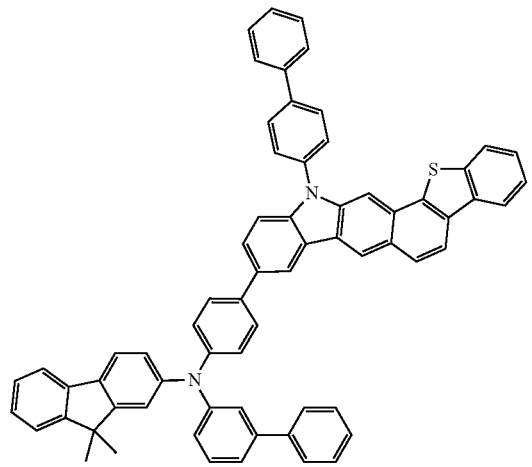
A 1-1-8
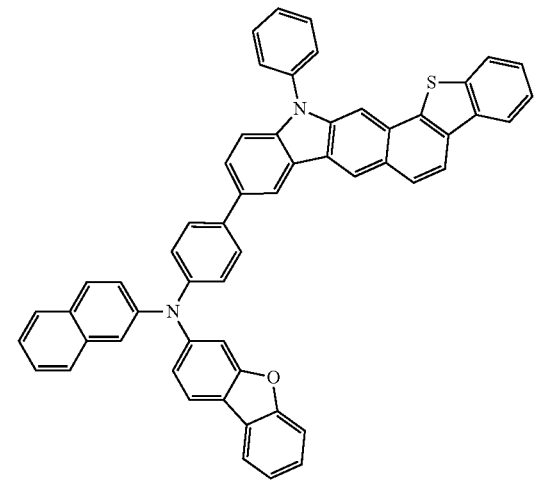
A 1-1-9
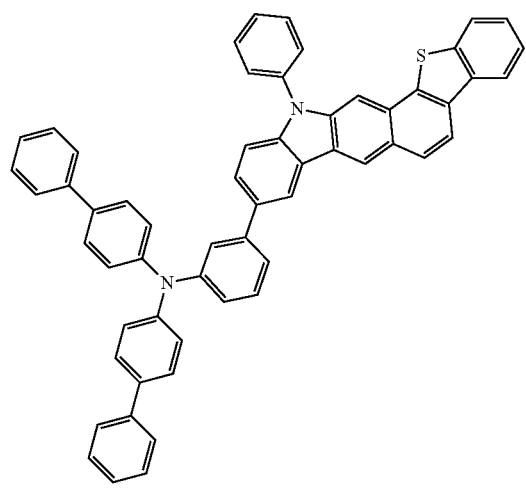
A 1-1-10
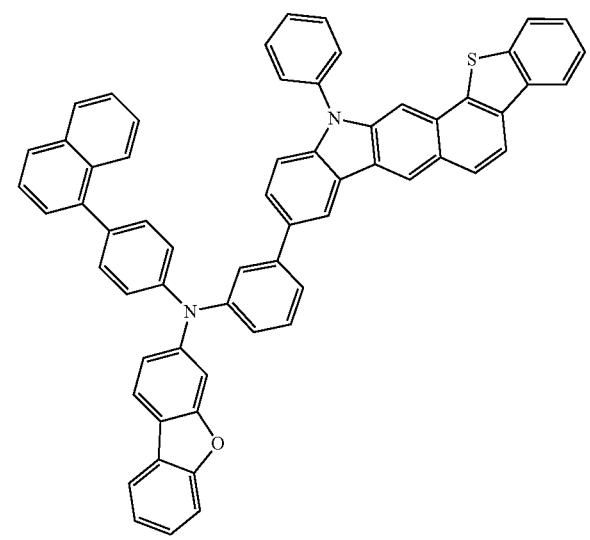
A 1-1-11
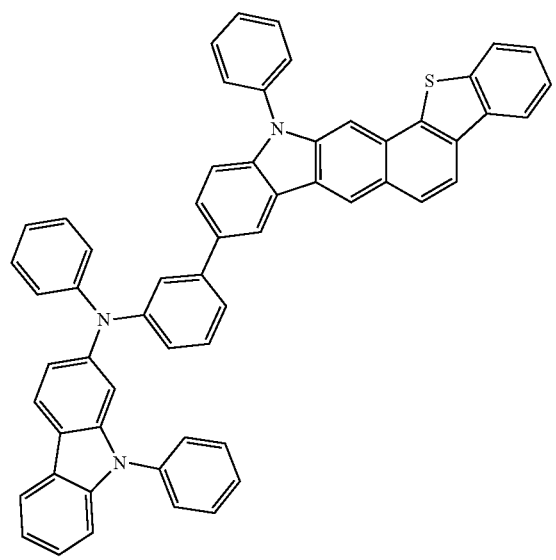
A 1-1-12
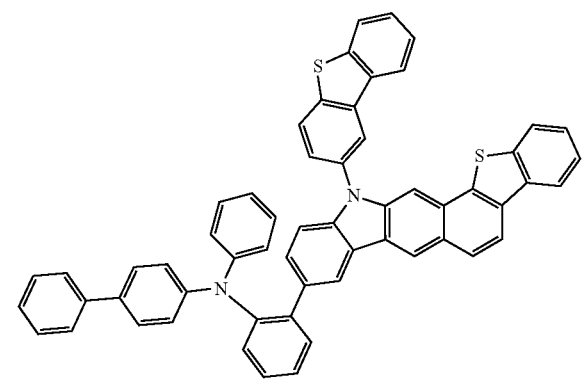

A 1-1-13
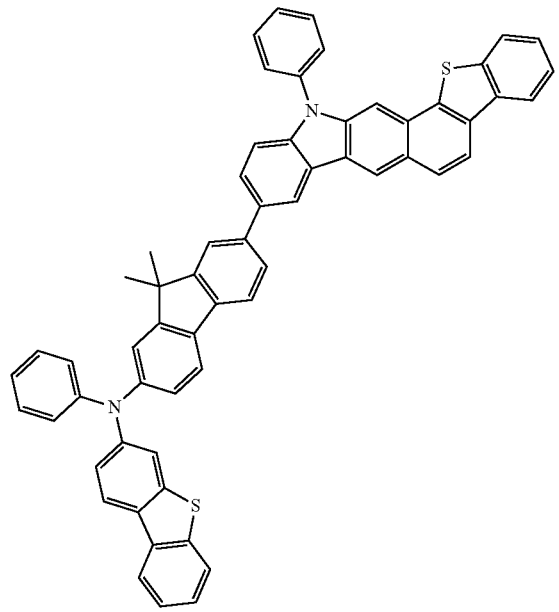
A 1-1-14
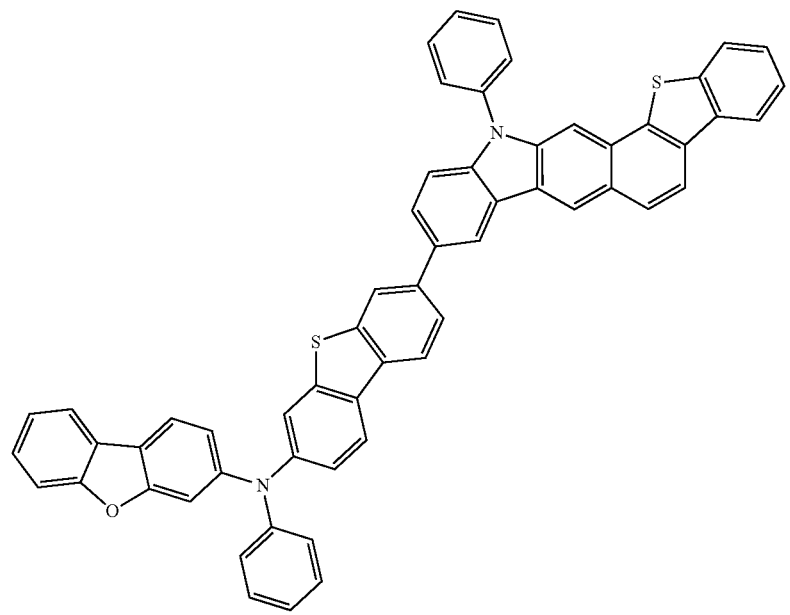

-continued
A 1-1-15
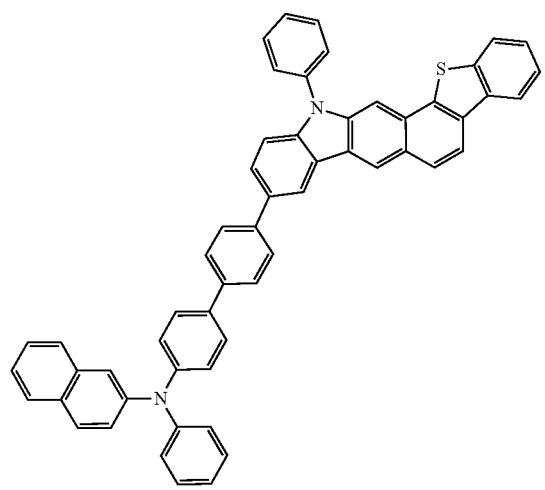
A 1-1-16
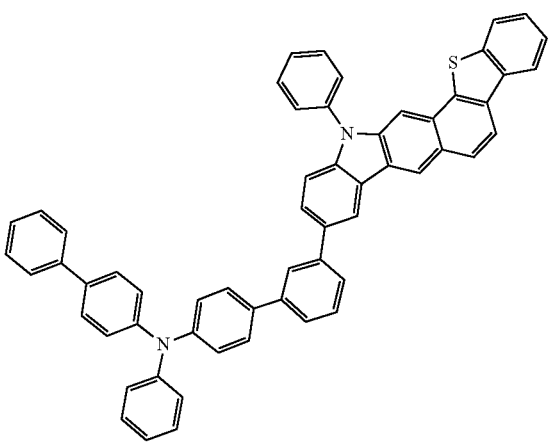
A 1-1-17
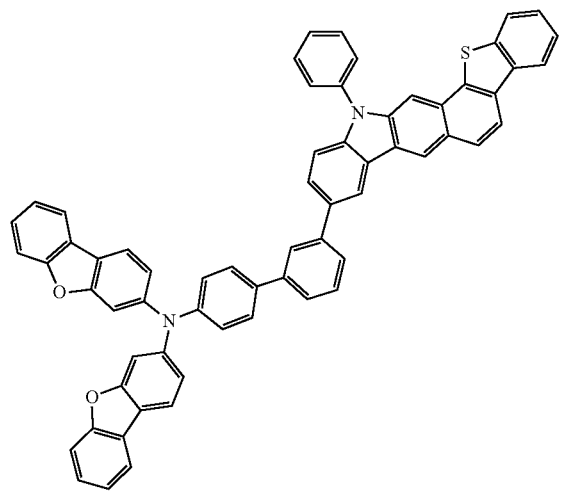
A 1-1-18
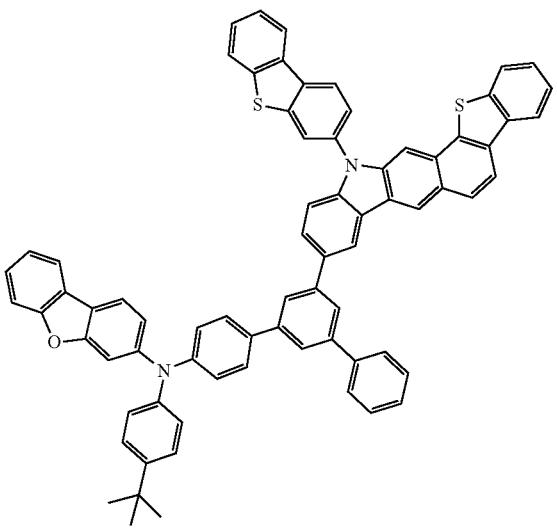
A 1-1-19
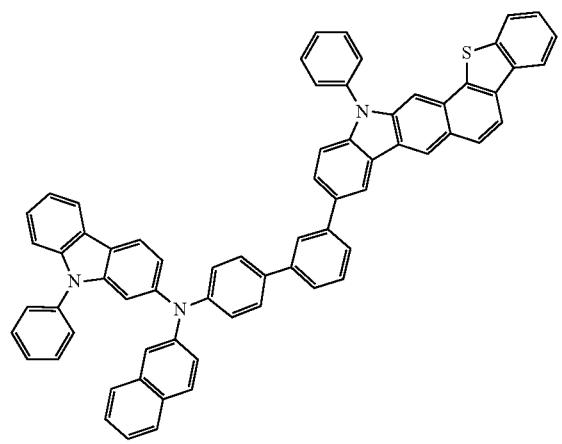

-continued
A 1-1-20
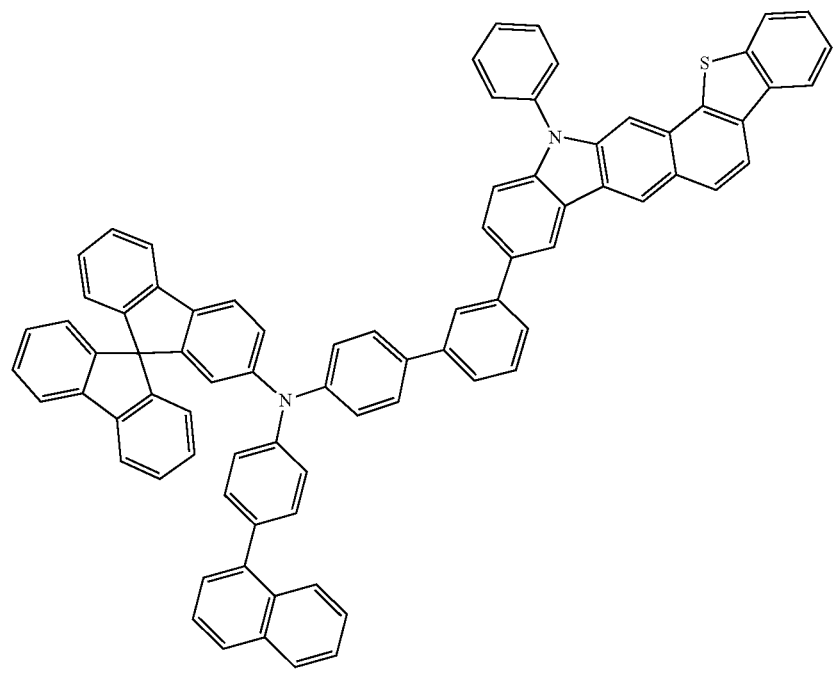
A 1-1-21
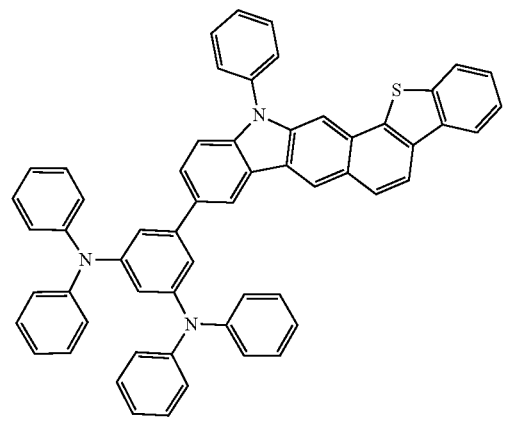
A 1-1-22
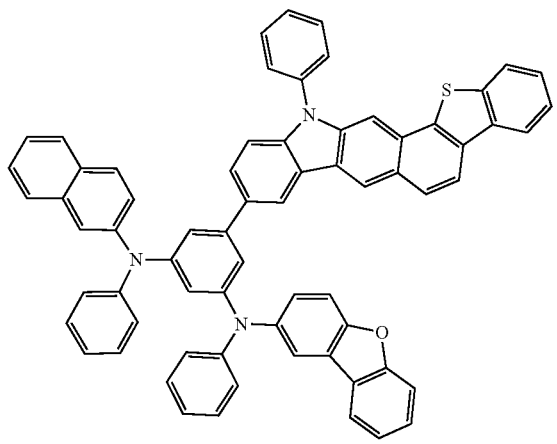
A 1-1-23
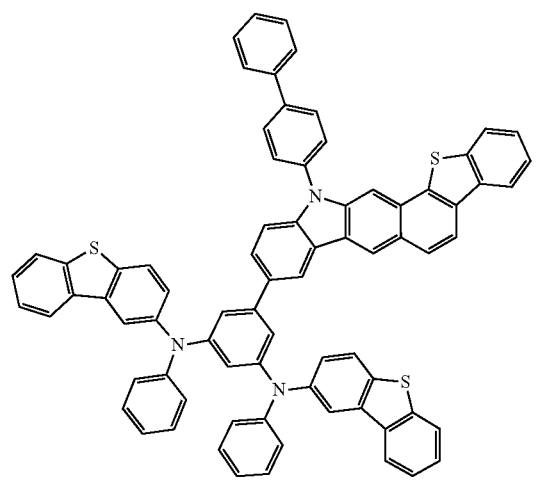
A 1-1-24
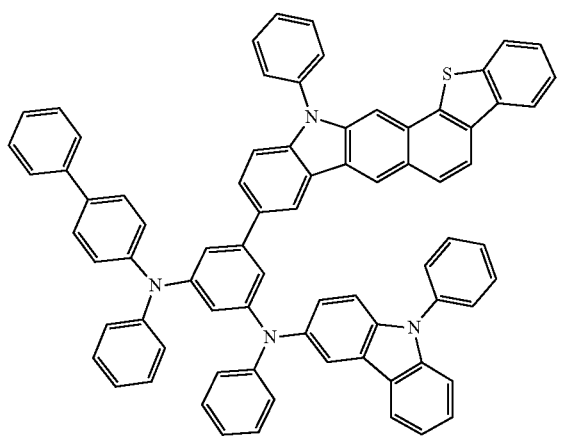

A 1-1-25
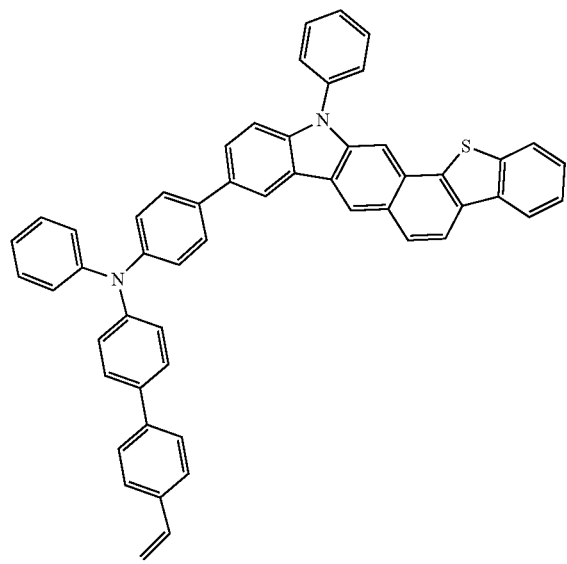
A 1-1-26
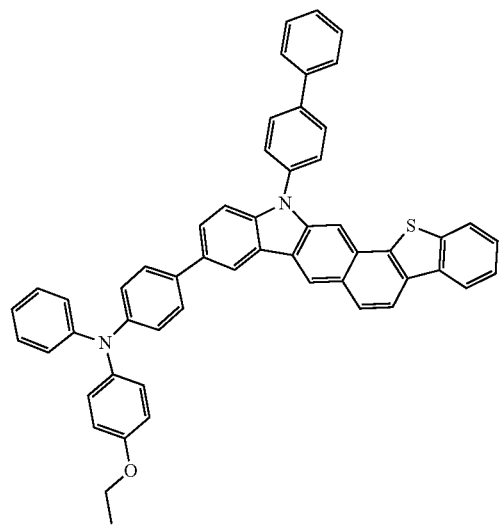
A 1-1-27
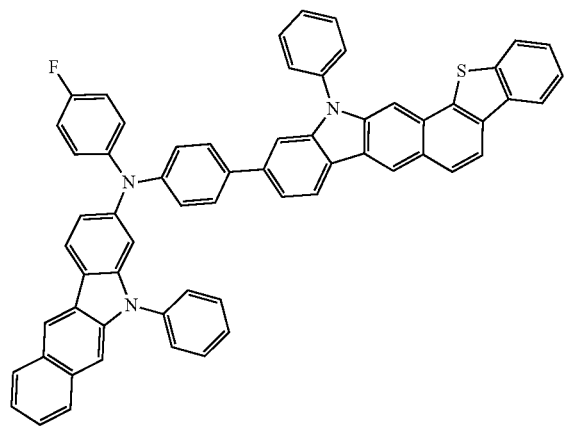
A 1-1-28
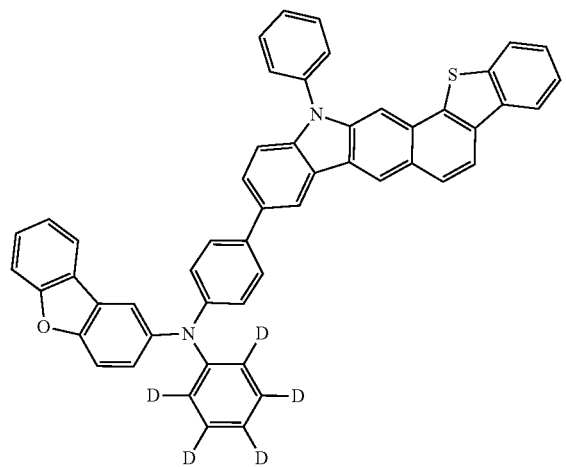

-continued
A 1-1-29
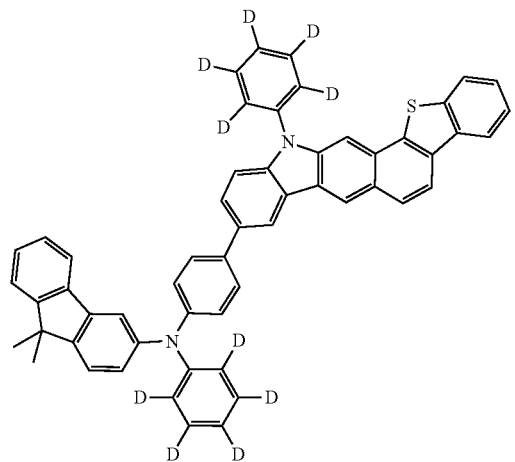
A 1-1-30
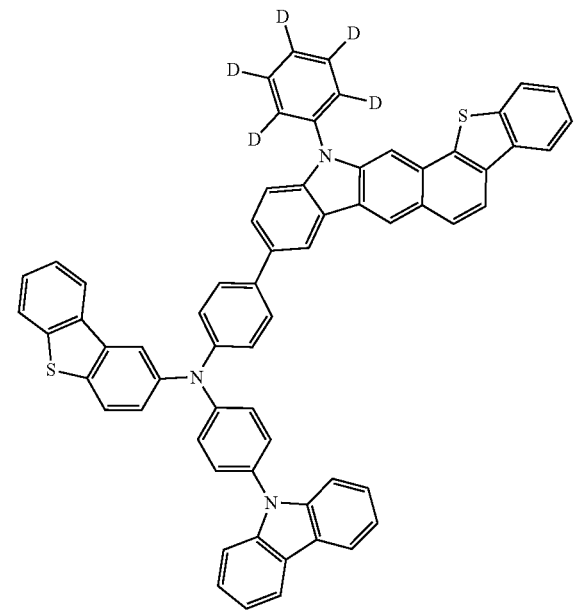
A 1-1-31
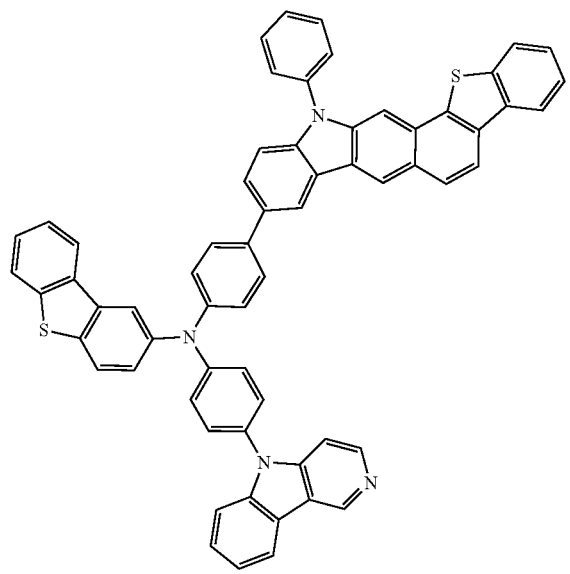
A 1-1-32
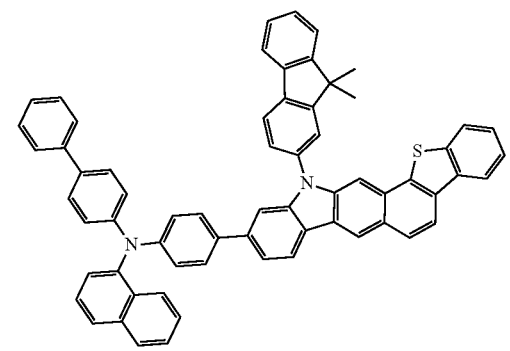
A 1-1-33
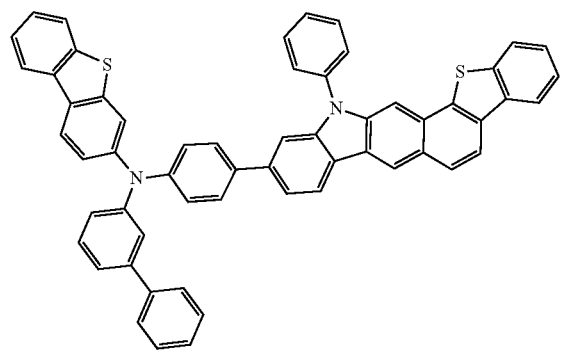
A 1-1-34
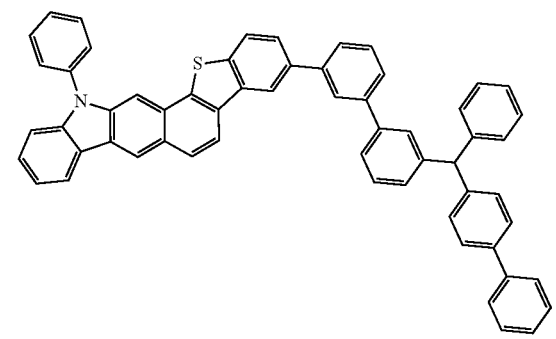

-continued
A 1-2-1
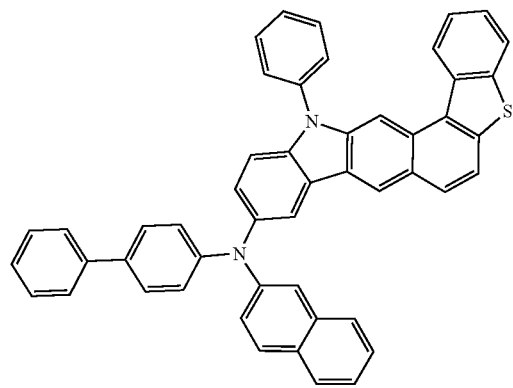
A 1-2-2
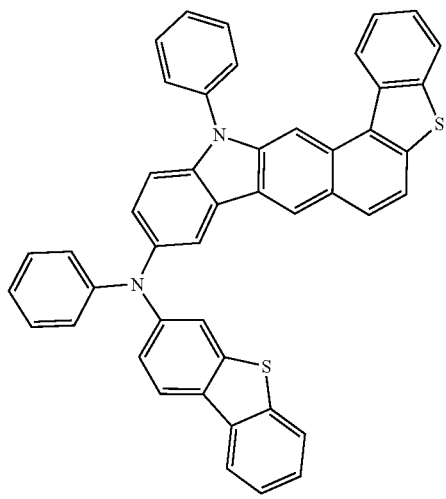
A 1-2-3
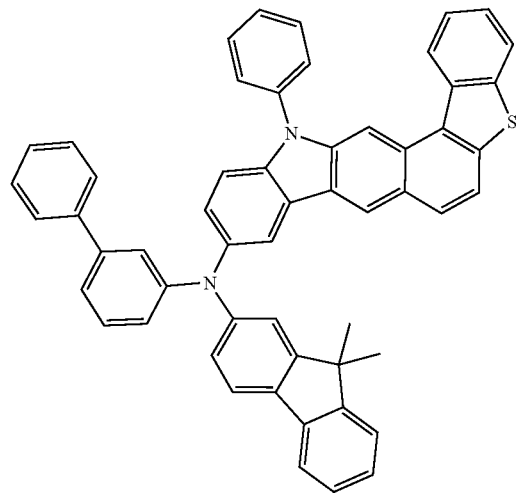
A 1-2-4
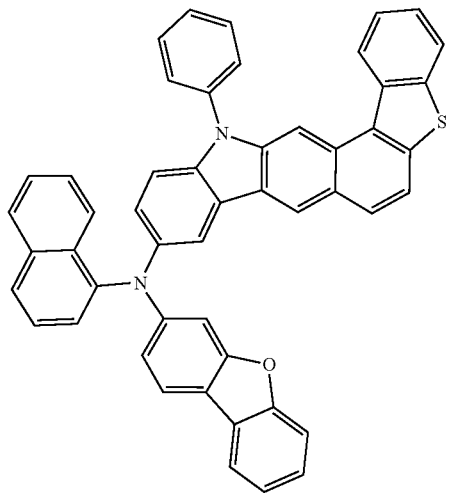
A 1-2-5
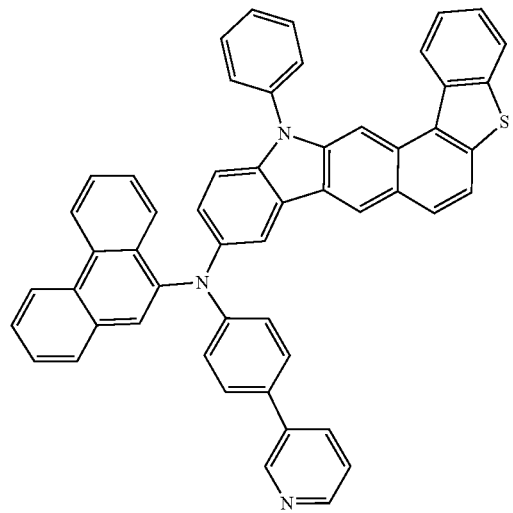
A 1-2-6
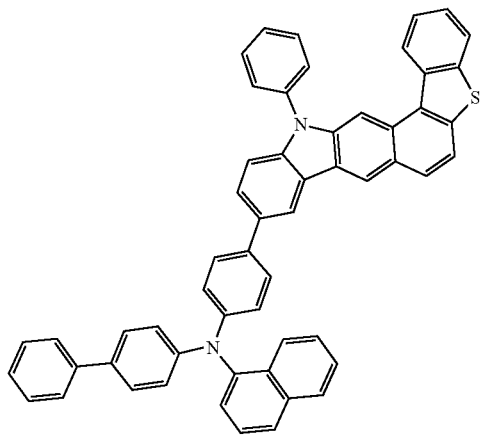

-continued
A 1-2-7
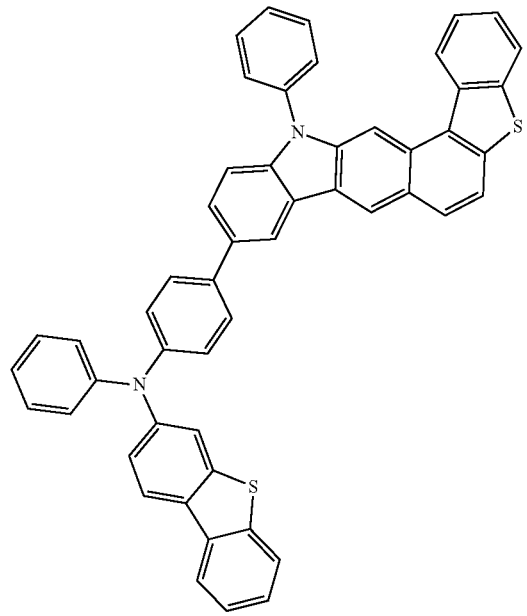
A 1-2-8
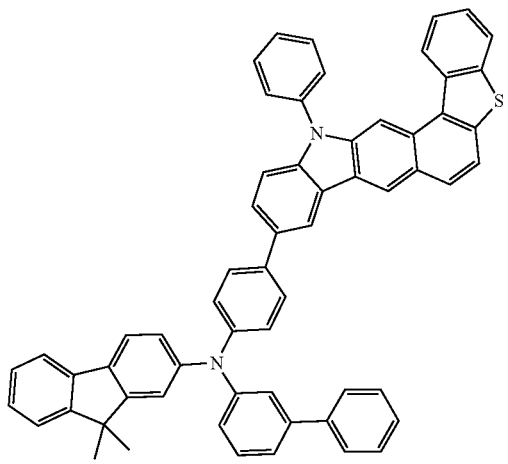
A 1-2-9
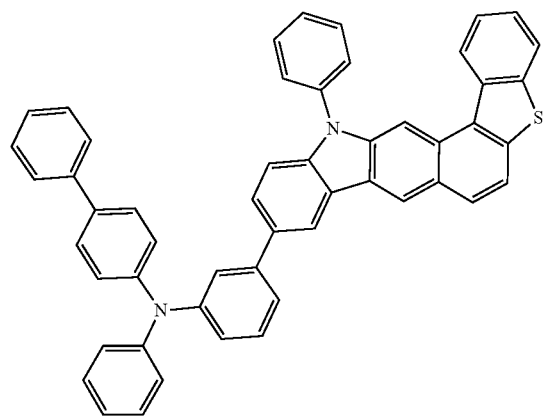
A 1-2-10
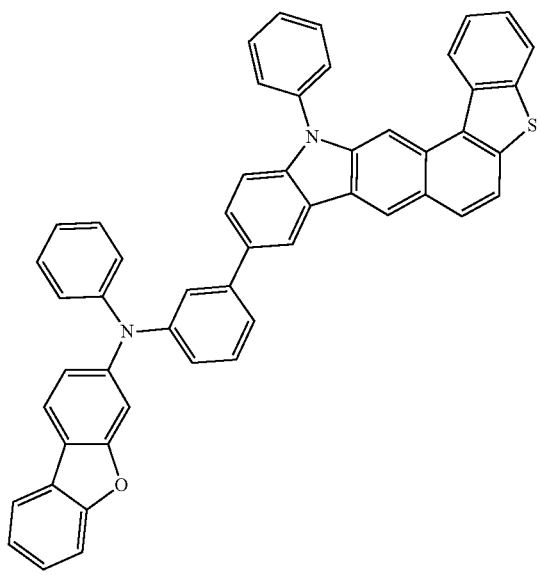

-continued
A 1-2-11
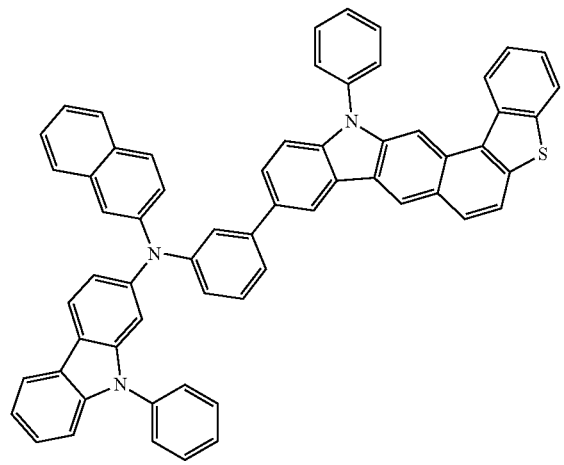
A 1-2-12
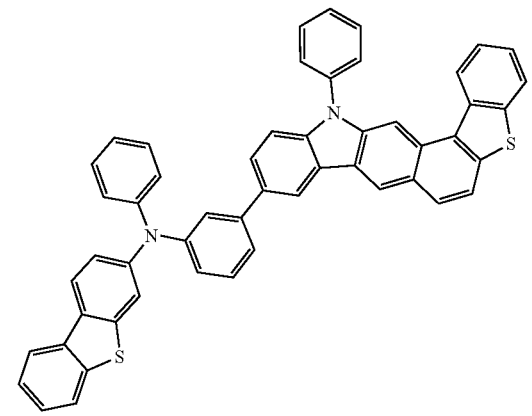
A 1-2-13
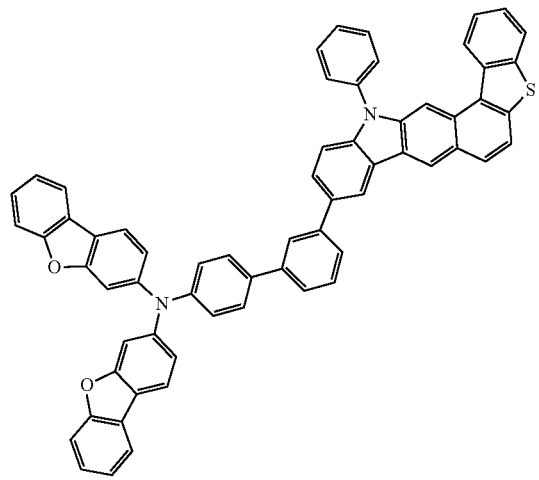
A 1-2-14
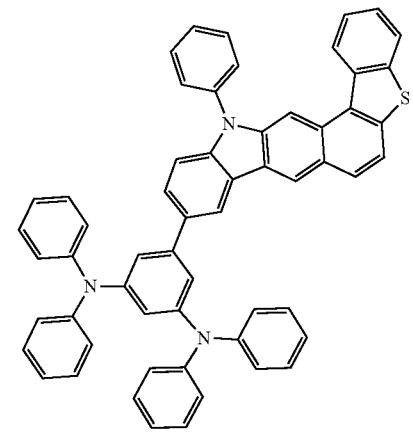
A 1-2-15
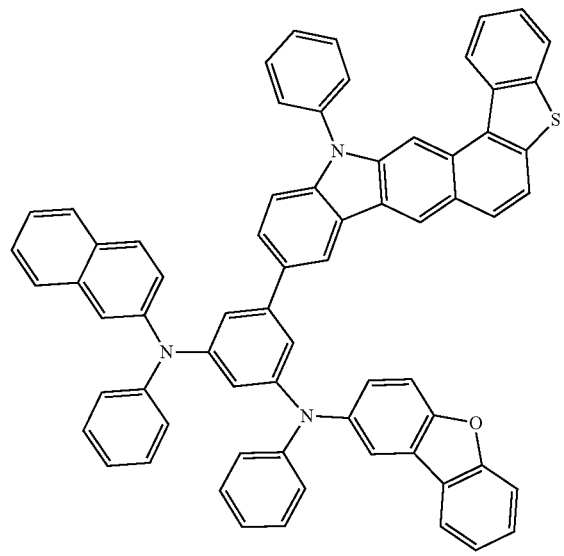
A 1-2-16
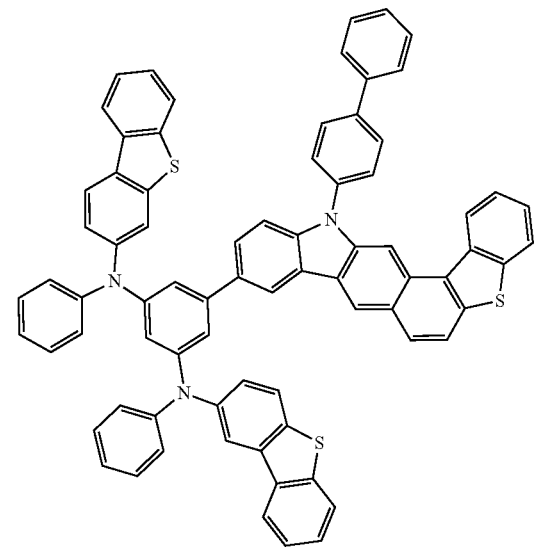

-continued
A 1-2-17
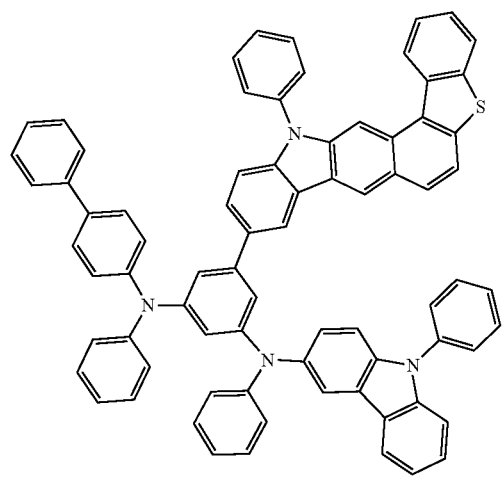
A 1-2-18
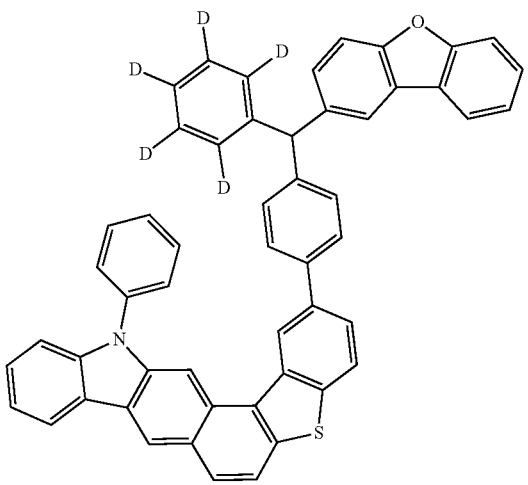
A 2-1-1
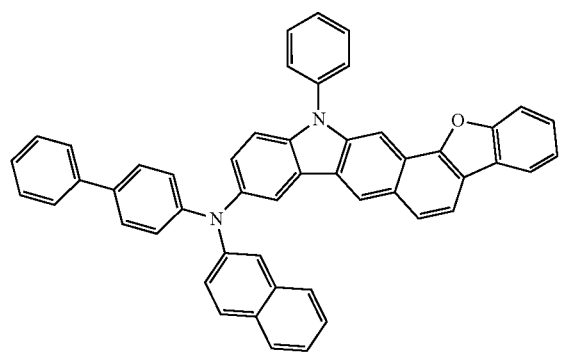
A 2-1-2
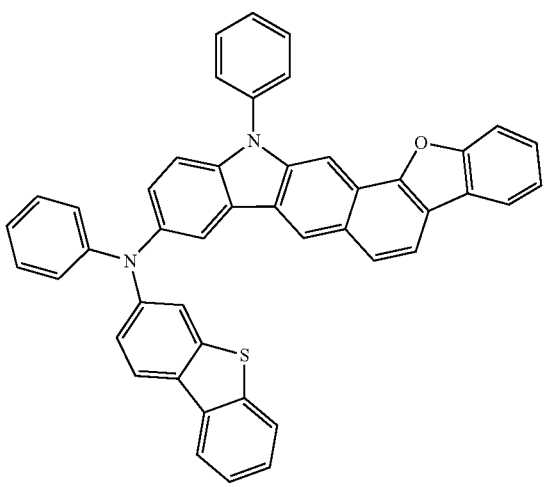
A 2-1-3
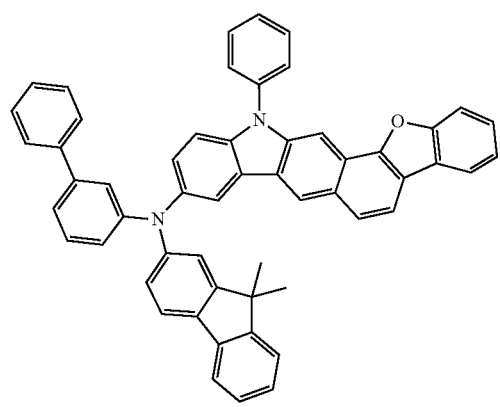
A 2-1-4
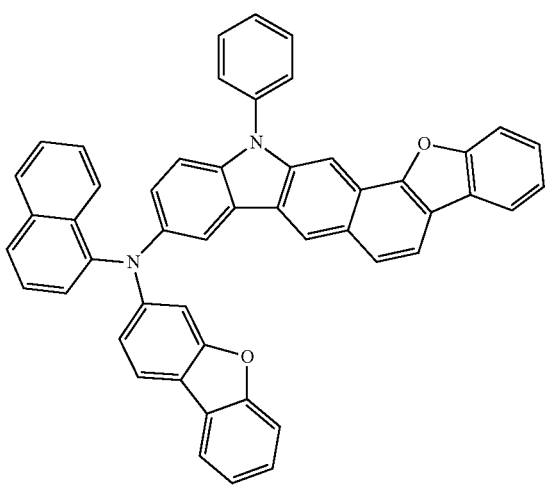

-continued
A 2-1-5
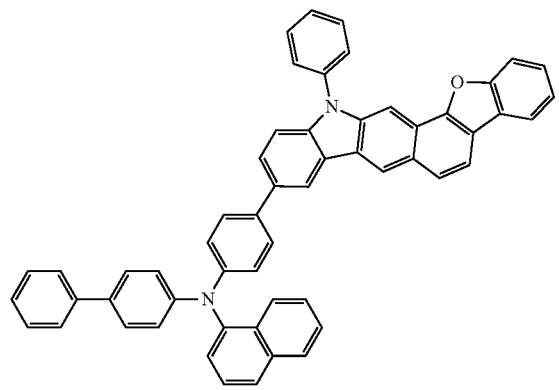
A 2-1-6
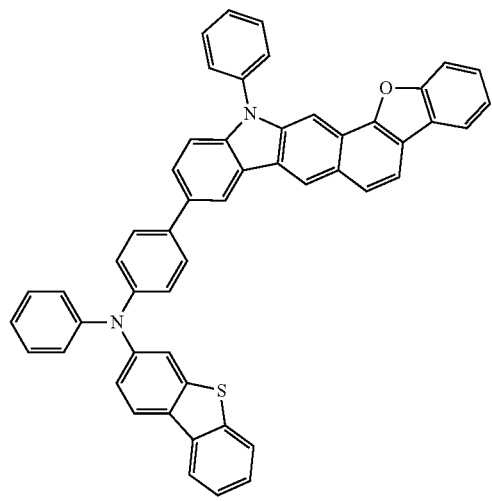
A 2-1-7
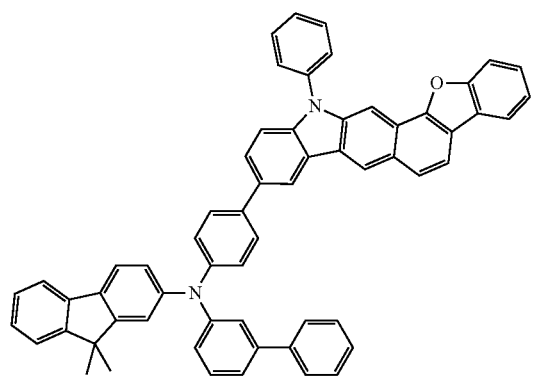
A 2-1-8
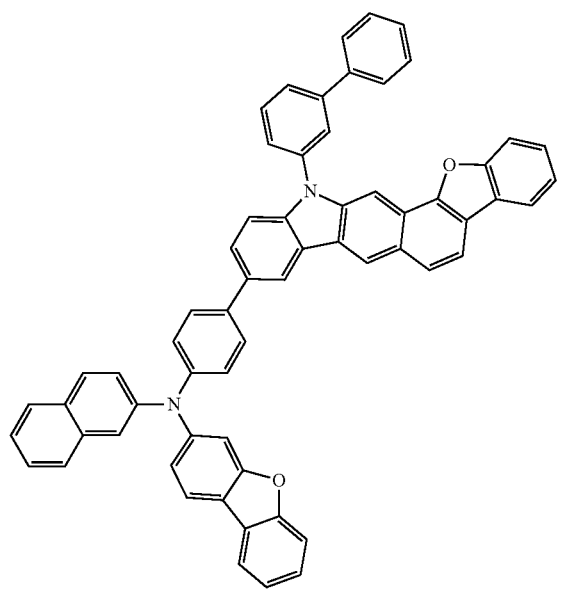

-continued
A 2-1-9
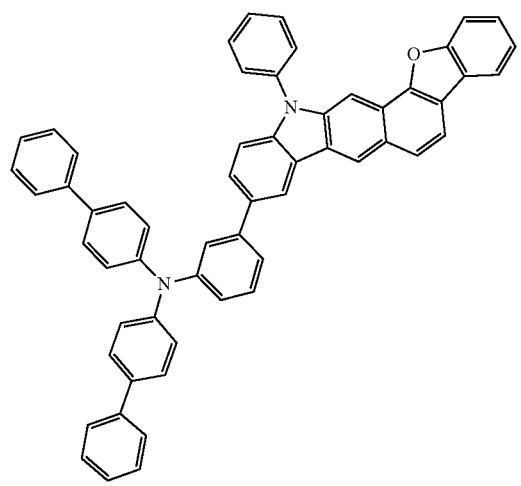
A 2-1-10
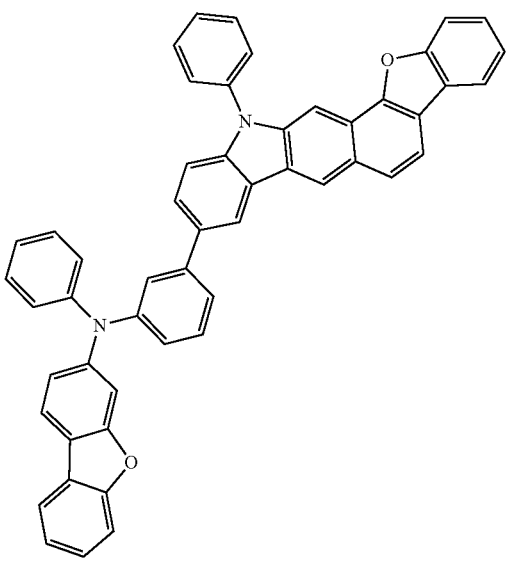
A 2-1-11
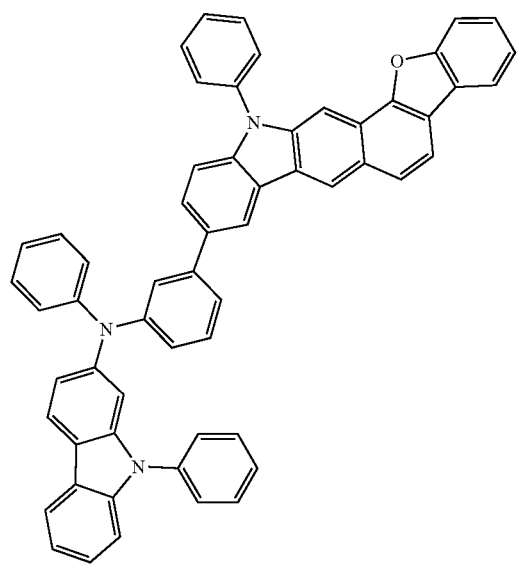
A 2-1-12
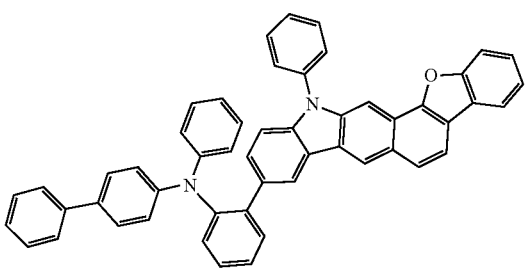
A 2-1-13
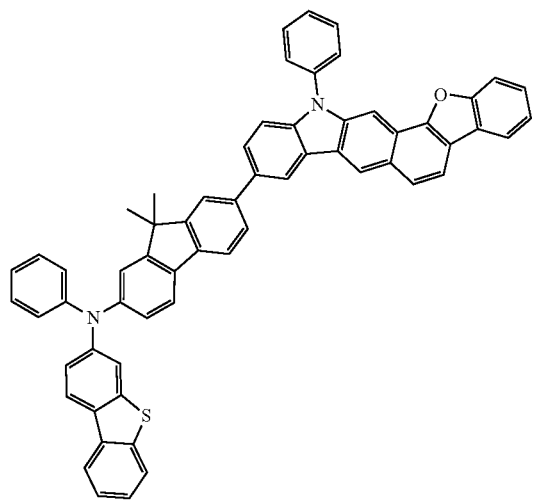

A 2-1-14
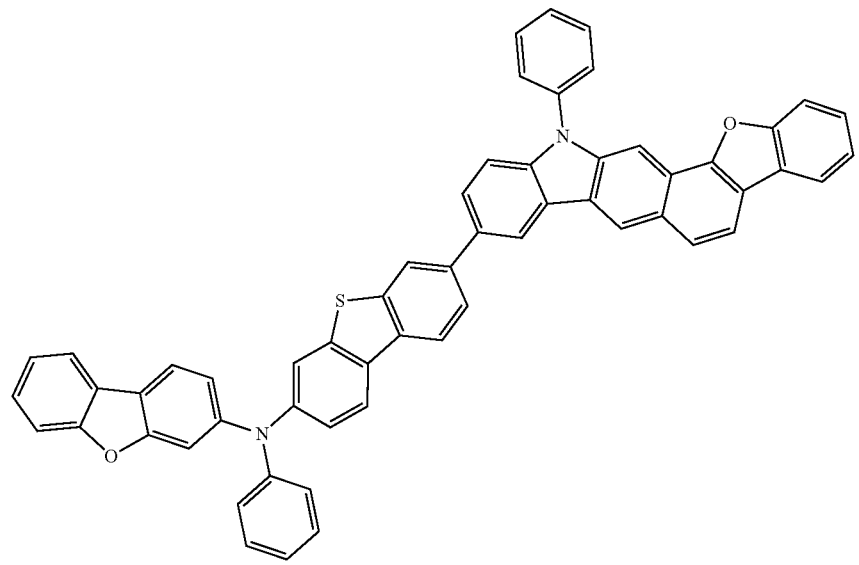
A 2-1-15
A 2-1-16
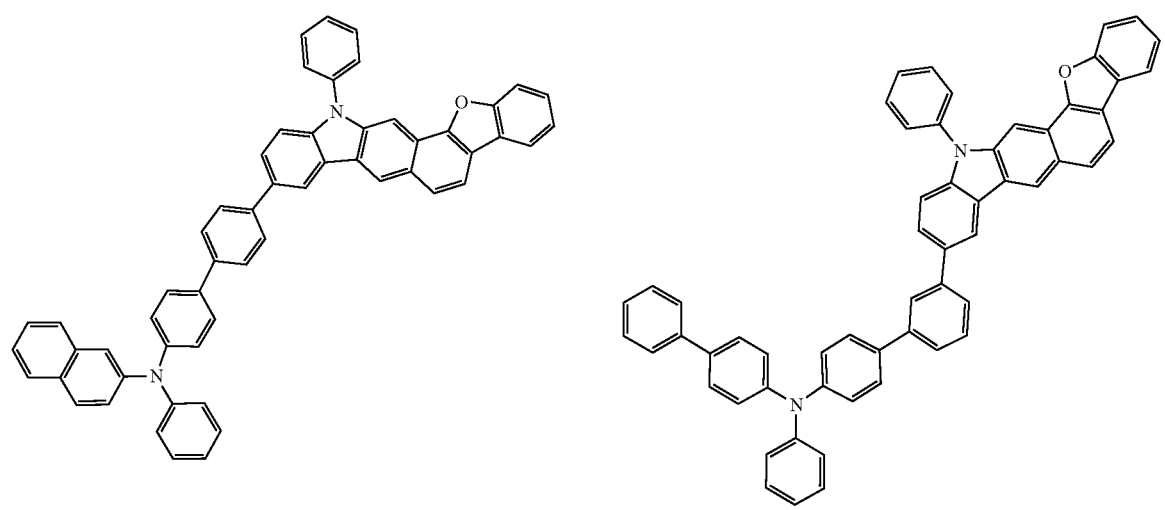

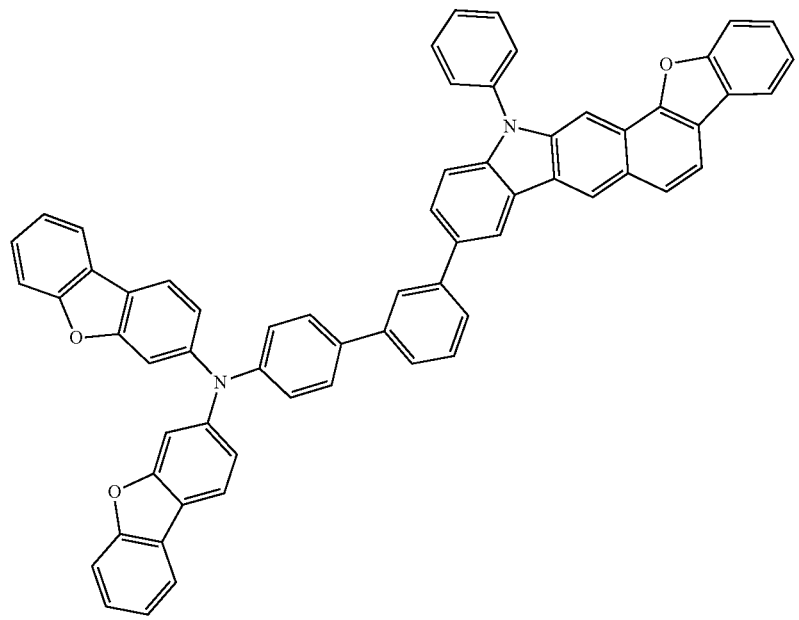
A 2-1-17
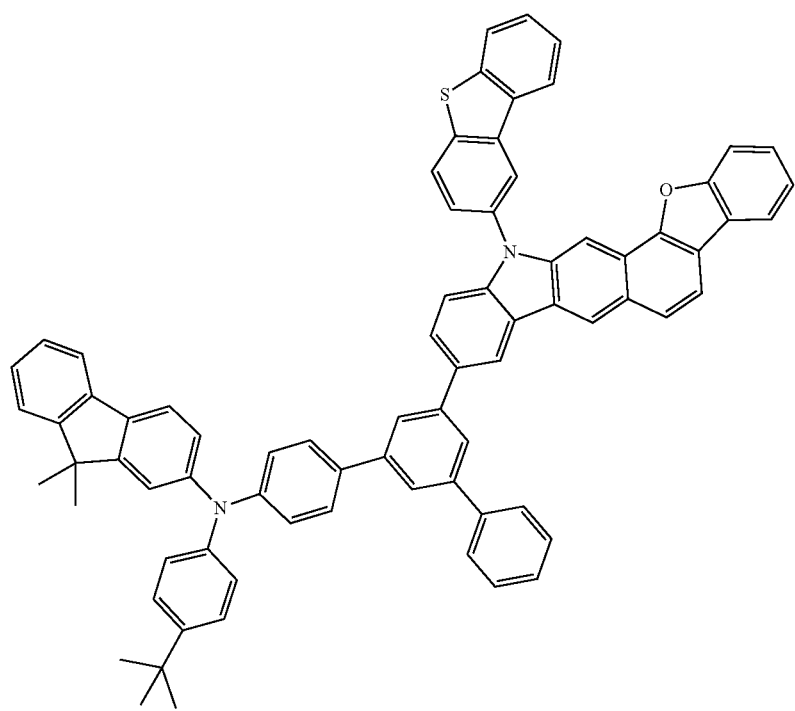
A 2-1-18

-continued
A 2-1-19
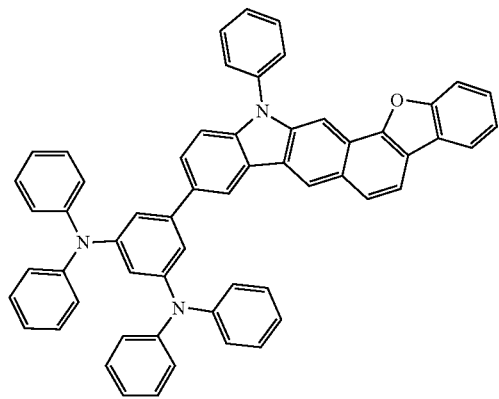
A 2-1-20
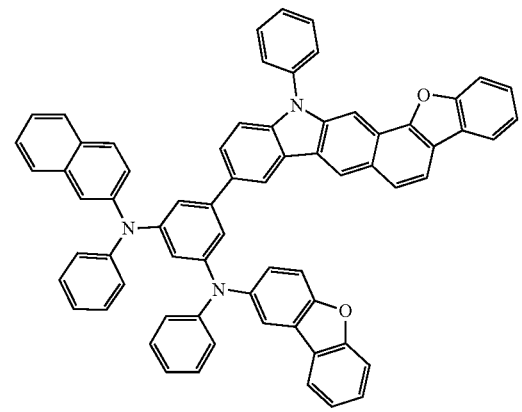
A 2-1-21
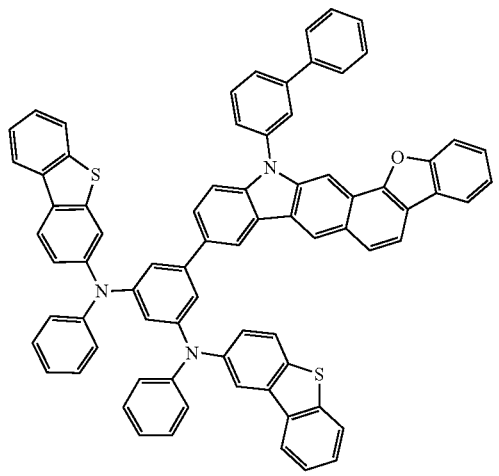
A 2-1-22
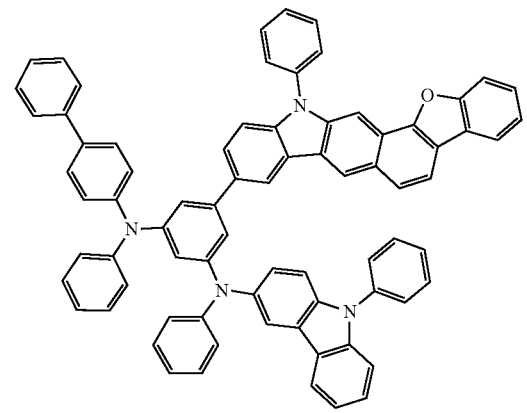
A 2-1-23
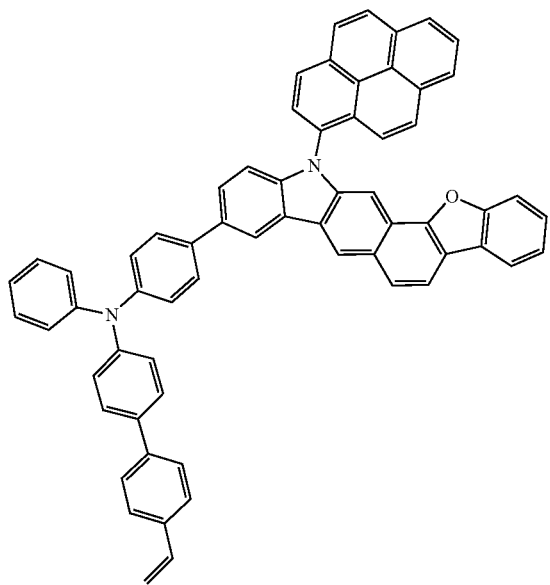
A 2-1-24
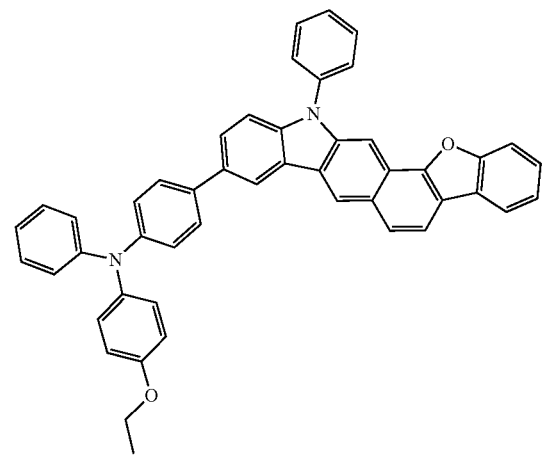

-continued
A 2-1-25
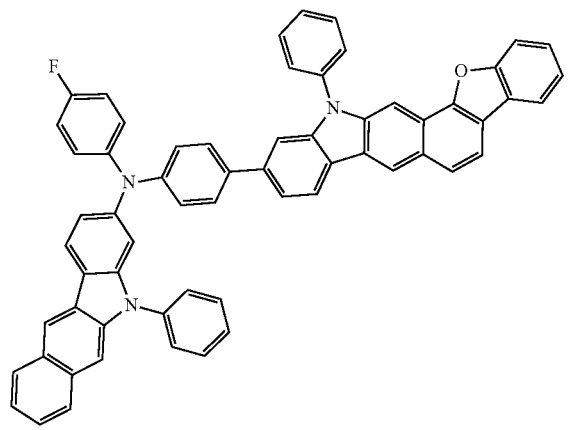
A 2-1-26
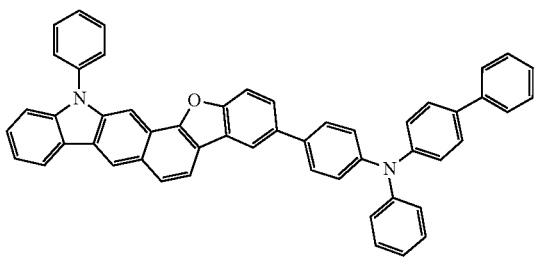
A 2-1-27
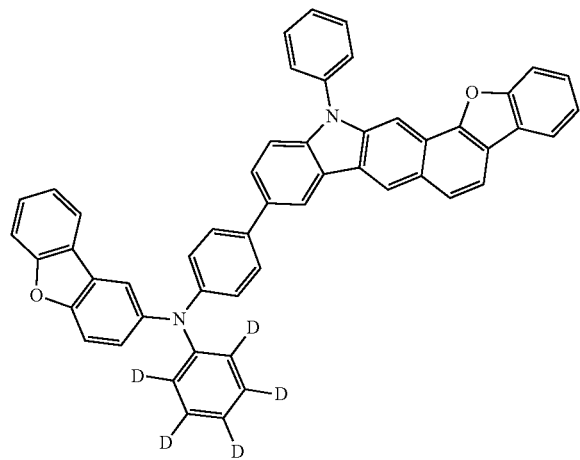
A 2-1-28
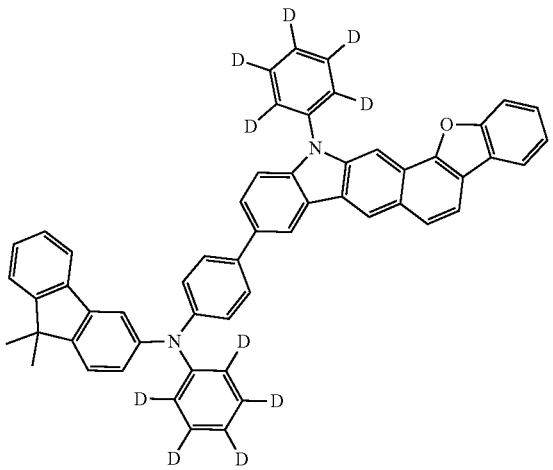
A 2-1-29
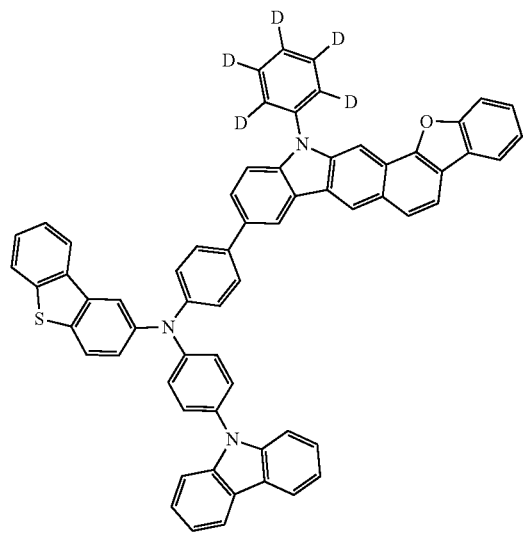
A 2-1-30
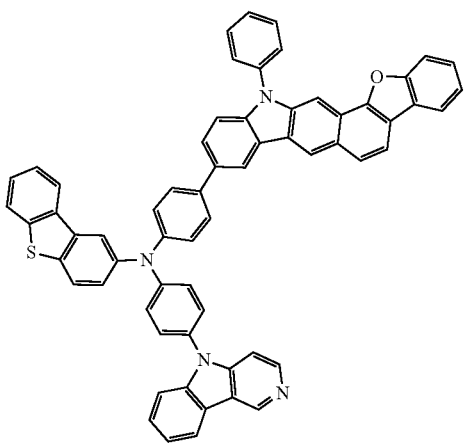

-continued
A 2-2-1
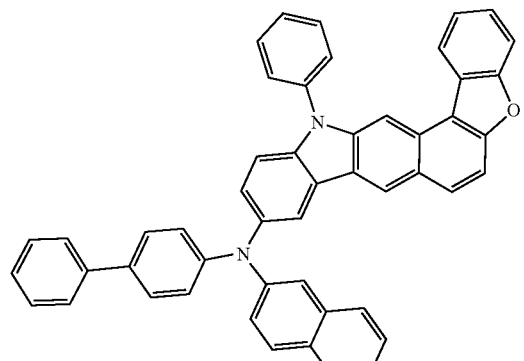
A 2-2-2
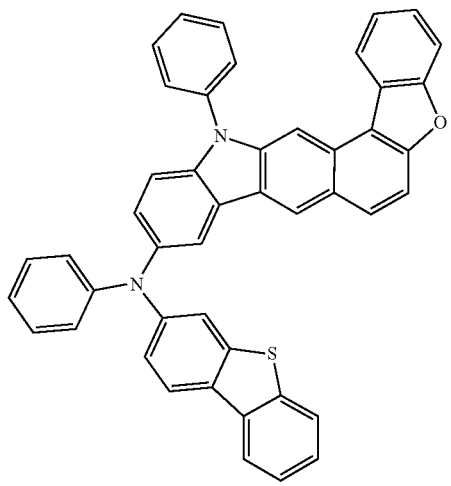
A 2-2-3
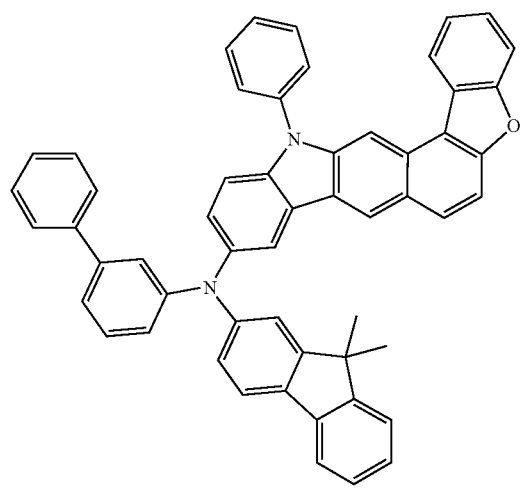
A 2-2-4
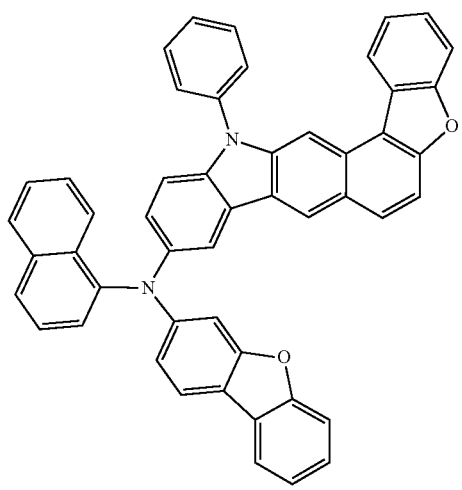
A 2-2-5
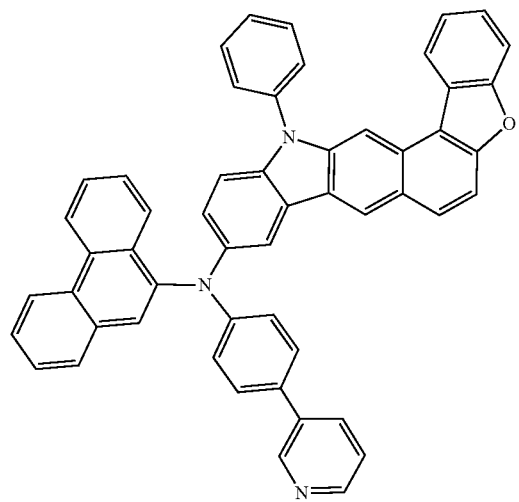
A 2-2-6
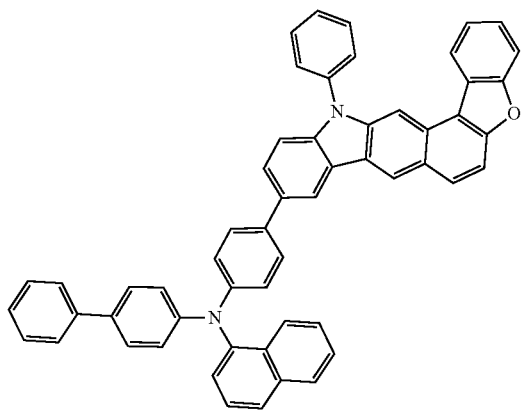

-continued
A 2-2-7
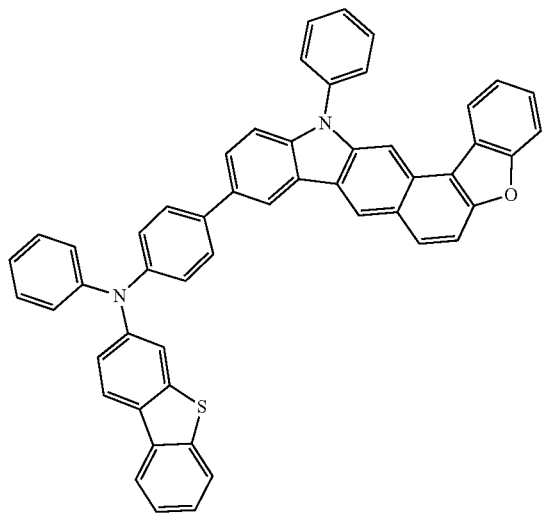
A 2-2-8
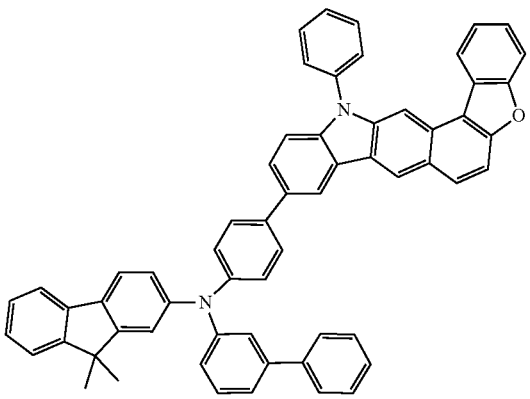
A 2-2-9
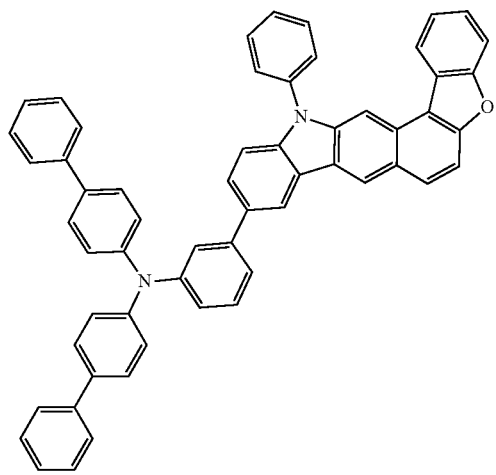
A 2-2-10
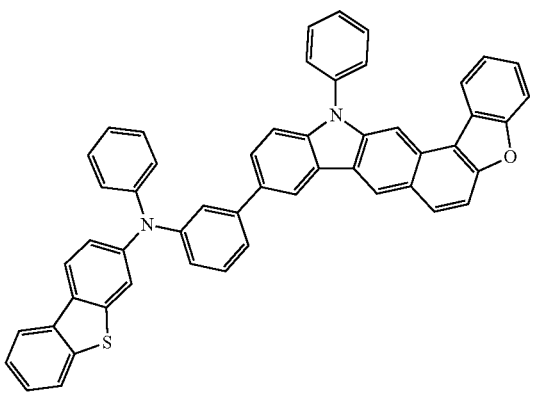
A 2-2-11
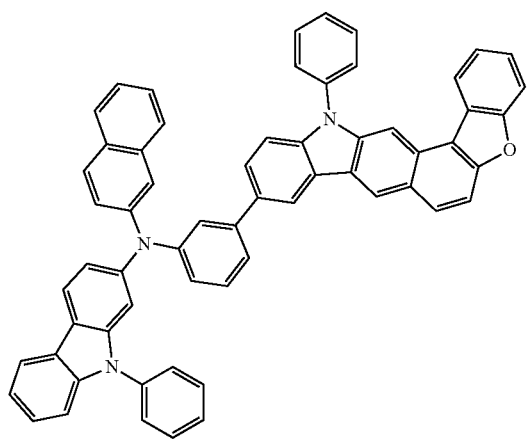
A 2-2-12
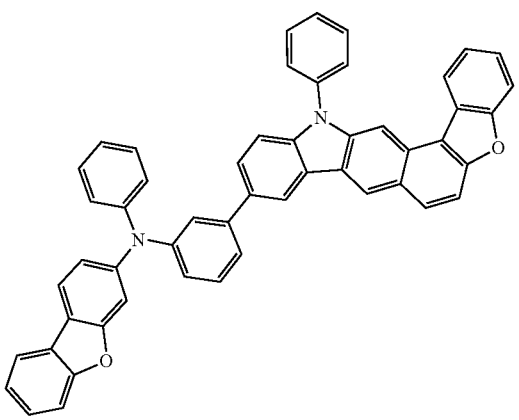

-continued
A 2-2-13
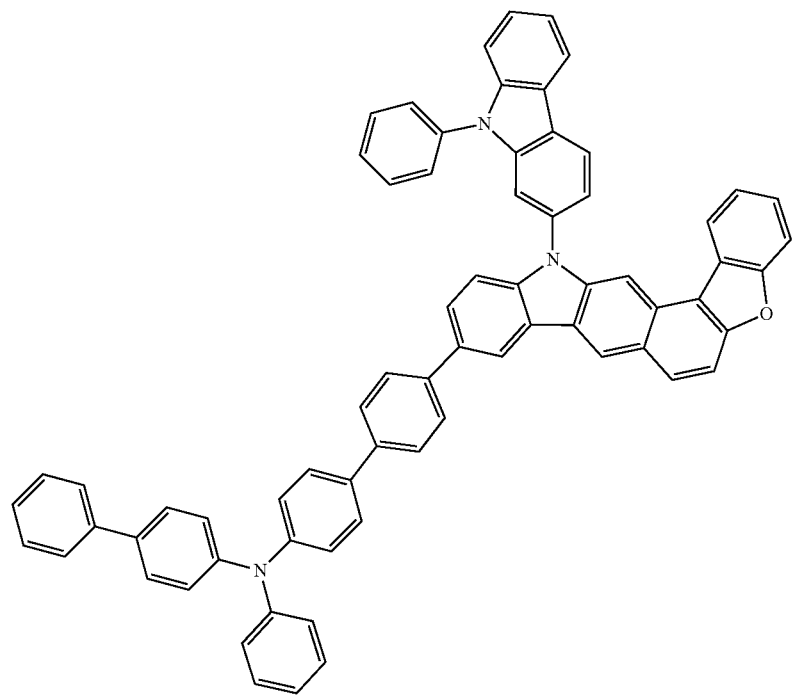
A 2-2-14
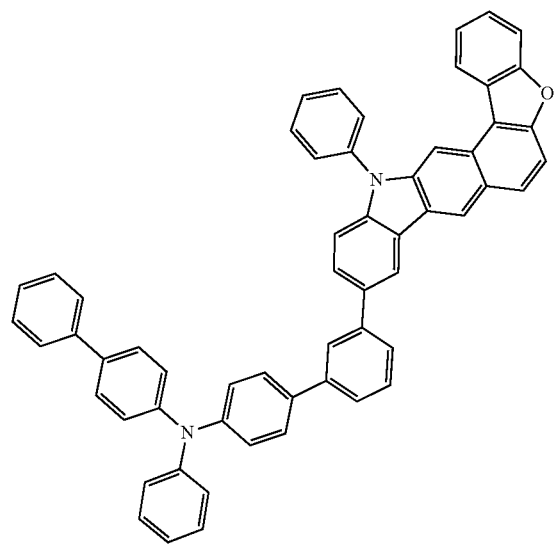

-continued
A 2-2-15
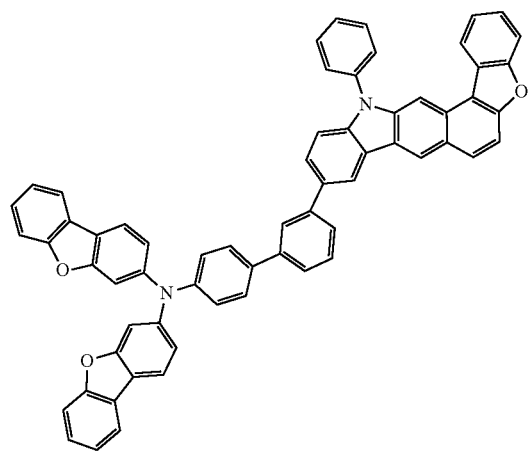
A 2-2-16
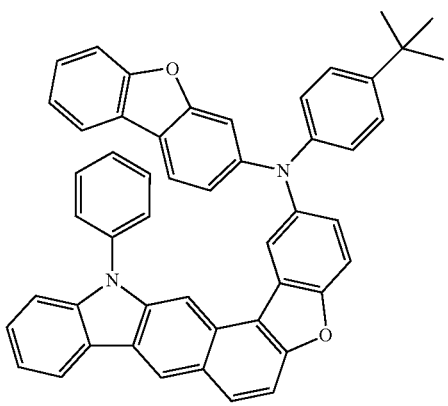
A 2-2-17
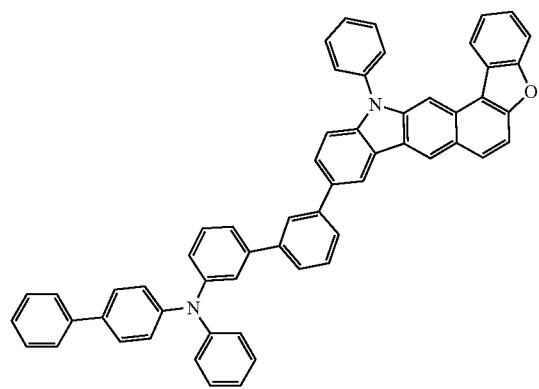
A 2-2-18
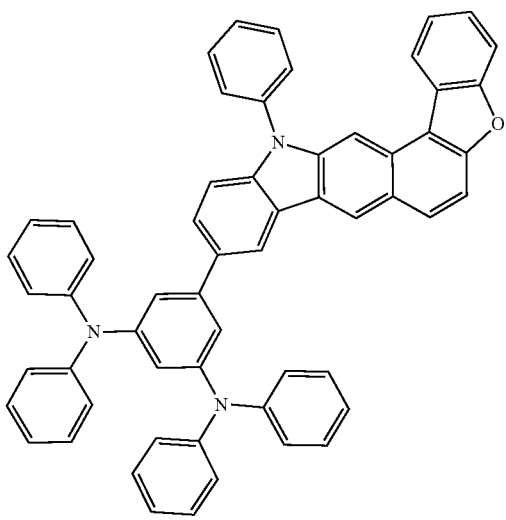
A 2-2-19
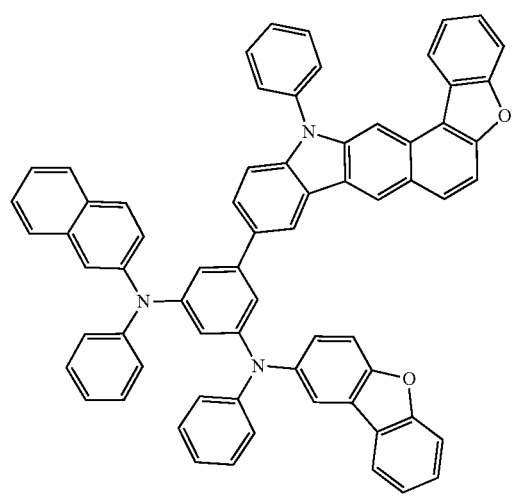
A 2-2-20
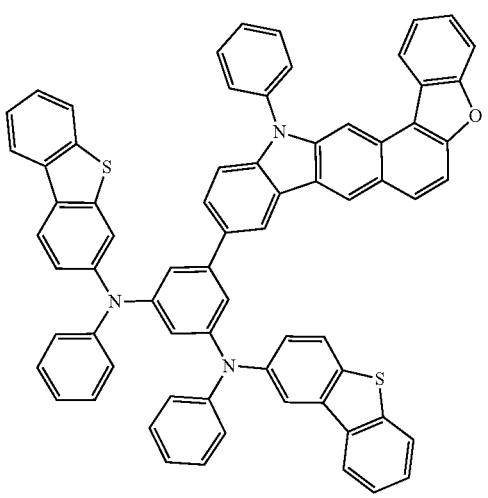

2-2-21
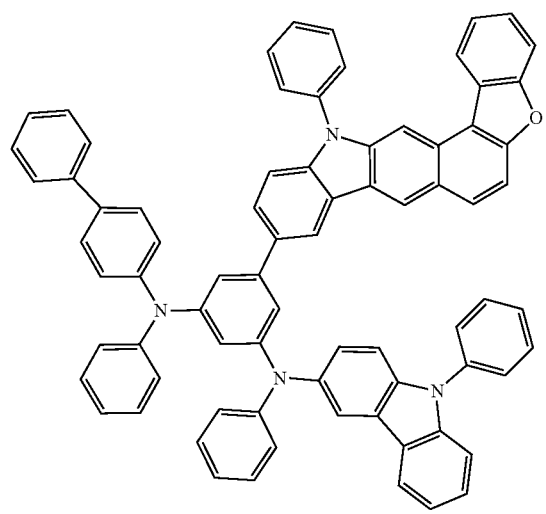
2-2-22
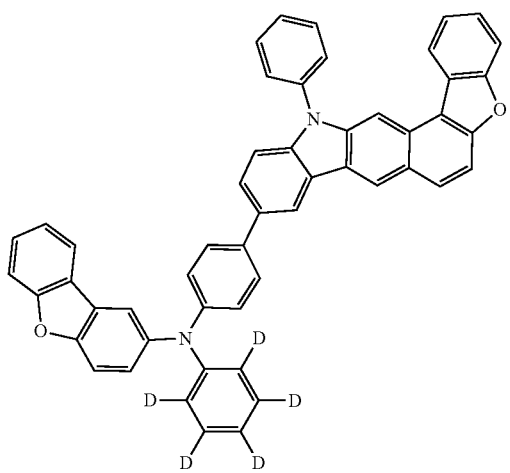
2-2-23
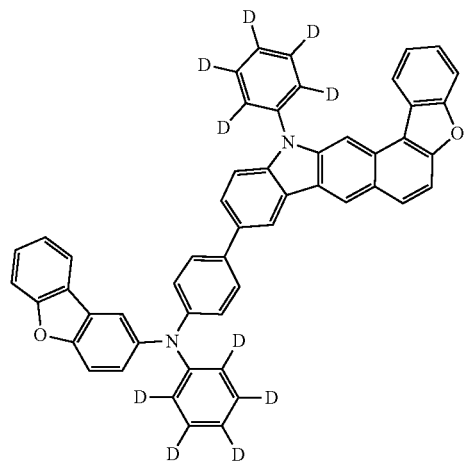
2-2-24
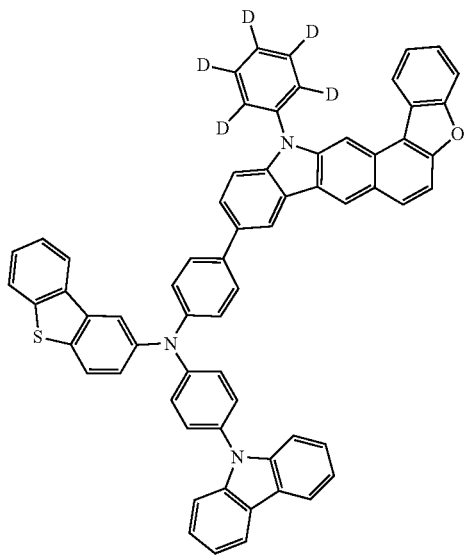

2-2-26
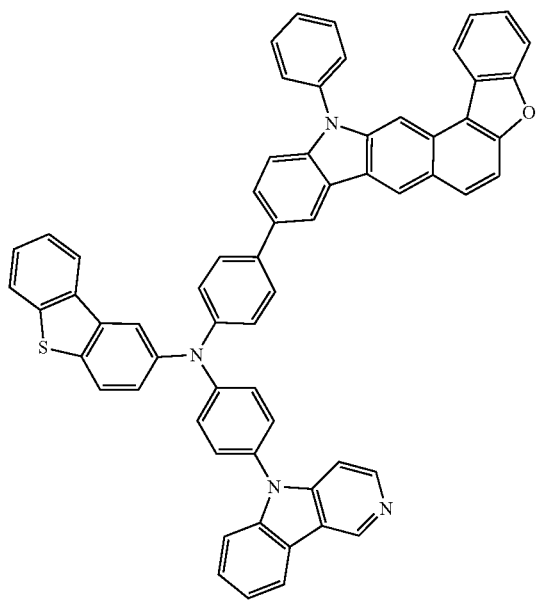
A 3-1-1
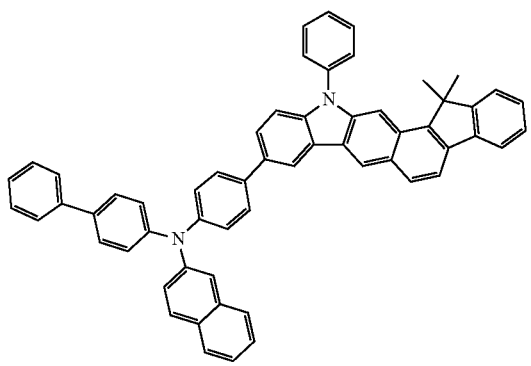
A 3-1-2
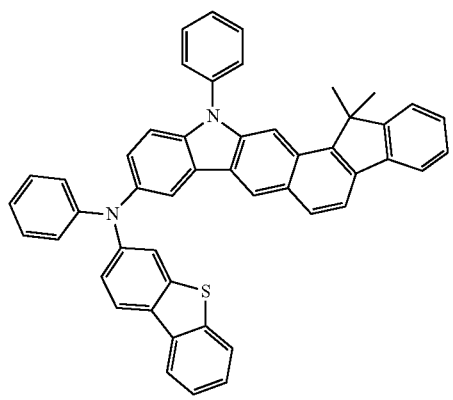
A 3-1-3
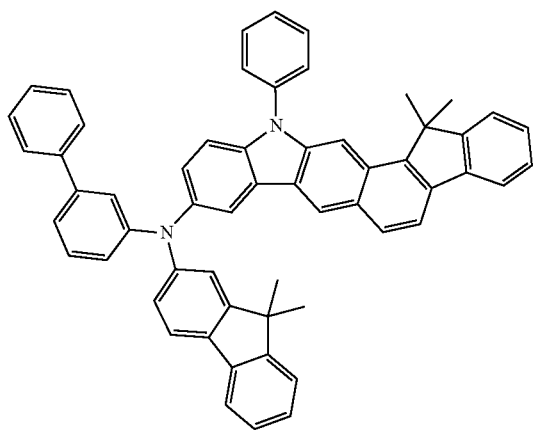
A 3-1-4
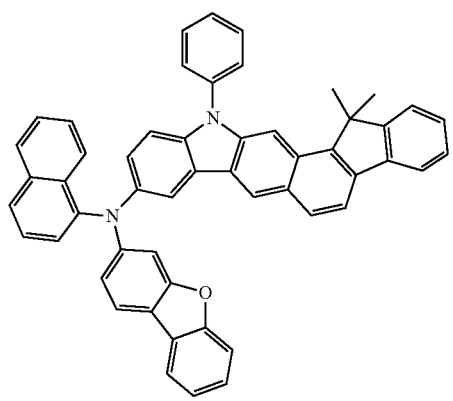
A 3-1-5
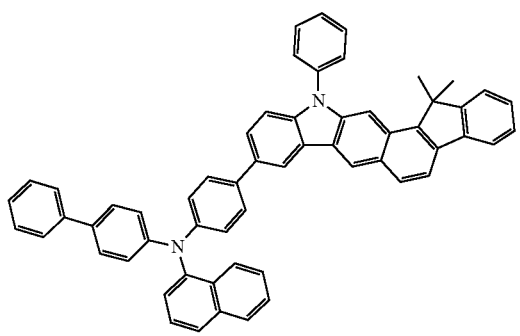

-continued
A 3-1-6
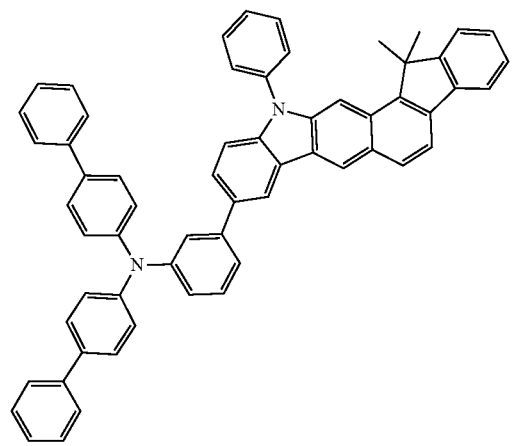
A 3-1-7
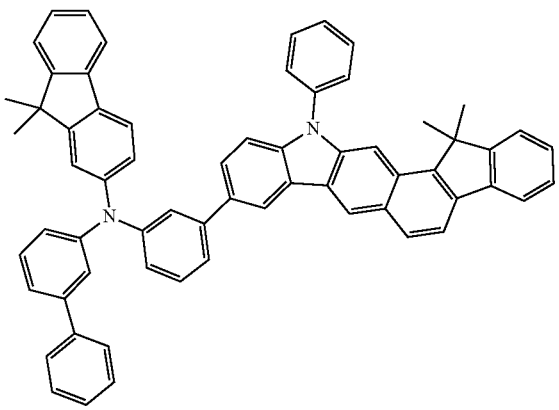
A 3-1-8
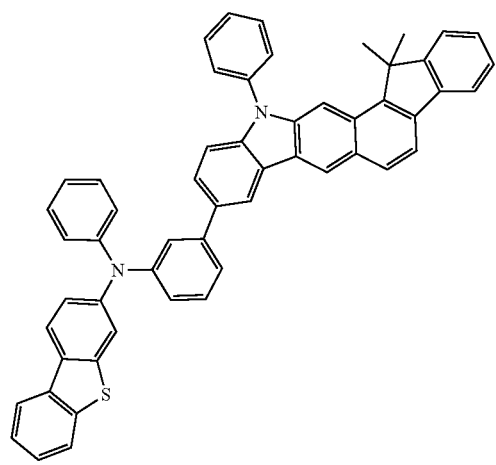
A 3-1-9
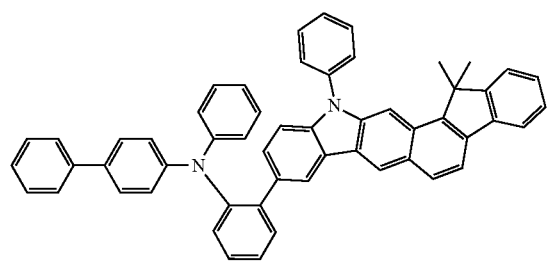
A 3-1-10
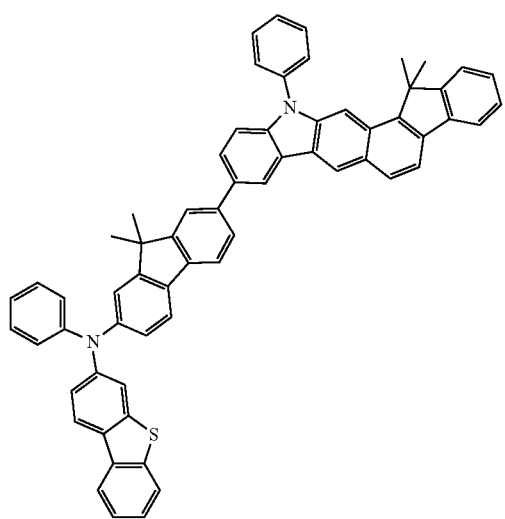

-continued
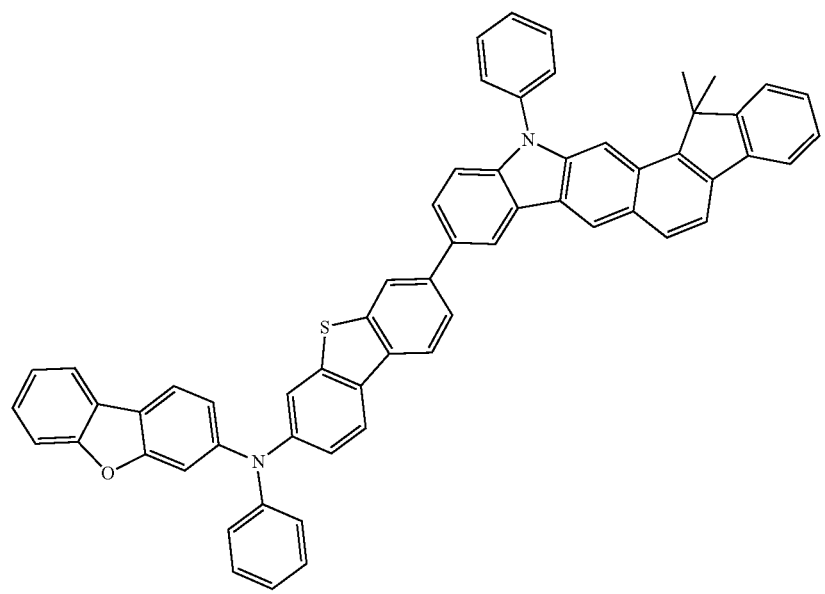
A 3-1-11
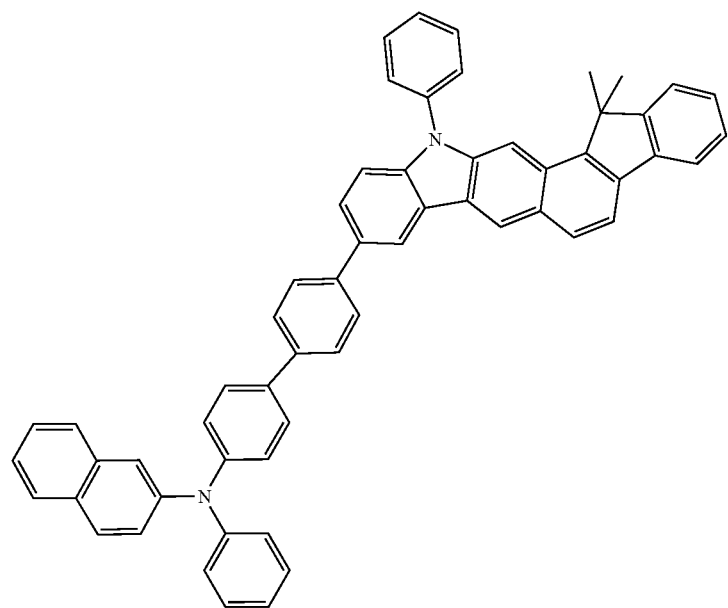
A 3-1-12

A 3-1-13
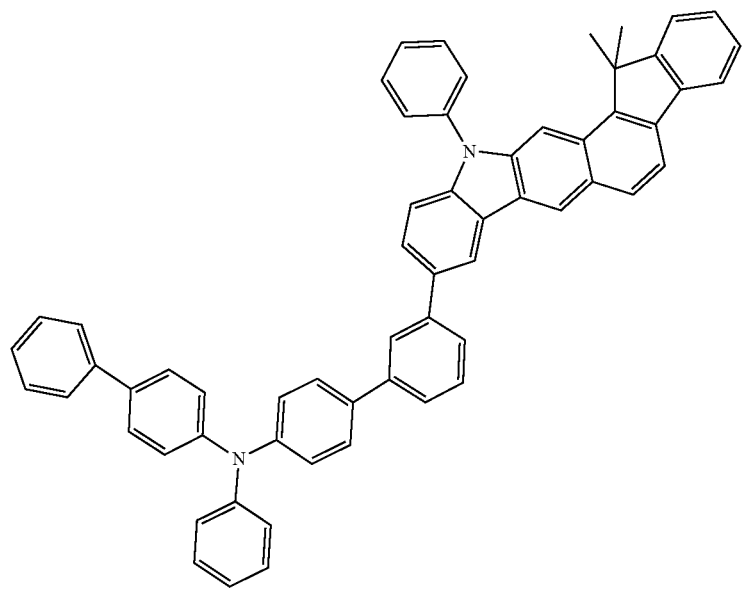
A 3-1-14
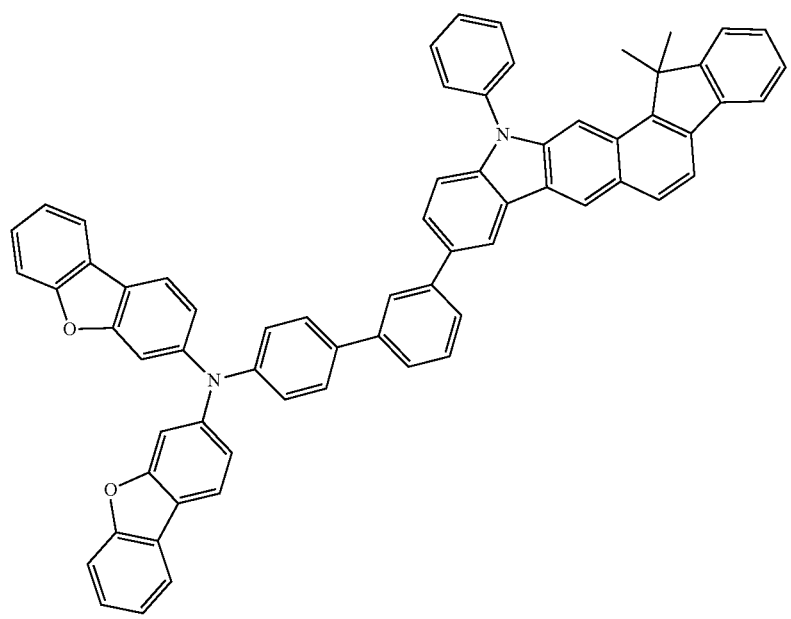
A 3-1-15
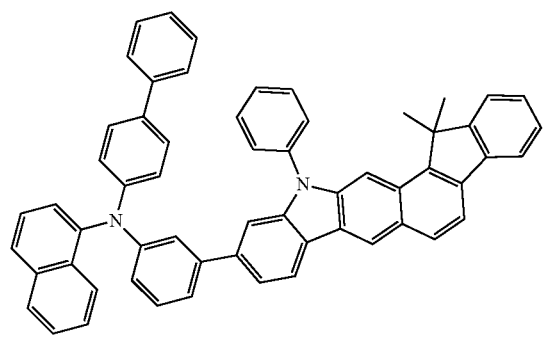
A 3-2-1
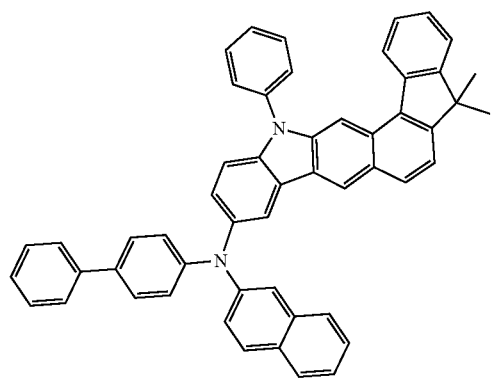

-continued
A 3-2-2
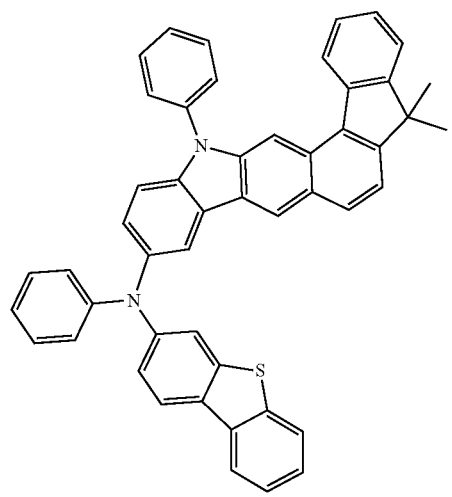
A 3-2-3
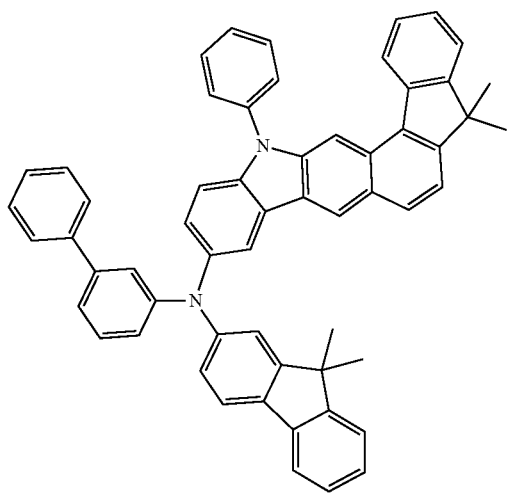
A 3-2-4
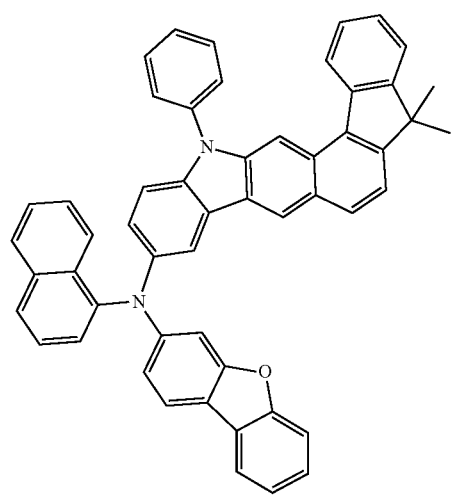
A 3-2-5
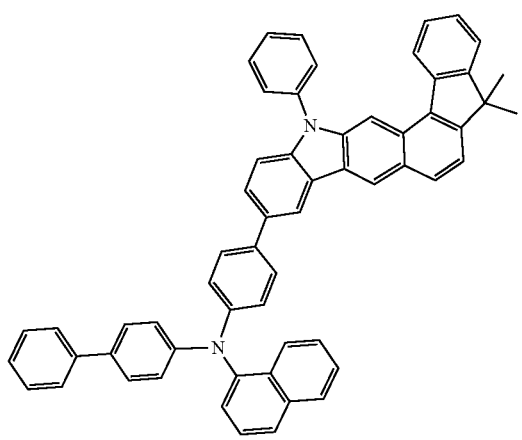
A 3-2-6
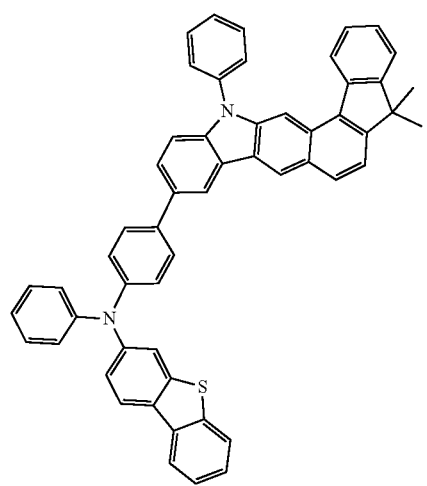
A 3-2-7
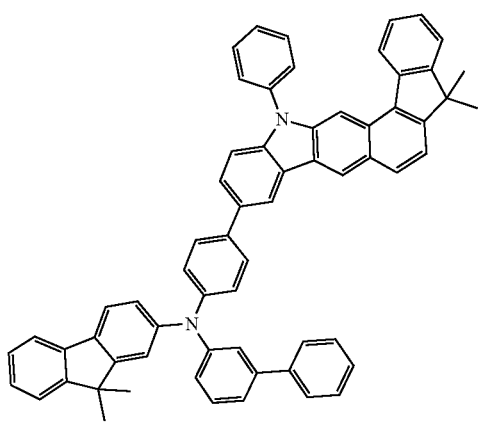

-continued
A 3-2-8
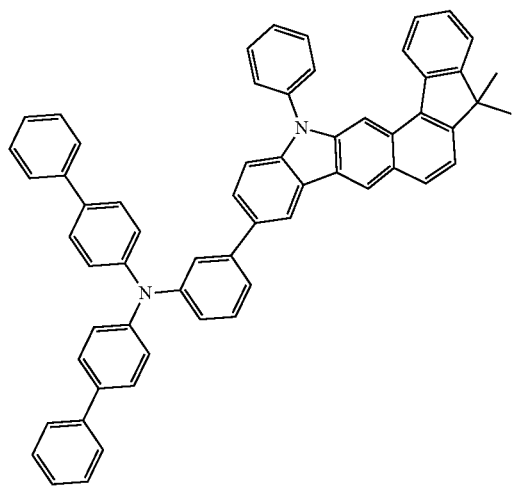
A 3-2-9
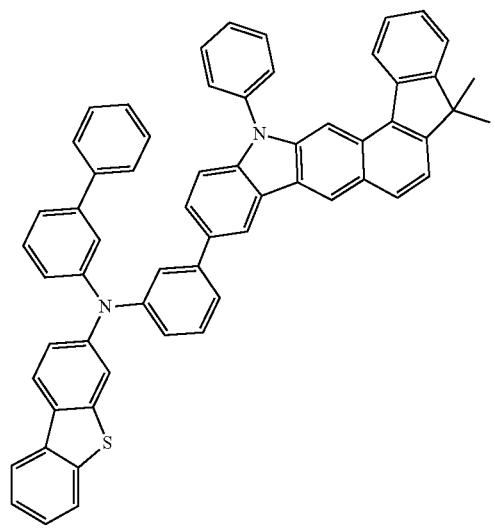
A 3-2-10
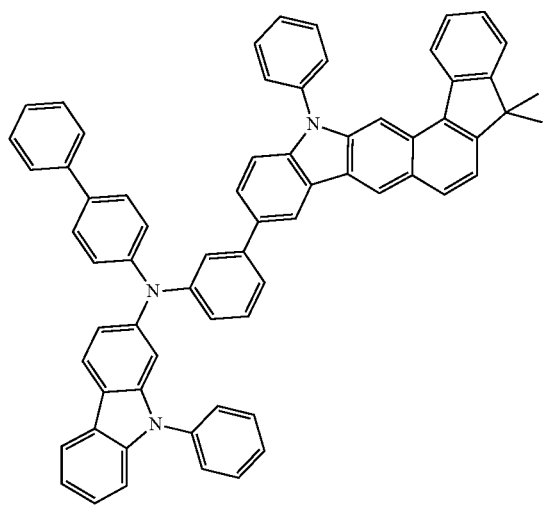
A 3-2-11
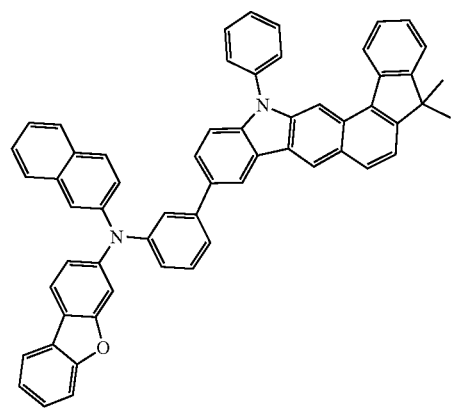
A 3-2-12
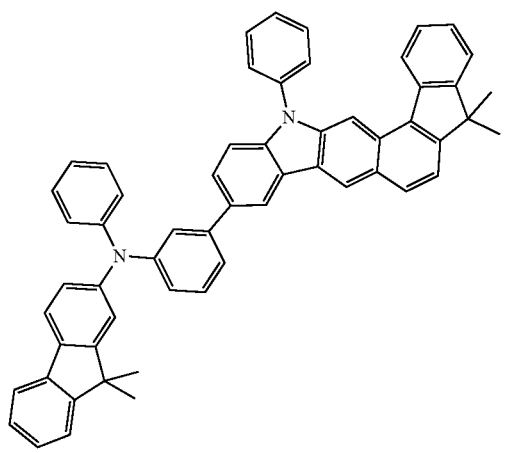
A 3-2-13
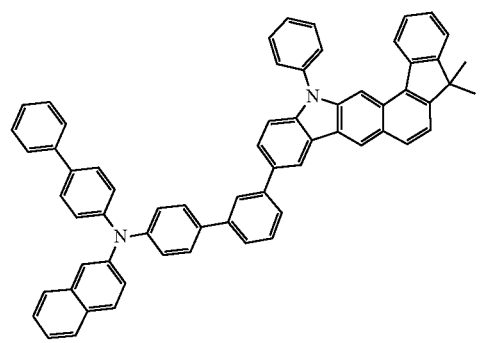

A 3-2-14
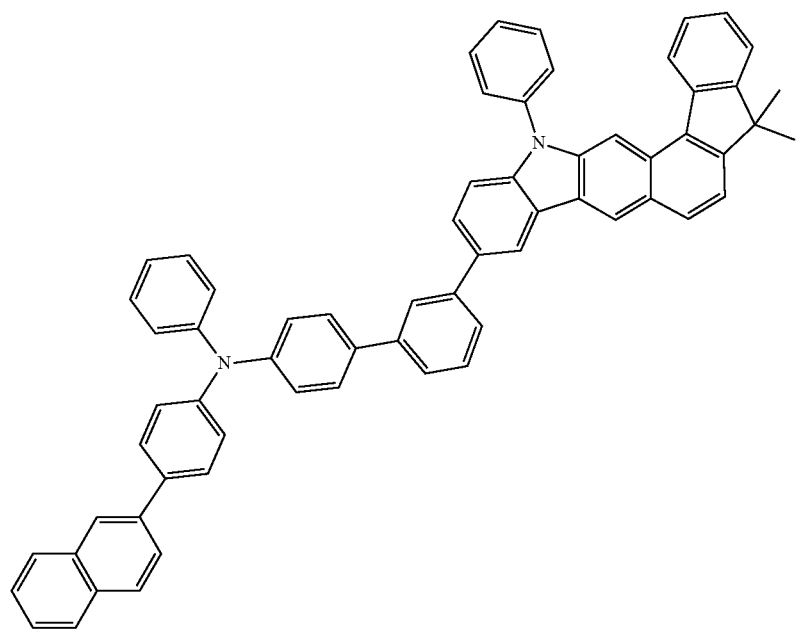
A 4-1-1
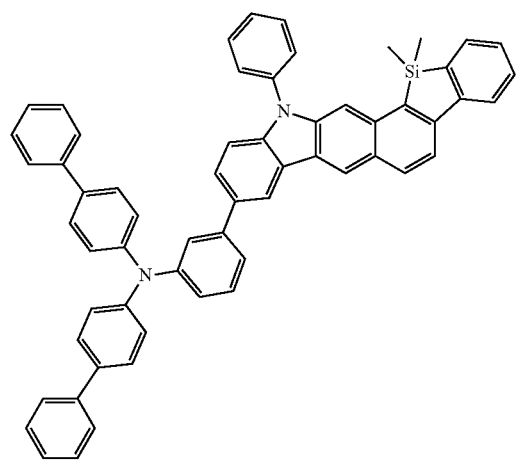
A 4-1-2
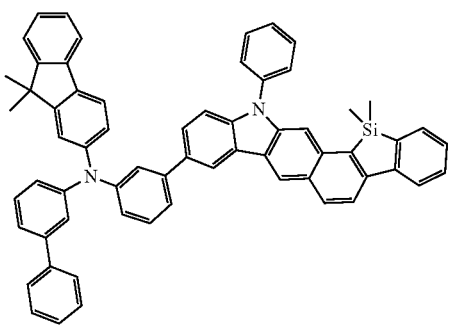
A 4-1-3
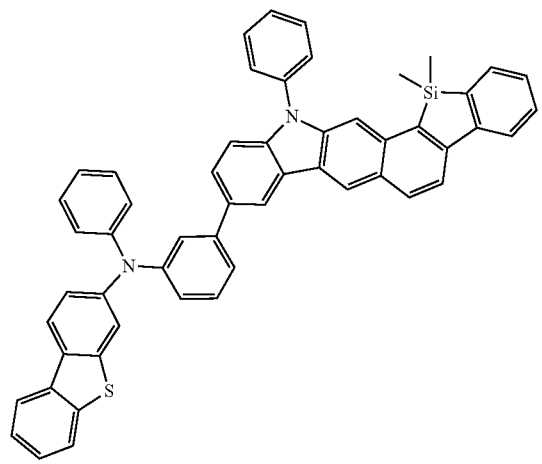
A 4-1-4
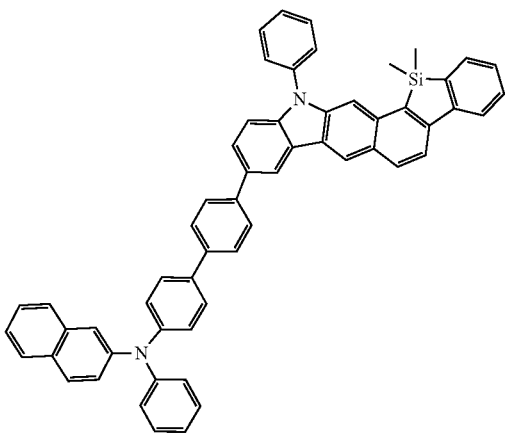

A 4-2-1
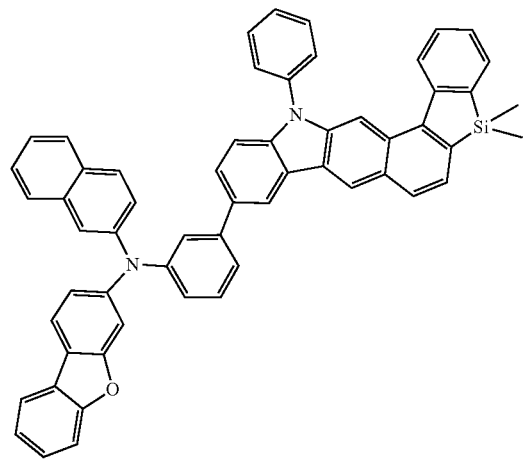
A 4-2-2
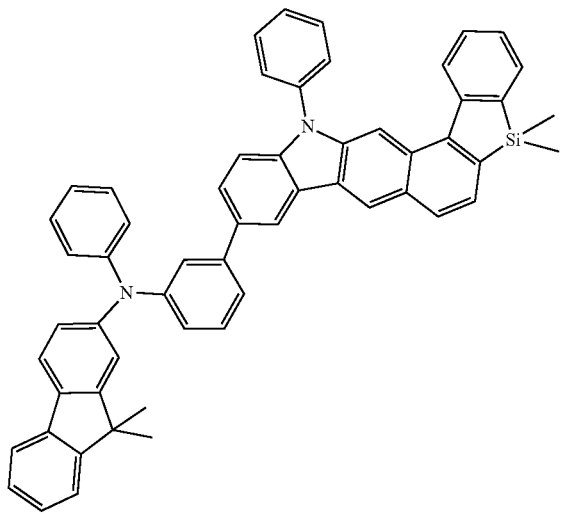
A 4-2-3
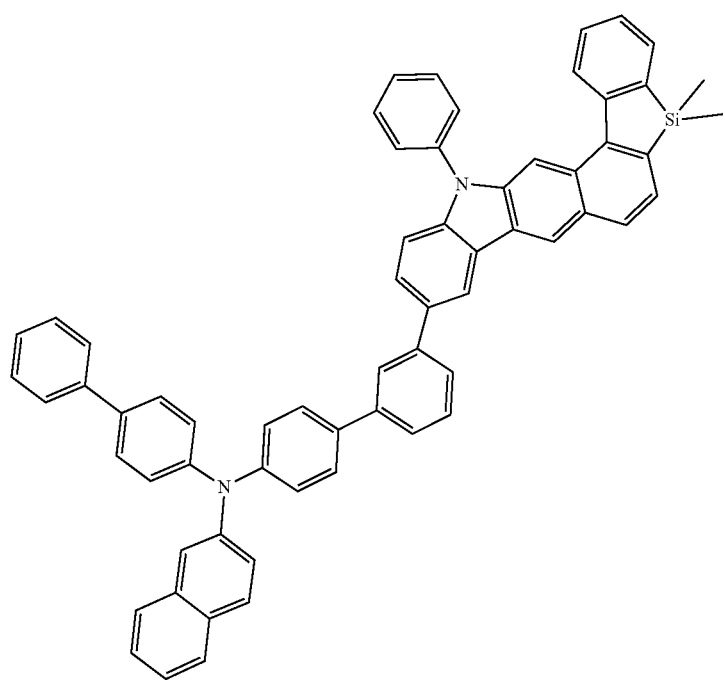

-continued

A 4-2-4

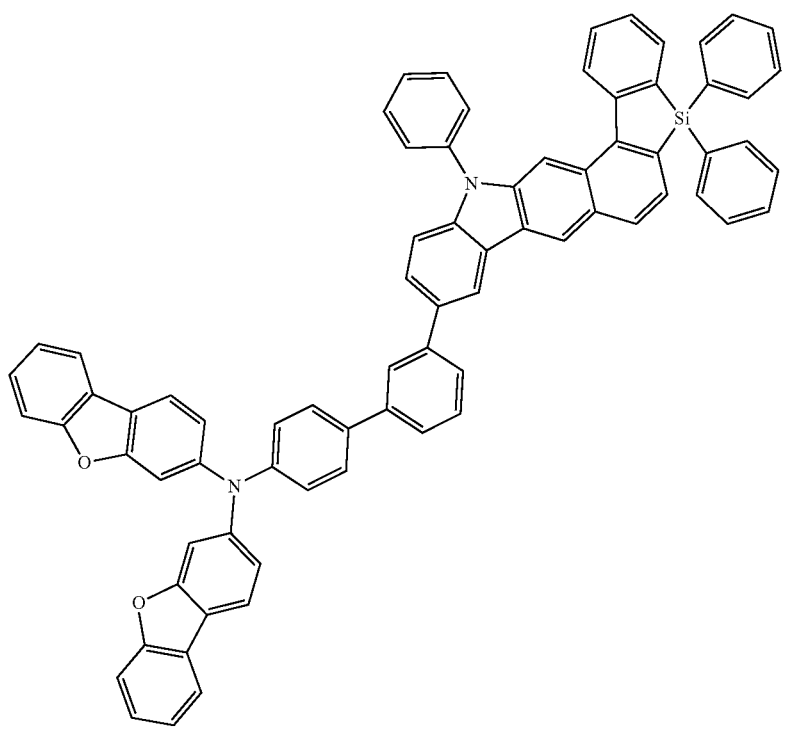

In another aspect of the present invention, the present invention provides an organic electric element comprising a first electrode, a second electrode, and an organic material layer formed between the first electrode and the second electrode and comprising the compound represented by formula 1. Here, the compound represented by formula 1 may be comprised in at least one layer of a hole injection layer, a hole transport layer, an emission-auxiliary layer and a light emitting layer, and may be comprised in a single compound or as a component of a mixture of two or more compounds.

That is, the compound represented by formula 1 may be used as material of a hole injection layer, a hole transport layer, an emission-auxiliary layer and/or a light emitting layer. Preferably, the compound represented by formula 1 may be used as phosphorescent, more preferably, as red phosphorescent host of the light emitting layer.

In another embodiment of the present invention, the present invention provides a organic electric element further comprising a layer for improving luminous efficiency formed on one side of the first electrode and/or one side of the second electrode, the side facing the organic material layer.

Hereinafter, synthesis method of the compound represented by Formula 1 according to one embodiment of the present invention and preparation method of an organic electric element will be described in detail by way of examples. However, the present invention is not limited to the following examples.

Synthesis Example

Illustratively, the compound (final products) according to the present invention may be synthesized by reacting Core and Sub 1 as shown in Reaction Scheme 1 or by reacting intermediate (C) and Sub 2 as shown in Reaction Scheme 2, but there is no limitation thereto.

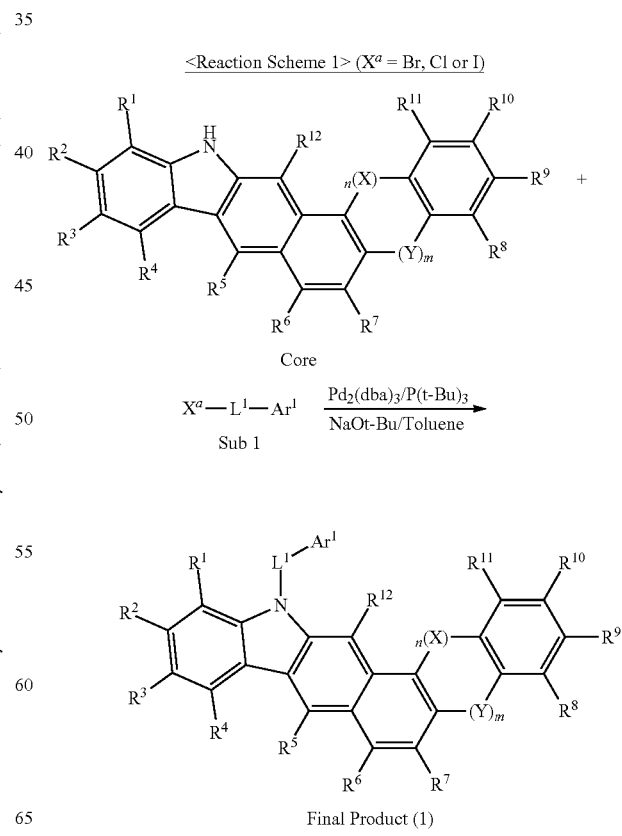

<Reaction Scheme 2> ($X^a$=Br, Cl or I, and symbol of each compound in the following reaction scheme is the same as defined in formula 6.)
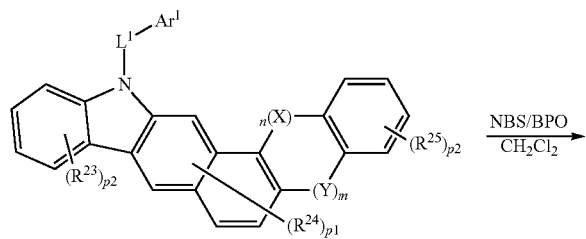 NBS/BPO / CH$_2$Cl$_2$ →
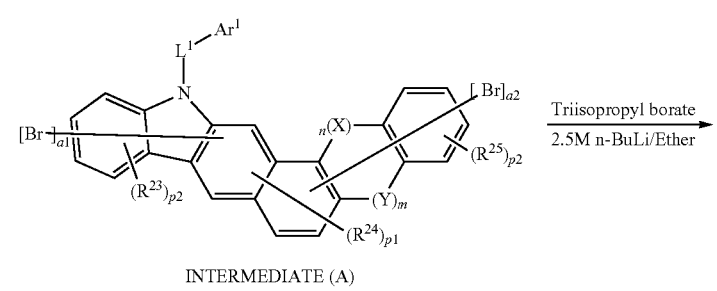 Triisopropyl borate / 2.5M n-BuLi/Ether →
INTERMEDIATE (A)
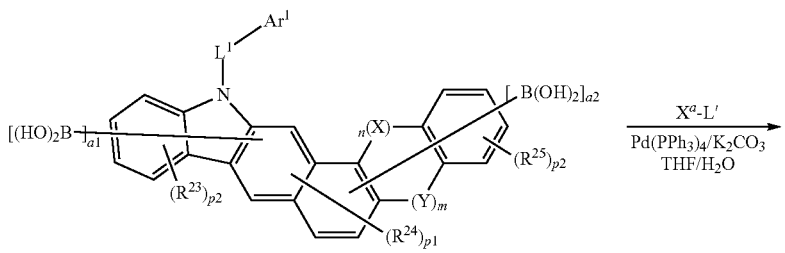 $X^a$-L' / Pd(PPh$_3$)$_4$/K$_2$CO$_3$ / THF/H$_2$O →
INTERMEDIATE (B)
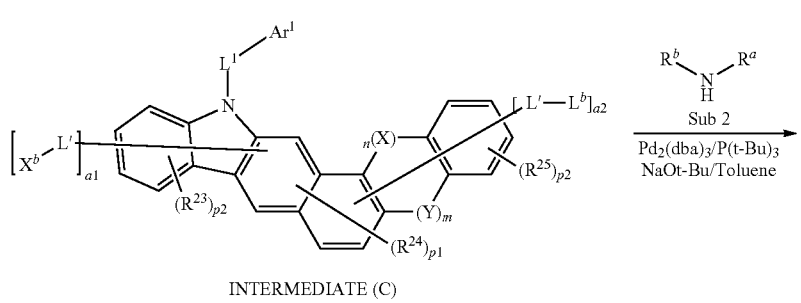 $R^b$-NH-$R^a$ Sub 2 / Pd$_2$(dba)$_3$/P(t-Bu)$_3$ / NaOt-Bu/Toluene →
INTERMEDIATE (C)
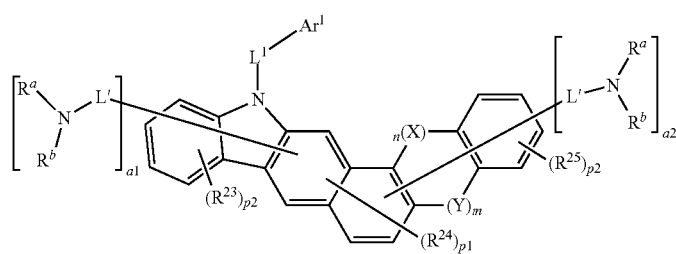
Final Product (2)

I. Synthesis of Core

1. Synthesis Example of Core ($X^a$: Br, Cl or I)

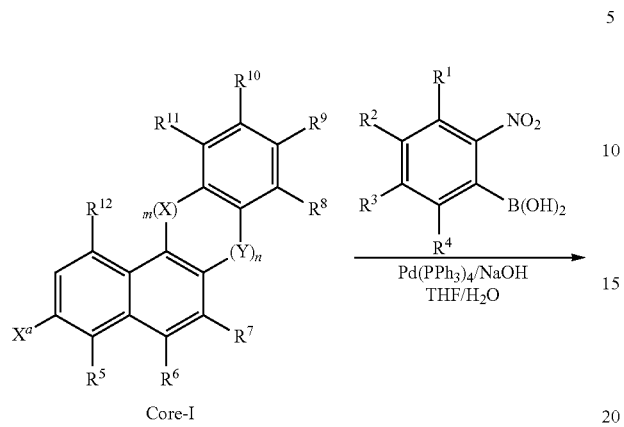

Core-I

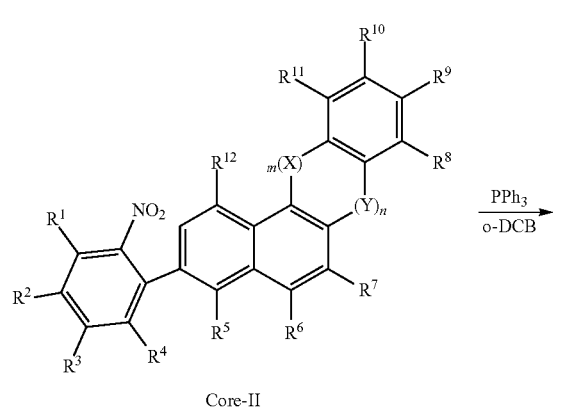

Core-II

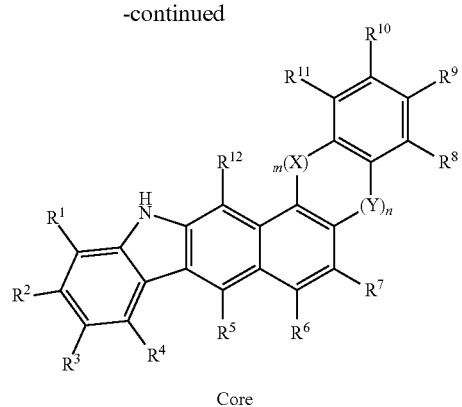

Core

Synthesis of Intermediate Core-II (2-nitrophenyl)boronic acid substituted with $R^1$-$R^4$ (1.1 eq.), $Pd(PPh_3)_4$ (0.03 eq.), NaOH (3 eq.) and water (2.2 mL/1 mmol) were added to the solution of Core-I (1 eq.) dissolved in THF (4.4 mL/1 mmol), and then followed by stirring the mixture under heating and refluxing. When the reaction was completed, the reaction product was extracted with ether and water. And then the organic layer was dried with $MgSO_4$ and concentrated. Then, the concentrate was separated by silica gel column and recrystallized to obtain Core-II.

Synthesis of Core

Core-II (1 eq) obtained in the above synthesis and triphenylphosphine (2.5 eq) were dissolved in dichlorobenzene (4 mL/1 mmol), and then the solution was heated and refluxed for 24 hours. When the reaction was completed, solvent was removed by distillation under reduced pressure, and then the residue was separated by silica gel column to obtain Core of the product.

Synthesis of Core 1-1 (X=S)

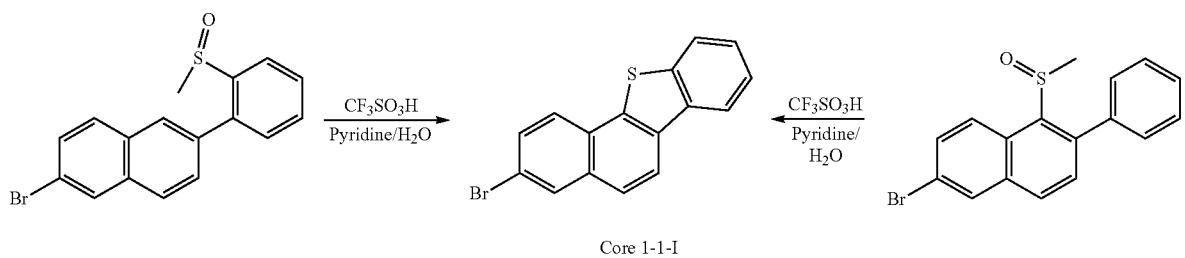

Core 1-1-I

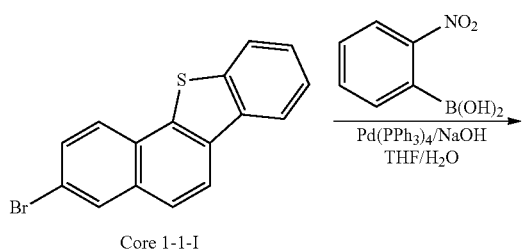

Core 1-1-I

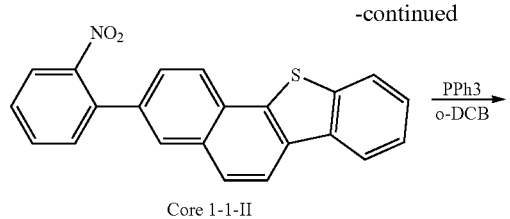
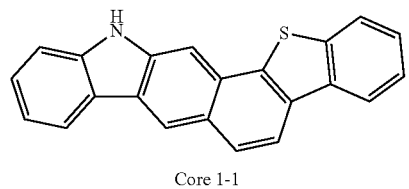

Core 1-1-II → Core 1-1

Synthesis of Core 1-1-I

Triflic acid (246.1 ml, 2780.59 mmol) was added to 2-bromo-6-(2-(methylsulfinyl)phenyl)naphthalene or 6-bromo-1-(methylsulfinyl)-2-phenylnaphthalene) (64 g, 185.38 mmol), and the mixture was stirred at room temperature. Subsequently, aqueous solution of pyridine (3248 ml, pyridine:H$_2$O=1:5) was slowly added dropwise, and followed by heating and refluxing the mixture for 30 minutes. When the reaction was completed, the reaction product was extracted with CH$_2$Cl$_2$ and water. And then, the organic layer was dried with MgSO$_4$ and concentrated. Then, the concentrate was separated by silica gel column and recrystallized to obtain 49.93 g (yield: 86%) of the product.

Synthesis of Intermediate Core 1-1-II 2-nitrophenyl)boronic acid (28.25 g, 169.24 mmol), Pd(PPh$_3$)$_4$ (5.33 g, 4.62 mmol), NaOH (18.46 g, 461.58 mmol) and water (338 ml) were added to the solution of Core 1-1-I (48.19 g, 153.86 mmol) dissolved in THF (677 ml), and then followed by string the mixture under heating and refluxing. When the reaction was completed, the reaction product was extracted with ether and water. And then, the organic layer was dried with MgSO$_4$ and concentrated. Then, the concentrate was separated by silica gel column and then recrystallized to obtain 48.67 g (yield: 89%) of the product.

Synthesis of Core 1-1

Core 1-1-II (48.67 g, 136.94 mmol) obtained in the above synthesis and triphenylphosphine (89.80 g, 342.35 mmol) were dissolved in o-dichlorobenzene (548 ml), and then the mixture was heated and refluxed for 24 hours. When the reaction is completed, solvent was removed by distillation under reduced pressure, and then the residue was separated by silica gel column to obtain 20.82 g (yield: 47%) of the product.

Synthesis of Core 1-7

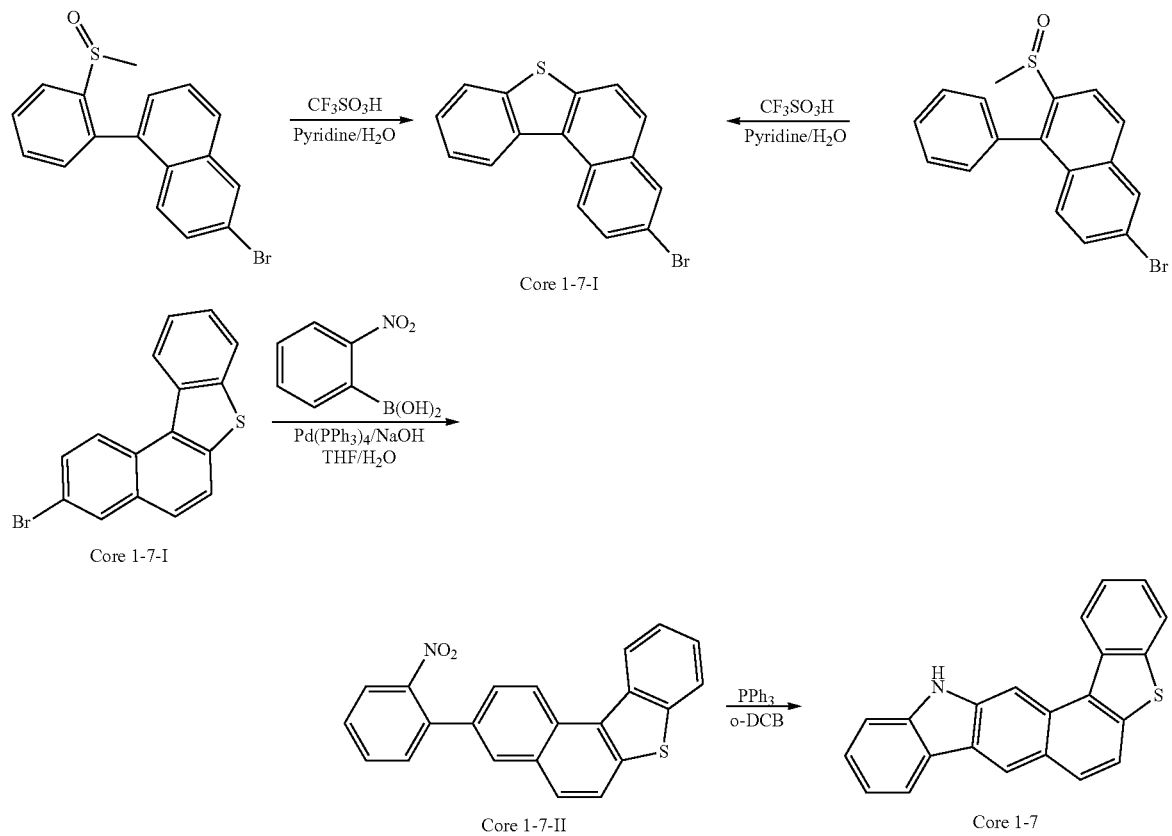

Synthesis of Core 1-7-I 48.19 g (yield: 83%) of the product was obtained by reacting the starting material 6-bromo-1-(2-(methyl sulfinyl)phenyl)naphthalene or 6-bromo-2-(methyl sulfinyl)-1-phenylnaphthalene (64 g, 185.37 mmol), triflic acid (246 ml, 2780.59 mmol) and aqueous solution of pyridine (3248 ml, pyridine:H₂O=1:5) by the same method as in synthesis example of Core 1-1-I.

Synthesis of Intermediate Core 1-7-II 47.57 g (yield: 87%) of the product was obtained by reacting Core 1-7-I (48.19 g, 153.86 mmol) obtained in the above synthesis, THF (677 ml), (2-nitrophenyl)boronic acid (28.25 g, 169.24 mmol), Pd(PPh₃)₄ (5.33 g, 4.62 mmol), NaOH (18.46 g, 461.58 mmol) and water (338 ml) by the same method as in synthesis example of Core 1-1-II.

Synthesis of Intermediate Core 1-7

19.93 g (yield: 45%) of the product was obtained by reacting Core 1-7-II (48.67 g, 136.94 mmol) obtained in the above synthesis, triphenylphosphine (89.80 g, 342.35 mmol) and o-dichlorobenzene (548 ml) by the same method as in synthesis example of Core 1-1.

Synthesis of Core 1-2

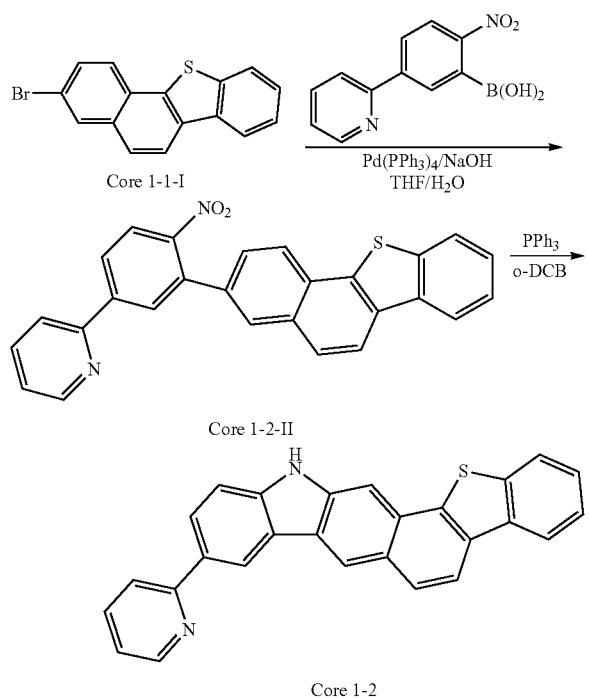

Synthesis of Intermediate Core 1-2-II 32.31 g (yield: 78%) of the product was obtained by reacting Core 1-1-I (30 g, 95.78 mmol), THF (421 ml), (2-nitro-5-(pyridin-2-yl)phenyl)boronic acid (25.71 g, 105.36 mmol), Pd(PPh₃)₄ (3.32 g, 2.87 mmol), NaOH (11.49 g, 287.35 mmol) and water (211 ml) by the same method as in synthesis example of Core 1-1-II.

Synthesis of Core 1-2

12.57 g (yield: 42%) of the product was obtained by reacting Core 1-2-II (32.31 g, 74.71 mmol), triphenylphosphine (48.99 g, 186.77 mmol) and o-dichlorobenzene (299 ml) by the same method as in synthesis example of Core 1-I.

Synthesis of Core 1-4

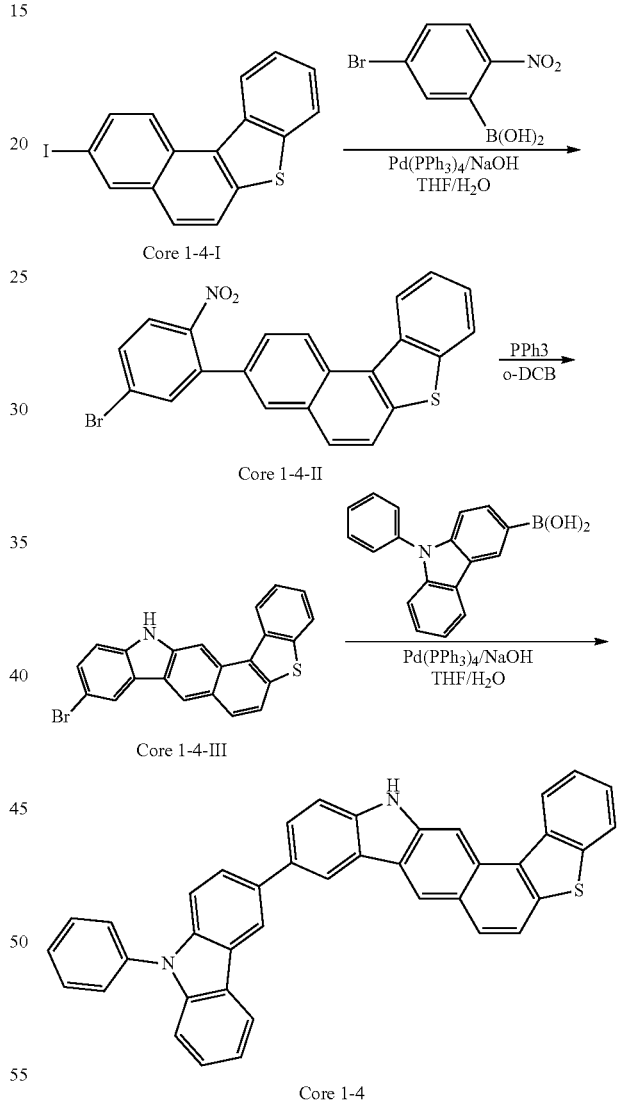

Synthesis of Intermediate Core 1-4-II 30.38 g (yield: 84%) of the product was obtained by reacting Core 1-4-I (30 g, 83.29 mmol), THF (366 ml), (5-bromo-2-nitrophenyl)boronic acid (22.52 g, 91.61 mmol), Pd(PPh₃)₄ (2.89 g, 2.5 mmol), NaOH (9.99 g, 249.85 mmol) and water (183 ml) by the same method as in synthesis example of Core 1-1-II.

Synthesis of Intermediate Core 1-4-III 12.57 g (yield: 42%) of the product was obtained by reacting Core 1-4-II (32.31 g, 74.71 mmol), triphenylphosphine (48.99 g, 186.77 mmol) and o-dichlorobenzene (299 ml) by the same method as in synthesis example of Core 1-1.

Synthesis of Core 1-4

15.35 g (yield: 87%) of the product was obtained by reacting Core 1-4-III (12.57 g, 31.25 mmol), THF (138 ml), (9-phenyl-9H-carbazol-3-yl)boronic acid (9.87 g, 34.37 mmol), $Pd(PPh_3)_4$ (1.08 g, 0.94 mmol), NaOH (3.75 g, 93.73 mmol) and water (68 ml) by the same method as in synthesis example of Core 1-I-II.

Synthesis of Core 1-8

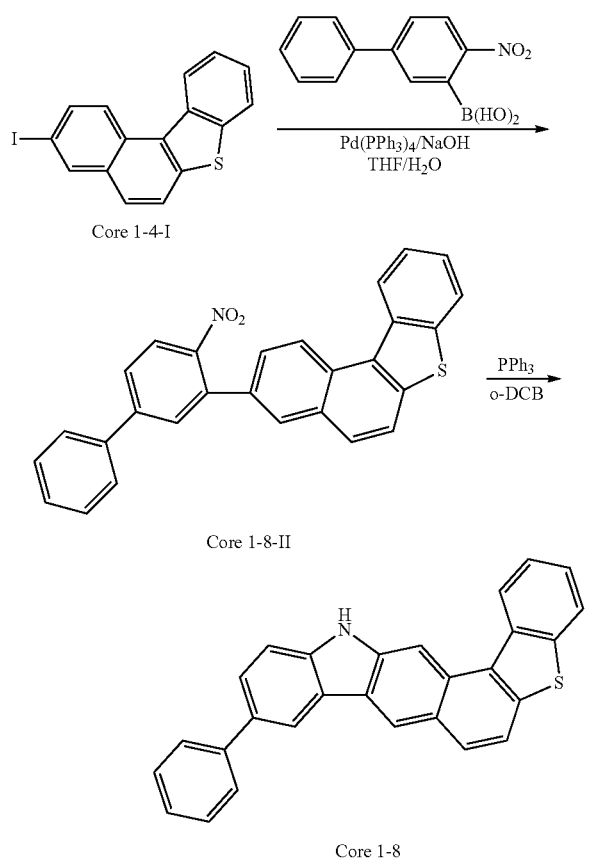

Synthesis of Intermediate Core 1-8-II 29.83 g (yield: 83%) of the product was obtained by reacting Core 1-4-I (30 g, 83.29 mmol), THF (366 ml), (4-nitro-[1,1'-biphenyl]-3-yl)boronic acid (22.26 g, 91.61 mmol), $Pd(PPh_3)_4$ (2.89 g, 2.5 mmol), NaOH (9.99 g, 249.85 mmol) and water (183 ml) by the same method as in synthesis example of Core 1-1-II.

Synthesis of Core 1-8

11.88 g (yield: 43%) of the product was obtained by reacting Core 1-8-II (29.83 g, 69.13 mmol), triphenylphosphine (45.33 g, 172.82 mmol) and o-dichlorobenzene (277 ml) by the same method as in synthesis example of Core 1-1.

Synthesis of Core 1-13 (X=O)

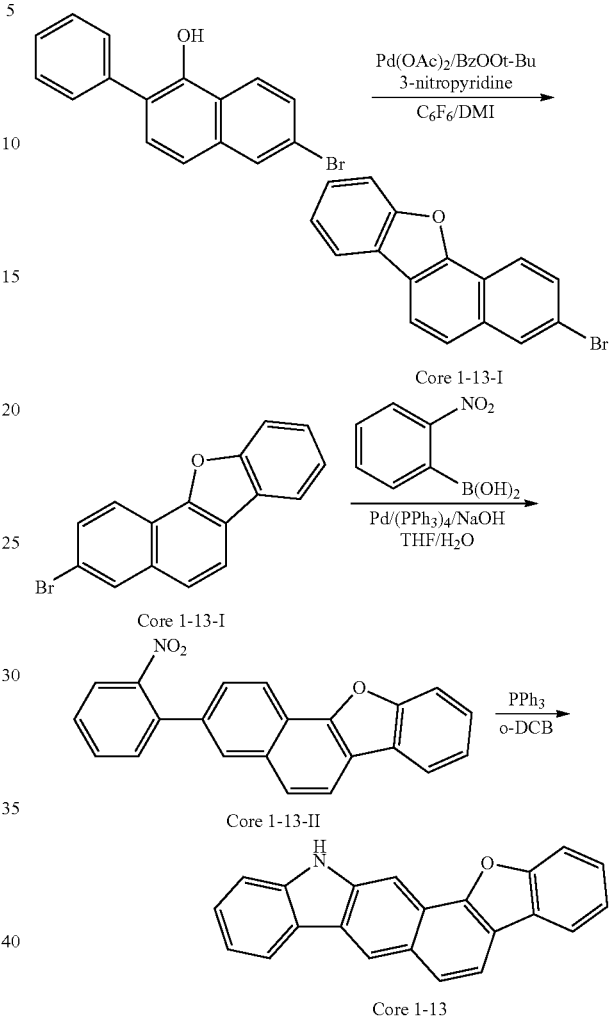

Synthesis of Intermediate Core 1-13-I 6-bromo-2-phenylnaphthalen-1-ol (200 g, 668.54 mmol), palladium acetate (1.5 g, 6.69 mmol) and 3-nitropyridine (165.93 g, 1337.08 mmol) were dissolved in the mixed solvent ($C_6H_6$:DMI=3:2). Then, BzOOt-Bu (1.30 g, 6.69 mmol) was added to the solution and followed by stirring the mixture at 90° C. for 4 hours. When the reaction was completed, the reaction product was extracted with $CH_2Cl_2$ and water. Then, the organic layer was dried with $MgSO_4$ and concentrated under reduced pressure. Then, the concentrate was separated by silica gel column and then recrystallized to obtain 89.40 g (yield: 45%) of the product.

Synthesis of Intermediate Core 1-13-II 47.39 g (yield: 83%) of the product was obtained by reacting Core 1-13-I (50 g, 168.27 mmol), THF (740 ml), (2-nitrophenyl)boronic acid (30.90 g, 185.09 mmol), $Pd(PPh_3)_4$ (5.83 g, 5.05 mmol), NaOH (20.19 g, 504.80 mmol) and water (370 ml) by the same method as in synthesis example of Core 1-1-II.

167

Synthesis of Core 1-13

18.89 g (yield: 44%) of the product was obtained by reacting Core 1-13-II (47.39 g 139.65 mmol), triphenylphosphine (91.57 g, 349.13 mmol) and o-dichlorobenzene (559 ml) by the same method as in synthesis example of Core 1-1.

Synthesis of Core 1-18

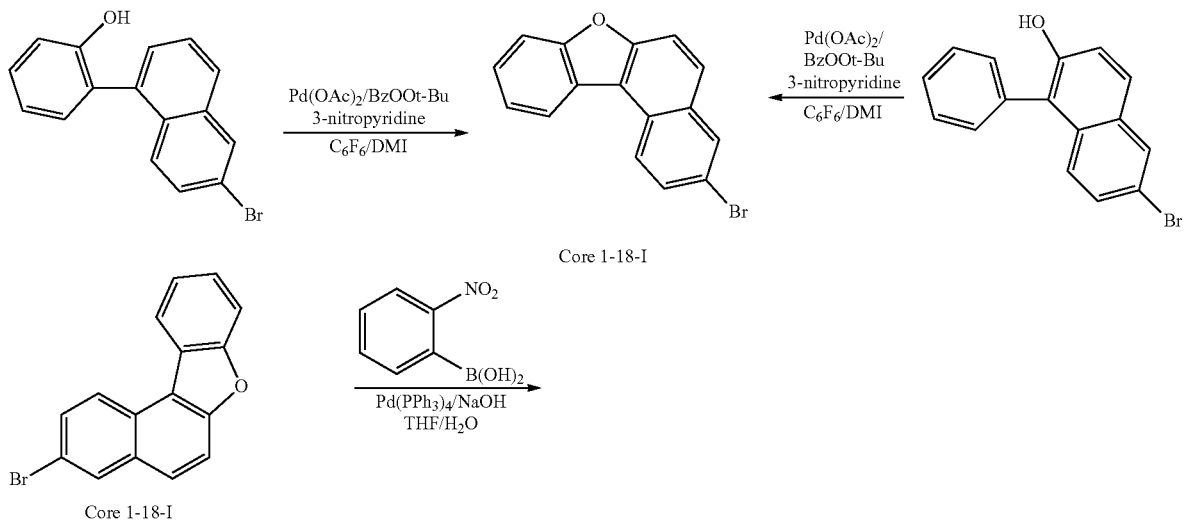

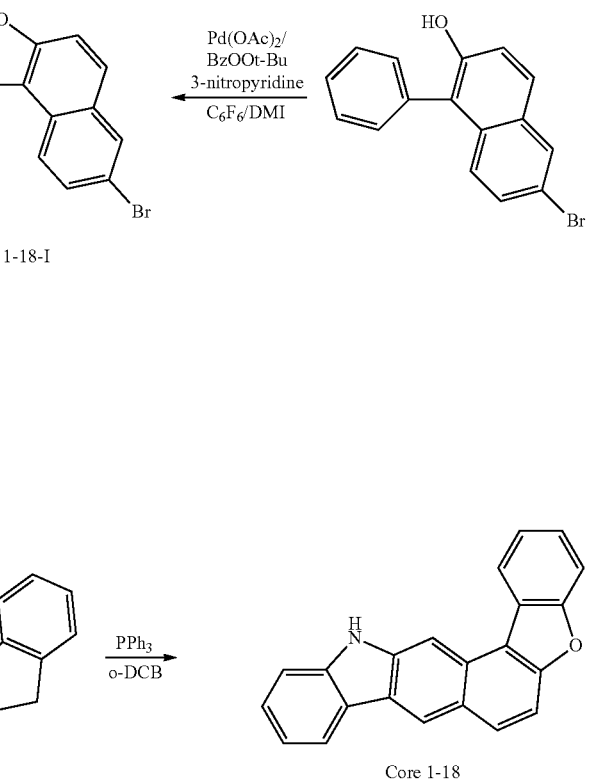

Synthesis of Intermediate Core 1-18-I 78.67 g (yield: 44%) of the product was obtained by reacting 2-(6-bromonaphthalen-1-yl)phenol or 6-bromo-1-phenylnaphthalen-2-ol (180 g, 601.69 mmol), Palladium acetate (1.35 g, 6.02 mmol), 3-nitropyridine (149.34 g, 1203.37 mmol) and BzOOt-Bu (1.17 g, 6.02 mmol) by the same method as in synthesis example of intermediate Core 1-13-I.

Synthesis of Intermediate Core 1-18-II 48.53 g (yield: 85%) of the product was obtained by reacting Core 1-18-I (50 g, 168.27 mmol), THF (740 ml), (2-nitrophenyl)boronic acid (30.90 g, 185.09 mmol), Pd(PPh$_3$)$_4$ (5.83 g, 5.05 mmol), NaOH (20.19 g, 504.80 mmol) and water (370 ml) by the same method as in synthesis example of Core 1-1-II.

168

Synthesis of Core 1-18

18.46 g (yield: 42%) of the product was obtained by reacting Core 1-18-II (48.53 g 143.01 mmol), triphenylphosphine (93.78 g, 357.53 mmol) and o-dichlorobenzene (572 ml) by the same method as in synthesis example of Core 1-1.

Synthesis of Core 1-21

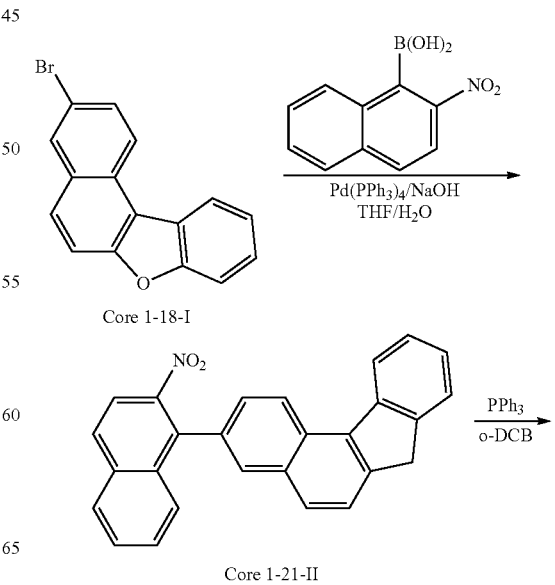

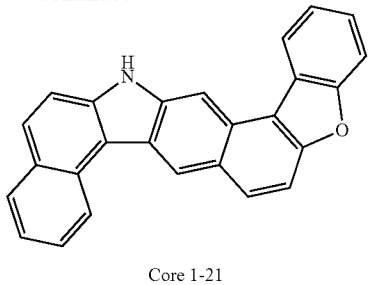

Core 1-21

Synthesis of Intermediate Core 1-21-II 46.52 g (yield: 71%) of the product was obtained by reacting Core 1-18-I (50 g, 168.27 mmol), THF (740 ml), (2-nitronaphthalen-1-yl)boronic acid (40.16 g, 185.09 mmol), Pd(PPh₃)₄ (5.83 g, 5.05 mmol), NaOH (20.19 g, 504.80 mmol) and water (370 ml) by the same method as in synthesis example of Core 1-1-II.

Synthesis of Core 1-21

17.49 g (yield: 41%) of the product was obtained by reacting Core 1-21-II (46.52 g, 119.47 mmol), triphenylphosphine (78.34 g, 298.67 mmol) and o-dichlorobenzene (478 ml) by the same method as in synthesis example of Core 1-1.

Synthesis of Core 1-24

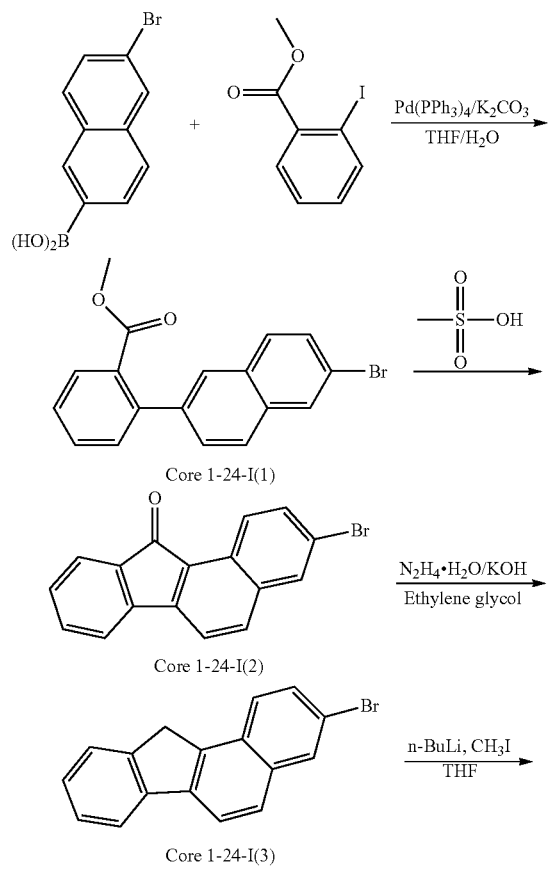

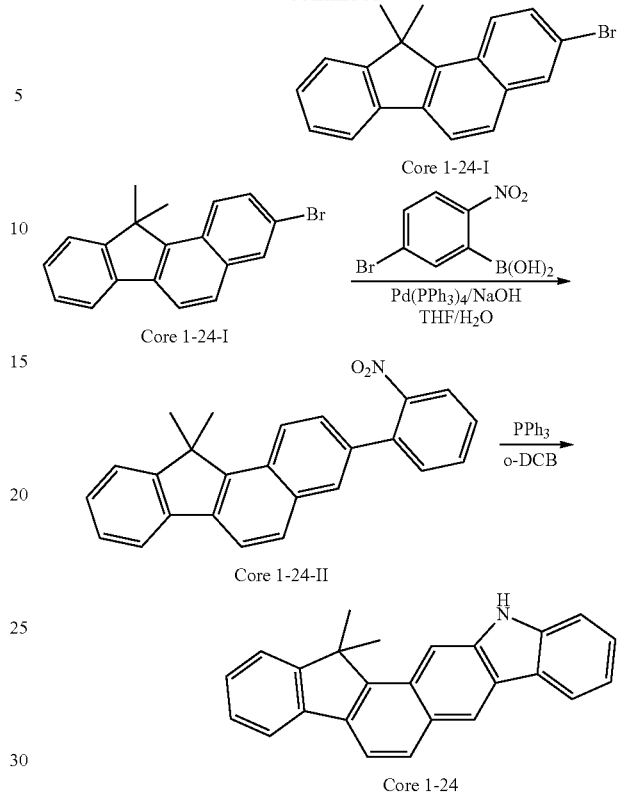

Synthesis of Intermediate Core 1-24-I(1)

(6-bromonaphthalen-2-yl)boronic acid (189.57 g, 755.61 mmol), Pd(PPh₃)₄ (23.81 g, 20.61 mmol), K₂CO₃ (284.82 g, 2060.75 mmol) and water (1511 ml) were added to the solution of methyl 2-iodobenzoate (180 g, 686.92 mmol) dissolved in THF (3022 ml) and then followed by stirring the mixture at 80° C. When the reaction was completed, the reaction product was extracted with CH₂Cl₂ and water. And then, the organic layer was dried with MgSO₄ and concentrated. Then, the concentrate was separated by silica gel column and then recrystallized to obtain 175.78 g (yield: 75%) of the product.

Synthesis of Intermediate Core 1-24-II(2)

Core 1-24-I(1) (120 g, 351.7 mmol) obtained in the above synthesis was dissolved in methanesulfonic acid (1143 ml), and then followed by stirring the mixture at 50~60° C. When the reaction was completed, the resultant was cooled to 0° C. and water was added to the resultant in order to obtain precipitate. The precipiated solid was filtered and washed with a small amount of water. Then, the filtered solid was dissolved in CH₂Cl₂ and the solution was dried with MgSO₄ and concentrated. The concentrate was separated by silica gel column and recrystallized to obtain 50.02 g (yield: 46%) of the product.

Synthesis of Intermediate Core 1-24-I(3)

Core 1-24-I(2)(60 g, 194.07 mmol) obtained in the above synthesis was dissolved in ethylene glycol (776 ml), and hydrazine monohydrate (291.46 g, 5822.23 mmol) and KOH (27.22 g, 485.19 mmol) were added to the solution. Then, the mixture was stirred at 185° ° C. When the reaction was completed, the resultant was cooled to 0° C. and water was added to the resultant in order to obtain precipitate. The precipiated solid was filtered and washed with a small amount of water. Then, the filtered solid was dissolved in CH$_2$Cl$_2$ and the solution was dried with MgSO$_4$ and concentrated. The concentrate was separated by silica gel column and recrystallized to obtain 26.35 g (yield: 46%) of the product.

Synthesis of Core 1-24-I n-BuLi (64.7 ml, 161.73 mmol) was added to the solution of Core 1-24-I(3) (50 g, 161.73 mmol) dissolved in THF (647 ml) at −78° C., and the mixture was stirred at room temperature for 1 hour. After the mixture was cooled to −78° C., CH$_3$I (57.39 g, 404.32 mmol) was added. Then, the mixture was stirred at room temperature for 3 hours. When the reaction was completed, water was added to the reaction product and then followed by extracting the mixture with diethyl ether. And then, the organic layer was dried with MgSO$_4$ and concentrated under reduced pressure. Then, the concentrate was separated by silica gel column applied ethyl acetate and n-hexan to obtain 20.05 g (yield: 42%) of the product.

Synthesis of Intermediate Core 1-24-II 17.45 g (yield: 77%) of the product was obtained by reacting Core 1-24-I (20.05 g, 62.03 mmol), THF (273 ml), (2-nitrophenyl)boronic acid (11.39 g, 68.23 mmol), Pd(PPh$_3$)$_4$ (2.15 g, 1.86 mmol), NaOH (7.44 g, 186.09 mmol) and water (136 ml) by the same method as in synthesis example of Core 1-1-II.

Synthesis of Core 1-24

6.85 g (yield: 43%) of the product was obtained by reacting Core 1-24-II (17.45 g, 47.75 mmol), triphenylphosphine (31.31 g, 119.38 mmol) and o-dichlorobenzene (191 ml) by the same method as in synthesis example of Core 1-1.

Synthesis of Core 1-27

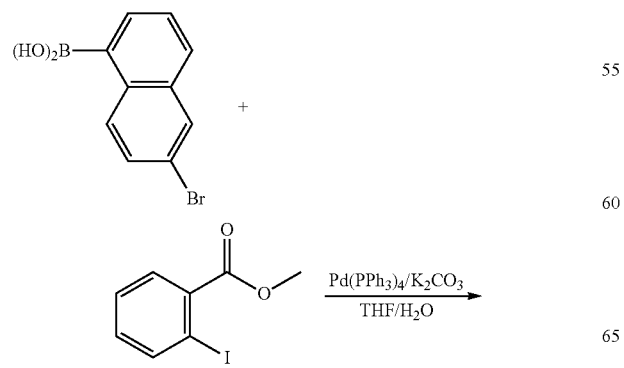

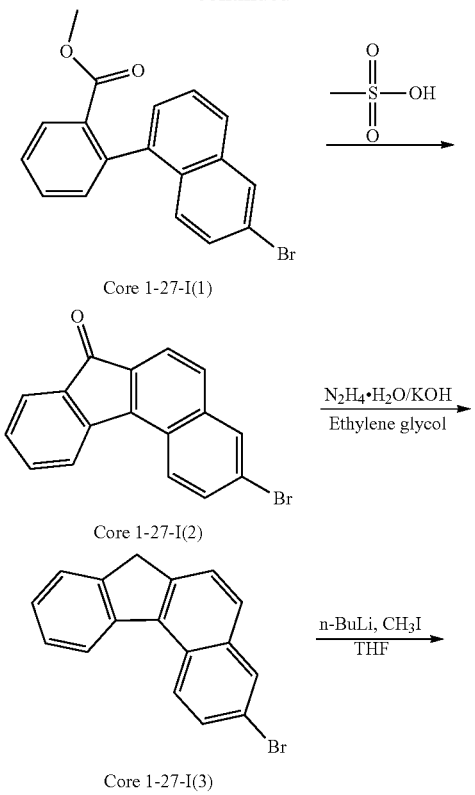

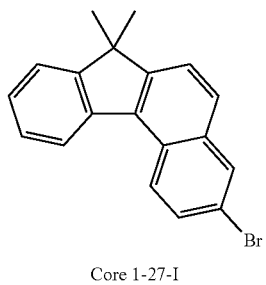

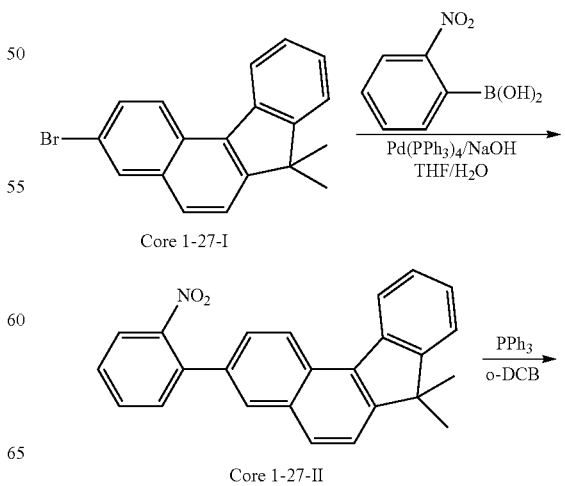

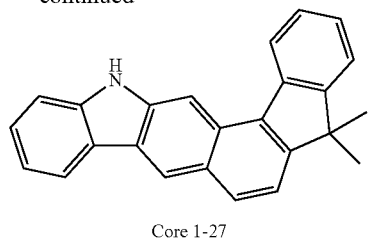

Core 1-27

Synthesis of Intermediate Core 1-27-I(1)

(6-bromonaphthalen-2-yl)boronic acid (189.57 g, 755.61 mmol), Pd(PPh3)4 (23.81 g, 20.61 mmol), K2CO3 (284.82 g, 2060.75 mmol) and water (1511 ml) were added to the solution of methyl 2-iodobenzoate (180 g, 686.92 mmol) dissolved in THF (3022 ml). Then the mixture was stirred at 80° C. When the reaction was completed, the reaction product was extracted with $CH_2Cl_2$ and water. And then, the organic layer was dried with $MgSO_4$ and concentrated. Then the concentrate was separated by silica gel column and recrystallized to obtain 180.47 g (yield: 77%) of the product.

Synthesis of Intermediate Core 1-27-I(2)

Core 1-27-I(1) (120 g, 351.7 mmol) obtained in the above synthesis was dissolved in methanesulfonic acid (1143 ml) and the solution was stirred at 50~60° C. When the reaction was completed, the resultant was cooled to 0° C. and water was added to the resultant in order to obtain precipitate. The precipiated solid was filtered and washed with a small amount of water. Then, the filtered solid was dissolved in $CH_2Cl_2$ and the solution was dried with $MgSO_4$ and concentrated. The concentrate was separated by silica gel column and recrystallized to obtain 46.75 g (yield: 43%) of the product.

Synthesis of Intermediate Core 1-27-I(3)

Core 1-27-I(2) (60 g, 194.07 mmol) obtained in the above synthesis was dissolved in ethylene glycol (776 ml), and hydrazine monohydrate (291.46 g, 5822.23 mmol) and KOH (27.22 g, 485.19 mmol) were added to the solution. Then the mixture was stirred at 185° ° C. When the reaction was completed, the resultant was cooled to 0° C. and water was added to the resultant in order to obtain precipitate. The precipiated solid was filtered and washed with a small amount of water. Then, the filtered solid was dissolved in $CH_2Cl_2$ and the solution was dried with $MgSO_4$ and concentrated. The concentrate was separated by silica gel column and recrystallized to obtain 26.92 g (yield: 47%) of the product.

Synthesis of Core 1-27-I n-BuLi (64.7 ml, 161.73 mmol) was added to the solution of Core 1-27-I(3) (50 g, 161.73 mmol) dissolved in THF (647 ml) at −78° C., and the mixture was stirred at room temperature for 1 hour. After the mixture was cooled to −78° C., $CH_3I$ (57.39 g, 404.32 mmol) was added. Then, the mixture was stirred at room temperature for 3 hours. When the reaction was completed, water was added to the reaction product and then followed by extracting the mixture with diethyl ether. And then, the organic layer was dried with $MgSO_4$ and concentrated under reduced pressure. Then, the concentrate was separated by silica gel column applied ethyl acetate and n-hexan to obtain 19.57 g (yield: 41%) of the product.

Synthesis of intermediate Core 1-27-II 14.80 g (yield: 75%) of the product was obtained by reacting Core 1-27-I (17.45 gg, 53.99 mmol), THF (238 ml), (2-nitrophenyl)boronic acid (9.91 g, 59.39 mmol), Pd(PPh3)4 (1.87 g, 1.62 mmol), NaOH (6.48 g, 161.96 mmol) and water (119 ml) by the same method as in synthesis example of Core 1-1-II.

Synthesis of Core 1-27

5.94 g (yield: 44%) of the product was obtained by reacting Core 1-24-II (14.80 g, 40.50 mmol), triphenylphosphine (26.56 g, 101.25 mmol) and o-dichlorobenzene (162 ml) by the same method as in synthesis example of Core 1-1.

2. Synthesis Example of Intermediate (C)

Synthesis of 1-1-1(C)

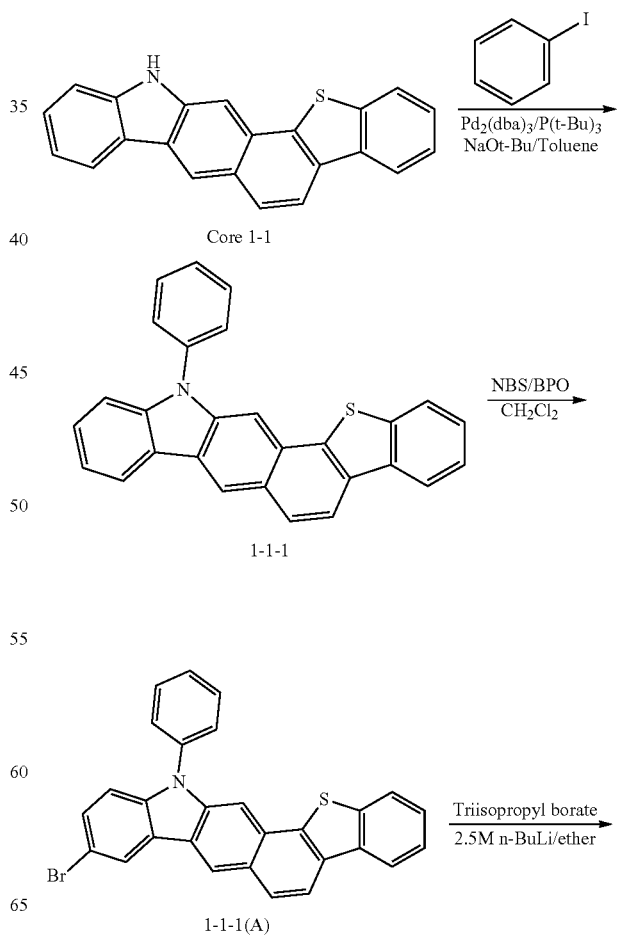

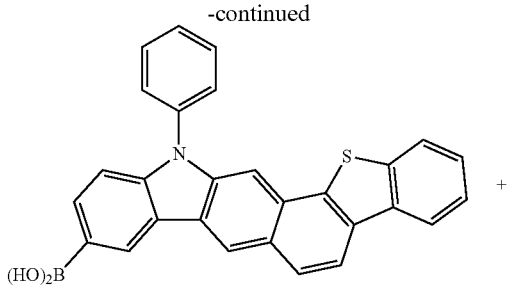

1-1-1(B)

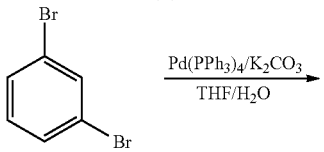

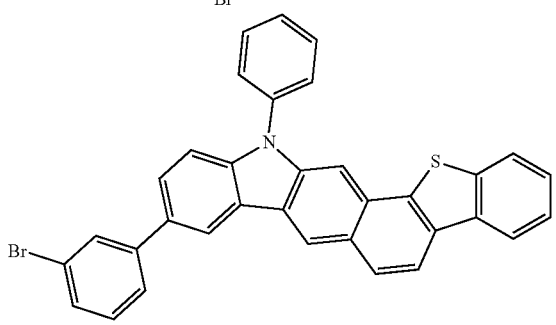

1-1-1(C)

Synthesis of 1-1-1

After mixing Core 1-1 (100 g, 309.21 mmol), iodobenzene (63.08 g, 309.21 mmol), Pd₂(dba)₃ (14.16 g, 15.46 mmol), P(t-Bu)₃ (6.26 g, 30.92 mmol), NaOt-Bu (44.57 g, 463.81 mmol) and toluene (3246 mL), the mixed reaction solution was stirred at 100° C. When the reaction was completed, the reaction product was extracted with ether and water. And then, the organic layer was dried with MgSO₄ and concentrated. Then, the concentrate was separated by silica gel column and recrystallized to obtain 107.47 g (yield: 87%) of the product.

Synthesis of 1-1-1(A)

Compound 1-1-1 (100 g, 250.31 mmol) obtained in the above synthesis, NBS(N-bromosuccinimide)(93.6 g, 525.64 mmol) and BPO (benzoylperoxide)(6.1 g, 25.03 mmol) were dissolved in CH₂Cl₂ (751 ml), and the mixture was stirred at room temperature for 3 hours. When the reaction was completed, aqueous solution of sodium bicarbonate was added to the reaction product. Then, the mixture was stirred for 30 minutes and extracted with CH₂Cl₂. And then the organic layer was dried with anhydrous MgSO₄, filtered under reduced pressure and concentrated under reduced pressure. Then, the concentrate was separated by silica gel column to obtain 77.84 g (yield: 65%) of the product.

Synthesis of 1-1-1(B)

Compound 1-1-1(A)(40 g, 83.6 mmol) obtained in the above synthesis was dissolved in anhydrous ether (293 ml), and n-BuLi (36.8 ml, 92 mmol) was slowly added to the solution at −78° C. Then the mixture was stirred at room temperature for 1 hour. After the mixture was cooled to −78° C., triisopropyl borate was added to the mixture. Then, the reaction solution was warmed gradually to room temperature and diluted with water. Then, HCl (2N) was added to the diluted reaction solution and followed by stirring the mixture. When the reaction was completed, the reaction product was extracted with ethyl acetate and water. Then the organic layer was dried with MgSO₄ and concentrated. Then, the concentrate was separated by silica gel column and recrystallized to obtain 25.58 g (yield: 69%) of the product.

Synthesis of 1-1-1(C)

23.04 g (yield: 72%) of the product was obtained by reacting Core 1-1-1(B) (25.58 g, 57.70 mmol), THF (254 ml), 1,3-dibromobenzene (13.61 g, 57.70 mmol), Pd(PPh₃)₄ (2.00 g, 1.73 mmol), K₂CO₃ (23.92 g, 173.10 mmol) and water (127 ml) by the same method as in synthesis example of Core 1-24-I(1).

Synthesis of 1-1-1(D)

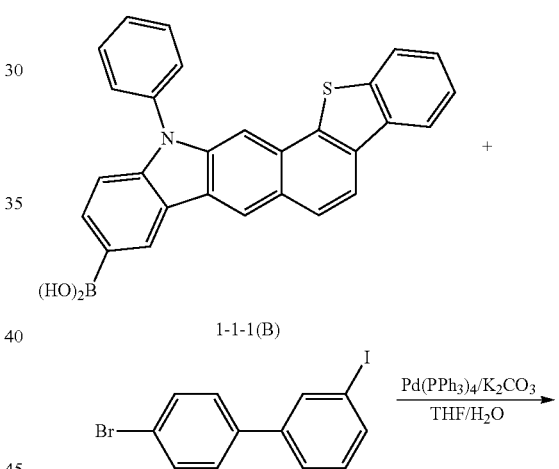

1-1-1(B)

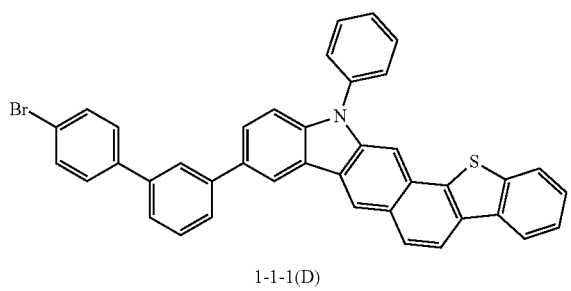

1-1-1(D)

21.05 g (yield: 74%) of the product was obtained by reacting Core 1-1-1(B) (20 g, 45.11 mmol), THF (199 ml), 4'-bromo-3-iodo-1,1'-biphenyl (16.20 g, 45.11 mmol), Pd(PPh₃)₄ (1.56 g, 1.35 mmol), K₂CO₃ (18.71 g, 135.34 mmol) and water (99.25 ml) by the same method as in synthesis example of Core 1-24-I(1).

Synthesis of 1-2-1(C)

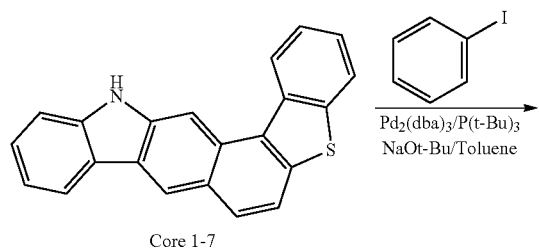

Core 1-7

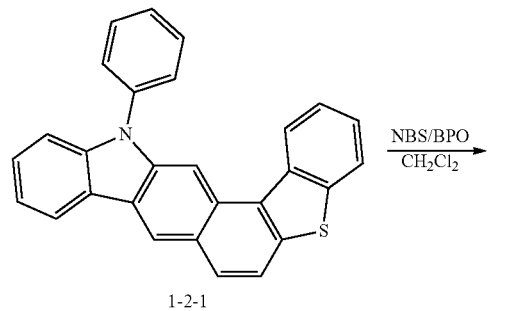

1-2-1

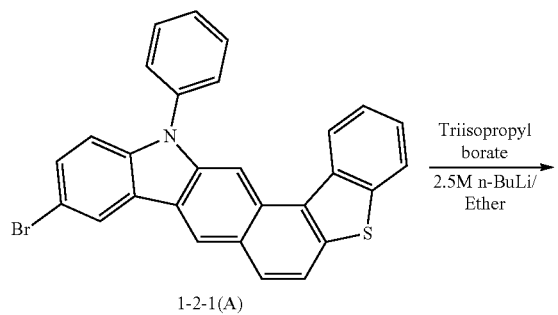

1-2-1(A)

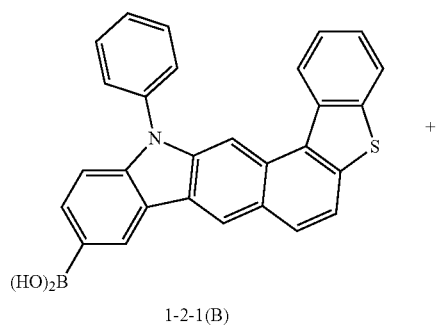

1-2-1(B)

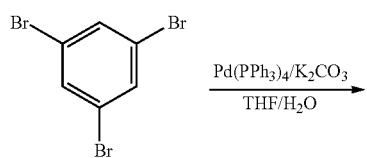

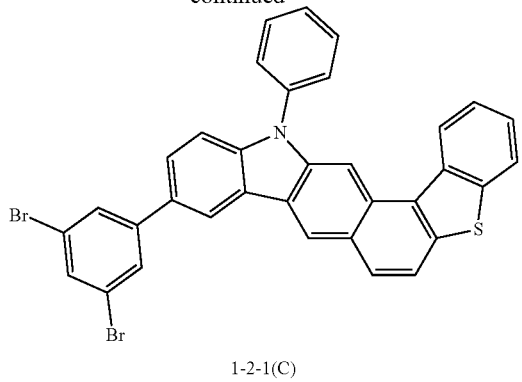

1-2-1(C)

Synthesis of 1-2-1

103.77 g (yield: 84%) of the product was obtained by reacting Core 1-7 (100 g, 309.21 mmol), iodobenzene (63.08 g, 309.21 mmol), Pd$_2$(dba)$_3$ (14.16 g, 15.46 mmol), P(t-Bu)$_3$ (6.26 g, 30.92 mmol), NaOt-Bu (44.57 g, 463.81 mmol) and toluene (3246 mL) by the same method as in synthesis example of 1-1-1.

Synthesis of 1-2-1(A)

36.14 g (yield: 62%) of the product was obtained by reacting Compound 1-2-1 (50 g, 105.13 mmol), NBS (39.3 g, 220.77 mmol), BPO (2.5 g, 10.51 mmol) and CH$_2$Cl$_2$ (315 ml) by the same method as in synthesis example of 1-1-1(A).

Synthesis of 1-2-1(B)

22 g (yield: 65%) of the product was obtained by reacting 1-2-1(A)(36.14 g, 65.2 mmol) obtained in the above synthesis, anhydrous Ether 228 ml, 2.5 M concentration of n-BuLi (28.68 ml, 71.7 mmol) and Tri isopropyl borate (18.39 g, 97.76 mmol) by the same method as in synthesis example of 1-1-1(B).

Synthesis of 1-2-1(C)

20.73 g (yield: 69%) of the product was obtained by reacting 1-2-1(B) (22 g, 42.35 mmol), THF (186 ml), 1,3,5-tribromobenzene (13.33 g, 42.35 mmol), Pd(PPh$_3$)$_4$ (1.47 g, 1.27 mmol), K$_2$CO$_3$ (17.56 g, 127.06 mmol) and water (93 ml) by the same method as in synthesis example of 1-1-1(C).

Synthesis of 2-1-2(B)

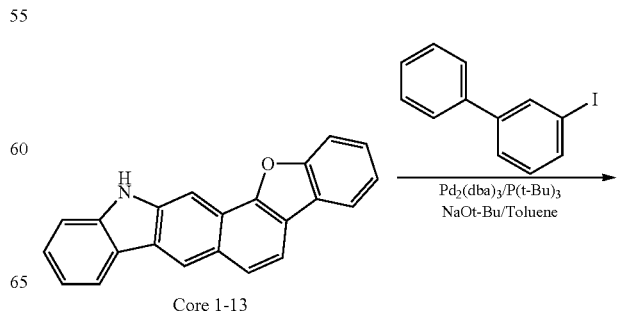

Core 1-13

-continued

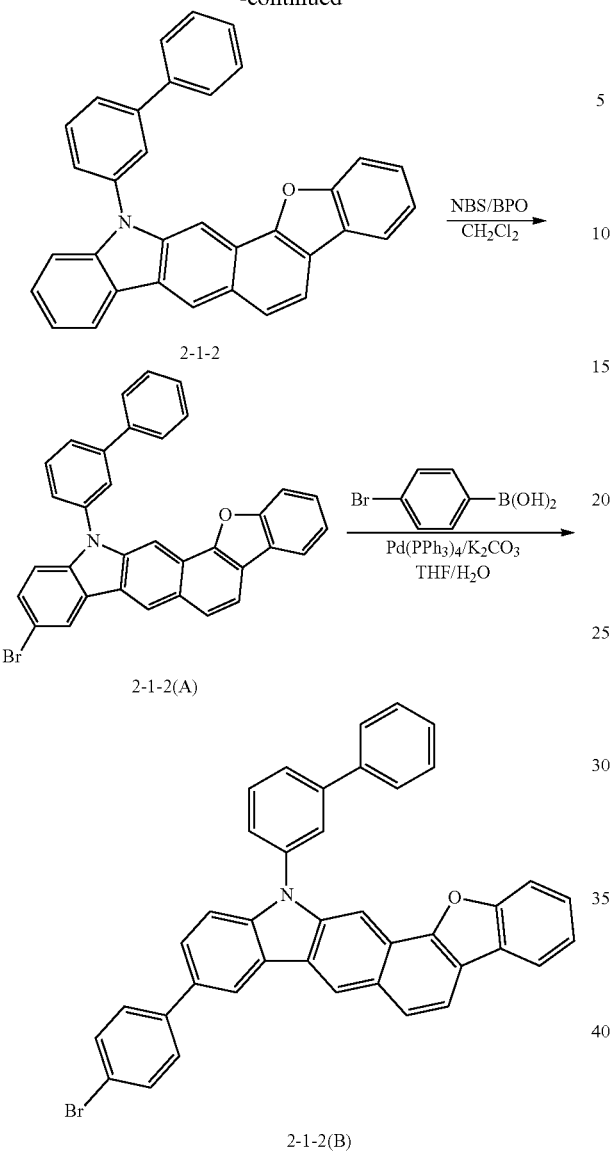

Synthesis of 2-1-2

128.59 g (yield: 86%) of the product was obtained by reacting Core 1-13 (100 g, 325.37 mmol), 3-iodo-1,1'-biphenyl (91.14 g, 325.37 mmol), Pd$_2$(dba)$_3$ (14.90 g, 16.27 mmol), P(t-Bu)$_3$ (6.58 g, 32.54 mmol), NaOt-Bu (46.90 g, 488.06 mmol) and toluene (3416 mL) by the same method as in synthesis example of 1-1-1.

Synthesis of 2-1-2(A)

36.17 g (yield: 60%) of the product was obtained by reacting compound 2-1-1 (50 g, 130.4 mmol), NBS (48.74 g, 273.84 mmol), BPO (3.16 g, 13.04 mmol) and CH$_2$Cl$_2$ (391 ml) by the same method as in synthesis example of 1-1-1(A).

Synthesis of 2-1-2(B)

20.73 g (yield: 69%) of the product was obtained by reacting 2-1-2(A) (36.17 g, 78.23 mmol), THF (186 ml), (4-bromophenyl)boronic acid (13.33 g, 42.35 mmol), Pd(PPh$_3$)$_4$ (1.47 g, 1.27 mmol), K$_2$CO$_3$ (17.56 g, 127.06 mmol) and water (93 ml) by the same method as in synthesis example of 1-1-1(C).

Synthesis of 2-1-2(C)

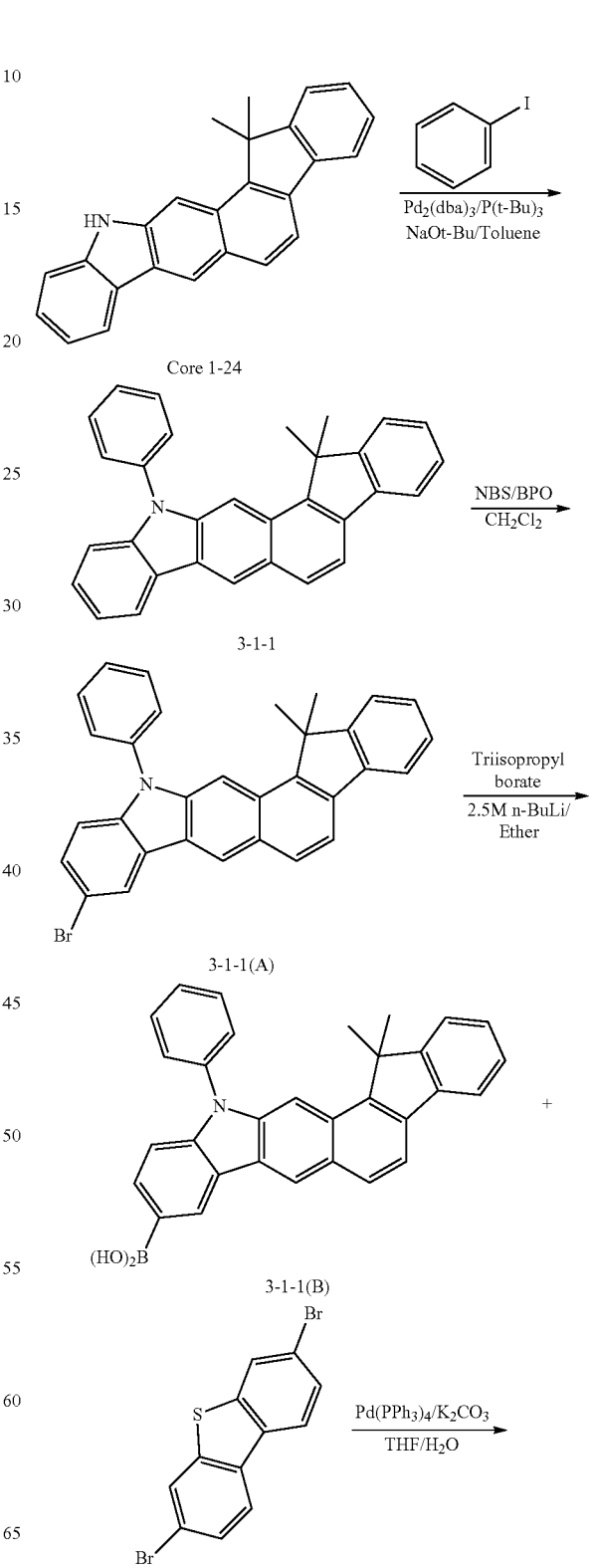

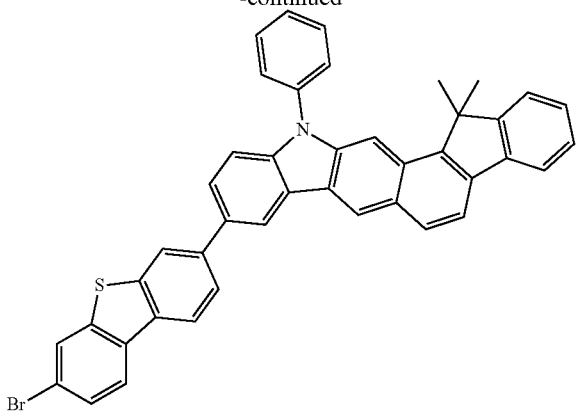

3-1-1(C)

Synthesis of 3-1-1

70.50 g (yield: 82%) of the product was obtained by reacting Core 1-24 (70 g, 209.94 mmol), iodobenzne (420.83 g, 209.94 mmol), Pd₂(dba)₃ (9.61 g, 10.5 mmol), P(t-Bu)₃ (4.25 g, 20.99 mmol), NaOt-Bu (30.26 g, 314.91 mmol) and toluene (2204 mL) by the same method as in synthesis example of 1-1-1.

Synthesis of 3-1-1(A)

41.50 g (yield: 58%) of the product was obtained by reacting compound 3-1-1 (60 g, 146.51 mmol) obtained in the above synthesis, NBS (54.76 g, 307.68 mmol), BPO (3.55 g, 14.65 mmol) and CH₂Cl₂ (439 ml) by the same method as in synthesis example of 1-1-1(A).

Synthesis of 3-1-1(B)

23.11 g (yield: 60%) of the product was obtained by reacting 3-1-1(A)(41.50 g, 84.97 mmol) obtained in the above synthesis, anhydrous Ether 297 ml, 2.5 M concentration of n-BuLi (37.38 ml, 93.46 mmol) and triisopropyl borate (23.97 g, 127.45 mmol) by the same method as in synthesis example of 1-1-1(B).

Synthesis of 3-1-1(C)

22.91 g (yield: 67%) of the product was obtained by reacting 3-1-1(B) (23.11 g, 50.98 mmol), THF (224 ml), 3,7-dibromodibenzo[b,d]thiophene (17.44 g, 50.98 mmol), Pd(PPh₃)₄ (1.77 g, 1.53 mmol), K₂CO₃ (21.14 g, 152.93 mmol) and water (112 ml) by the same method as in synthesis example of 1-1-1(C).

Synthesis of 3-2-1(C)

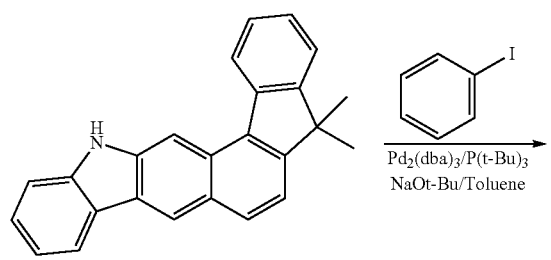

Core 1-27

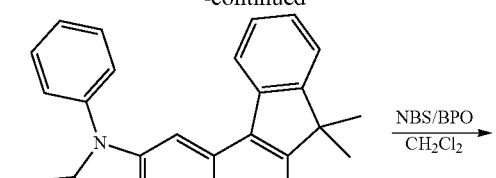

3-2-1

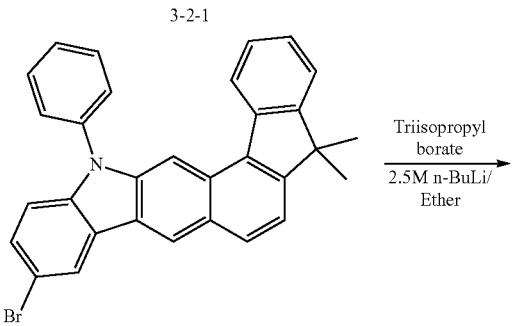

3-2-1(A)

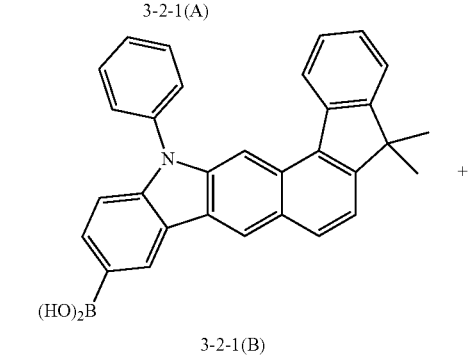

3-2-1(B)

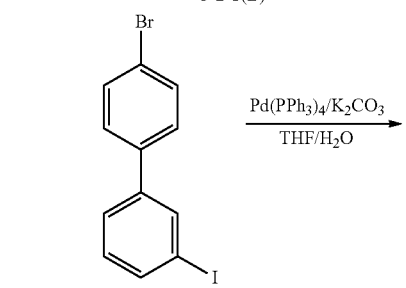

3-2-1(C)

Synthesis of 3-2-1

68.78 g (yield: 80%) of the product was obtained by reacting Core 1-27 (70 g, 209.94 mmol), iodobenzne (42.83 g, 209.94 mmol), Pd$_2$(dba)$_3$ (9.61 g, 10.5 mmol), P(t-Bu)$_3$ (4.25 g, 20.99 mmol), NaOt-Bu (30.26 g, 314.91 mmol) and toluene (2204 mL) by the same method as in synthesis example of 1-1-1.

Synthesis of 3-2-1(A)

40.07 g (yield: 56%) of the product was obtained by reacting compound 3-2-1 (60 g, 146.51 mmol) obtained in the above synthesis, NBS (54.76 g, 307.68 mmol), BPO (3.55 g, 14.65 mmol) and CH$_2$Cl$_2$ (439 ml) by the same method as in synthesis example of 1-1-1(A).

Synthesis of 3-2-1(B)

23.06 g (yield: 62%) of the product was obtained by reacting 3-2-1(A)(40.07 g, 82.04 mmol) obtained in the above synthesis, anhydrous Ether 287 ml, 2.5 M concentration of n-BuLi (36.1 ml, 90.24 mmol) and triisopropyl borate (23.14 g, 123.06 mmol) by the same method as in synthesis example of 1-1-1(B).

Synthesis of 3-2-1(C)

22.17 g (yield: 65%) of the product was obtained by reacting 3-2-1(B)(23.06 g, 50.87 mmol), THF (223 ml), 4'-bromo-3-iodo-1,1'-biphenyl (17.40 g, 50.87 mmol), Pd(PPh$_3$)$_4$ (1.76 g, 1.53 mmol), K$_2$CO$_3$ (21.09 g, 152.60 mmol) and water (111 ml) by the same method as in synthesis example of 1-1-1(C).

TABLE 1

| FD-MS of Core intermediates | | | |
|---|---|---|---|
| compound | FD-MS | compound | FD-MS |
| 1-1-1(A) | m/z = 477.02(C$_{28}$H$_{16}$BrNS = 478.40) | 1-1-1(B) | m/z = 443.12(C$_{28}$H$_{18}$BNO$_2$S = 443.32) |
| 1-1-1(C) | m/z = 553.05(C$_{34}$H$_{20}$BrNS = 554.50) | 1-1-1(D) | m/z = 629.08(C$_{40}$H$_{24}$BrNS = 630.59) |
| 1-2-1(A) | m/z = 477.02(C$_{28}$H$_{16}$BrNS = 478.40) | 1-2-1(B) | m/z = 443.12(C$_{28}$H$_{18}$BNO$_2$S = 443.32) |
| 1-2-1(C) | m/z = 630.96(C$_{34}$H$_{19}$Br$_2$NS = 633.39) | 2-1-2(A) | m/z = 537.07(C$_{34}$H$_{20}$BrNO = 538.43) |
| 2-1-2(B) | m/z = 613.10(C$_{40}$H$_{24}$BrNO = 614.53) | 3-1-1(A) | m/z = 487.09(C$_{31}$H$_{22}$BrN = 488.42) |
| 3-1-1(B) | m/z = 453.19(C$_{31}$H$_{24}$BNO$_2$ = 453.34) | 3-1-1(C) | m/z = 669.11(C$_{43}$H$_{28}$BrNS = 670.66) |
| 3-2-1(A) | m/z = 487.09(C$_{31}$H$_{22}$BrN = 488.42) | 3-2-1(B) | m/z = 453.19(C$_{31}$H$_{24}$BNO$_2$ = 453.34) |
| 3-2-1(C) | m/z = 639.16(C$_{43}$H$_{30}$BrN = 640.61) | | |

Example of Core 1

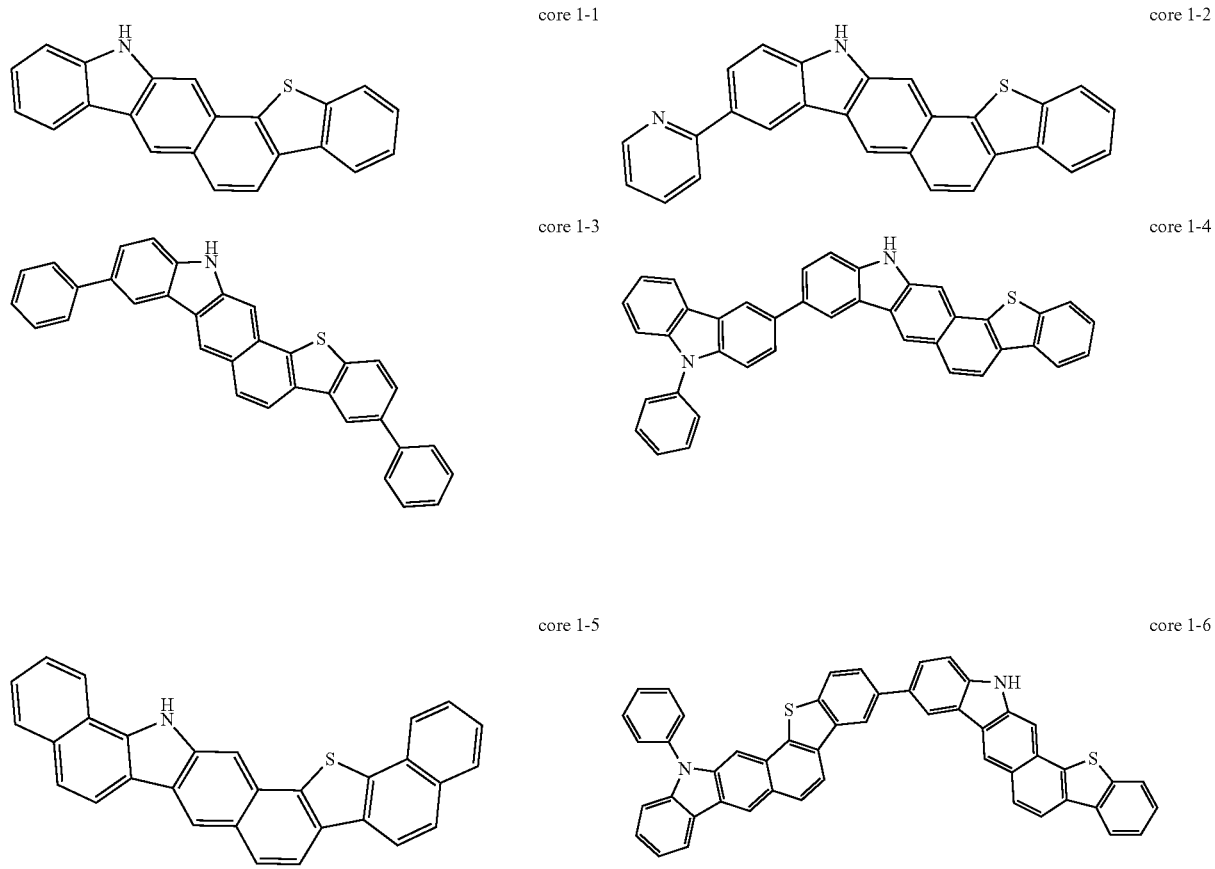

-continued
core 1-7
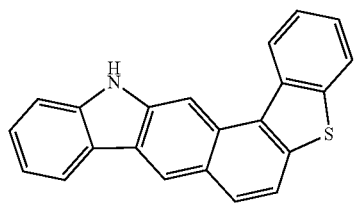
core 1-8
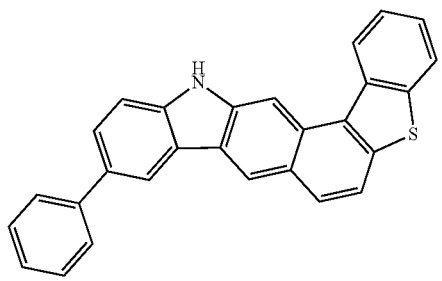
core 1-9
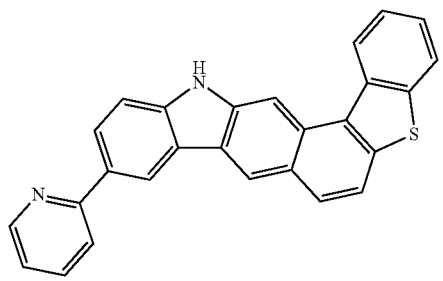
core 1-10
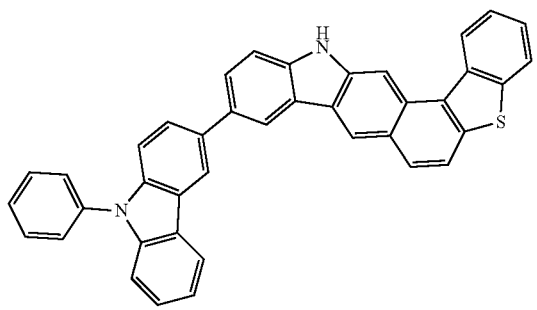
core 1-11
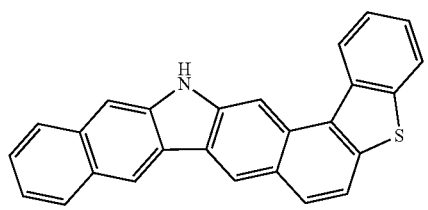
core 1-12
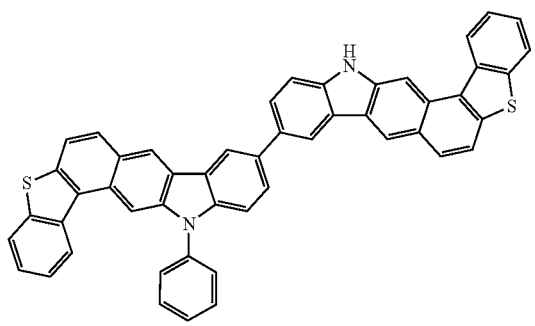
core 1-13
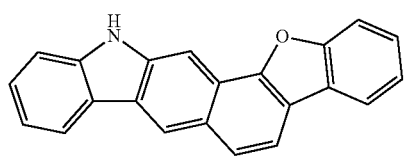
core 1-14
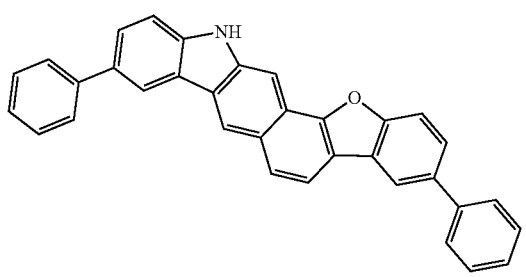
core 1-15
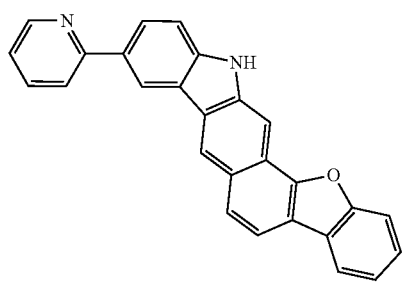
core 1-16
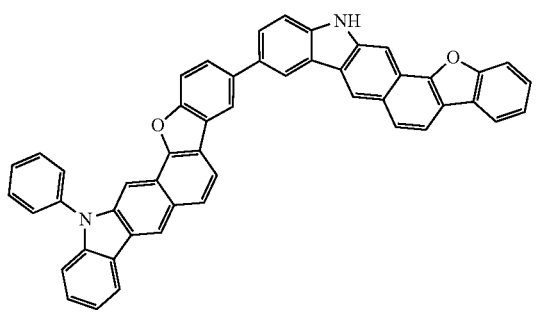

-continued
core 1-17
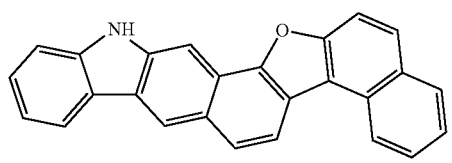
core 1-18
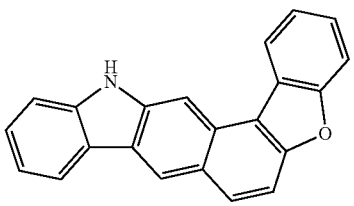
core 1-19
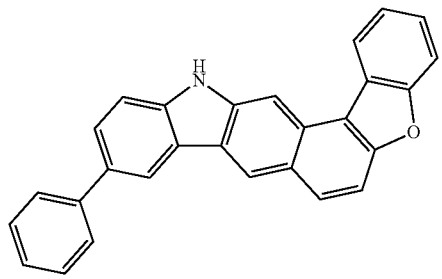
core 1-20
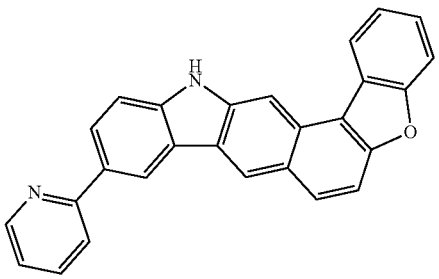
core 1-21
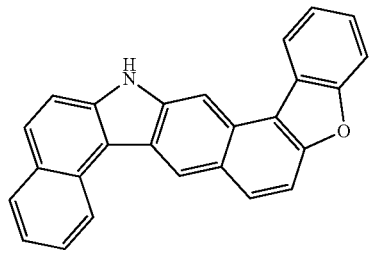
core 1-22
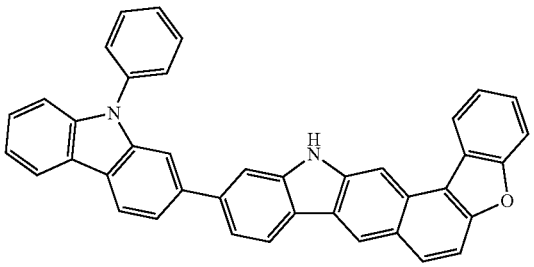
core 1-23
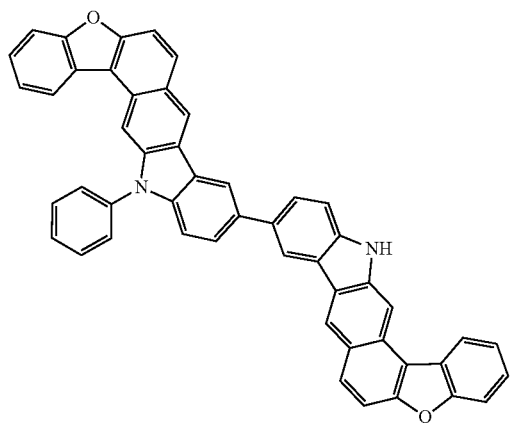
core 1-24
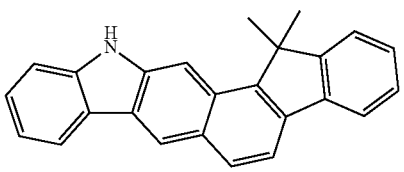
core 1-25
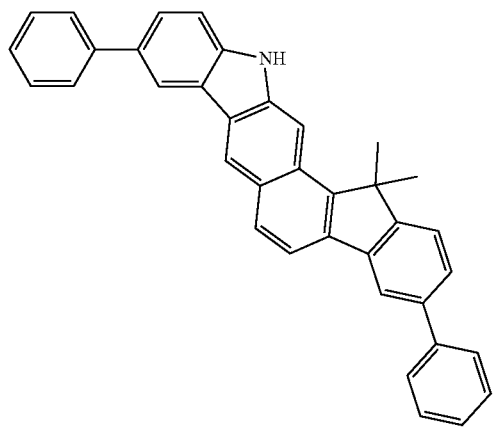

core 1-26

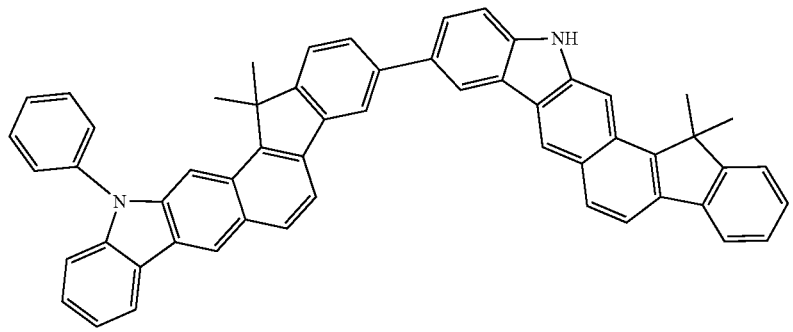

core 1-27

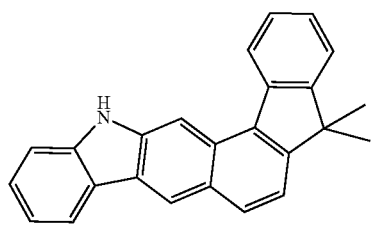

core 1-28

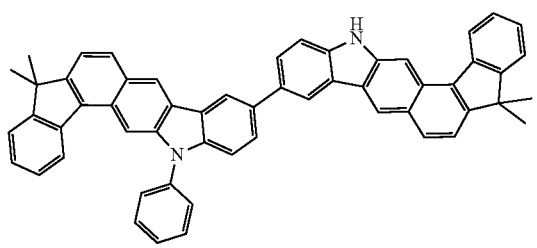

core 1-29

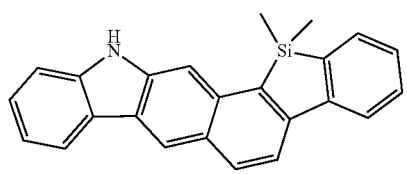

core 1-30

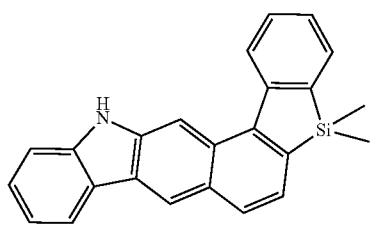

core 1-31

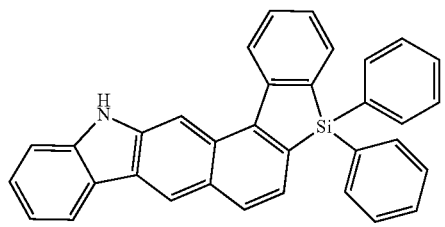

TABLE 2

| FD-MS of Core | | | |
|---|---|---|---|
| compound | FD-MS | compound | FD-MS |
| Core 1-1 | m/z = 323.08($C_{22}H_{13}NS$ = 323.41) | Core 1-2 | m/z = 400.10($C_{27}H_{16}N_2S$ = 400.49) |
| Core 1-3 | m/z = 475.14($C_{34}H_{21}NS$ = 475.60) | Core 1-4 | m/z = 564.17($C_{40}H_{24}N_2S$ = 564.70) |
| Core 1-5 | m/z = 423.11($C_{30}H_{17}NS$ = 423.53) | Core 1-6 | m/z = 720.17($C_{50}H_{28}N_2S_2$ = 720.90) |
| Core 1-7 | m/z = 323.08($C_{22}H_{13}NS$ = 323.41) | Core 1-8 | m/z = 399.11($C_{28}H_{17}NS$ = 399.51) |
| Core 1-9 | m/z = 400.10($C_{27}H_{16}N_2S$ = 400.49) | Core 1-10 | m/z = 564.17($C_{40}H_{24}N_2S$ = 564.70) |
| Core 1-11 | m/z = 373.09($C_{26}H_{15}NS$ = 373.47) | Core 1-12 | m/z = 720.17($C_{50}H_{28}N_2S_2$ = 720.90) |
| Core 1-13 | m/z = 307.10($C_{22}H_{13}NO$ = 307.34) | Core 1-14 | m/z = 459.16($C_{34}H_{21}NO$ = 459.54) |
| Core 1-15 | m/z = 384.13($C_{27}H_{16}N_2O$ = 384.43) | Core 1-16 | m/z = 688.22($C_{50}H_{28}N_2O_2$ = 688.77) |
| Core 1-17 | m/z = 357.12($C_{26}H_{15}NO$ = 357.40) | Core 1-18 | m/z = 307.10($C_{22}H_{13}NO$ = 307.34) |
| Core 1-19 | m/z = 383.13($C_{28}H_{17}NO$ = 383.44) | Core 1-20 | m/z = 384.13($C_{27}H_{16}N_2O$ = 384.43) |
| Core 1-21 | m/z = 357.12($C_{26}H_{15}NO$ = 357.40) | Core 1-22 | m/z = 548.19($C_{40}H_{24}N_2O$ = 548.63) |
| Core 1-23 | m/z = 688.22($C_{50}H_{28}N_2O_2$ = 688.77) | Core 1-24 | m/z = 333.15($C_{25}H_{19}N$ = 333.43) |
| Core 1-25 | m/z = 485.21($C_{37}H_{27}N$ = 485.62) | Core 1-26 | m/z = 740.32($C_{56}H_{40}N_2$ = 740.93) |
| Core 1-27 | m/z = 333.15($C_{25}H_{19}N$ = 333.43) | Core 1-28 | m/z = 740.32($C_{56}H_{40}N_2$ = 740.93) |
| Core 1-29 | m/z = 349.13($C_{24}H_{19}NSi$ = 349.50) | Core 1-30 | m/z = 349.13($C_{24}H_{19}NSi$ = 349.50) |
| Core 1-31 | m/z = 473.16($C_{34}H_{23}NSi$ = 473.64) | | |

II. Synthesis of Sub 1

Synthesis of Sub 1-12

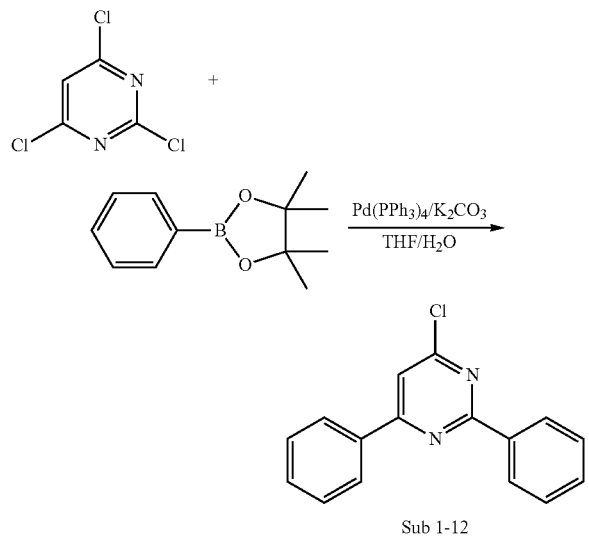

Sub 1-12

Phenylboronic acid pinacol ester (22.3 g, 109 mmol), THF (240 ml), 2,4,6-trichloropyrimidine (10 g, 54.5 mmol), Pd(PPh$_3$)$_4$ (3.8 g, 3.27 mmol), K$_2$CO$_3$ (45.2 g, 327 mmol), water (120 ml) were mixed, and then the mixed solution was stirred at 90° C. When the reaction was completed, the reaction product was extracted with CH$_2$Cl$_2$ and water. And then, the organic layer was dried with MgSO$_4$ and concentrated. Then, the concentrate was separated by silica gel column and recrystallized to obtain 9.5 g (yield: 65%) of the product.

Synthesis of Sub 1-14

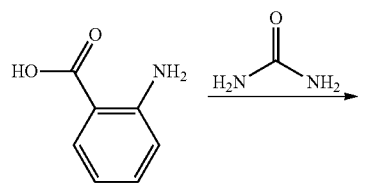

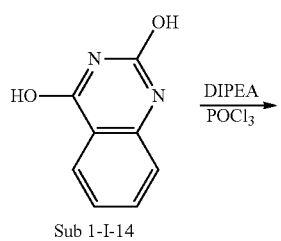

Sub 1-I-14

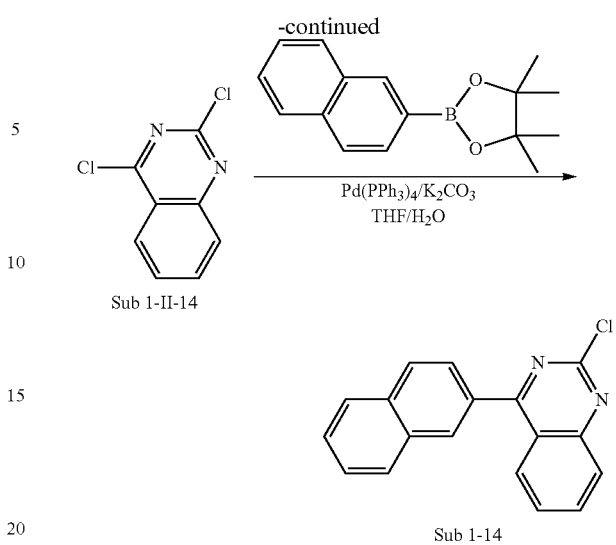

Sub 1-II-14

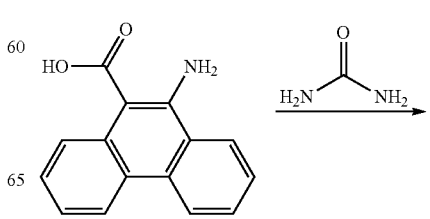

Sub 1-14

Synthesis of Sub 1-I-14

The mixture of 2-aminobenzoic acid (15.22 g, 111 mmol) and urea (46.66 g, 776.9 mmol) was stirred at 160° C. After the progress of reaction was confirmed by TLC, the reaction solution was cooled to 100° C. Then, water (55 ml) was added to the reaction solution and the mixture was stirred for 1 hour. When the reaction was completed, the produced solid was filtered under reduced pressure, washed with water, and dried to obtain 14.58 g (yield: 81%) of the product.

Synthesis of Sub 1-II-14

Sub 1-I-14 (14.58 g, 89.9 mmol) obtained in the above synthesis was dissolved in POCl$_3$ (60 ml). Then, N,N-Diisopropylethylamine (29.05 g, 224.8 mmol) was slowly added to the solution and the mixture was stirred at 90° C. When the reaction was completed, the reaction product was concentrated. Then, ice water (120 ml) was added to the reaction product and the reaction product was stirred at room temperature for 1 hour. Then, the produced solid was filtered under reduced pressure and dried to obtain 15.39 g (yield: 86%) of the product.

Synthesis of Sub 1-14

9.64 g (yield: 49%) of the product was obtained by reacting phenylboronic acid pinacol ester (19.2 g, 75.4 mmol), THF (332 ml), 2,4-dichloroquinazoline (15 g, 75.4 mmol), Pd(PPh$_3$)$_4$ (2.6 g, 2.26 mmol), K$_2$CO$_3$ (31.2 g, 226 mmol) and water (166 ml) by the same method as in synthesis example of Sub 1-12.

Synthesis of Sub 1-28

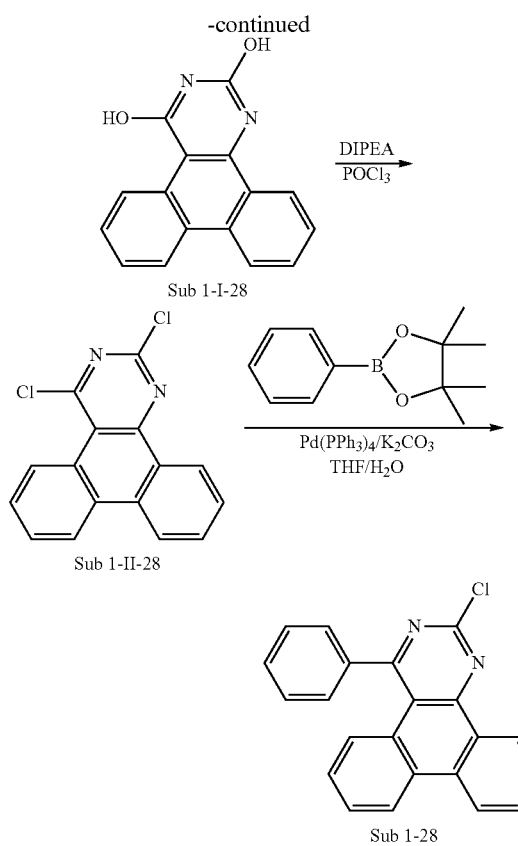

Synthesis of Sub 1-I-28

41.94 g (yield: 63%) of the product was obtained by reacting 10-aminophenanthrene-9-carboxylic acid (60.22 g, 253.8 mmol), urea (106.71 g, 1776.8 mmol) and water (130 ml) by the same method as in synthesis example of Sub 1-I-14.

Synthesis of Sub 1-II-28

40.19 g (yield: 84%) of the product was obtained by reacting Sub 1-II-28 (41.94 g, 159.9 mmol) obtained in the above synthesis, $POCl_3$ (110 ml) and N,N-Diisopropylethylamine (51.67 g, 399.8 mmol) by the same method as in synthesis example of Sub 1-11-14.

Synthesis of Sub 1-28

23.81 g (yield: 52%) of the product was obtained by reacting Sub 1-I-28 (40.19 g, 134.3 mmol) obtained in the above synthesis, 4,4,5,5-tetramethyl-2-phenyl-1,3,2-dioxaborolane (30.16 g, 147.8 mmol), $Pd(PPh_3)_4$ (6.21 g, 5.4 mmol), $K_2CO_3$ (55.7 g, 403 mmol), THF and water by the same method as in synthesis example of Sub 1-14.

Synthesis of Sub 1-36

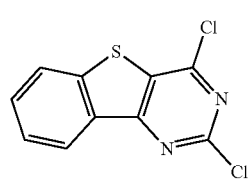

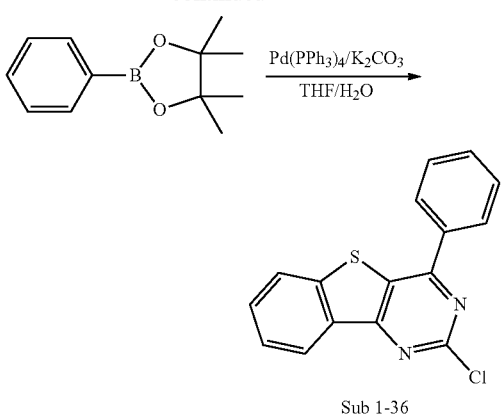

9.21 g (yield: 44%) of the product was obtained by reacting phenylboronic acid pinacol ester (14.4 g, 70.6 mmol), THF (310 ml), 2,4-dichlorobenzo[4,5]thieno[3,2-d]pyrimidine (18 g, 70.6 mmol), $Pd(PPh_3)_4$ (2.4 g, 2.1 mmol), $K_2CO_3$ (29.3 g, 212 mmol) and water (155 ml) by the same method as in synthesis example of Sub 1-14.

Example of Sub 1

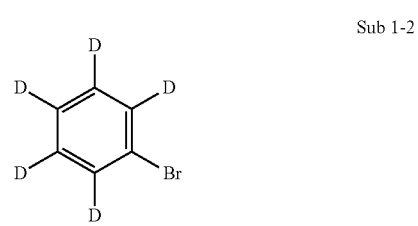

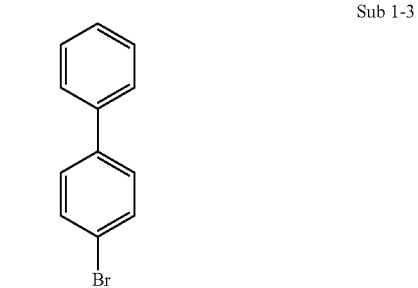

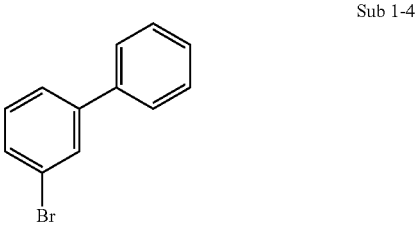

195
-continued
Sub 1-5
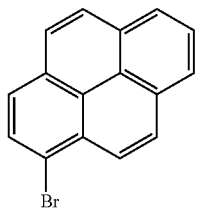
Sub 1-6
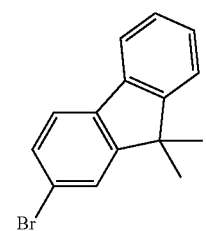
Sub 1-7
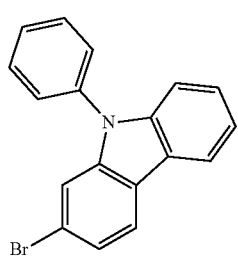
Sub 1-8
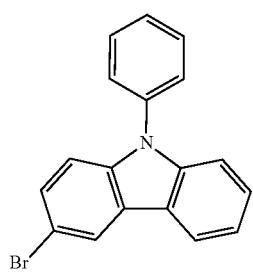
Sub 1-9
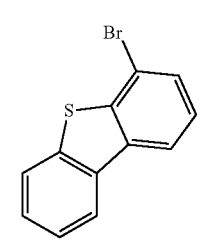
Sub 1-10
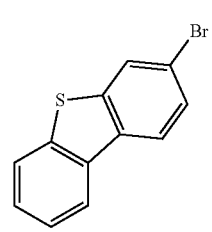
Sub 1-11
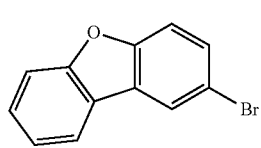
196
-continued
Sub 1-12
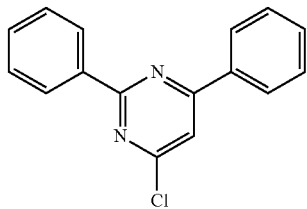
Sub 1-13
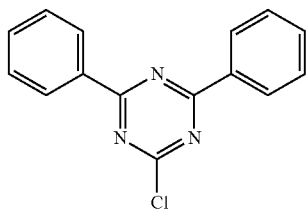
Sub 1-14
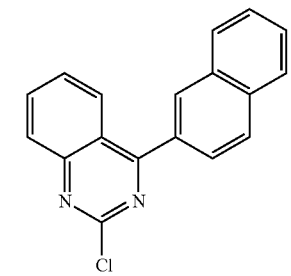
Sub 1-15
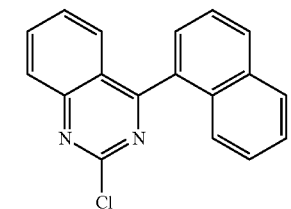
Sub 1-16
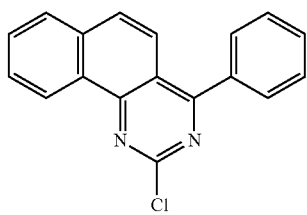
Sub 1-17
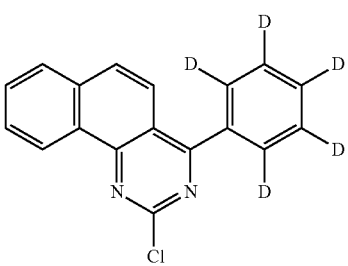

Sub 1-18
Sub 1-19
Sub 1-20
Sub 1-21
Sub 1-22
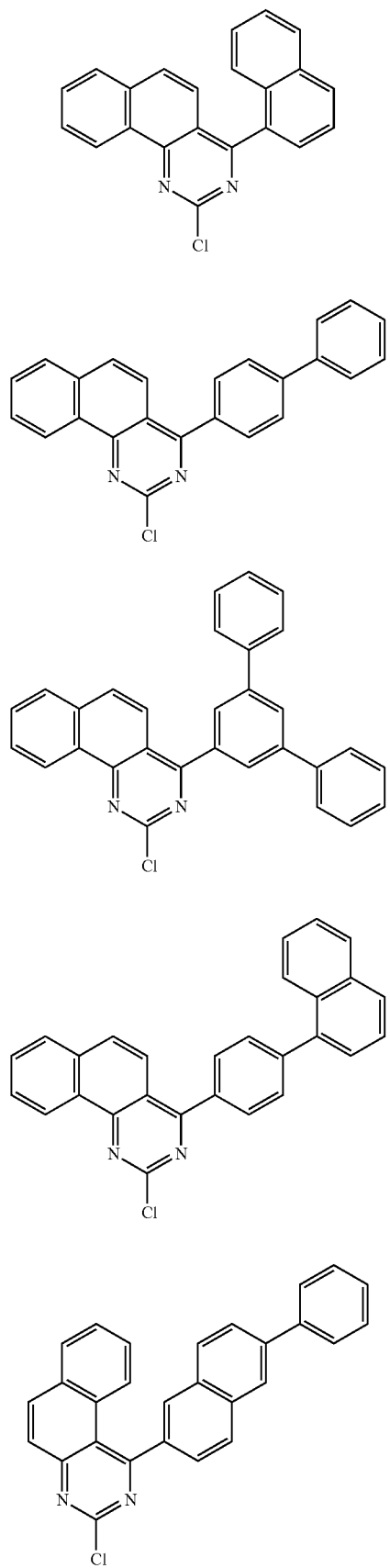
Sub 1-23
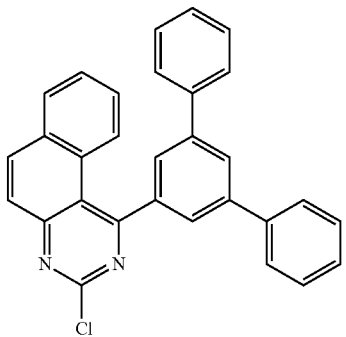
Sub 1-24
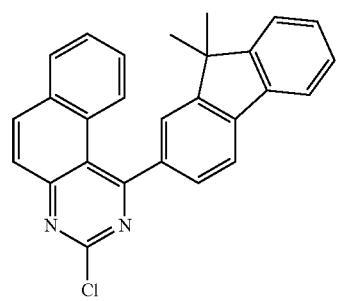
Sub 1-25
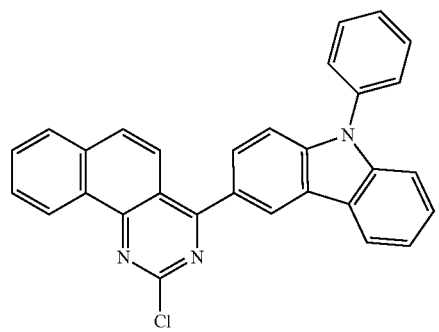
Sub 1-26
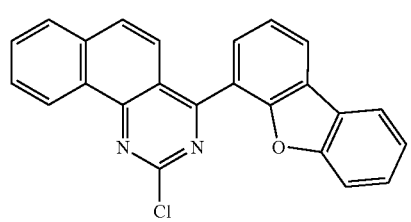
Sub 1-27
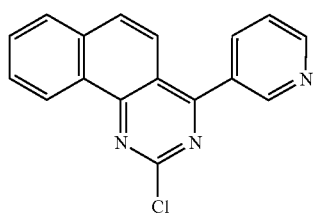

-continued
Sub 1-28
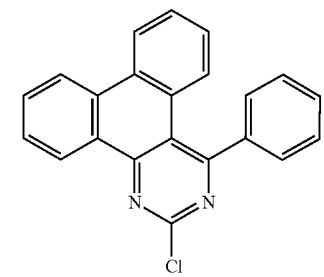
Sub 1-29
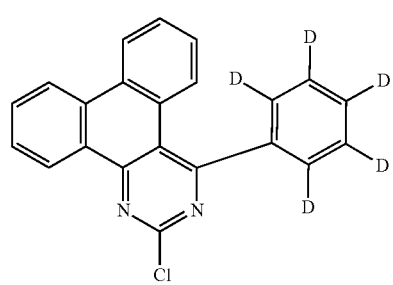
Sub 1-30
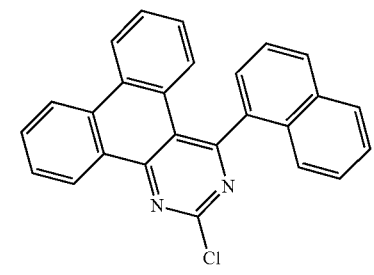
Sub 1-31
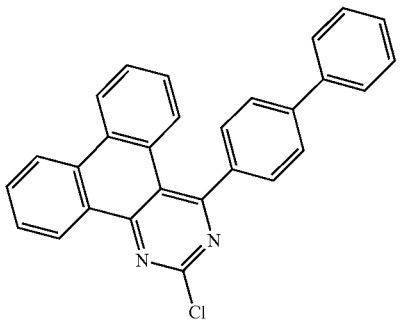
Sub 1-32
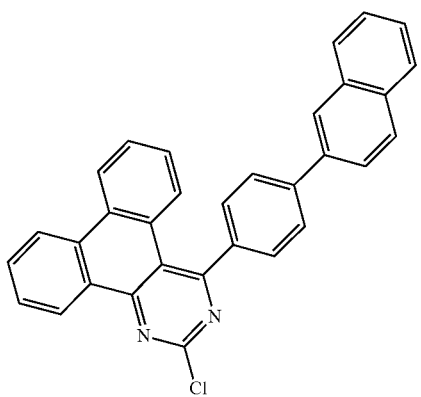
-continued
Sub 1-33
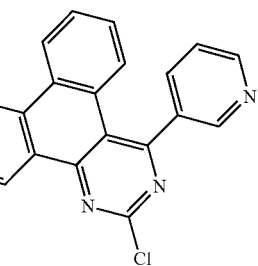
Sub 1-34
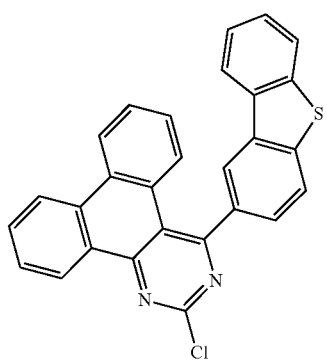
Sub 1-35
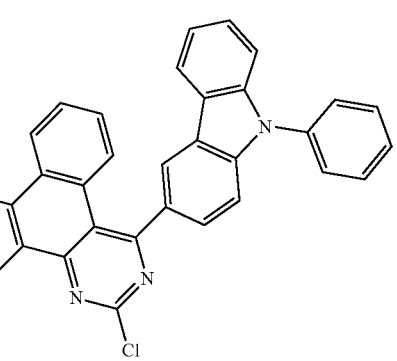
Sub 1-36
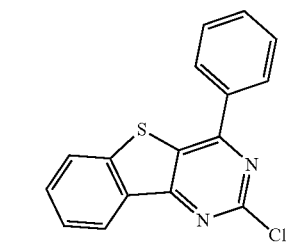
Sub 1-37
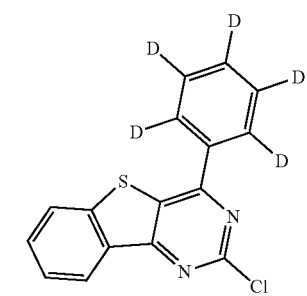

| 201 -continued | 202 -continued |
|---|---|
| Sub 1-38 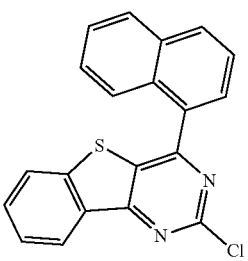 | Sub 1-42 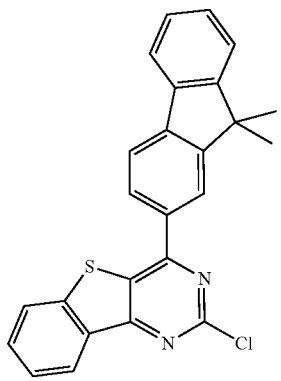 |
| Sub 1-39 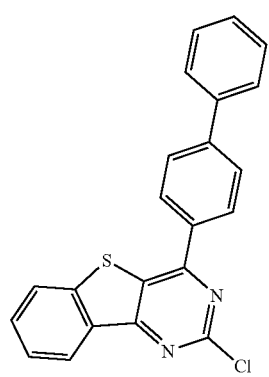 | Sub 1-43 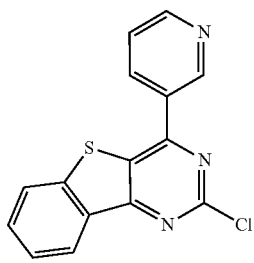 |
| Sub 1-40 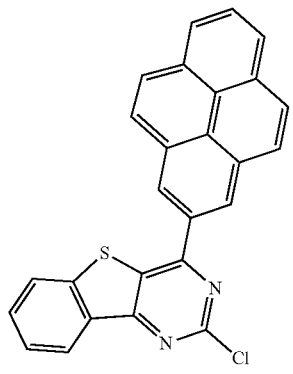 | Sub 1-44 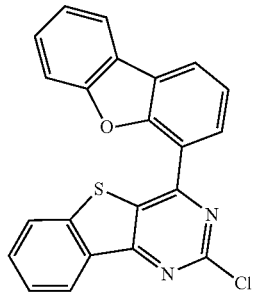 |
|  | Sub 1-45 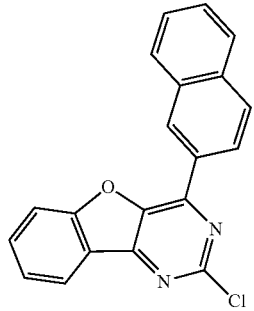 |
| Sub 1-41 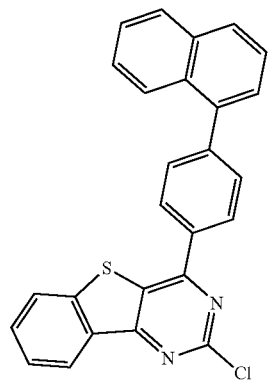 | Sub 1-46 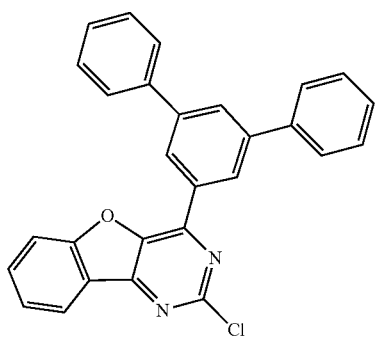 |

Sub 1-47
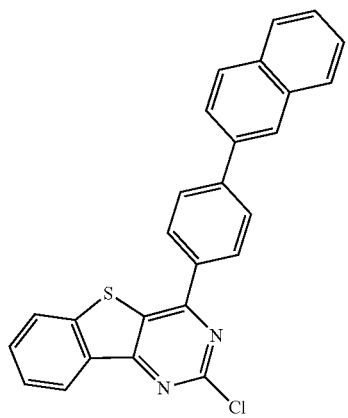
Sub 1-48
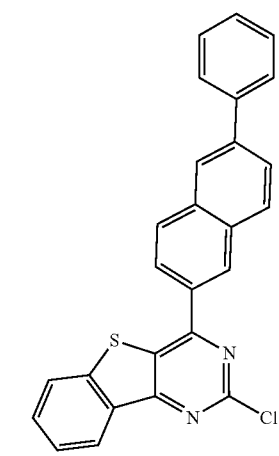
Sub 1-49
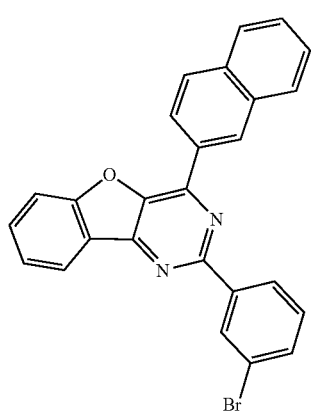
Sub 1-50
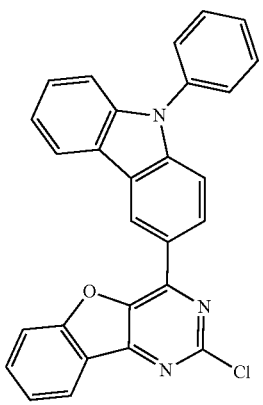
Sub 1-51
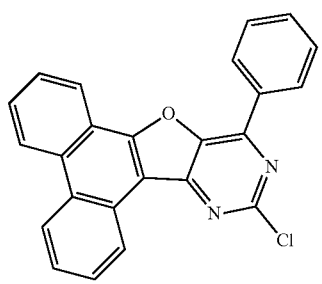
Sub 1-52
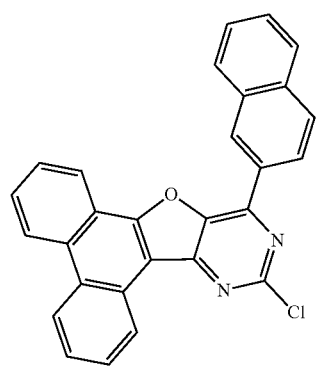
Sub 1-53
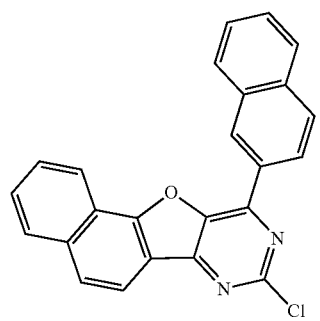

Sub 1-54
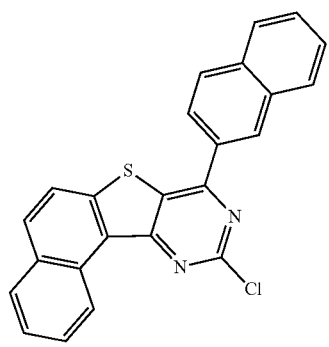
Sub 1-55
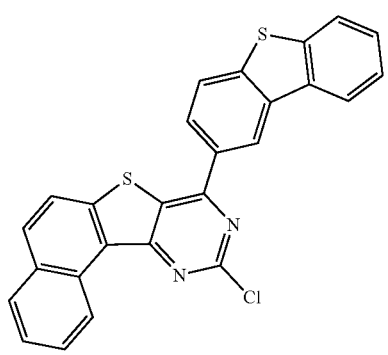
Sub 1-56
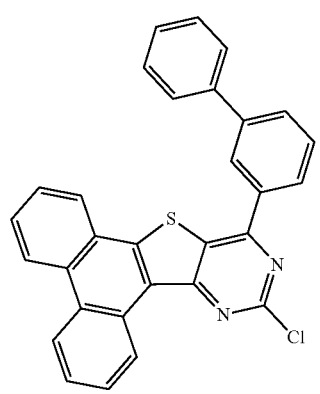
Sub 1-57
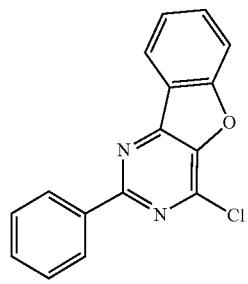
Sub 1-58
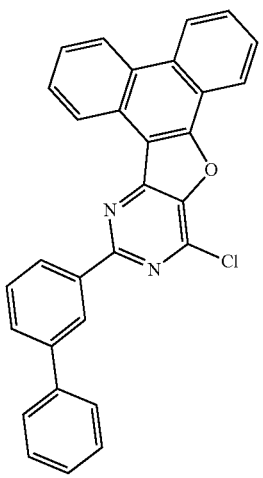
Sub 1-59
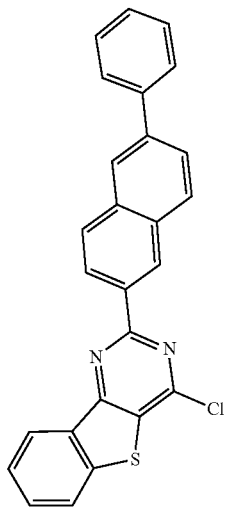
Sub 1-60
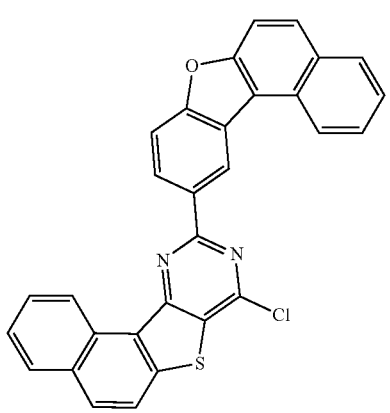

Sub 1-61
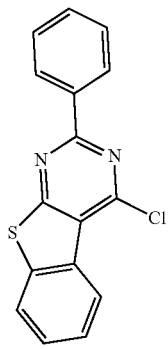
Sub 1-62
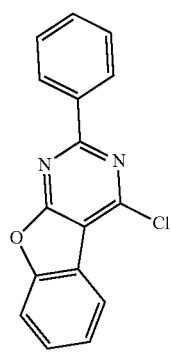
Sub 1-63
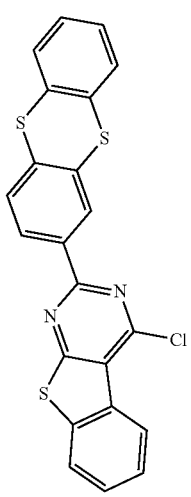
Sub 1-64
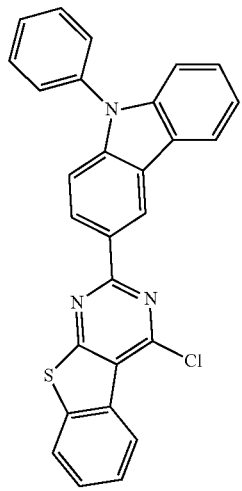
Sub 1-65
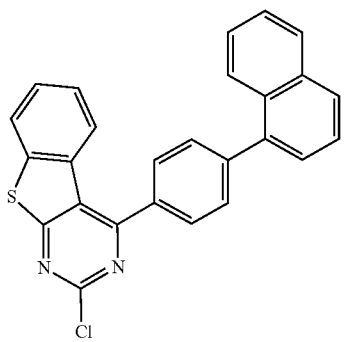
Sub 1-66
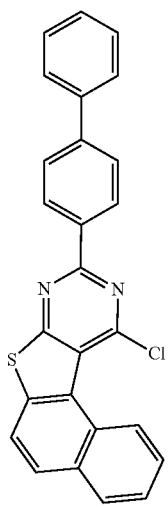

Sub 1-67
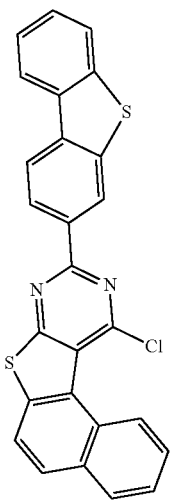
Sub 1-70
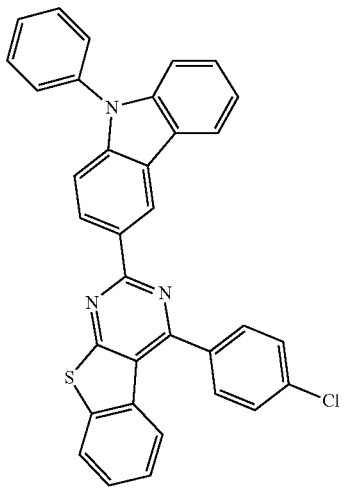
Sub 1-68
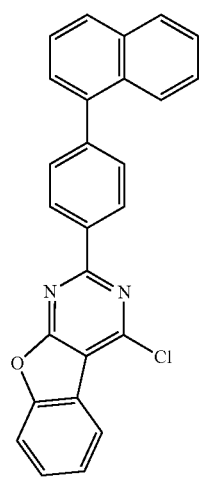
Sub 1-71
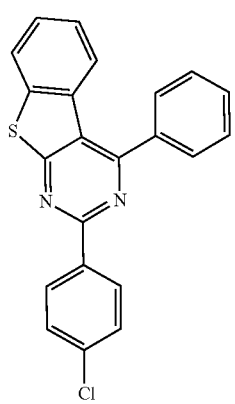
Sub 1-69
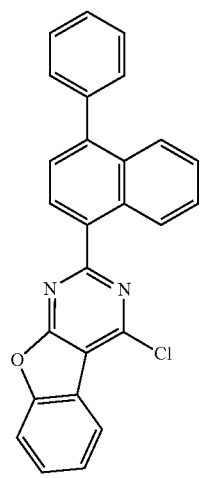
Sub 1-72
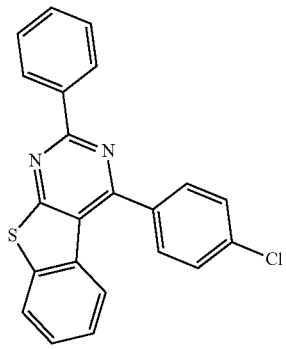

211
-continued
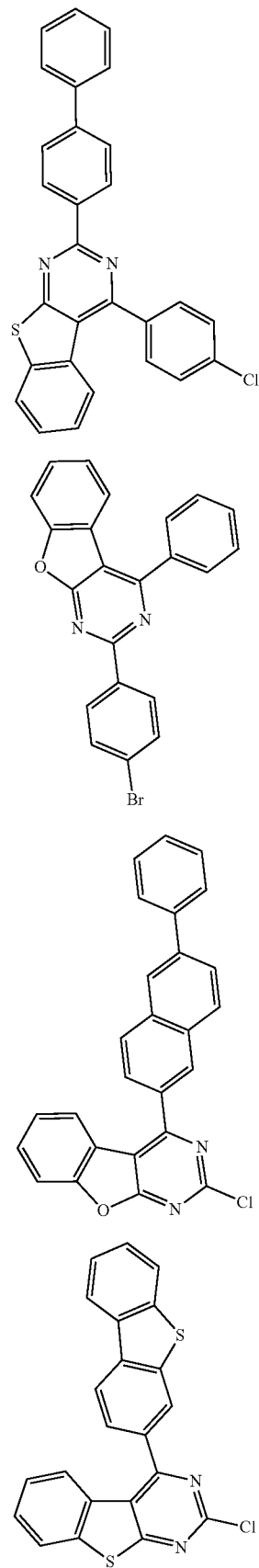
212
-continued
Sub 1-73
Sub 1-77
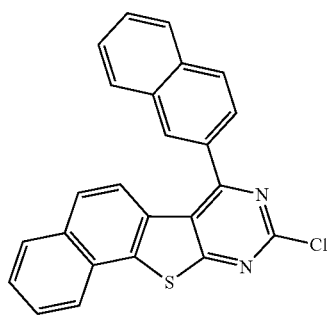
Sub 1-74
Sub 1-78
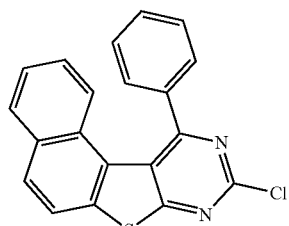
Sub 1-75
Sub 1-79
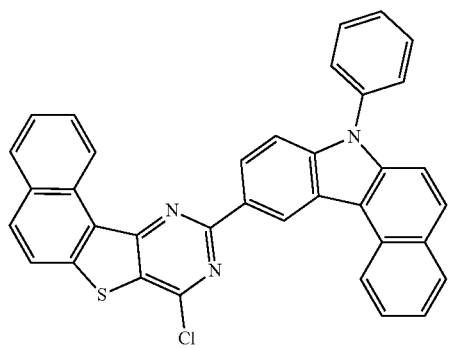
Sub 1-76
Sub 1-80
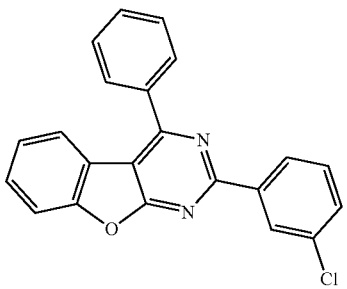
Sub 1-81
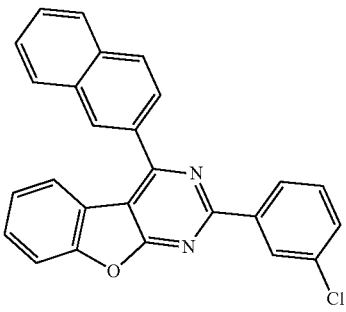

Sub 1-82
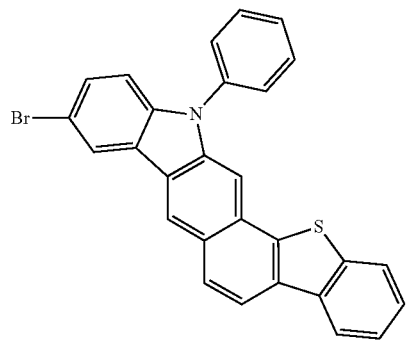
Sub 1-83
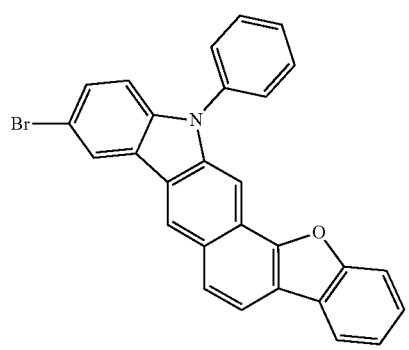
Sub 1-84
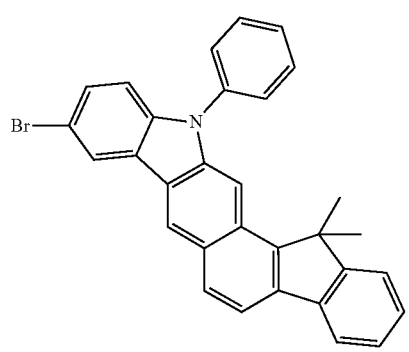
Sub 1-85
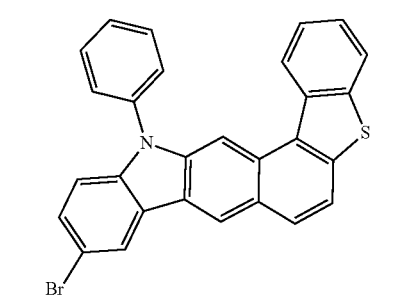
Sub 1-86
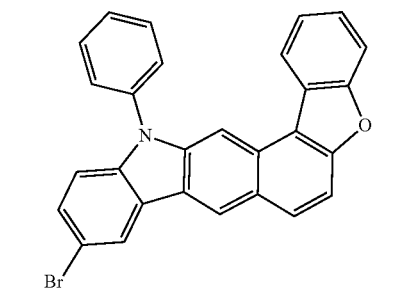
Sub 1-87
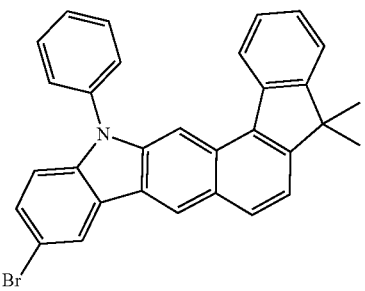
Sub 1-88
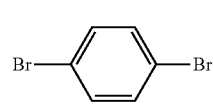
Sub 1-89
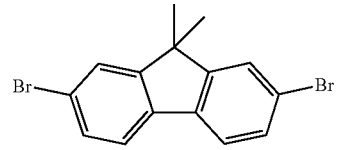
Sub 1-90
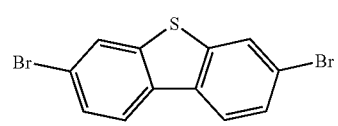
Sub 1-91
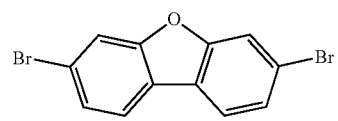
Sub 1-92
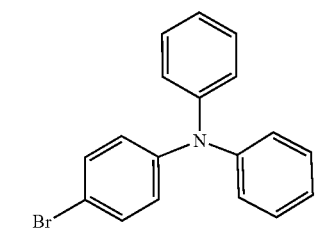
Sub 1-93
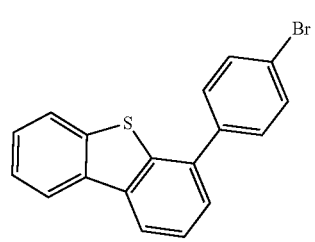

TABLE 3

| compound | FD-MS | compound | FD-MS |
|---|---|---|---|
| Sub 1-3 | m/z = 231.99($C_{12}H_9Br$ = 233.10) | Sub 1-6 | m/z = 272.02($C_{15}H_{13}Br$ = 273.17) |
| Sub 1-11 | m/z = 245.97($C_{12}H_7BrO$ = 247.09) | Sub 1-12 | m/z = 266.06($C_{16}H_{11}ClN_2$ = 266.72) |
| Sub 1-21 | m/z = 416.11($C_{28}H_{17}ClN_2$ = 416.90) | Sub 1-34 | m/z = 446.06($C_{28}H_{15}ClN_2S$ = 446.95) |
| Sub 1-49 | m/z = 450.04($C_{26}H_{15}BrN_2O$ = 451.31) | Sub 1-74 | m/z = 400.02($C_{22}H_{13}BrN_2O$ = 401.26) |
| Sub 1-78 | m/z = 346.03($C_{20}H_{11}ClN_2S$ = 346.83) | Sub 1-90 | m/z = 339.86($C_{12}H_6Br_2S$ = 342.05) |

III. Synthesis Example of Sub 2

Sub 2 of reaction scheme 2 may be synthesized according to, but not limited to, the following reaction scheme.

Reaction Scheme 3 (Here, Hal is Br or Cl)

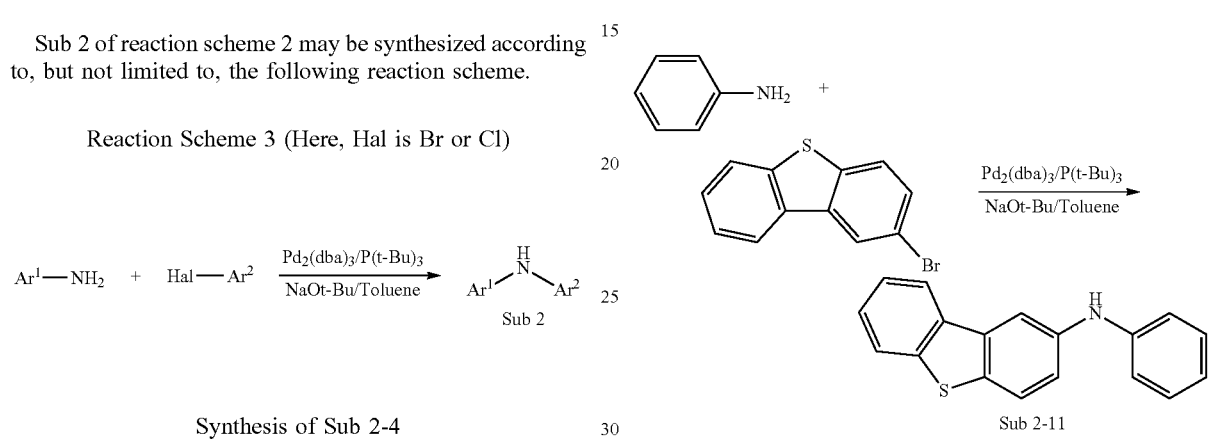

Synthesis of Sub 2-4

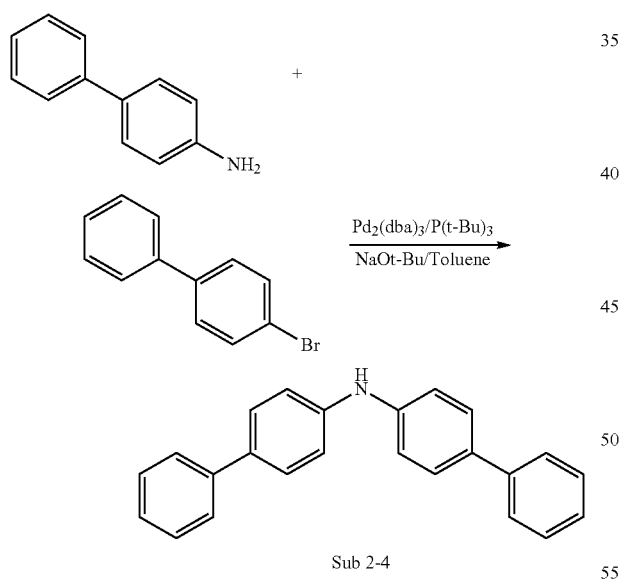

The reaction solution mixed with 4-Aminobiphenyl(5.23 g, 30.9 mmol), 4-Bromobiphenyl(7.2 g, 30.9 mmol), $Pd_2(dba)_3$ (1.41 g, 1.54 mmol), P(t-Bu)$_3$ (0.62 g, 3.1 mmol), NaOt-Bu (8.91 g, 92.7 mmol) and toluene (324 mL) was stirred at 100° C. for 24 hours under refluxing. When the reaction was completed, the reaction product was extracted with ether and water. And then, the organic layer was dried with $MgSO_4$ and concentrated. Then, the concentrate was separated by silica gel column and recrystallized to obtain 6.75 g (yield: 68%) of the product.

Synthesis of Sub 2-11

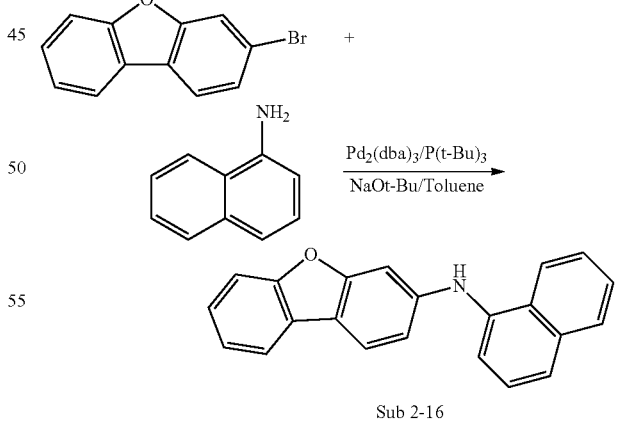

12.1 g (yield: 77%) of the product was obtained by reacting 2-bromodibenzo[b,d]thiophene (15 g, 57 mmol), aniline (5.31 g, 57 mmol), Pd$_2$(dba)$_3$ (2.61 g, 2.85 mmol), P(t-Bu)$_3$ (1.15 g, 5.7 mmol), NaOt-Bu (16.4 g, 171 mmol) and toluene (598 mL) by the same method as in synthesis example of Sub 2-4.

Synthesis of Sub 2-16

8.07 g (yield: 80%) of the product was obtained by reacting the starting material 3-bromodibenzo[b,d]furan (8.06 g, 32.6 mmol), naphthalen-1-amine (9.34 g, 65.2 mmol), Pd$_2$(dba)$_3$ (0.9 g, 1 mmol), 50% P(t-Bu)$_3$ (1.3 ml, 2.6 mmol), NaOt-Bu (9.41 g, 97.9 mmol) and toluene by the same method as in synthesis example of Sub 2-4.

Synthesis of Sub 2-9

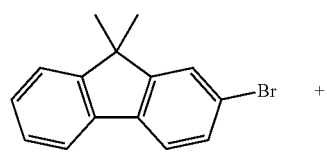

+

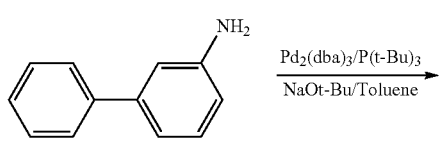

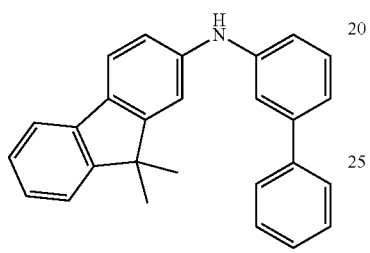

Sub 2-9

11.73 g (yield: 82%) of the product was obtained by reacting the starting material 2-bromo-9,9-dimethyl-9H-fluorene (10.81 g, 39.6 mmol), [1,1'-biphenyl]-4-amine (13.39 g, 79.1 mmol), Pd$_2$(dba)$_3$ (1.09 g, 1.2 mmol), 50% P(t-Bu)$_3$ (1.5 ml, 3.2 mmol), NaOt-Bu (11.41 g, 118.7 mmol) and toluene by the same method as in synthesis example of Sub 2-4.

TABLE 4

FD-MS of Sub 2

| compound | FD-MS | compound | FD-MS |
|---|---|---|---|
| Sub 2-4 | m/z = 321.15(C$_{24}$H$_{19}$N = 321.41) | Sub 2-6 | m/z = 295.14(C$_{22}$H$_{17}$N = 295.38) |
| Sub 2-9 | m/z = 361.18(C$_{27}$H$_{23}$N = 361.48) | Sub 2-11 | m/z = 275.08(C$_{18}$H$_{13}$NS = 275.37) |
| Sub 2-12 | m/z = 275.08(C$_{18}$H$_{13}$NS = 275.37) | Sub 2-15 | m/z = 259.10(C$_{18}$H$_{13}$NO = 259.30) |
| Sub 2-16 | m/z = 309.12(C$_{22}$H$_{15}$NO = 309.36) | Sub 2-18 | m/z = 385.15(C$_{28}$H$_{19}$NO = 385.46) |
| Sub 2-26 | m/z = 384.16(C$_{28}$H$_{20}$N$_2$ = 384.47) | | |

Example of Sub 2

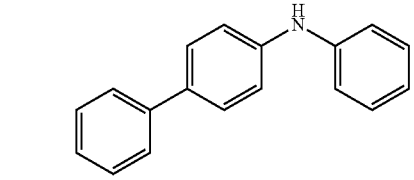

Sub 2-3

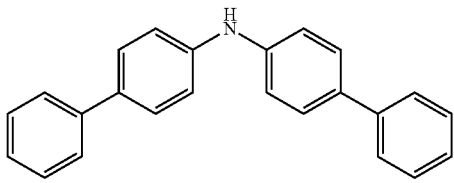

Sub 2-4

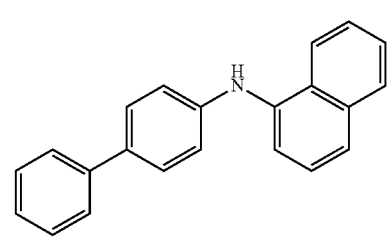

Sub 2-5

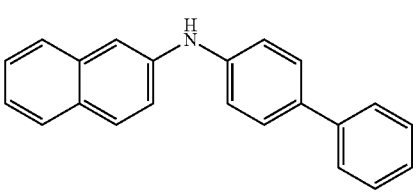

Sub 2-6

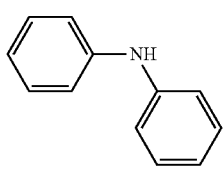

Sub 2-1

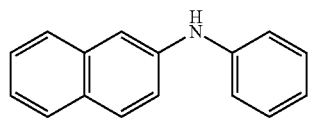

Sub 2-2

-continued

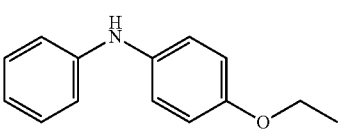

Sub 2-7

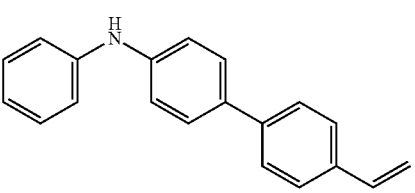

Sub 2-8

Sub 2-9
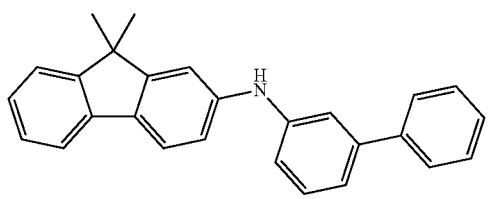
Sub 2-10
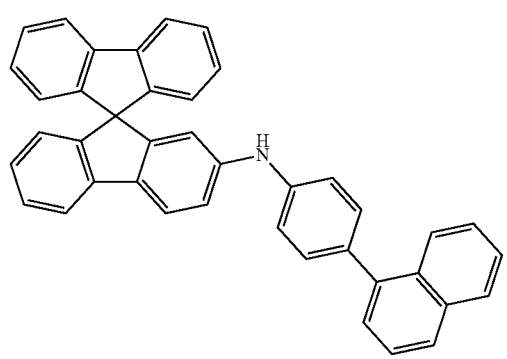
Sub 2-11
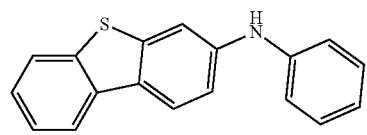
Sub 2-12
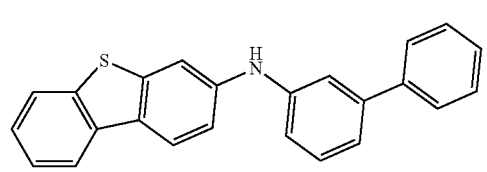
Sub 2-13
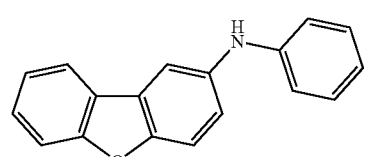
Sub 2-14
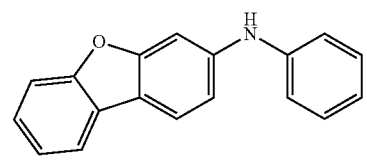
Sub 2-15
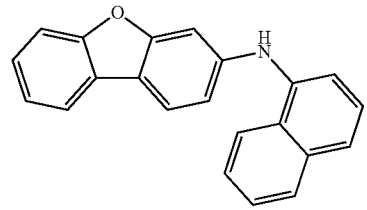
Sub 2-16
Sub 2-17
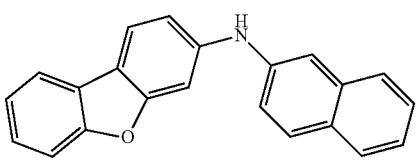
Sub 2-18
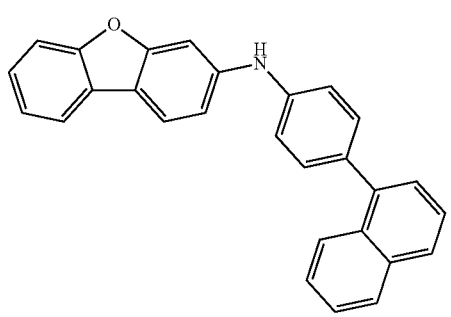
Sub 2-19
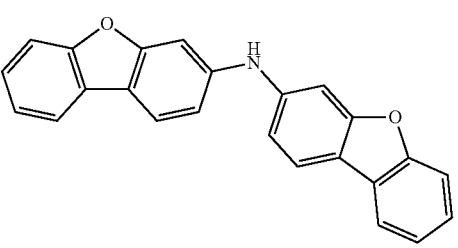
Sub 2-20
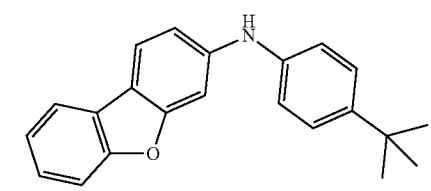
Sub 2-21
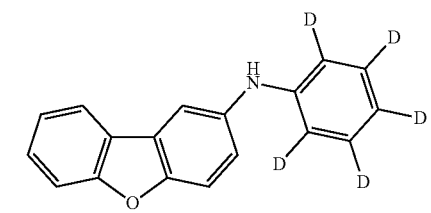
Sub 2-22
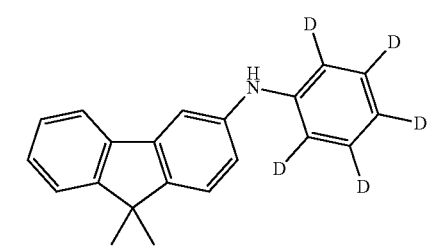
Sub 2-23
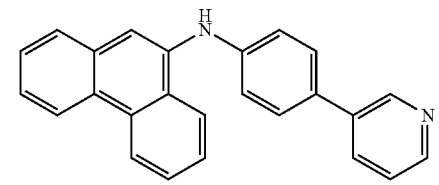

IV. Final Product(1)

Synthesis of 1-1-5

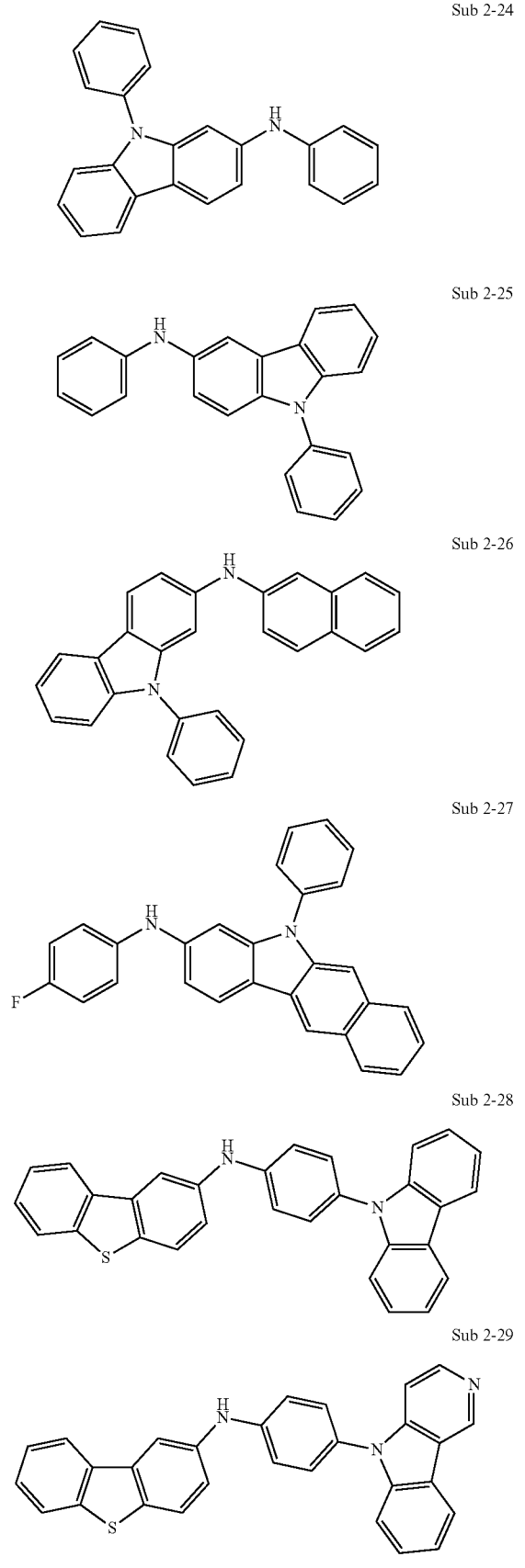

The reaction solution mixed with Core 1-1 (5.4 g, 16.7 mmol), Sub 1-6 (4.56 g, 16.7 mmol), Pd₂(dba)₃ (0.76 g, 0.84 mmol), P(t-Bu)₃ (0.34 g, 1.67 mmol), NaOt-Bu (2.41 g, 25.05 mmol) and toluene (175 mL) was stirred at 100° C. When the reaction was completed, the reaction product was extracted with ether and water. And then, the organic layer was dried with MgSO₄ and concentrated. Then, the concentrate was separated by silica gel column and recrystallized to obtain 7.06 g (yield: 82%) of the product.

Synthesis of 1-1-2

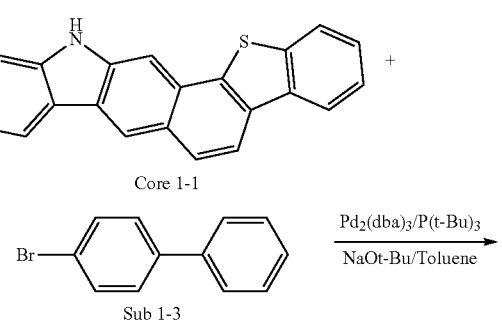

223
-continued

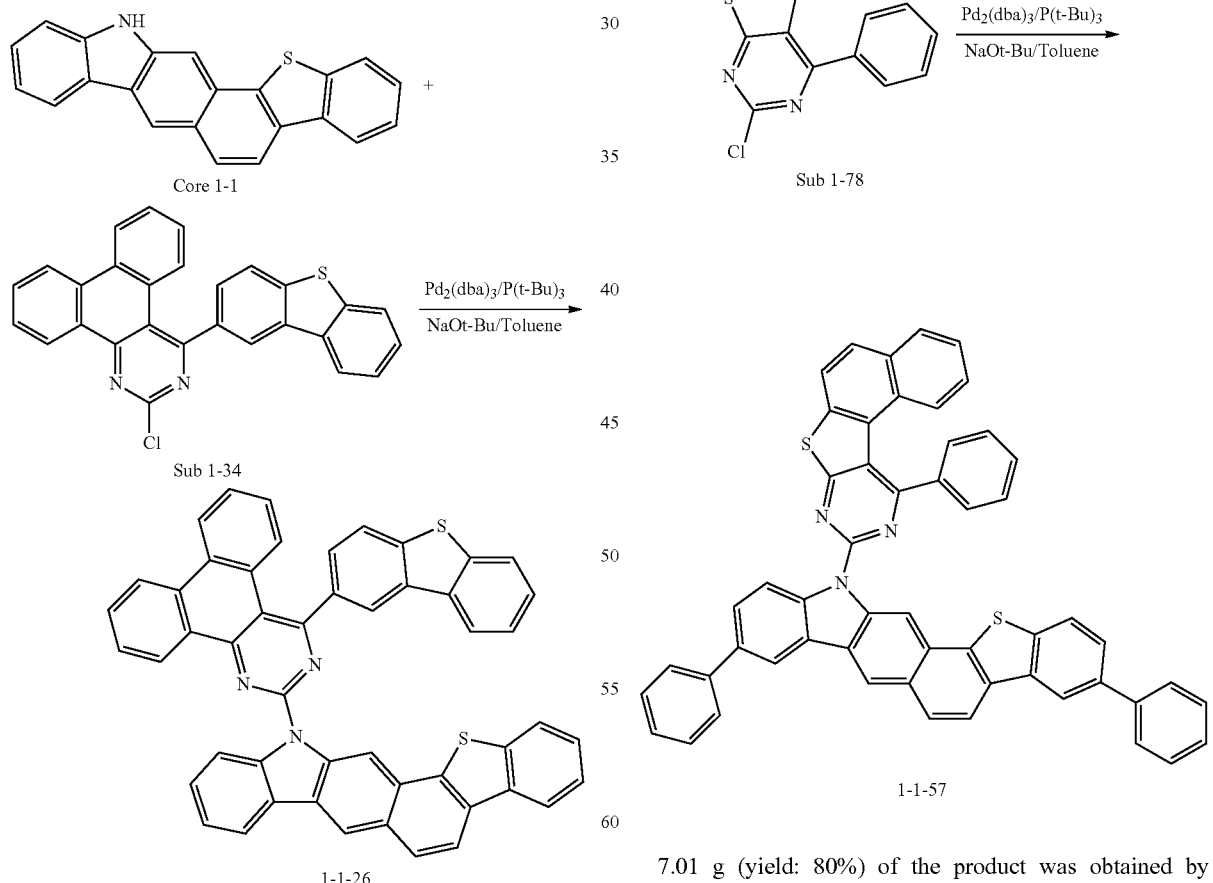

1-1-2

7.08 g (yield: 86%) of the product was obtained by reacting Core 1-1 (5.6 g, 17.32 mmol), Sub 1-3 (4.04 g, 17.32 mmol), Pd$_2$(dba)$_3$ (0.79 g, 0.87 mmol), P(t-Bu)$_3$ (0.35 g, 1.73 mmol), NaOt-Bu (2.50 g, 25.97 mmol) and toluene (181 mL) by the same method as in synthesis example of 1-1-5.

Synthesis of 1-1-26

Core 1-1

Sub 1-34

1-1-26

7.07 g (yield: 82%) of the product was obtained by reacting Core 1-1 (3.8 g, 11.75 mmol), Sub 1-34 (5.25 g, 11.75 mmol), Pd$_2$(dba)$_3$ (0.54 g, 0.59 mmol), P(t-Bu)$_3$ (0.24 g, 1.18 mmol), NaOt-Bu (1.69 g, 17.63 mmol) and toluene (123 mL) by the same method as in synthesis example of 1-1-5.

Synthesis of 1-1-57

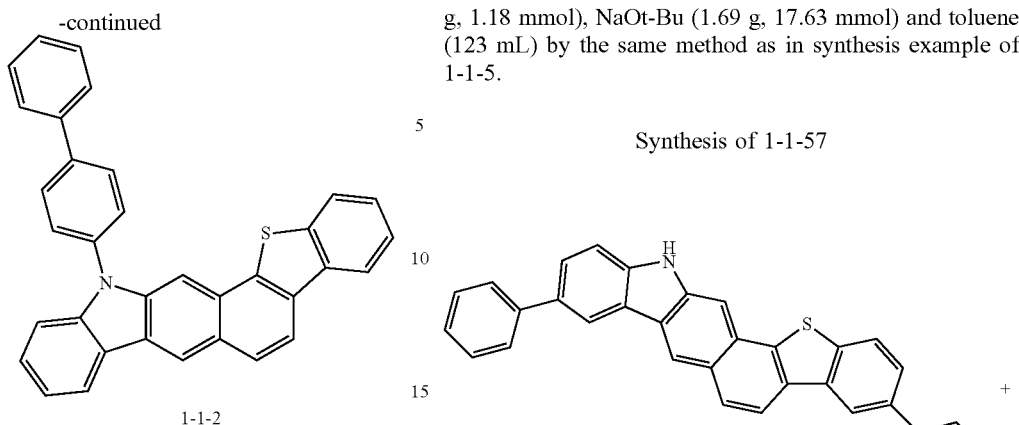

Core 1-3

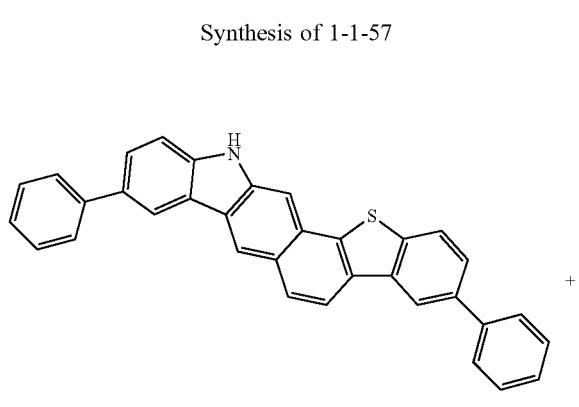

Sub 1-78

1-1-57

7.01 g (yield: 80%) of the product was obtained by reacting Core 1-3 (5.3 g, 11.14 mmol), Sub 1-78 (3.87 g, 11.14 mmol), Pd$_2$(dba)$_3$ (0.51 g, 0.55 mmol), P(t-Bu)$_3$ (0.23 g, 1.11 mmol), NaOt-Bu (1.61 g, 16.72 mmol) and toluene (117 mL) by the same method as in synthesis example of 1-1-5.

Synthesis of 1-1-54

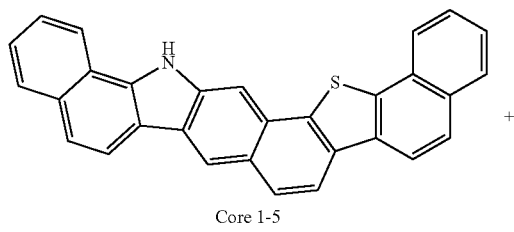

Core 1-5 +

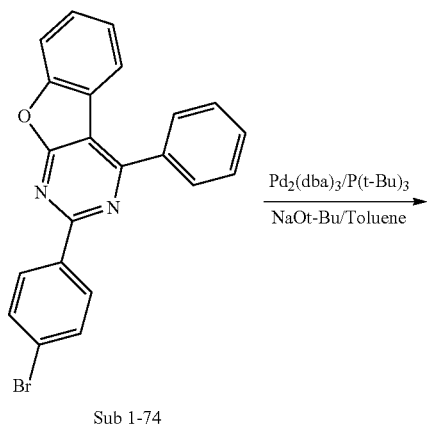

Sub 1-74

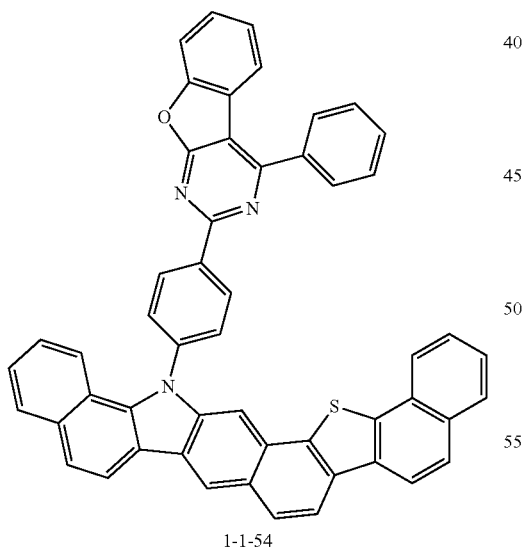

1-1-54

7.11 g (yield: 75%) of the product was obtained by reacting Core 1-5 (5.4 g, 12.75 mmol), Sub 1-74 (5.12 g, 12.75 mmol), Pd₂(dba)₃ (0.58 g, 0.64 mmol), P(t-Bu)₃ (0.26 g, 1.28 mmol), NaOt-Bu (1.84 g, 19.13 mmol) and toluene (134 mL) by the same method as in synthesis example of 1-1-5.

Synthesis of 1-1-61

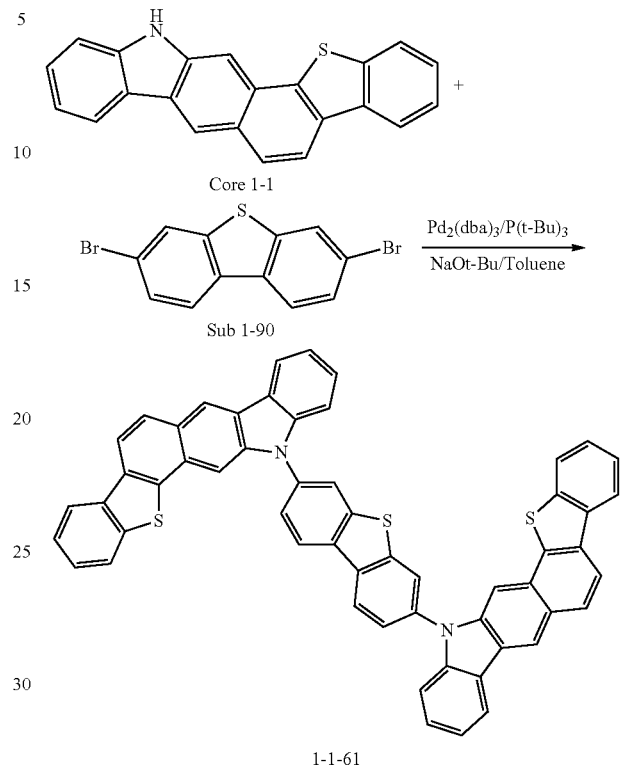

13.43 g (yield: 75%) of the product was obtained by reacting Core 1-1 (7 g, 21.64 mmol), Sub 1-90 (3.7 g, 10.82 mmol), Pd₂(dba)₃ (0.99 g, 1.08 mmol), P(t-Bu)₃ (0.44 g, 2.16 mmol), NaOt-Bu (5.20 g, 54.11 mmol) and toluene (227 mL) by the same method as in synthesis example of 1-1-5.

Synthesis of 2-1-15

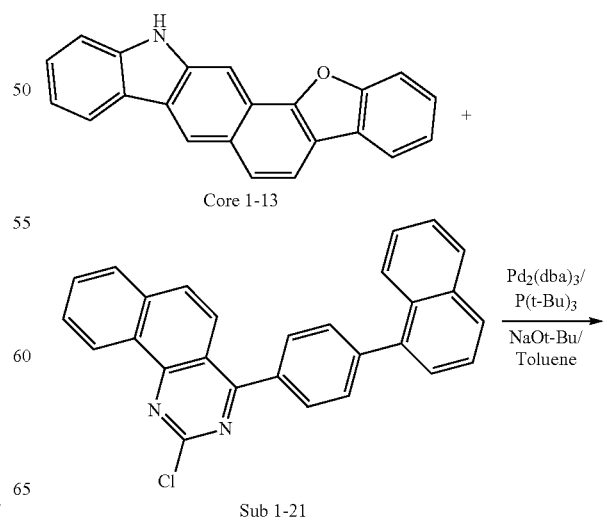

-continued

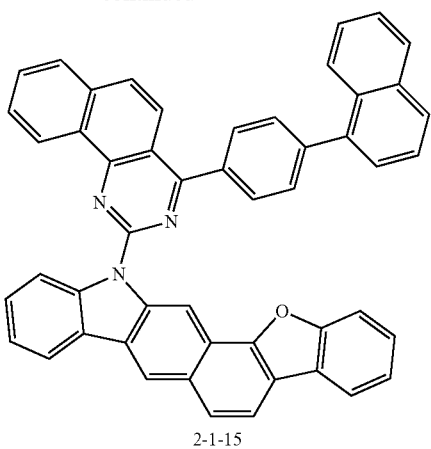

2-1-15

7.16 g (yield: 78%) of the product was obtained by reacting Core 1-13 (4.1 g, 13.34 mmol), Sub 1-21 (5.56 g, 13.34 mmol), Pd₂(dba)₃ (0.61 g, 0.67 mmol), P(t-Bu)₃ (0.27 g, 1.33 mmol), NaOt-Bu (1.92 g, 20.01 mmol) and toluene (140 mL) by the same method as in synthesis example of 1-1-5.

Synthesis of 2-2-7

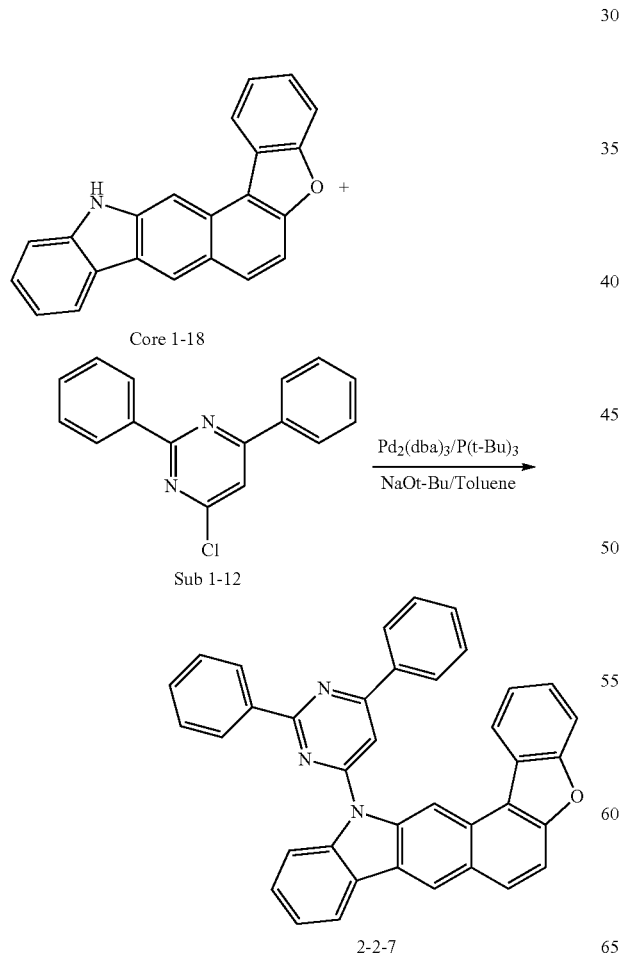

2-2-7

7.05 g (yield: 76%) of the product was obtained by reacting Core 1-18 (5.3 g, 17.25 mmol), Sub 1-12 (4.60 g, 17.25 mmol), Pd₂(dba)₃ (0.79 g, 0.86 mmol), P(t-Bu)₃ (0.35 g, 1.72 mmol), NaOt-Bu (2.49 g, 25.87 mmol) and toluene (18 mL) by the same method as in synthesis example of 1-1-5.

Synthesis of 3-1-4

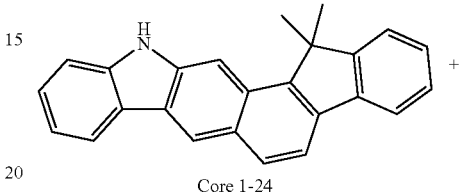

Core 1-24

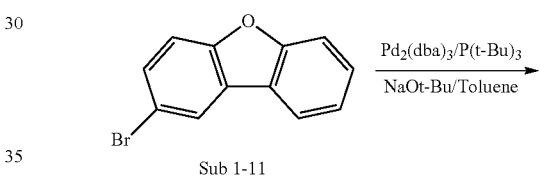

Sub 1-11

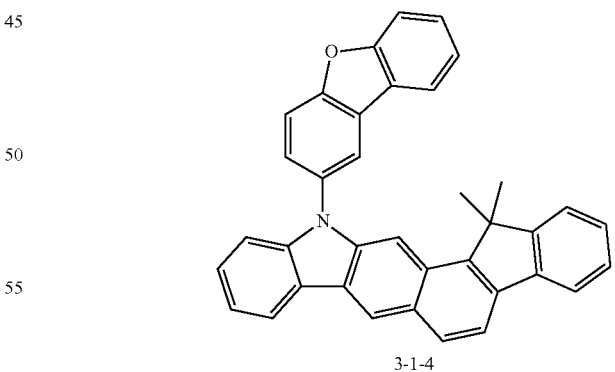

3-1-4

7.01 g (yield: 78%) of the product was obtained by reacting Core 1-24 (6 g, 18 mmol), Sub 1-11 (4.45 g, 18 mmol), Pd₂(dba)₃ (0.82 g, 0.90 mmol), P(t-Bu)₃ (0.36 g, 1.8 mmol), NaOt-Bu (2.59 g, 26.99 mmol) and toluene (189 mL) by the same method as in synthesis example of 1-1-5.

229
Synthesis of 3-2-12
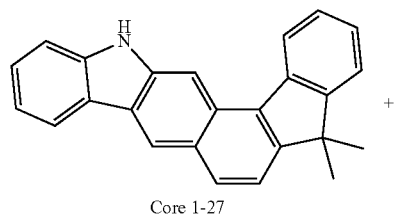
Core 1-27
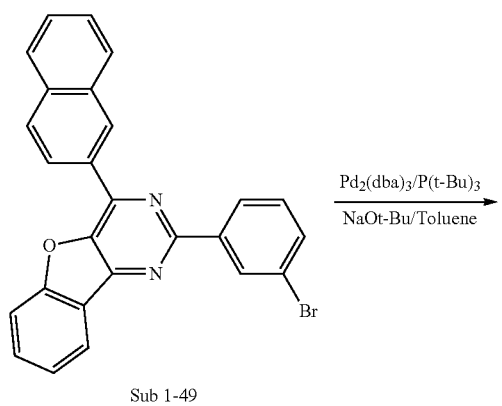
Sub 1-49
230
-continued
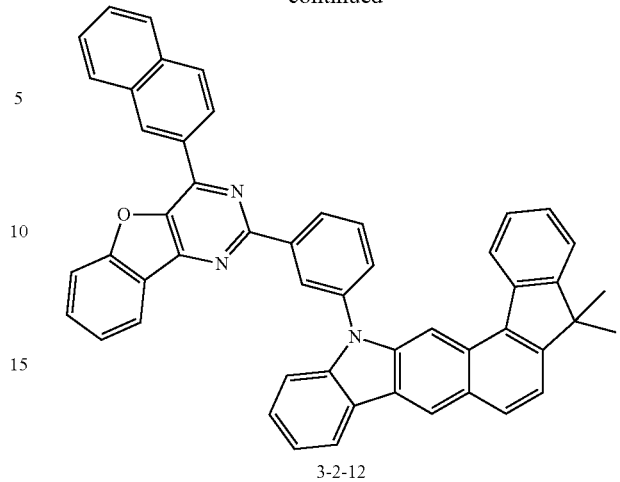
3-2-12
7.09 g (yield: 73%) of the product was obtained by reacting Core 1-27 (4.6 g, 13.8 mmol), Sub 1-49 (6.23 g, 13.8 mmol), Pd$_2$(dba)$_3$ (0.63 g, 0.69 mmol), P(t-Bu)$_3$ (0.28 g, 1.38 mmol), NaOt-Bu (1.99 g, 20.69 mmol) and toluene (145 mL) by the same method as in synthesis example of 1-1-5.
V. Synthesis of Final Product(2)
Synthesis of A 1-1-1
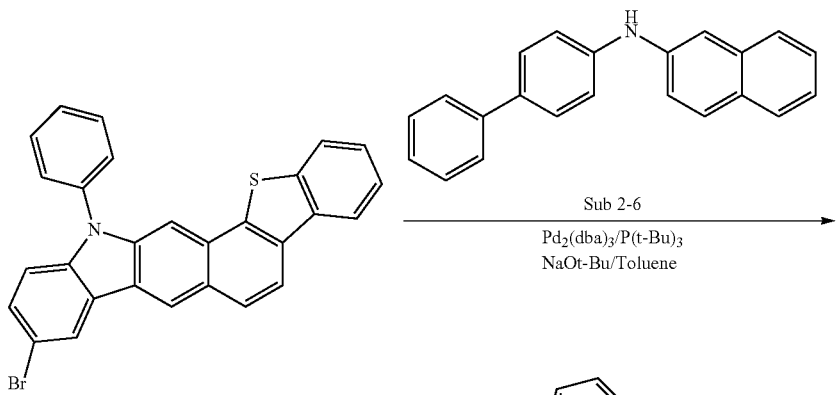
1-1-1(A)
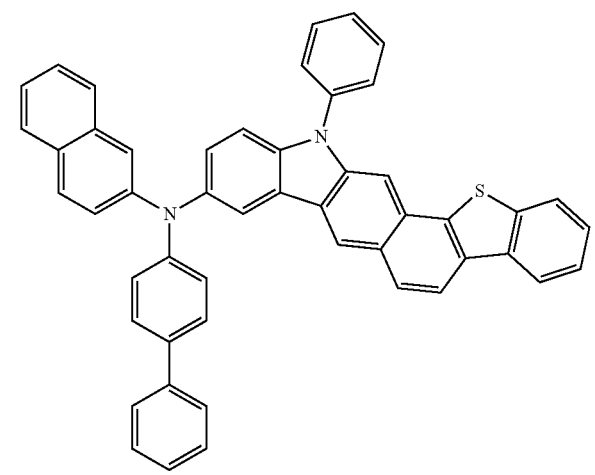
A 1-1-1

The reaction solution mixed with 1-1-1(A) (5.9 g, 12.33 mmol), Sub 2-6 (3.64 g, 12.33 mmol), Pd$_2$(dba)$_3$ (0.56 g, 0.62 mmol), P(t-Bu)$_3$ (0.25 g, 1.23 mmol), NaOt-Bu (1.78 g, 18.5 mmol) and toluene (129 mL) was stirred at 100° C. When the reaction was completed, the reaction product was extracted with ether and water. And then, the organic layer was dried with MgSO$_4$ and concentrated. Then, the concentrate was separated by silica gel column and recrystallized to obtain 7.09 g (yield: 83%) of the product.

Synthesis of A 1-1-19

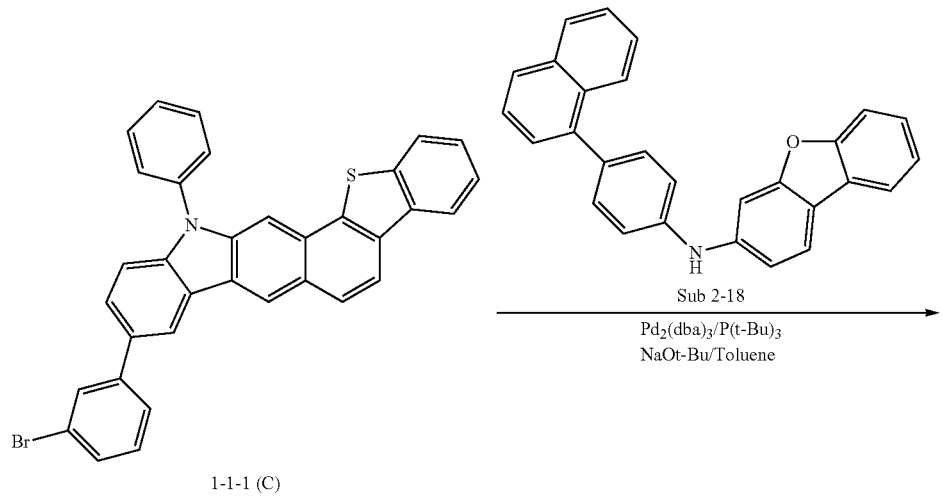

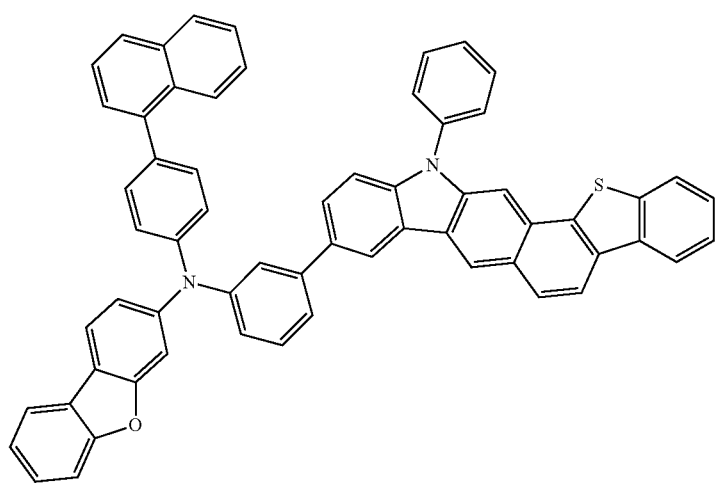

A 1-1-19

7.10 g (yield: 79%) of the product was obtained by reacting 1-1-1(C) (5.8 g, 10.46 mmol), Sub 2-18 (4.03 g, 10.46 mmol), Pd$_2$(dba)$_3$ (0.48 g, 0.52 mmol), P(t-Bu)$_3$ (0.21 g, 1.05 mmol), NaOt-Bu (1.51 g, 15.69 mmol) and toluene (110 mL) by the same method as in synthesis example of A 1-1-1.

Synthesis of A 1-1-28
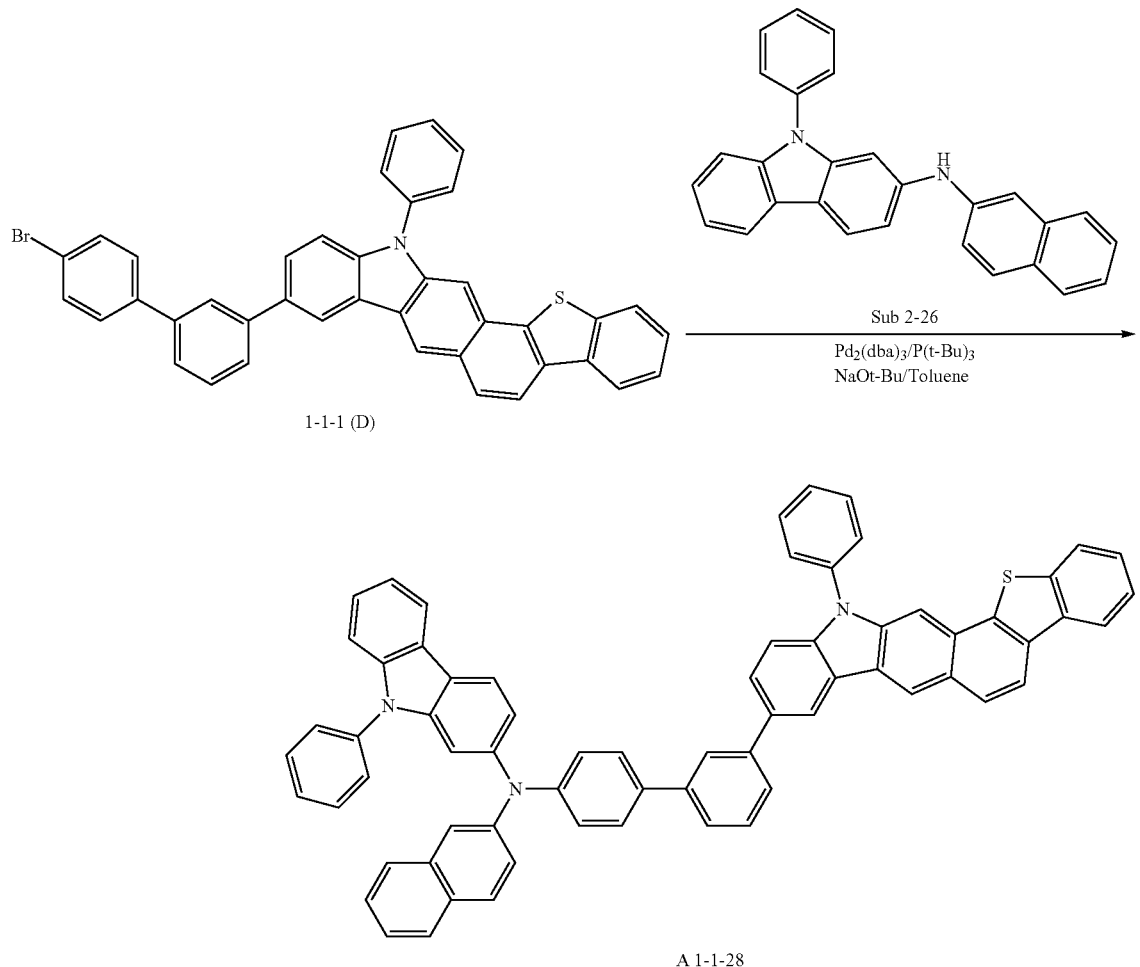
7.07 g (yield: 77%) of the product was obtained by reacting 1-1-1(D) (6.2 g, 9.83 mmol), Sub 2-26 (3.78 g, 9.83 mmol), Pd$_2$(dba)$_3$ (0.45 g, 0.49 mmol), P(t-Bu)$_3$ (0.20 g, 0.98 mmol), NaOt-Bu (1.42 g, 14.75 mmol) and toluene (103 mL) by the same method as in synthesis example of A 1-1-1.
Synthesis of A 1-2-26
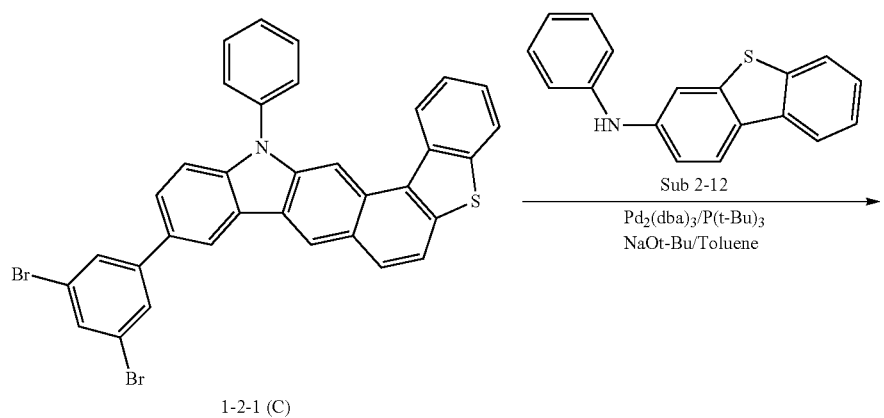

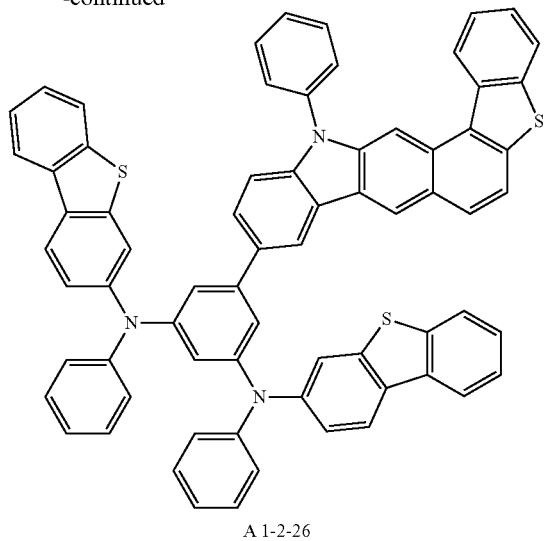
A 1-2-26
7.05 g (yield: 74%) of the product was obtained by reacting 1-2-1(C) (5.9 g, 9.32 mmol), Sub 2-12 (5.13 g, 18.63 mmol), Pd$_2$(dba)$_3$ (0.85 g, 0.93 mmol), P(t-Bu)$_3$ (0.38 g, 1.86 mmol), NaOt-Bu (2.69 g, 27.95 mmol) and toluene (98 mL) by the same method as in synthesis example of A 1-1-1.
Synthesis of A 2-1-14
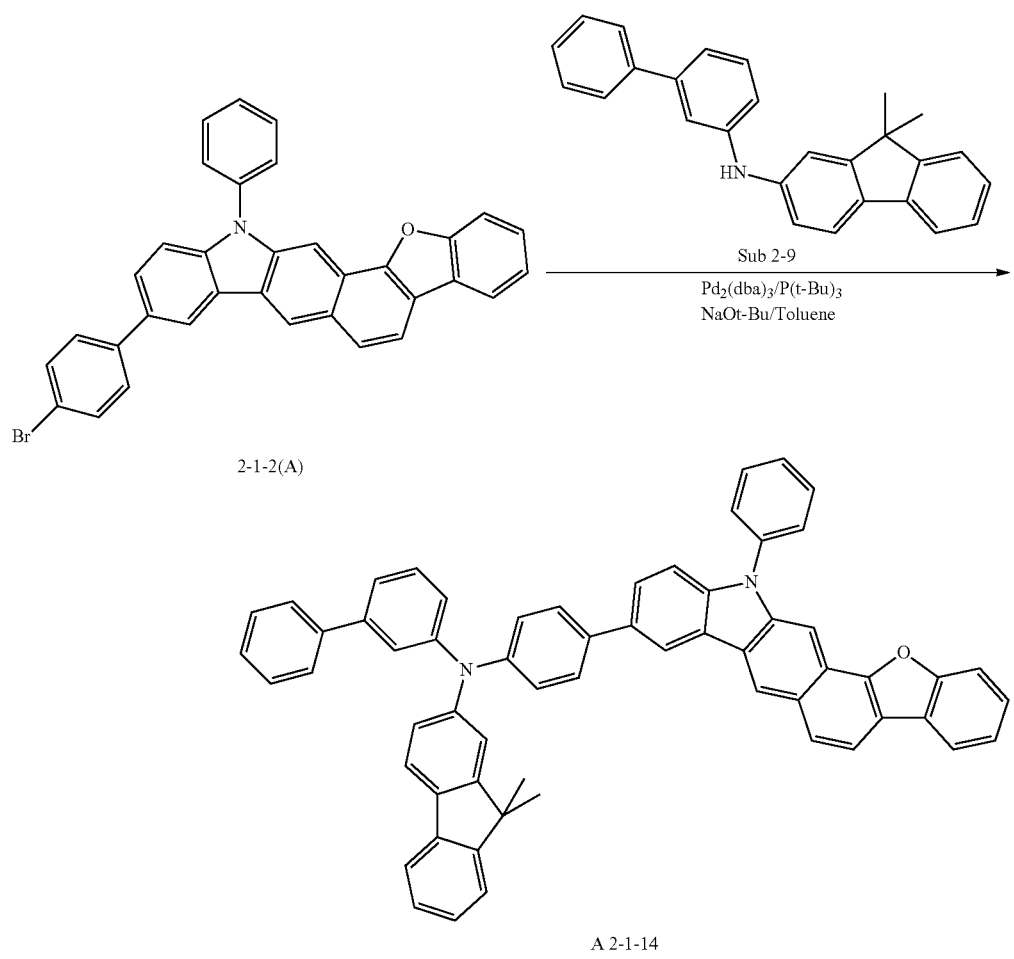
A 2-1-14

7.01 g (yield: 72%) of the product was obtained by reacting 2-1-2(A) (6.4 g, 11.89 mmol), Sub 2-9 (4.3 g, 11.89 mmol), Pd$_2$(dba)$_3$ (0.54 g, 0.59 mmol), P(t-Bu)$_3$ (0.24 g, 1.19 mmol), NaOt-Bu (1.71 g, 17.83 mmol) and toluene (125 mL) by the same method as in synthesis example of A 1-1-1.

Synthesis of A 3-1-10

7.09 g (yield: 70%) of the product was obtained by reacting 3-1-1(C) (8 g, 11.93 mmol), Sub 2-15 (3.09 g, 11.93 mmol), Pd$_2$(dba)$_3$ (0.55 g, 0.6 mmol), P(t-Bu)$_3$ (0.24 g, 1.19 mmol), NaOt-Bu (1.72 g, 17.89 mmol) and toluene (125 mL) by the same method as in synthesis example of A 1-1-1.

The FD-MS values of compounds 1-1-1 to 3-2-10 and A 1-1-1 to A 3-1-10 of the present invention manufactured according to the above synthesis examples are shown in Table 5 below.

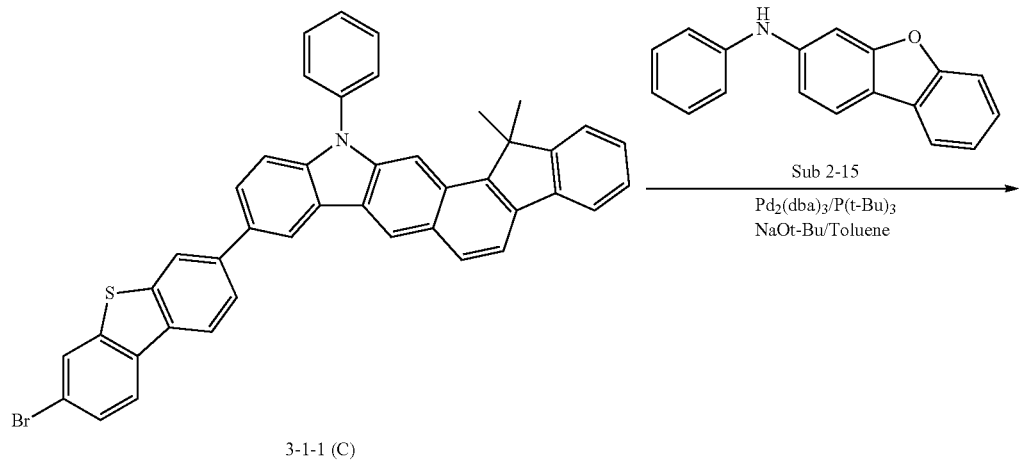

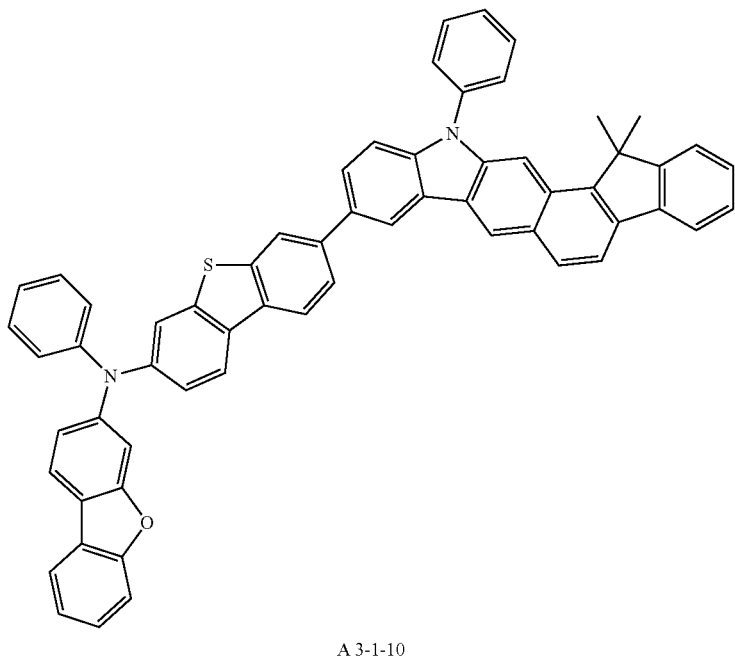

TABLE 5

FD-MS of final products

| compound | FD-MS | compound | FD-MS |
|---|---|---|---|
| 1-1-1 | m/z = 399.11($C_{28}H_{17}NS$ = 399.51) | 1-1-2 | m/z = 475.14($C_{34}H_{21}NS$ = 475.60) |
| 1-1-5 | m/z = 515.17($C_{37}H_{25}NS$ = 515.67) | 1-1-7 | m/z = 489.12($C_{34}H_{19}NOS$ = 489.59) |
| 1-1-10 | m/z = 577.16($C_{40}H_{23}N_3S$ = 577.70) | 1-1-10 | m/z = 627.18($C_{44}H_{25}N_3S$ = 627.75) |
| 1-1-23 | m/z = 677.19($C_{48}H_{27}N_3S$ = 677.81) | 1-1-26 | m/z = 733.16($C_{50}H_{27}N_3S_2$ = 733.90) |
| 1-1-31 | m/z = 633.13($C_{42}H_{23}N_3S_2$ = 633.78) | 1-1-40 | m/z = 693.19($C_{48}H_{27}N_3OS$ = 693.81) |
| 1-1-53 | m/z = 743.20($C_{52}H_{29}N_3OS$ = 743.87) | 1-1-56 | m/z = 785.20($C_{54}H_{31}N_3S_2$ = 785.97) |
| 1-1-57 | m/z = 900.24($C_{62}H_{36}N_4S_2$ = 901.11) | 1-1-60 | m/z = 826.16($C_{56}H_{30}N_2S_3$ = 827.05) |
| 1-2-1 | m/z = 399.11($C_{28}H_{37}NS$ = 399.51) | 1-2-20 | m/z = 677.19($C_{48}H_{27}N_3S$ = 677.81) |
| 1-2-41 | m/z = 689.11($C_{44}H_{23}N_3S_3$ = 689.87) | 2-1-2 | m/z = 383.13($C_{28}H_{17}NO$ = 383.44) |
| 2-1-15 | m/z = 687.23($C_{50}H_{29}N_3O$ = 687.78) | 2-1-26 | m/z = 717.19($C_{50}H_{27}N_3OS$ = 717.83) |
| 2-1-32 | m/z = 643.17($C_{44}H_{25}N_3OS$ = 643.75) | 2-1-37 | m/z = 657.15($C_{44}H_{23}N_3O_2S$ = 657.74) |
| 2-2-1 | m/z = 383.13($C_{28}H_{37}NO$ = 383.44) | 2-2-7 | m/z = 537.18($C_{38}H_{23}N_3O$ = 537.61) |
| 2-2-20 | m/z = 661.22($C_{38}H_{27}N_3O$ = 661.75) | 2-2-29 | m/z = 643.17($C_{44}H_{25}N_3OS$ = 643.75) |
| 3-1-1 | m/z = 409.18($C_{31}H_{23}N$ = 409.52) | 3-1-4 | m/z = 499.19($C_{37}H_{25}NO$ = 499.60) |
| 3-1-11 | m/z = 637.25($C_{47}H_{31}N$ = 637.77) | 3-2-12 | m/z = 703.26($C_{51}H_{33}N_3O$ = 703.83) |
| 3-2-16 | m/z = 643.21($C_{45}H_{29}N_3S$ = 643.80) | 3-2-1 | m/z = 409.18($C_{31}H_{23}N$ = 409.52) |
| 3-2-9 | m/z = 637.25($C_{47}H_{31}N_3$ = 637.77) | 3-2-10 | m/z = 693.22($C_{49}H_{31}N_3S$ = 693.86) |
| A 1-1-1 | m/z = 692.23($C_5H_3N_2S$ = 692.87) | A 1-1-2 | m/z = 672.17($C_{46}H_{28}N_2S_2$ = 672.86) |
| A 1-1-5 | m/z = 768.26($C_{56}H_{38}N_2S$ = 768.96) | A 1-1-8 | m/z = 782.24($C_{56}H_{34}N_2OS$ = 782.95) |
| A 1-1-9 | m/z = 794.28($C_{58}H_{38}N_2S$ = 795.00) | A 1-1-10 | m/z = 858.27($C_{62}H_{38}N_2OS$ = 859.04) |
| A 1-1-15 | m/z = 768.26($C_{56}H_{36}N_2S$ = 768.96) | A 1-1-16 | m/z = 794.28($C_{58}H_{38}N_2S$ = 795.00) |
| A 1-1-19 | m/z = 858.27($C_{62}H_{38}N_2OS$ = 859.04) | A 1-1-21 | m/z = 809.29($C_{58}H_{39}N_3S$ = 810.02) |
| A 1-1-28 | m/z = 933.32($C_{68}H_{43}N_3S$ = 934.15) | A 1-2-26 | m/z = 1021.26($C_{70}H_{43}N_3S_3$ = 1022.31) |
| A 2-1-1 | m/z = 676.25($C_{50}H_{32}N_2O$ = 676.80) | A 2-1-5 | m/z = 752.28($C_{56}H_{36}N_2O$ = 752.90) |
| A 2-1-10 | m/z = 716.25($C_{52}H_{32}N_2O_2$ = 716.82) | A 2-1-14 | m/z = 818.33($C_{61}H_{42}N_2O$ = 819.00) |
| A 2-1-15 | m/z = 752.28($C_{56}H_{36}N_2O$ = 752.90) | A 2-1-16 | m/z = 778.30($C_{58}H_{38}N_2O$ = 778.94) |
| A 2-2-1 | m/z = 676.25($C_{50}H_{32}N_2O$ = 676.80) | A 2-2-6 | m/z = 752.28($C_{56}H_{36}N_2O$ = 752.90) |
| A 2-2-9 | m/z = 778.30($C_{58}H_{38}N_2O$ = 778.94) | A 3-1-1 | m/z = 702.30($C_{53}H_{38}N_2$ = 702.88) |
| A 3-1-5 | m/z = 778.33($C_{59}H_{42}N_2$ = 778.98) | A 3-1-6 | m/z = 804.35($C_{61}H_{44}N_2$ = 805.02) |
| A 3-1-10 | m/z = 818.33($C_{63}H_{42}N_2O$ = 819.00) | | |

In the above, even though an exemplary synthesis example of the present invention represented by the Formula 1 are described, all of them are based on Buchwald-Hartwig cross coupling reaction, Pd(II)-catalyzed oxidative cyclization reaction (*Org. Lett.* 2011, 13, 5504), Miyaura boration reaction and Suzuki cross-coupling reaction. It will be understood by those skilled in the art that the above reaction proceeds even when other substituents (substituents of $R^1$-$R^{12}$, $L^1$, $Ar^1$ and the like) defined in Formula 1 are bonded, in addition to the substituents described in the specific synthesis example.

The above reactions will proceed even if a substituent not specifically mentioned is attached. (A method of synthesizing a core containing Si is described in J. AM. CHEM. SOC. 2008, 130, 7670-7685)

Fabrication and Evaluation of Organic Electronic Element

[Example 1] Red OLED (Phosphorescent Host)

Organic light emitting diodes (OLEDs) were fabricated according to a conventional method by using a compound of the present invention as luminous host material of a light emitting layer. First, an ITO layer (anode) was formed on a glass substrate, and then a film of $N^1$-(naphthalen-2-yl)-$N^4$,$N^4$-bis(4-(naphthalen-2-yl(phenyl)amino)phenyl)-$N^1$-phenylbenzene-1,4-diamine (hereinafter, "2-TNATA") was vacuum-deposited on the ITO layer to form a hole injection layer with a thickness of 60 nm. Subsequently, a film of NPD as a hole transport compound was vacuum-deposited with a thickness of 60 nm on the hole injection layer to form a hole transport layer. A light emitting layer with a thickness of 30 nm was formed on the hole transport layer by depositing the compound 1-1-1 of the present invention as a host material and (piq)$_2$Ir(acac) as a dopant material in a weight ratio of 90:10. Next, (1,1'-bisphenyl)-4-olato)bis(2-methyl-8-quinolinolato)aluminum (hereinafter, "BAlq") was vacuum-deposited with a thickness of 10 nm on the light emitting layer to form a hole blocking layer, and a film of tris(8-quinolinolato)aluminum (hereinafter abbreviated as "Alq$_3$") was formed with a thickness of 40 nm to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 2] to [Example 25] Red OLED

The OLEDs were fabricated in the same manner as described in Example 1, except that any one of the compounds of the present invention described in Table 6 below was used as the red host material of a light emitting layer, instead of the inventive compound 1-1-1.

[Comparative Example 1] to [Comparative Example 4]

The OLEDs were fabricated in the same manner as described in Example 1, except that any one of the following Comparative compounds 1 to 4 was used as host material of a light emitting layer, instead of the inventive compound 1-1-1.

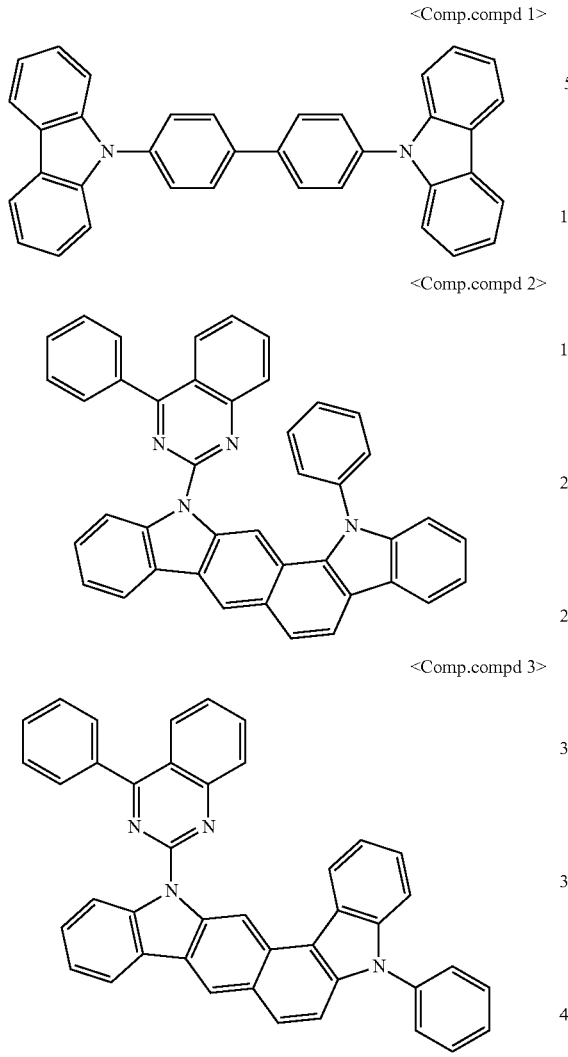
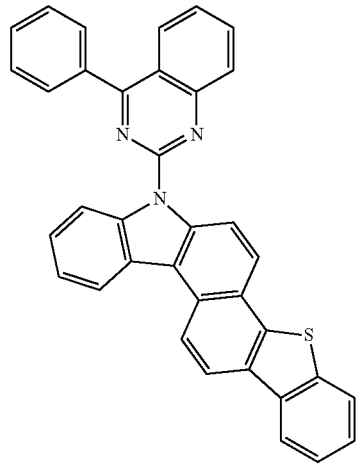

Electroluminescence (EL) characteristics were measured with a PR-650(Photoresearch) by applying a forward bias DC voltage to the OLEDs prepared in Examples 1 to 25 of the present invention and Comparative Examples 1 to 4. And, the T95 life time was measured using a life time measuring apparatus manufactured by Macscience Inc. at reference brightness of 2500 cd/m². The measured results are shown in Table 6 below.

TABLE 6

|  | compound | Voltage (V) | Current Density (mA/cm²) | Brightness (cd/m²) | Efficiency (cd/A) | Lifetime T(95) | CIE X | CIE Y |
|---|---|---|---|---|---|---|---|---|
| comp. Ex(1) | comp. Com 1 | 6.6 | 35.2 | 2500 | 7.1 | 63.3 | 0.65 | 0.31 |
| comp. Ex(2) | comp. Com 2 | 6.3 | 27.2 | 2500 | 8.5 | 79.5 | 0.66 | 0.32 |
| comp. Ex(3) | comp. Com 3 | 6.2 | 29.1 | 2500 | 7.7 | 71.5 | 0.65 | 0.32 |
| comp. Ex(4) | comp. Com 4 | 6.2 | 32.1 | 2500 | 9.1 | 86.2 | 0.65 | 0.31 |
| Ex.(1) | Com. 1-1-1 | 5.4 | 20.3 | 2500 | 12.3 | 120.1 | 0.66 | 0.31 |
| Ex.(2) | Com. 1-1-4 | 5.3 | 19.5 | 2500 | 12.8 | 123.7 | 0.65 | 0.32 |
| Ex.(3) | Com. 1-1-7 | 5.4 | 20.2 | 2500 | 12.4 | 132 | 0.66 | 0.32 |
| Ex.(4) | Com. 1-1-10 | 5.4 | 20.5 | 2500 | 12.2 | 136 | 0.66 | 0.31 |
| Ex.(5) | Com. 1-1-13 | 5.3 | 19.8 | 2500 | 12.6 | 139.2 | 0.66 | 0.31 |
| Ex.(6) | Com. 1-1-23 | 5.3 | 18.8 | 2500 | 13.3 | 142.4 | 0.65 | 0.31 |
| Ex.(7) | Com. 1-1-31 | 5.1 | 14.2 | 2500 | 17.6 | 157.7 | 0.66 | 0.31 |
| Ex.(8) | Com. 1-1-41 | 5.1 | 15.2 | 2500 | 16.5 | 150.3 | 0.65 | 0.31 |
| Ex.(9) | Com. 1-1-58 | 5.3 | 14.9 | 2500 | 16.8 | 147.2 | 0.66 | 0.32 |
| Ex.(10) | Com. 1-2-1 | 5.4 | 20.8 | 2500 | 12 | 117.7 | 0.65 | 0.31 |
| Ex.(11) | Com. 1-2-20 | 5.4 | 19.5 | 2500 | 12.8 | 138.7 | 0.66 | 0.32 |
| Ex.(12) | Com. 1-2-41 | 5.3 | 16.2 | 2500 | 15.4 | 142.3 | 0.66 | 0.32 |
| Ex.(13) | Com. 2-1-2 | 5.4 | 21.2 | 2500 | 11.8 | 115.4 | 0.66 | 0.31 |
| Ex.(14) | Com. 2-1-26 | 5.4 | 19.4 | 2500 | 12.9 | 139.6 | 0.66 | 0.32 |
| Ex.(15) | Com. 2-1-32 | 5.3 | 16.4 | 2500 | 15.2 | 136.2 | 0.66 | 0.32 |
| Ex.(16) | Com. 2-1-37 | 5.2 | 14.8 | 2500 | 16.9 | 149.2 | 0.66 | 0.31 |
| Ex.(17) | Com. 2-2-1 | 5.3 | 21.0 | 2500 | 11.9 | 113.7 | 0.66 | 0.31 |

TABLE 6-continued

| compound | | Voltage (V) | Current Density (mA/cm$^2$) | Brightness (cd/m$^2$) | Efficiency (cd/A) | Lifetime T(95) | CIE X | CIE Y |
|---|---|---|---|---|---|---|---|---|
| Ex.(18) | Com. 2-2-20 | 5.3 | 20.3 | 2500 | 12.3 | 131.2 | 0.66 | 0.31 |
| Ex.(19) | Com. 2-2-29 | 5.2 | 16.9 | 2500 | 14.8 | 134.5 | 0.65 | 0.31 |
| Ex.(20) | Com. 3-1-1 | 5.5 | 22.5 | 2500 | 10.9 | 109.7 | 0.66 | 0.32 |
| Ex.(21) | Com. 3-1-11 | 5.5 | 21.4 | 2500 | 11.7 | 116.9 | 0.66 | 0.31 |
| Ex.(22) | Com. 3-1-16 | 5.5 | 18.9 | 2500 | 13.2 | 125.6 | 0.66 | 0.31 |
| Ex.(23) | Com. 3-2-1 | 5.5 | 23.8 | 2500 | 9.5 | 98.7 | 0.66 | 0.31 |
| Ex.(24) | Com. 3-2-9 | 5.5 | 22.5 | 2500 | 10.1 | 111.5 | 0.65 | 0.31 |
| Ex.(25) | Com. 3-2-10 | 5.5 | 20.5 | 2500 | 12.2 | 120.2 | 0.66 | 0.31 |

From the results shown in Table 6 above, it is confirmed that the luminous efficiency and lifetime of device are remarkably improved when the compound according to an embodiment of the present invention was used as a phosphorescent host material of a light emitting layer, compared with any one of Comparative compounds 1 to 4

Particularly, comparing six-ring heterocyclic compounds comprising two 5-membered rings, while the Comparative compounds 2 and 3 are each N—N type having N as a hetero atom in two 5-membered, the compounds of the present invention are the type having different hetero atoms such as N—S, N—O, N—CR'R" or N—SiR'R". It was confirmed that the the luminous efficiency and lifetime of device are remarkably improved when the inventive compound was used as a phosphorescent host material, compared to the Comparative compound.

Generally, when molecules are stacked, they have strong electrical interactions as the number of adjacent π-electrongs increases, which is closely related to the charge carrier mobility.

In the case of the N—N type six-ring cyclic compound of Comparative Compound 2 and Comparative Compound 3, when molecules are stacked, the order of intermolecular arrangement shows the form of edge-to-face due to heterocyclic core having the homo-type such as N—N type. It is believed that this causes low charge carrier mobility and low oxidation stability.

In addition, comparing the comparative compounds 2 and 3, their core has the same fused position and two hetero atoms comprised in the core are opposite to each other in direction. It can be seen that the Comparative compound 2 in which two heteroatoms are located in the same direction with respect to the axis shows the better performance than the Comparative compound 3 in which two heteroatoms are located in the opposite direction. It is considered that this is because the Comparative compound 3 has a relatively non-linear structure compared to the Comparative compound 2 and thus the charge transfer from the host to the dopant is not smooth as the difference of the T1 value between the host and the dopant increases.

The six-ring cyclic compound of the present invention has a heterocyclic core in which heteroatoms are different from each other. Therefore, the compound of the present invention has the antiparallel cofacial it-stacking structure as the molecular packing structure. This allows the molecules to be arranged as form of the face-to-face. It is believed that the steric effect of Ar1 bonded to heteroatom N, wherein the heteroatom arranged asymmetrically is the cause of the packing structure, causes significantly higher carrier mobility and thus the efficiency of device is increased and the lifetime of device is significantly increased due to high oxidation stability.

In addition, comparing Comparative compound 4 with the compound of the present invention, T1 and the energy band gap are dependent on the fused position of the six-ring cyclic compound, that is, the degree of twist of the molecular, wherein Comparative compound 4 and the inventive compound are similar in having N—S type in the six-ring cyclic compound, but have difference in the fused position of carbazole core.

The core of the inventive compound has a structure that is less bent than the Comparative compound 4, and thus the T1 value of the inventive compound is relatively lower. Therefore, it is seen that the efficiency is increased because the charge transfer from the host to the dopant is smooth and the number of surplus polarons is decreased.

Particularly, the compound having a specific substituent such as benzothienopyrimidine or benzofuropyrimidine of the inventive compounds exhibits the best device results, compared to the compound having general aryl groups or general heterocyclic groups as a substituent. It is believed that this is because the inventive compound has a structure suitable for accommodating both holes and electrons by introducing two nitrogen atoms (N) into the core (dibenzothiophene, dibenzofuran) having strong hole characteristics, resulting in the easier charge balance of holes and electrons and thus the light emission in the light emitting layer is performed efficiently.

From the result of table 6 above, it is suggested that the efficiency and the lifetime may be dependent on the type of heteroatom included in six-ring cyclic compound. That is, it is seen that the band gap, the electrical characteristics, the interface characteristics and the like can be largely changed depending on the kind and the bonding position of substituent. Particularly, in the case of phosphorescent host, because the correlation of the hole transfer layer and the dopant is grasped, even if a similar core is used, it will be very difficult to deduce the excellent electrical characteristics of the inventive compound showing in the phosphorescent host.

[Example 26] Green OLED (a Hole Transport Layer)

Organic light emitting diodes (OLEDs) were fabricated according to a conventional method by using a compound of the present invention as a hole transport layer material. First, an ITO layer (anode) was formed on a glass substrate, and then 2-TNATA was vacuum-deposited on the ITO layer to form a hole injection layer with a thickness of 60 nm. Subsequently, the compound A 1-1-1 of the present invention was vacuum-deposited with a thickness of 60 nm on the hole injection layer to form a hole transport layer. Subsequently, a light emitting layer with a thickness of 30 nm was formed on the hole transport layer by depositing 4,4'-N,N'- dicarbazole-biphenyl (hereinafter, "CBP") as a host material and tris(2-phenylpyridine)-iridium (hereinafter, "Ir(ppy)₃") as a dopant material in a weight ratio of 90:10. Next, BAlq was vacuum-deposited with a thickness of 10 nm on the light emitting layer to form a hole blocking layer, and Alq₃ was vacuum-deposited with a thickness of 40 nm on the hole blocking layer to form an electron transport layer. Next, LiF as halogenated alkali metal was deposited with a thickness of 0.2 nm on the electron transport layer to form an electron injection layer, and then Al was deposited with a thickness of 150 nm on the electron injection layer to form a cathode. In this way, the OLED was completed.

[Example 27] to [Example 49] Green OLED (a Hole Transport Layer)

The OLEDs were fabricated in the same manner as described in Example 26, except that any one of the compounds 1-1-2 to A 3-1-6 of the present invention described in Table 7 below was used as the hole transport layer material, instead of the inventive compound A 1-1-1.

[Comparative Example 5] to [Comparative Example 7]

Comparative example 5 was fabricated in the same manner as described in example 26 above, except that comparative compound 5 was used as the hole transport layer material, instead of the inventive compound A 1-1-1.

Comparative example 6 was fabricated in the same manner as described in example 26 above, except that comparative compound 6 instead of the compound A 1-1-1 of the present invention was used as the hole transport layer material.

Comparative example 7 was fabricated in the same manner as described in example 26 above, except that comparative compound 7 instead of the compound A 1-1-1 of the present invention was used as the hole transport layer material.

<Comp.compd 5>

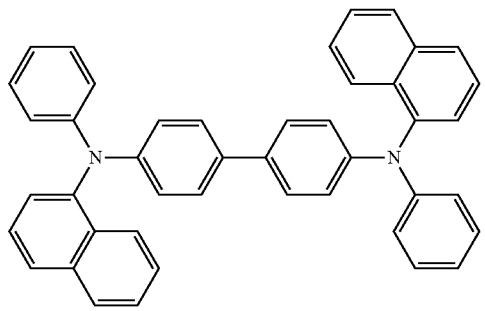

<Comp.compd 6>

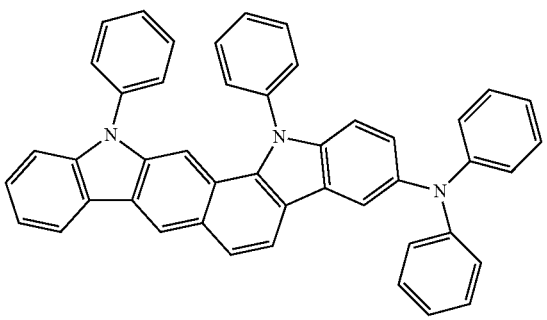

<Comp.compd 7>

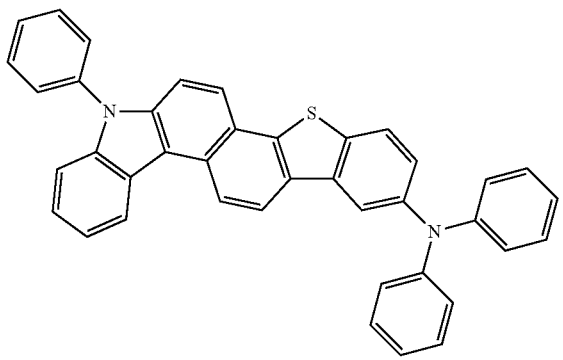

Electroluminescence (EL) characteristics were measured with a PR-650(Photoresearch) by applying a forward bias DC voltage to the OLEDs prepared in Examples 26 to 49 of the present invention and Comparative Examples 5 to 7. And, the T95 life time was measured using a life time measuring apparatus manufactured by Macscience Inc. at reference brightness of 5000 cd/m². The measured results are shown in Table 7 below.

TABLE 7

| | compound | Voltage (V) | Current Density (mA/cm²) | Brightness (cd/m²) | Efficiency (cd/A) | Lifetime T(95) | CIE x | y |
|---|---|---|---|---|---|---|---|---|
| comp. Ex(5) | comp. Com 5 | 5.8 | 21.7 | 5000 | 23 | 59.6 | 0.33 | 0.62 |
| comp. Ex(6) | comp. Com 6 | 5.7 | 18.7 | 5000 | 25.7 | 77 | 0.33 | 0.61 |
| comp. Ex(7) | comp. Com 7 | 5.5 | 17.7 | 5000 | 28.2 | 89.9 | 0.32 | 0.62 |
| Ex.(26) | Com. A 1-1-1 | 5.2 | 12.3 | 5000 | 40.6 | 141.2 | 0.33 | 0.61 |
| Ex.(27) | Com. A 1-1-2 | 5.3 | 11.5 | 5000 | 43.5 | 145.1 | 0.33 | 0.61 |
| Ex.(28) | Com. A 1-1-5 | 5.2 | 10.7 | 5000 | 46.7 | 149.3 | 0.33 | 0.61 |

TABLE 7-continued

|  | compound | Voltage (V) | Current Density (mA/cm$^2$) | Brightness (cd/m$^2$) | Efficiency (cd/A) | Lifetime T(95) | CIE x | CIE y |
|---|---|---|---|---|---|---|---|---|
| Ex.(29) | Com. A 1-1-8 | 5.2 | 10.3 | 5000 | 48.5 | 153.4 | 0.33 | 0.62 |
| Ex.(30) | Com. A 1-1-9 | 5.1 | 9.5 | 5000 | 52.6 | 158.2 | 0.33 | 0.62 |
| Ex.(31) | Com. A 1-1-10 | 5.1 | 9.4 | 5000 | 53.3 | 164.4 | 0.32 | 0.62 |
| Ex.(32) | Com. A 1-1-11 | 5.1 | 9.5 | 5000 | 52.8 | 161.5 | 0.32 | 0.62 |
| Ex.(33) | Com. A 1-1-15 | 5.2 | 9.7 | 5000 | 51.3 | 156.6 | 0.33 | 0.62 |
| Ex.(34) | Com. A 1-1-16 | 5.1 | 9.5 | 5000 | 52.8 | 159.2 | 0.32 | 0.62 |
| Ex.(35) | Com. A 1-1-21 | 5.2 | 11.0 | 5000 | 45.5 | 152.8 | 0.32 | 0.62 |
| Ex.(36) | Com. A 1-2-1 | 5.3 | 12.7 | 5000 | 39.5 | 136.2 | 0.32 | 0.61 |
| Ex.(37) | Com. A 1-2-6 | 5.3 | 11.9 | 5000 | 42.1 | 139.7 | 0.32 | 0.61 |
| Ex.(38) | Com. A 1-2-9 | 5.3 | 11.3 | 5000 | 44.3 | 142.8 | 0.33 | 0.61 |
| Ex.(39) | Com. A 2-1-1 | 5.3 | 14.0 | 5000 | 35.6 | 130.2 | 0.33 | 0.62 |
| Ex.(40) | Com. A 2-1-5 | 5.3 | 13.2 | 5000 | 37.8 | 133.5 | 0.32 | 0.62 |
| Ex.(41) | Com. A 2-1-10 | 5.3 | 12.5 | 5000 | 40.1 | 137.3 | 0.32 | 0.61 |
| Ex.(42) | Com. A 2-1-15 | 5.3 | 14.0 | 5000 | 35.8 | 132.2 | 0.32 | 0.61 |
| Ex.(43) | Com. A 2-1-16 | 5.3 | 13.4 | 5000 | 37.4 | 138.6 | 0.32 | 0.61 |
| Ex.(44) | Com. A 2-2-1 | 5.3 | 15.1 | 5000 | 33.2 | 125.2 | 0.33 | 0.62 |
| Ex.(45) | Com. A 2-2-6 | 5.3 | 14.2 | 5000 | 35.1 | 127.8 | 0.33 | 0.62 |
| Ex.(46) | Com. A 2-2-9 | 5.3 | 13.3 | 5000 | 37.6 | 130.4 | 0.32 | 0.62 |
| Ex.(47) | Com. A 3-1-1 | 5.4 | 16.3 | 5000 | 30.7 | 120.1 | 0.32 | 0.62 |
| Ex.(48) | Com. A 3-1-5 | 5.4 | 15.9 | 5000 | 31.5 | 122.9 | 0.33 | 0.62 |
| Ex.(49) | Com. A 3-1-6 | 5.4 | 15.3 | 5000 | 34.7 | 128 | 0.33 | 0.61 |

From the results shown in Table 7, it is confirmed that the luminous efficiency and lifetime of the organic electroluminescent device are remarkably improved when compounds of the present invention were used as a hole transport layer material, compared with Comparative compounds 5 to 7.

The inventive compound capable of using as hole transport layer material by introducing —N(R$^a$) (R$^b$) into a 6-ring heterocyclic core of the inventive compound has a high HOMO energy level, wherein HOMO energy level is the intrinsic properties of the material. This causes the charge balance to increases and the surplus polaron to decrease in the light emitting layer, and thus the interface deterioration and dopant quenching due to the surplus polar are reduced.

In the case of the N—N type six-ring cyclic compound of Comparative Compound 6, when molecules are stacked, the order of the intermolecular arrangement becomes the form of the edge-to-face since the heterocyclic core is the homo type of N—N type. It is considered that this causes low charge carrier mobility and low oxidation stability.

The packing structure of the molecule of the inventive compound comprising a six-ring cyclic compound is an antiparallel cofacial π-stacking structure since the inventive compound has the heterocyclic core in which heteroatoms are different from each other. This allows the molecules to be arranged as form of the face-to-face. It is believed that the steric effect of Ar1 bonded to heteroatom N, wherein the heteroatom arranged asymmetrically is the cause of the packing structure, causes significantly higher carrier mobility and thus the efficiency of device is increased and the lifetime of device is significantly increased due to high oxidation stability.

In addition, among the compounds of the present invention, the compound of non-linear type exhibited more performance than that of linear type, wherein non-linear type means that the core and the amine group are bonded to the linker (L$^1$, L') at the ortho- or meta-position and linear type means that the core and the amine group are bonded to the linker (L$^1$, L') at the para position. It is considered that this is because the bonding angle becomes smaller and thus T1 value becomes higher, resulting in improving the ability capable of blocking electron.

It is confirmed that the lifetime is remarkably improved as well as the low driving voltage and high luminous efficiency even when the compound of the present invention was used as a hole transporting layer material.

From the results shown in Table 7, it is difficult to infer the efficiency and lifetime due to the difference in the fused position and type and arrangement of heteroatom in the six-ring cyclic compound.

Although exemplary embodiments of the present invention have been described for illustrative purposes, those skilled in the art will appreciate that various modifications, additions and substitutions are possible, without departing from the scope and spirit of the invention as disclosed in the accompanying claims. Therefore, the embodiment disclosed in the present invention is intended to illustrate the scope of the technical idea of the present invention, and the scope of the present invention is not limited by the embodiment. The scope of the present invention shall be construed on the basis of the accompanying claims, and it shall be construed that all of the technical ideas included within the scope equivalent to the claims belong to the present invention.

The invention claimed is:

1. A compound of Formula 4 or 5:

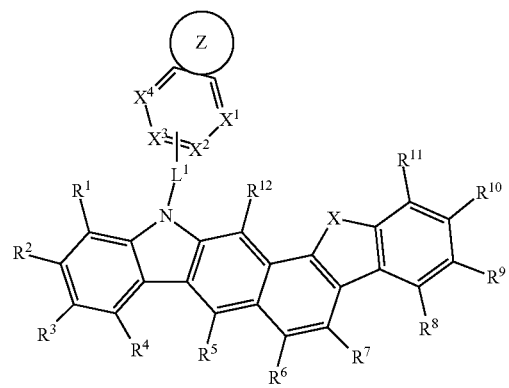

<Formula 4>

<Formula 5>

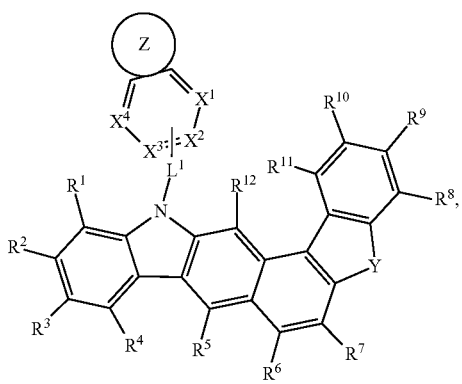

wherein:

X and Y are each O or S, $R^1$ to $R^{12}$ are each independently selected from the group consisting of hydrogen, deuterium, a halogen, a $C_6$-$C_{60}$ aryl group, a fluorenyl group, a $C_2$-$C_{60}$ heterocyclic group comprising at least one heteroatom selected from the group consisting of O, N, S, Si, and P, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_1$-$C_{50}$ alkynyl group, a $C_1$-$C_{30}$ alkoxyl group, a $C_6$-$C_{30}$ aryloxyl group, and -L'—N($R^a$)($R^b$), and neighboring groups of $R^1$ to $R^{12}$ are optionally linked to each other to form a ring, wherein L' is selected from the group consisting of a single bond; a $C_1$-$C_{60}$ arylene group; a fluorenylene group; a $C_2$-$C_{60}$ heterocyclic group comprising at least one heteroatom selected from the group consisting of O, N, S, Si, and P; and a fused ring of a $C_3$-$C_{60}$ aliphatic ring and a $C_6$-$C_{60}$ aromatic ring, and L' may be further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group and -N($R^a$)($R^b$), $R^a$ and $R^b$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a fused ring of a $C_3$-$C_{60}$ aliphatic ring and a $C_6$-$C_{60}$ aromatic ring, $L^1$ is selected from the group consisting of a single bond; a $C_6$-$C_{60}$ arylene group; a fluorenylene group; a $C_2$-$C_{60}$ heterocyclic group comprising at least one heteroatom selected from the group consisting of O, N, S, Si, and P; a fused ring formed by a $C_6$-$C_{60}$ aromatic ring and a $C_3$-$C_{60}$ aliphatic ring, and the moiety

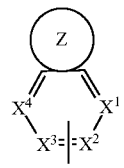

is represented by one of Formulas Z-3 to Z-10 and Z-15 to Z-22:

<FormulaZ-3>

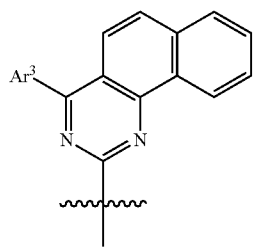

<FormulaZ-4>

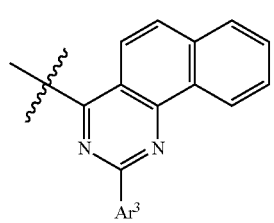

<FormulaZ-5>

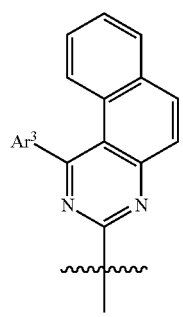

<FormulaZ-6>

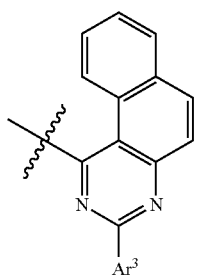

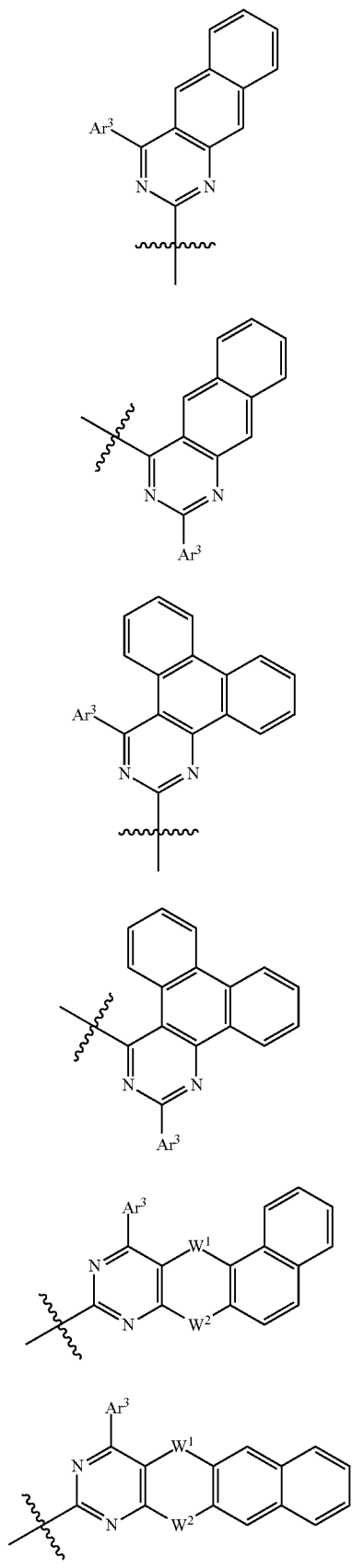

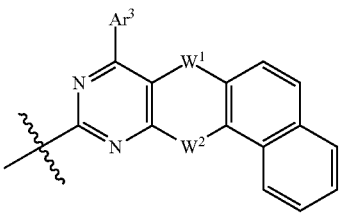

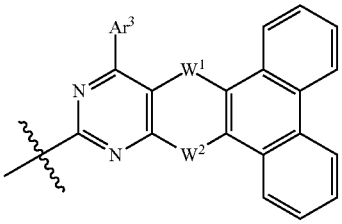

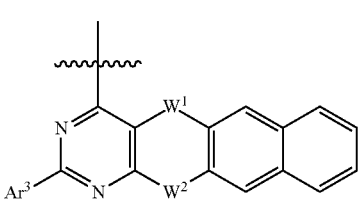

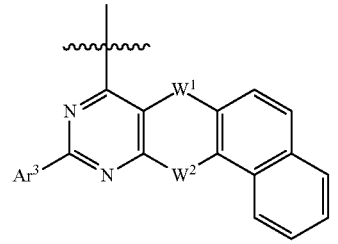

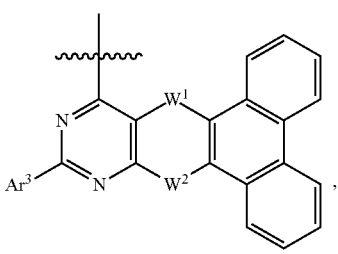

in Formulas Z-3 to Z10 and Z15 to Z-22:

$W^1$ and $W^2$ are each independently a single bond, $C(R^{13})(R^{14})$, $N(Ar^2)$, O or S, $Ar^2$ and $Ar^3$ is selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group comprising at least one heteroatom selected from the group consisting of O, N, S, Si, and P, and -L'-N($R^a$)($R^b$), and $R^{13}$ and $R^{14}$ are each independently selected from the group consisting of hydrogen, deuterium, a $C_1$-$C_{50}$) alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxyl group, a $C_1$-$C_{30}$ silyl group, a $C_6$-$C_{60}$ aryl group, a $C_2$-$C_{60}$ heterocyclic group comprising at least one heteroatom selected from the group consisting of O, N, S, Si, and P, a fluorenyl group, a fused ring group of a $C_6$-$C_{60}$ aromatic ring and a $C_3$-$C_{60}$ aliphatic ring, and -L'-N($R^a$)($R^b$), and $R^{13}$ and $R^{14}$ is optionally linked to each other to form a spiro-compound together with C to which $R^{13}$ and $R^{14}$ are bond.

2. The compound of claim 1, wherein L' is selected from the group of the following Formulas:

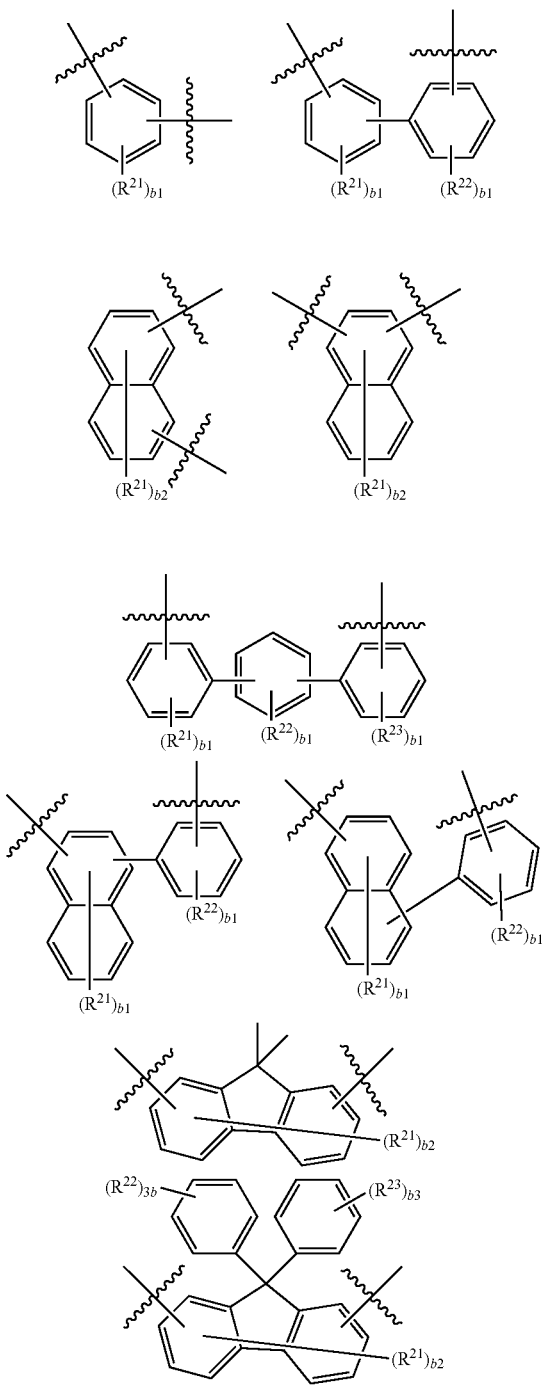

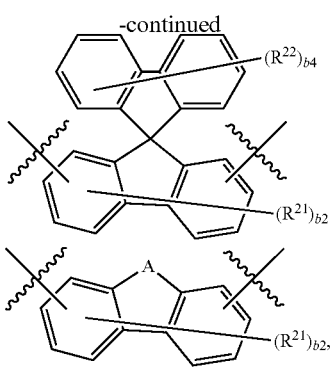

in the Formulas, $R^{21}$ to $R^{23}$ are each independently selected from the group consisting of hydrogen, deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group, and —N($R^a$)($R^b$), wherein $R^a$ and $R^b$ are the same as defined in claim 1, b1 is an integer of 0 to 4, b2 is an integer of 0 to 6, b3 is an integer of 0 to 5, b4 is an integer of 0 to 8, and when b1 to b4 are each an integer of 2 or more, neighboring $R^{21}$ to neighboring $R^{23}$ are optionally linked to each other to form a ring, and A is N($Ar^2$), O, S, C($R^{13}$)($R^{14}$) or Si($R^{13}$)($R^{14}$), wherein $Ar^2$ is the same as $Ar^2$ defined in claim 1 and $R^{13}$ and $R^{14}$ are the same as defined in claim 1.

3. An organic electric element comprising a first electrode, a second electrode, and an organic material layer formed between the first electrode and the second electrode, wherein the organic material layer comprises the compound of claim 1.

4. The organic electric element of claim 3, wherein the compound is comprised in at least one layer of a hole injection layer, a hole transport layer, an emission-auxiliary layer and a light emitting layer.

5. The organic electric element of claim 4, wherein the compound is used as phosphorescent host material of the light emitting layer.

6. The organic electric element of claim 4, wherein the compound is used as red phosphorescent host material of the light emitting layer.

7. The organic electric element of claim 3, further comprising a layer for improving luminous efficiency formed on one side of the first electrode and/or one side of the second electrode, the side facing the organic material layer.

8. The organic electric element of claim 3, wherein the organic material layer is formed by one of the processes of spin coating, nozzle printing, inkjet printing, slot coating, dip coating and roll-to-roll.

9. An electronic device comprising a display device and a control unit for driving the display device, wherein the display device comprises the organic electric element of claim 3.

10. The electronic device of claim 9, wherein the organic electric element is an organic light emitting diode, an organic solar cell, an organic photo conductor, an organic transistor, or an element for monochromatic or white illumination.

11. A compound represented by Formula 6:

[Formula 6]

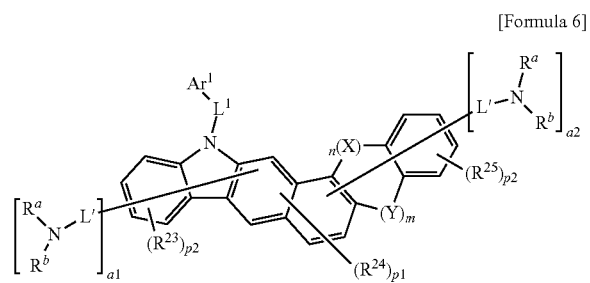

wherein:
a1 and a2 are each an integer of 0 or 1 and a1+a2=1, and p1 and p2 are each an integer of 0 to 4,
$Ar^1$ is selected from the group consisting of a $C_6$-$C_{60}$ aryl group, a fluorenyl group, a fused ring group of a $C_3$-$C_{60}$ aliphatic ring and a $C_6$-$C_{60}$ aromatic ring, a $C_2$-$C_{60}$ heterocyclic group including at least one heteroatom of O, N, S, Si or P, and -L'-$N(R^a)(R^b)$,
X and Y are each independently O, S, $C(R^{13})(R^{14})$, wherein $R^{13}$ and $R^{14}$ are each independently selected from the group consisting of hydrogen, deuterium, a $C_1$-$C_{50}$ alkyl group, a $C_2$-$C_{30}$ alkenyl group, a $C_2$-$C_{30}$ alkynyl group, a $C_1$-$C_{30}$ alkoxyl group, a $C_6$-$C_{30}$ aryloxyl group, a $C_1$-$C_{30}$ silyl group, a $C_6$-$C_{60}$ aryl group, a $C_2$-$C_{60}$ heterocyclic group comprising at least one heteroatom selected from the group consisting of O, N, S, Si, and P, a fluorenyl group, a fused ring group of a $C_6$-$C_{60}$ aromatic ring and a $C_3$-$C_{60}$ aliphatic ring, and -L'-$N(R^a)(R^b)$, and $R^{13}$ and $R^{14}$ is optionally linked to each other to form a spiro-compound together with C or Si to which $R^{13}$ and $R^{14}$ are bond,
m and n are each an integer of 0 or 1, and m+n is an integer of 1 or 2,
$R^{23}$, $R^{24}$ and $R^{25}$ are each independently selected from the group consisting of hydrogen, deuterium, a halogen, a $C_6$-$C_{60}$ aryl group, a fluorenyl group, a $C_2$-$C_{60}$ heterocyclic group comprising at least one heteroatom selected from the group consisting of O, N, S, Si, and P, a fused ring group of a $C_6$-$C_{60}$ aromatic ring and a $C_3$-$C_{60}$ aliphatic ring, a $C_1$-$C_{50}$ alkyl group, a $C_2$-$C_{20}$ alkenyl group, a $C_1$-$C_{50}$ alkynyl group, a $C_1$-$C_{30}$ alkoxyl group, a $C_6$-$C_{30}$ aryloxyl group, and -L'-$N(R^a)(R^b)$, and neighboring groups of $R^{23}$, $R^{24}$ and $R^{25}$ are optionally linked to each other to form a ring,
$L^1$ is selected from the group consisting of a single bond; a $C_6$-$C_{60}$ arylene group; a fluorenylene group; a $C_2$-$C_{60}$ heterocyclic group comprising at least one heteroatom selected from the group consisting of O, N, S, Si, and P; a fused ring formed by a $C_6$-$C_{60}$ aromatic ring and a $C_3$-$C_{60}$ aliphatic ring,
L' is selected from the group consisting of a single bond; a $C_6$-$C_{60}$ arylene group; a fluorenylene group; a $C_2$-$C_{60}$ heterocyclic group comprising at least one heteroatom selected from the group consisting of O, N, S, Si, and P; and a fused ring of a $C_3$-$C_{60}$ aliphatic ring and a $C_6$-$C_{60}$ aromatic ring, and L' may be further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group, a $C_8$-$C_{20}$ arylalkenyl group and —$N(R^a)(R^b)$, $R^a$ and $R^b$ are each independently selected from the group consisting of a $C_6$-$C_{60}$ aryl group; a fluorenyl group; a $C_2$-$C_{60}$ heterocyclic group containing at least one heteroatom selected from the group consisting of O, N, S, Si, and P; and a fused ring of a $C_3$-$C_{60}$ aliphatic ring and a $C_6$-$C_{60}$ aromatic ring, and
where $R^{23}$ to $R^{25}$, $L^1$, $Ar^1$, $R^a$ and $R^b$ are each an aryl group, a fluorenyl group, a heterocyclic group, a fused ring group, an alkyl group, an alkenyl group, an alkynyl group, an alkoxyl group, an aryloxy group, an arylene group or a fluorenylene group, they may be each further substituted with one or more substituents selected from the group consisting of deuterium, halogen, a silane group, a siloxane group, a boron group, a germanium group, a cyano group, a nitro group, a $C_1$-$C_{20}$ alkylthio group, a $C_1$-$C_{20}$ alkoxyl group, a $C_1$-$C_{20}$ alkyl group, a $C_2$-$C_{20}$ alkenyl group, a $C_2$-$C_{20}$ alkynyl group, a $C_6$-$C_{20}$ aryl group, a $C_6$-$C_{20}$ aryl group substituted with deuterium, a fluorenyl group, a $C_2$-$C_{20}$ heterocyclic group containing at least one heteroatom selected from the group consisting of O, N, S, Si, and P, a $C_3$-$C_{20}$ cycloalkyl group, a $C_7$-$C_{20}$ arylalkyl group and a $C_8$-$C_{20}$ arylalkenyl group.

12. An organic electric element comprising a first electrode, a second electrode, and an organic material layer formed between the first electrode and the second electrode, wherein the organic material layer comprises the compound of claim 11.

13. An electronic device comprising a display device and a control unit for driving the display device, wherein the display device comprises the organic electric element of claim 12.

14. A compound selected from the group consisting of the following compounds:

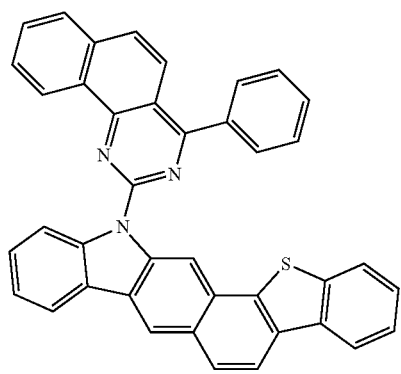
1-1-11
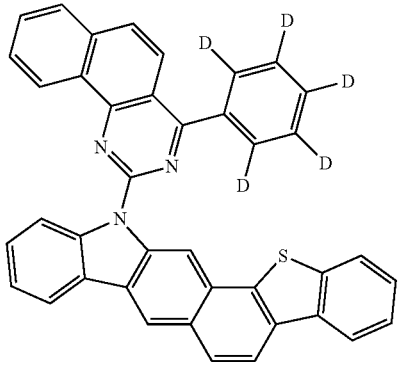
1-1-12
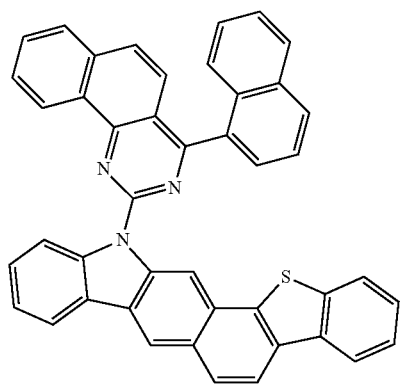
1-1-13
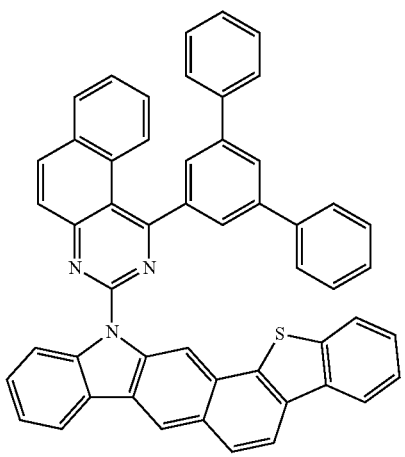
1-1-14
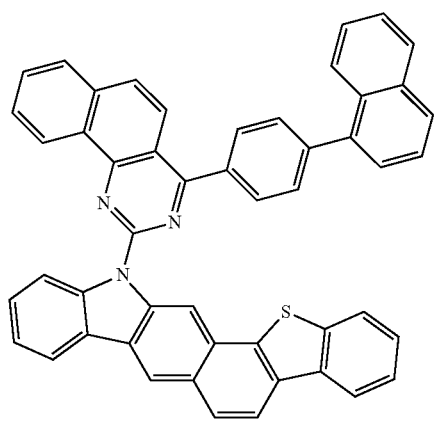
1-1-15
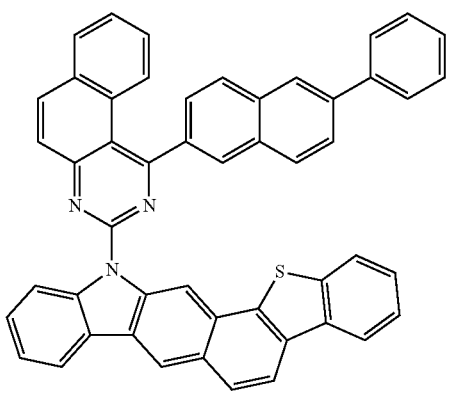
1-1-16

1-1-17
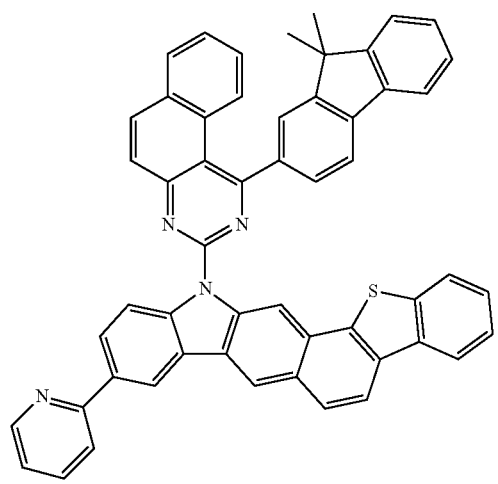
1-1-18
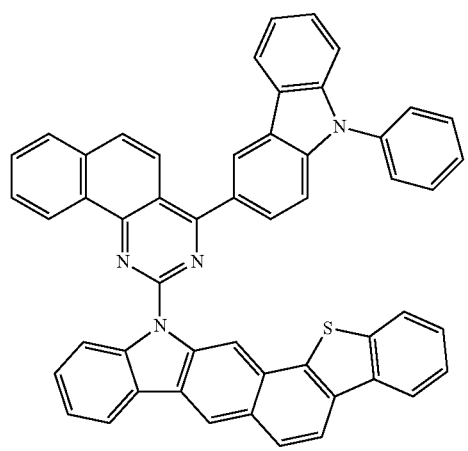
1-1-19
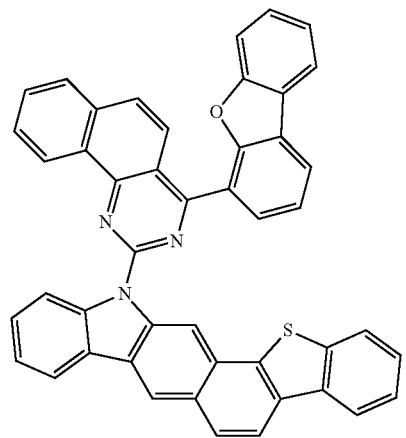
1-1-20
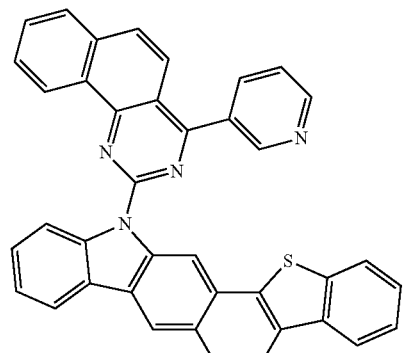
1-1-21
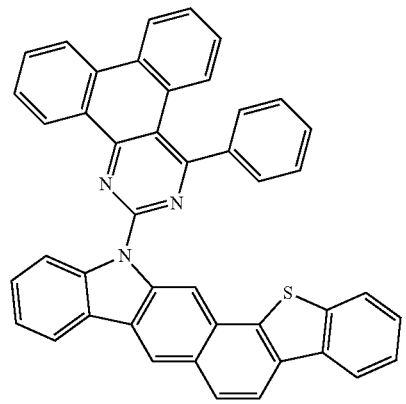
1-1-22
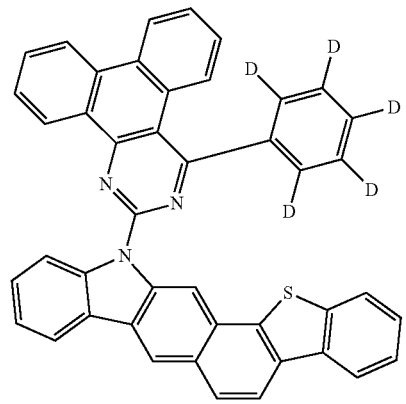

-continued
1-1-23
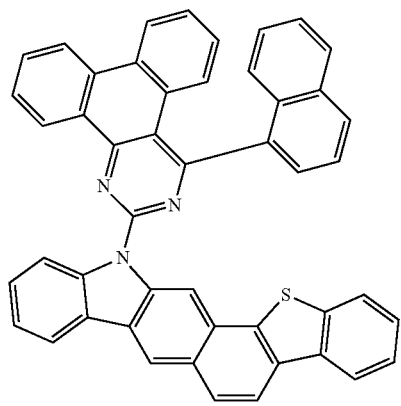
1-1-24
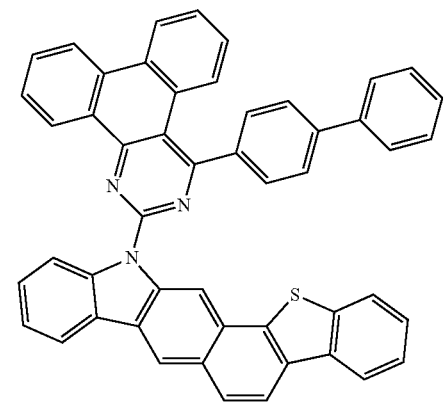
1-1-25
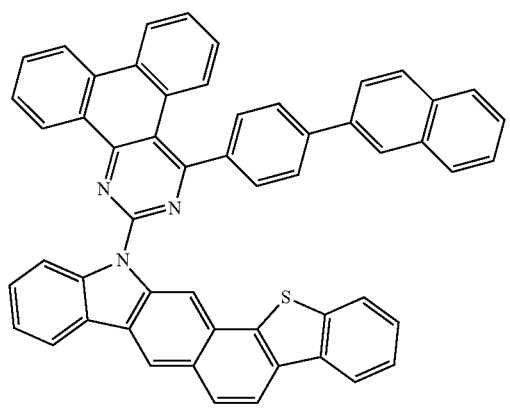
1-1-26
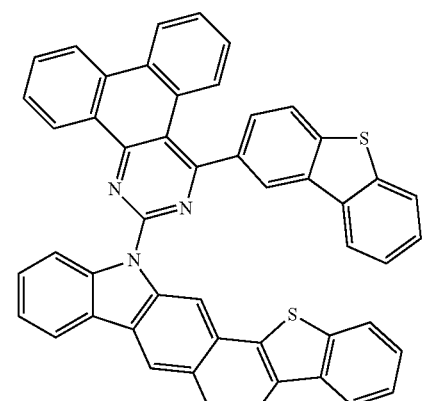
1-1-27
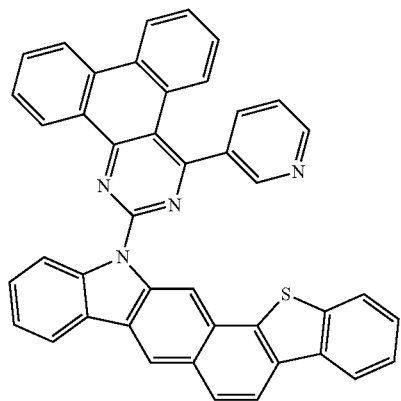
1-1-28
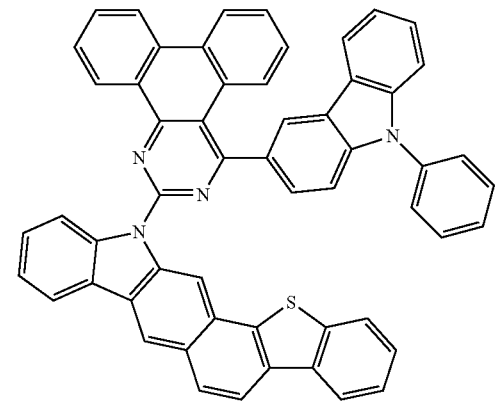
1-1-43
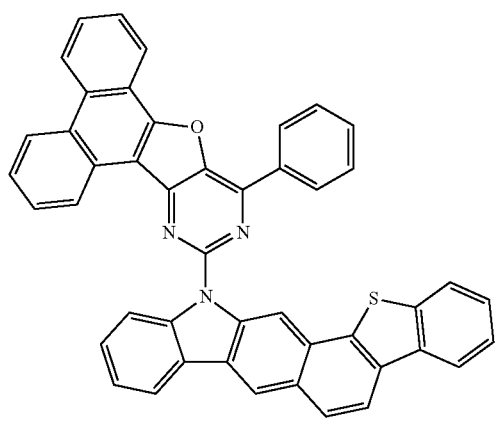
1-1-44
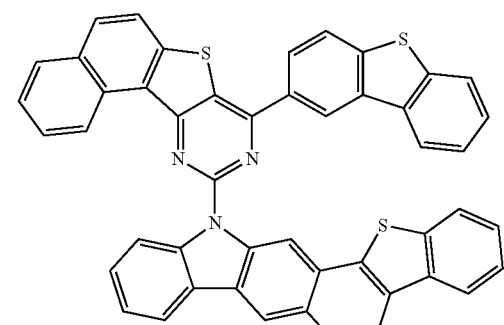

1-1-46 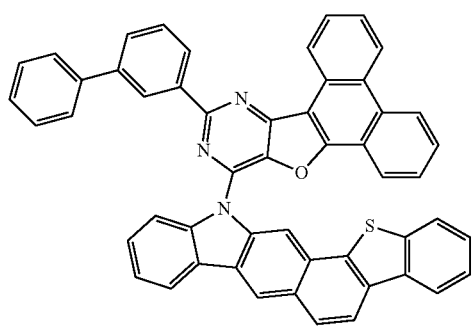
1-1-48 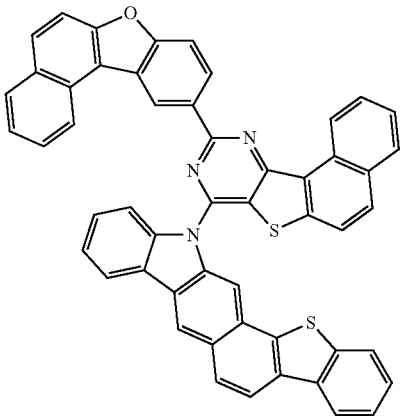
1-1-55 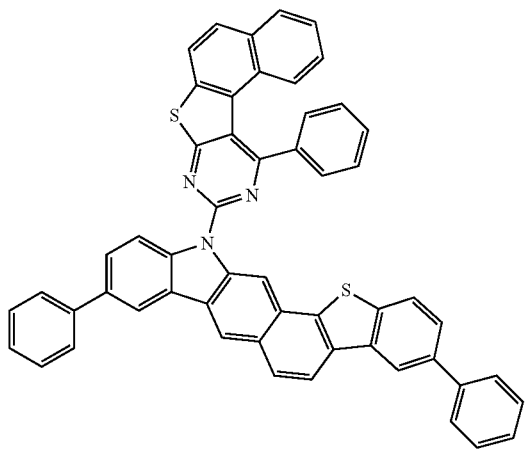
1-1-59 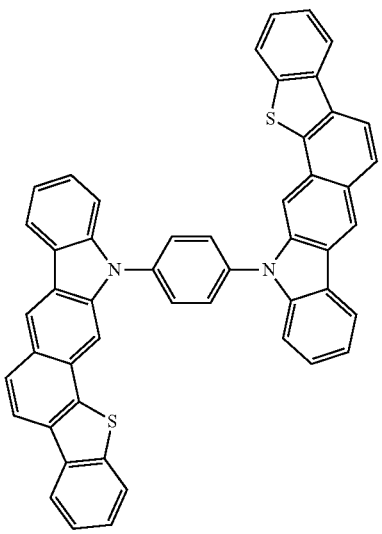
1-1-60 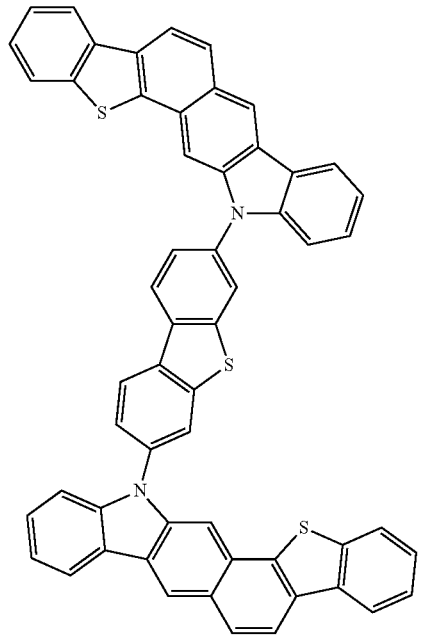
1-1-61 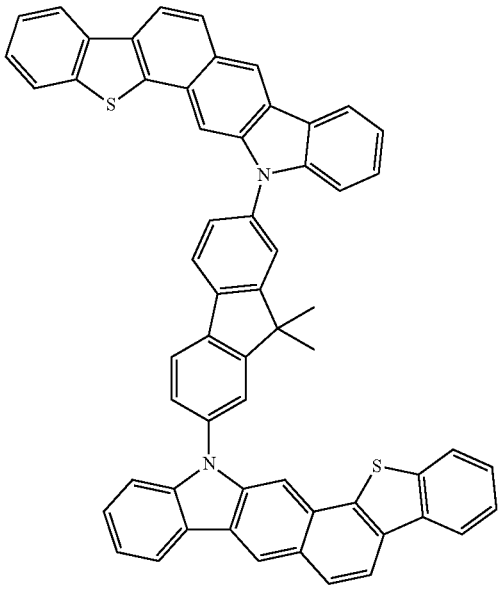

-continued
1-1-62
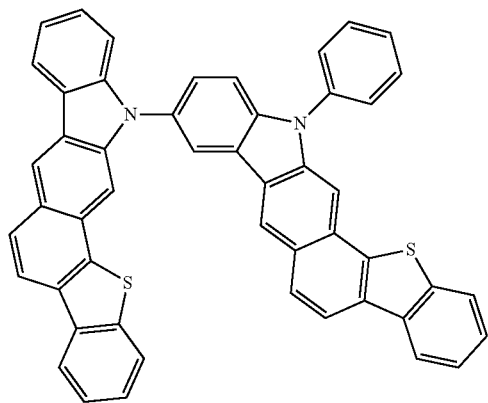
1-1-63
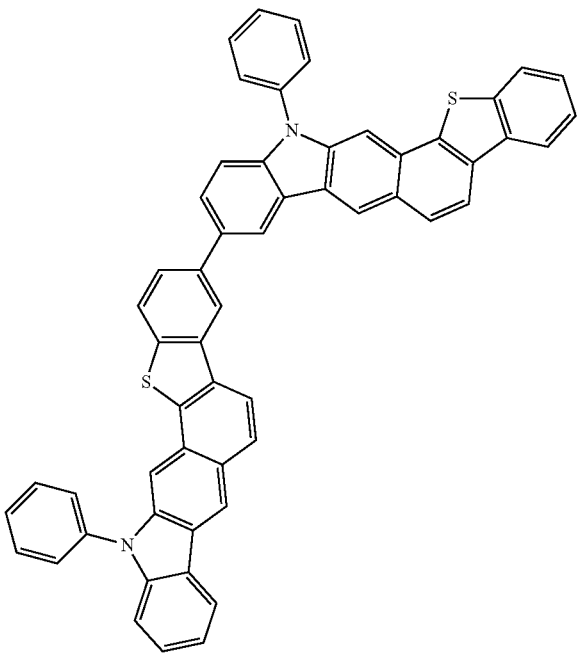
1-2-9
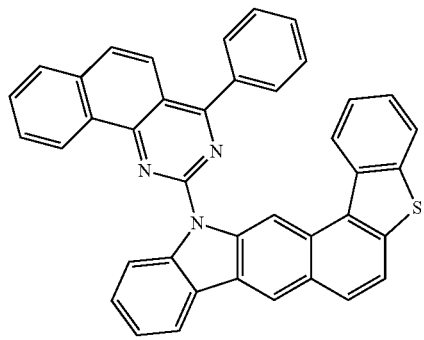
1-2-10
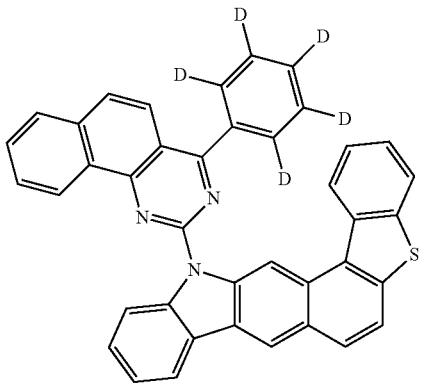
1-2-11
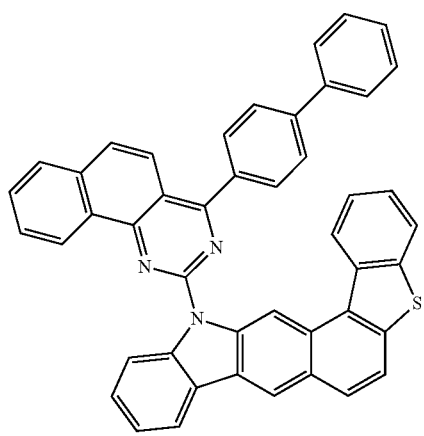
1-2-12
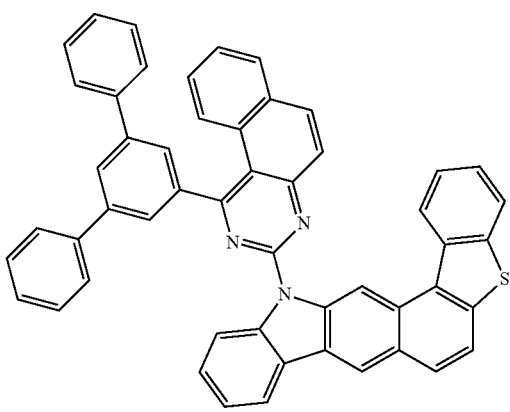

-continued
1-2-13
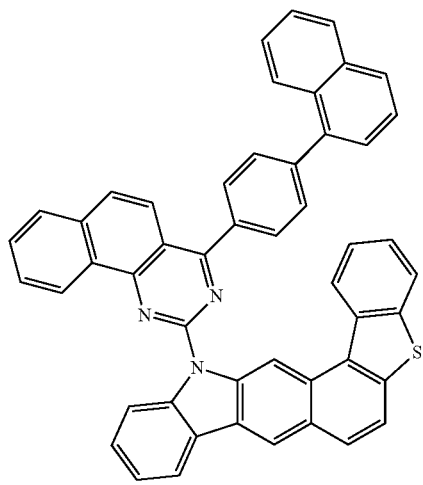
1-2-14
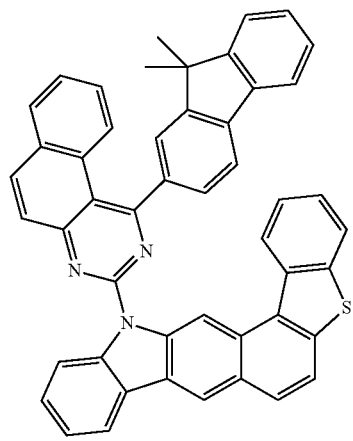
1-2-15
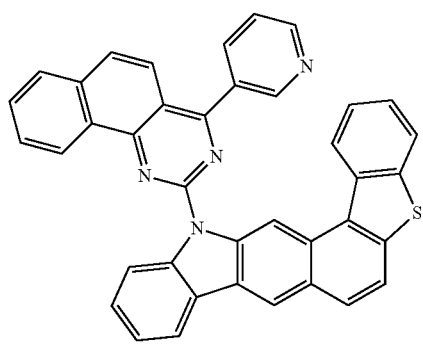
1-2-16
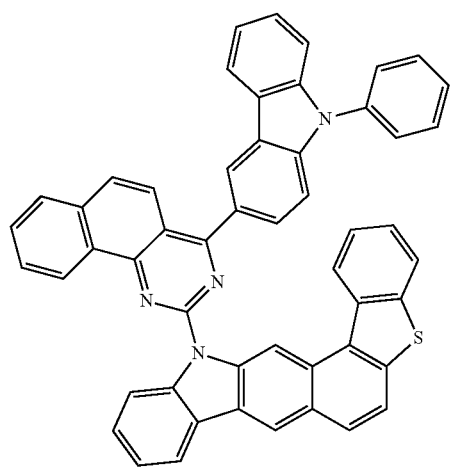
1-2-17
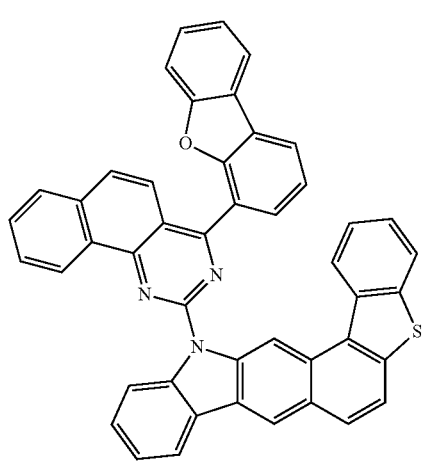
1-2-18
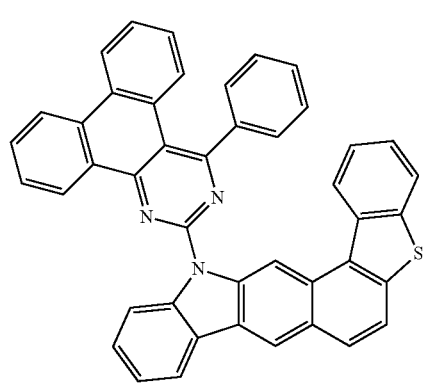

-continued
1-2-19
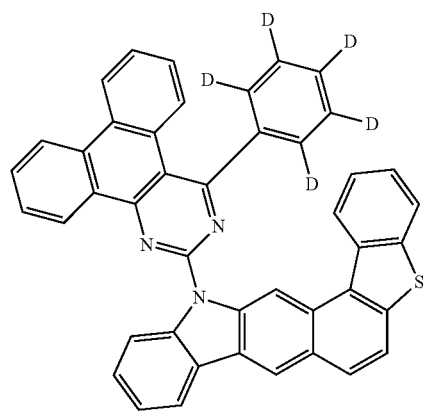
1-2-20
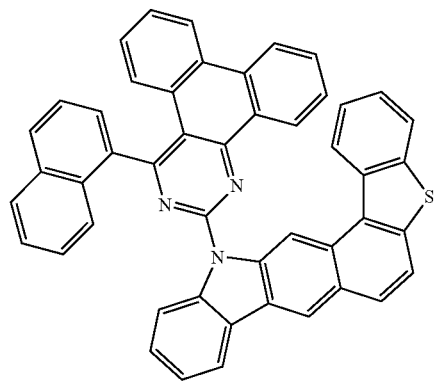
1-2-21
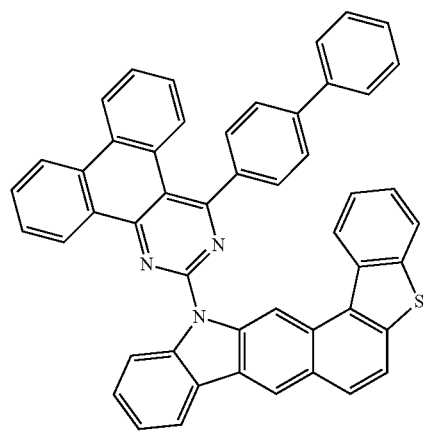
1-2-22
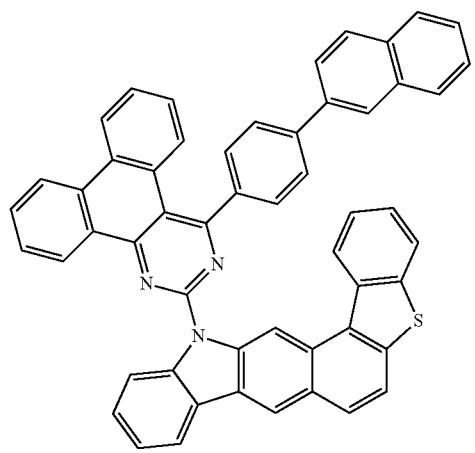
1-2-23
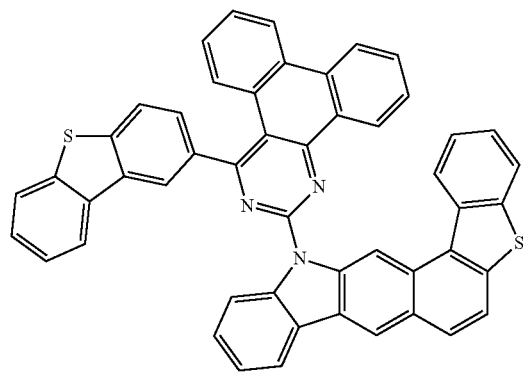
1-2-24
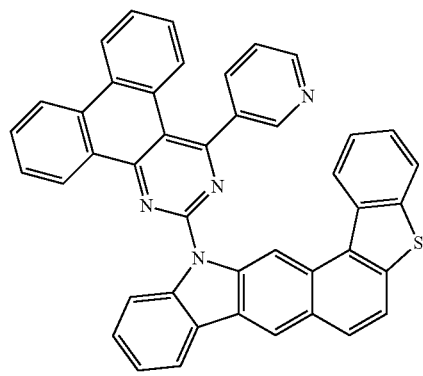

-continued
1-2-25
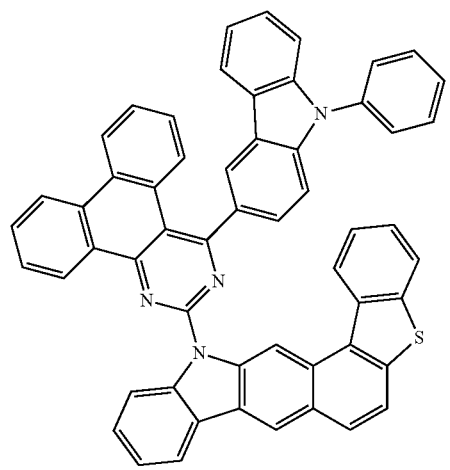
1-2-38
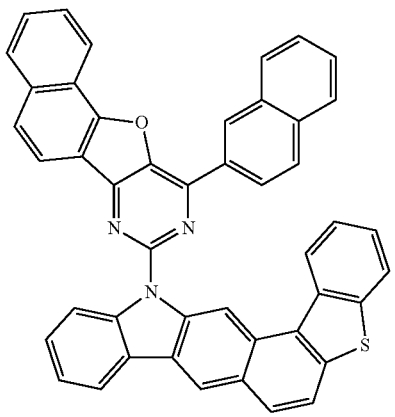
1-2-39
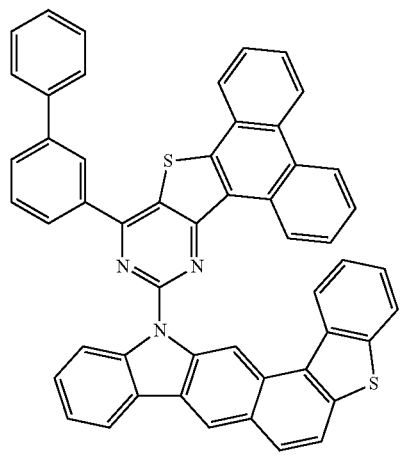
1-2-40
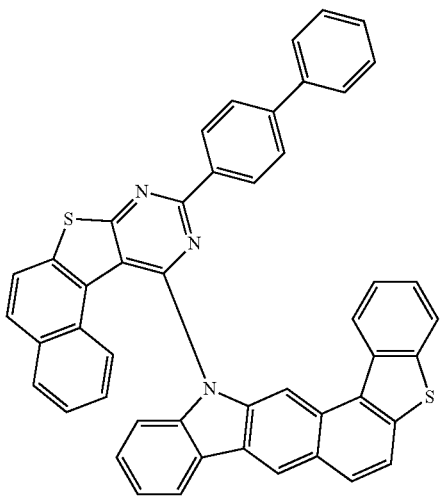
1-2-42
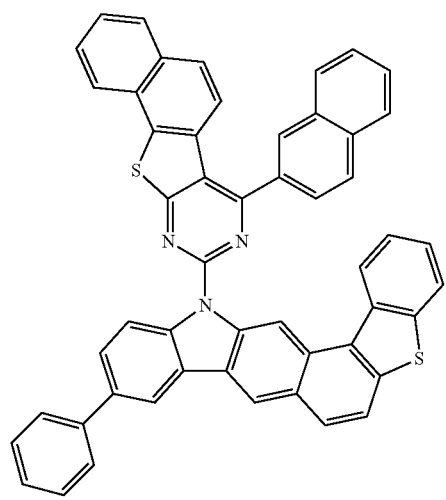
1-2-46
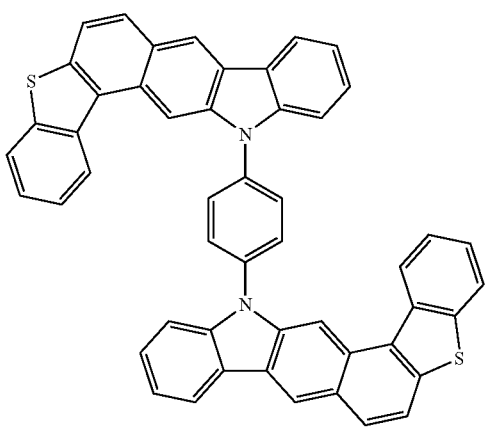

-continued
1-2-47
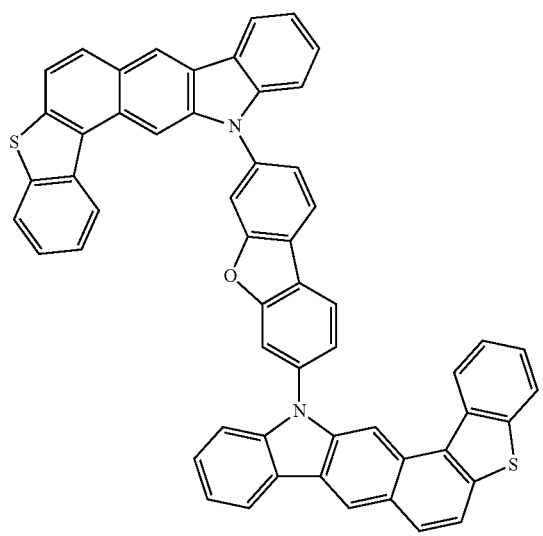
1-2-48
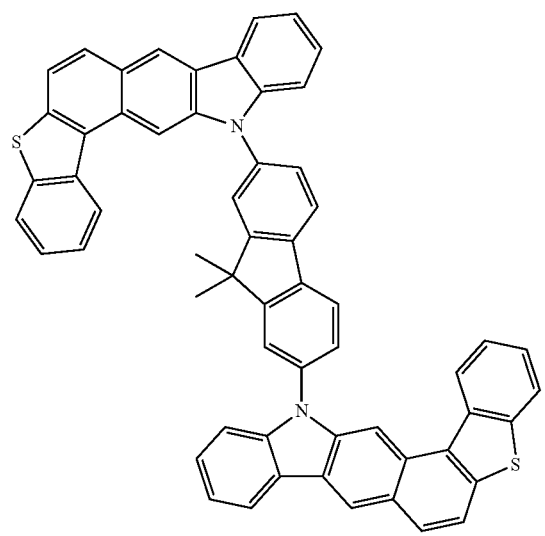
1-2-49
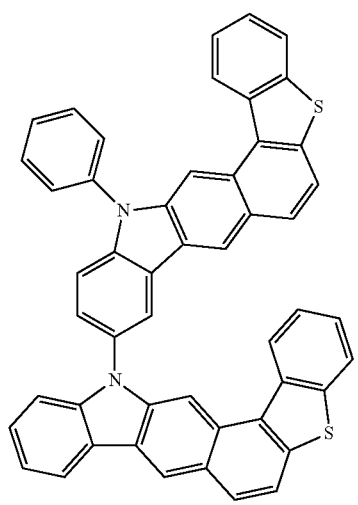
1-2-50
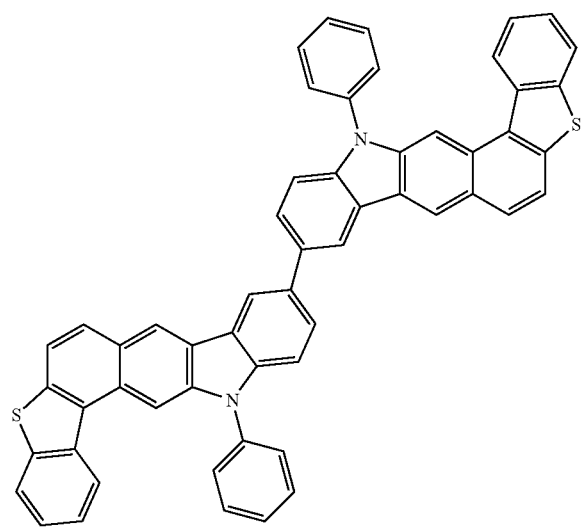
2-1-11
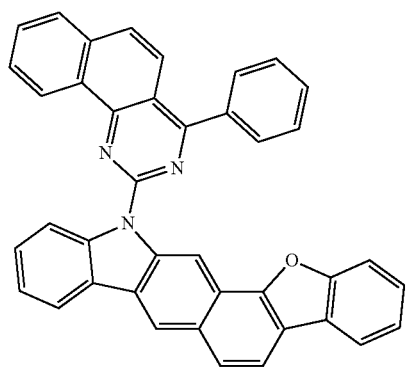
2-1-12
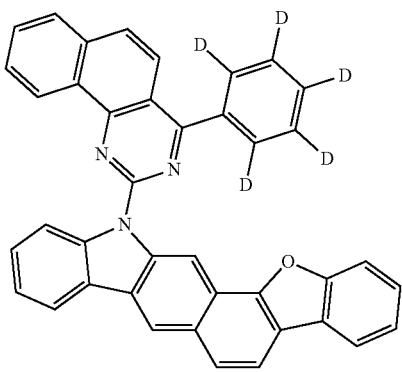

-continued
2-1-13
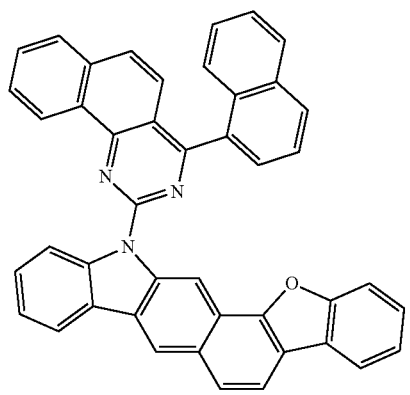
2-1-14
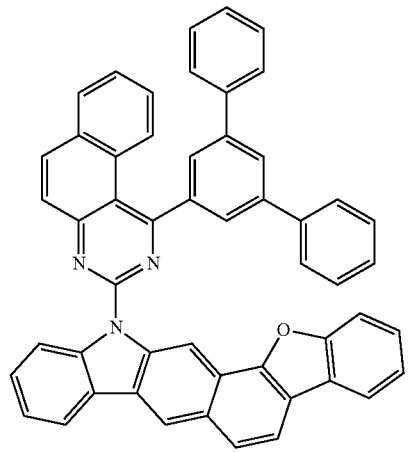
2-1-15
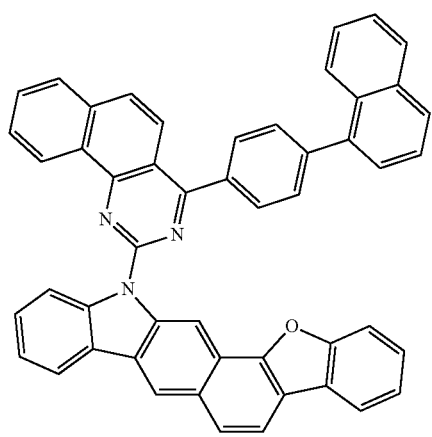
2-1-16
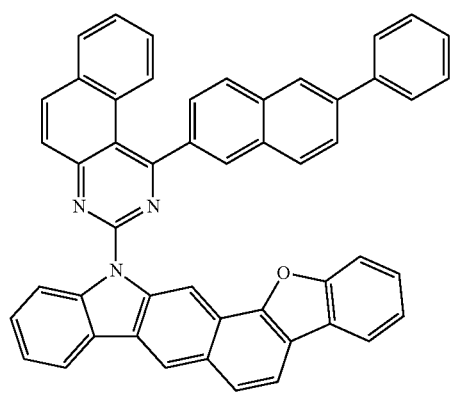
2-1-17
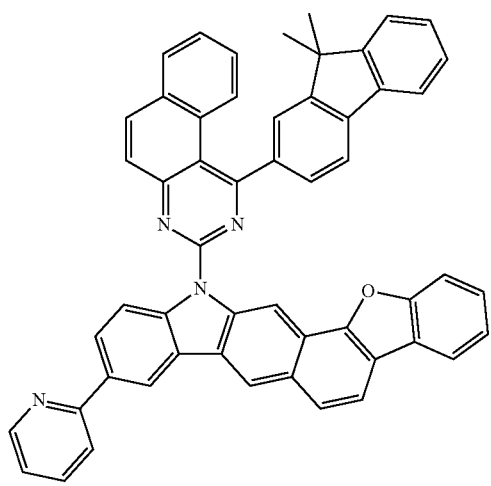
2-1-18
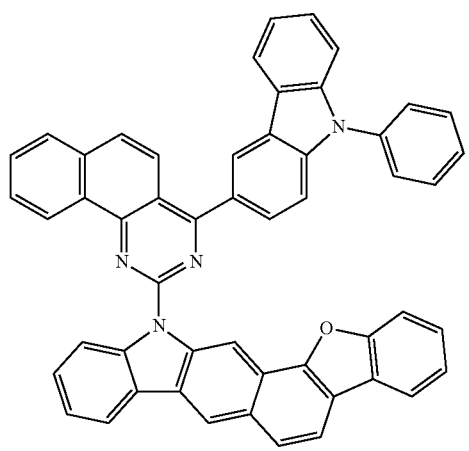

-continued
2-1-19
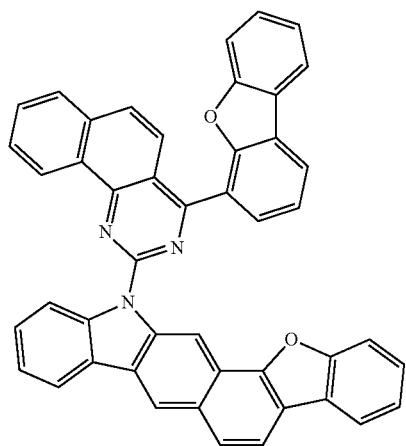
2-1-20
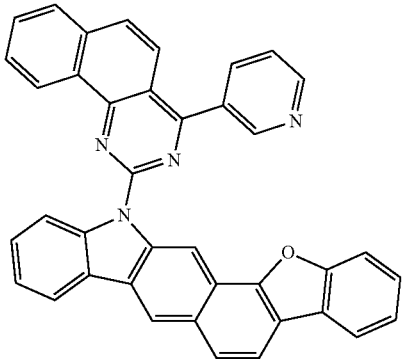
2-1-21
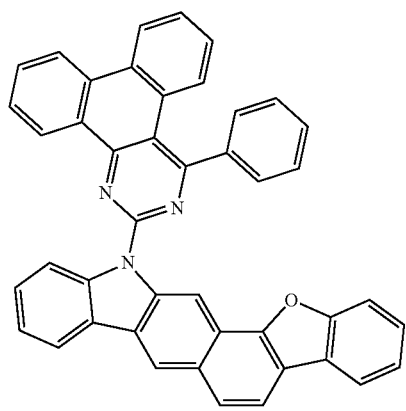
2-1-22
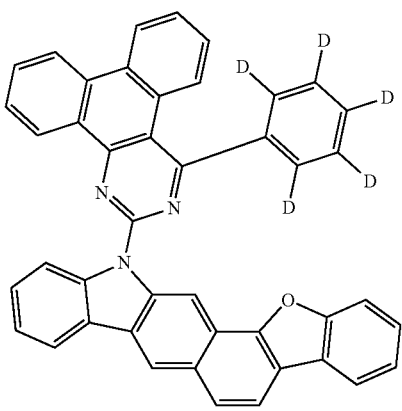
2-1-23
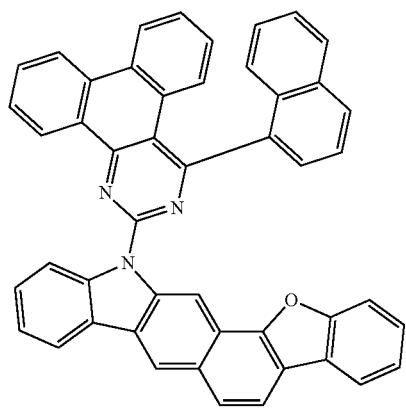
2-1-24
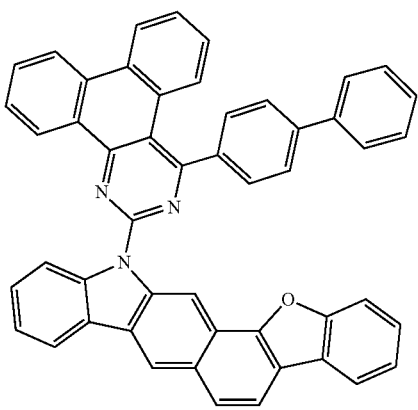

-continued
2-1-25
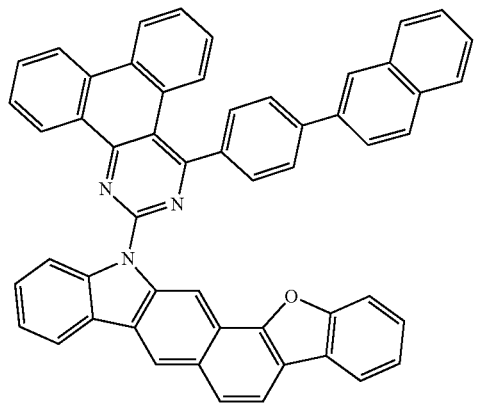
2-1-26
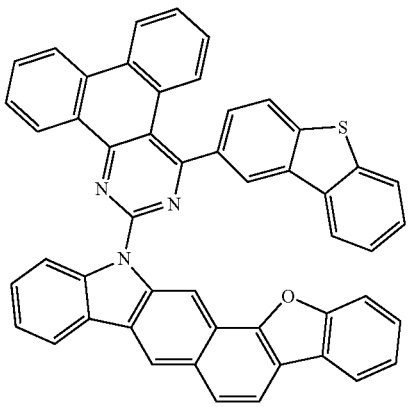
2-1-27
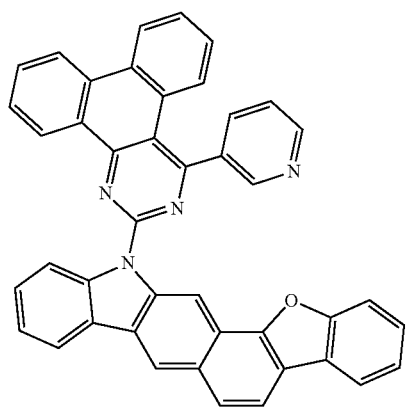
2-1-28
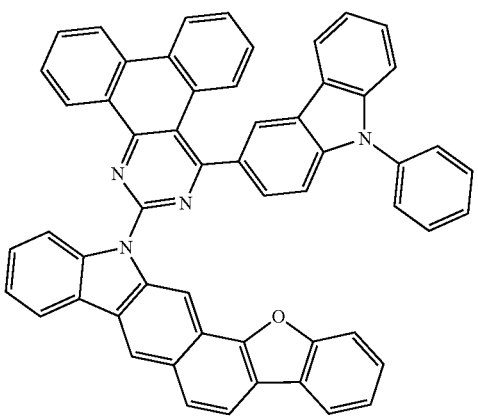
2-1-42
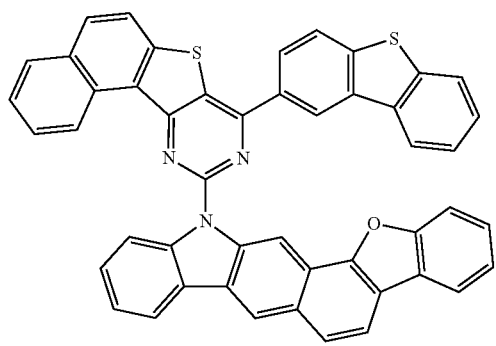
2-1-43
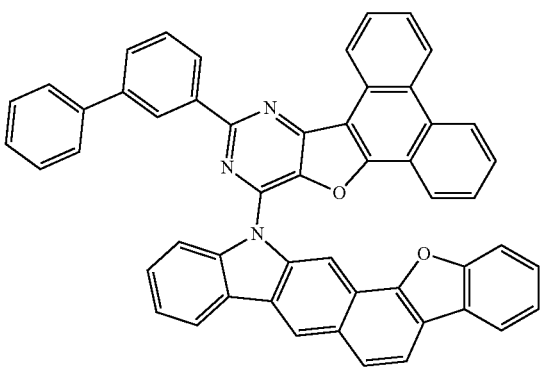

-continued
2-1-45
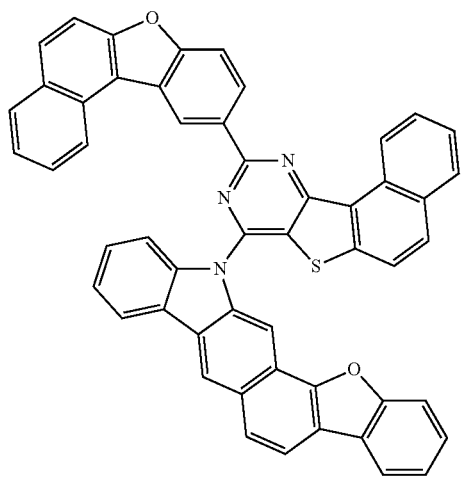
2-1-47
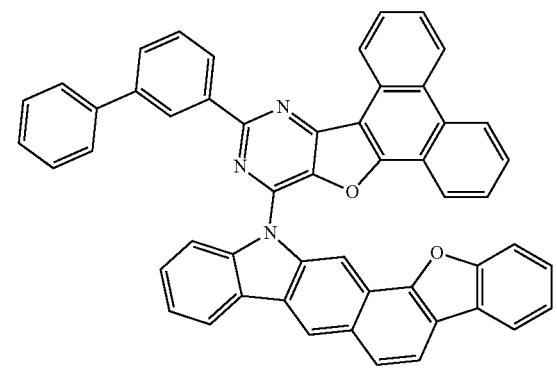
2-1-48
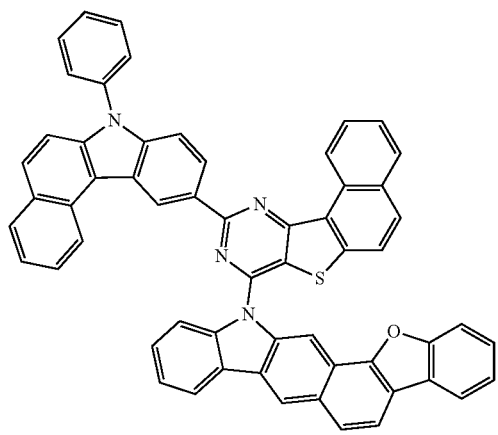
2-1-54
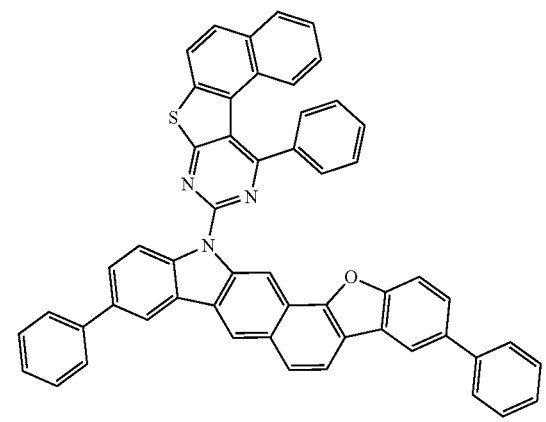
2-1-56
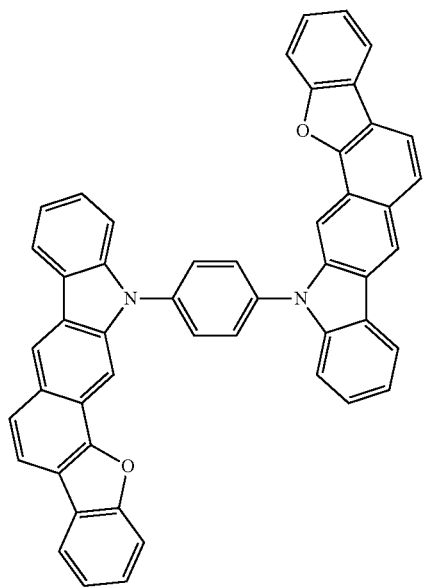
2-1-57
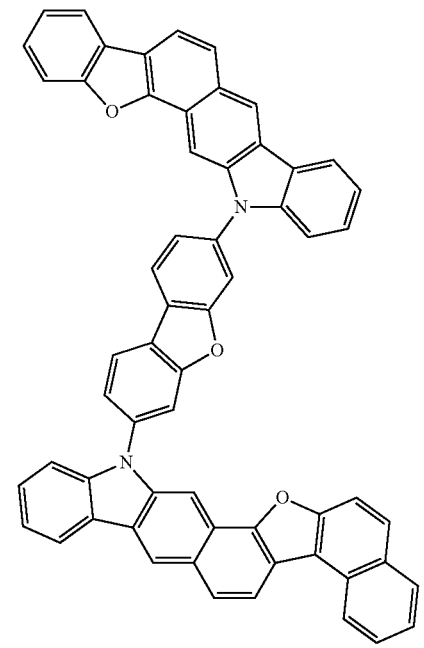

2-1-58
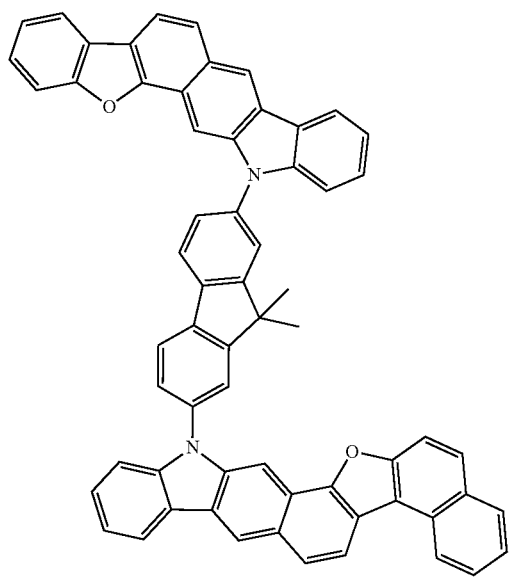
2-1-59
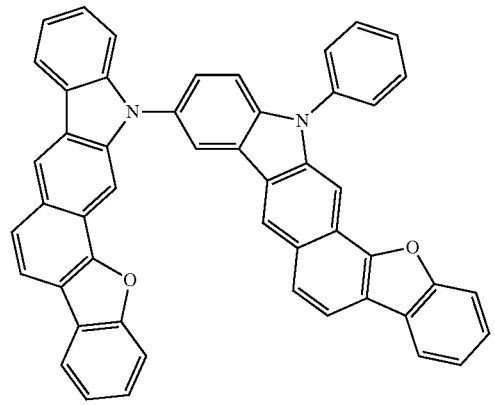
2-1-60
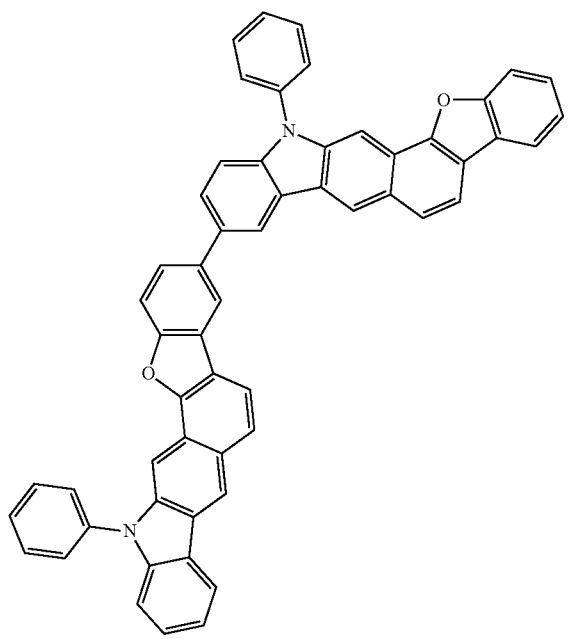
2-2-9
2-2-10
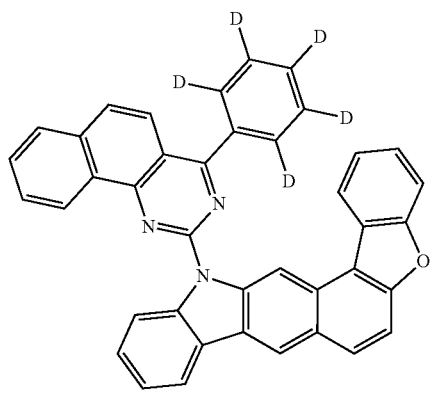
2-2-11
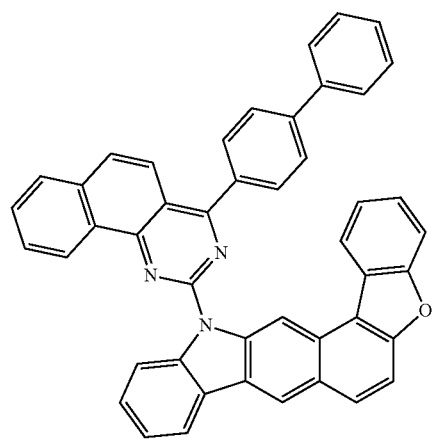

-continued
2-2-12
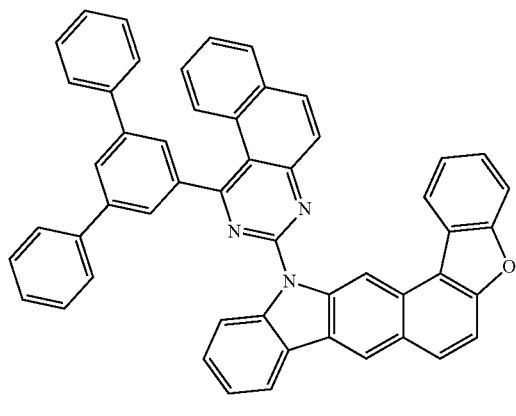
2-2-13
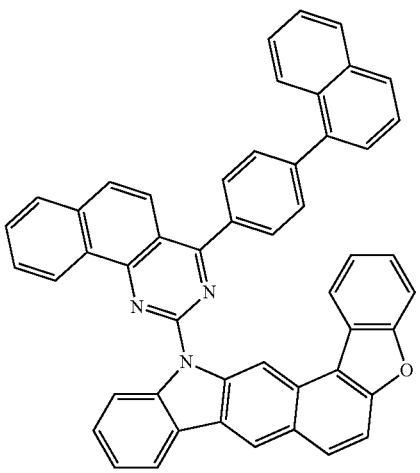
2-2-14
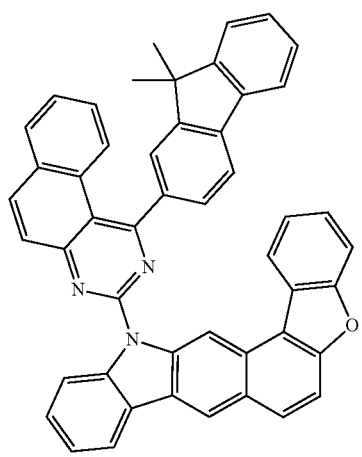
2-2-15
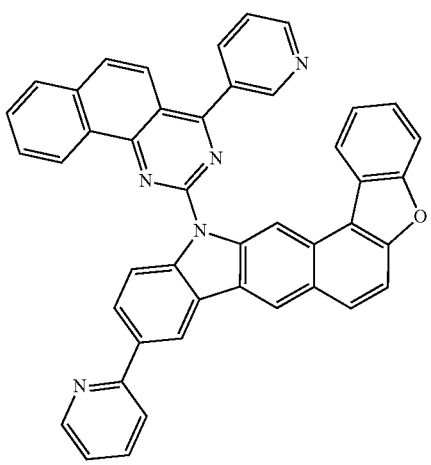
2-2-16
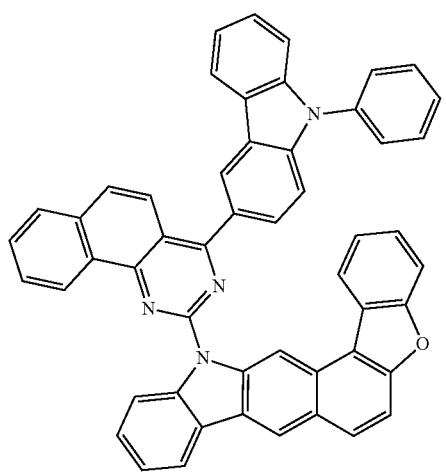
2-2-17
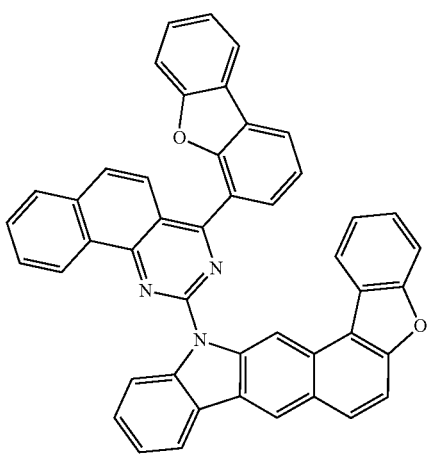

-continued
2-2-18
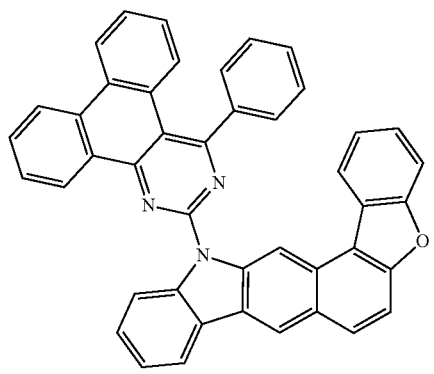
2-2-19
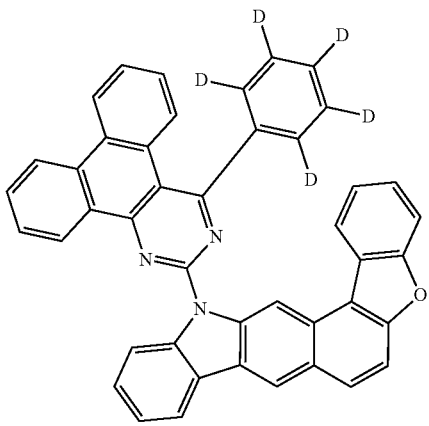
2-2-20
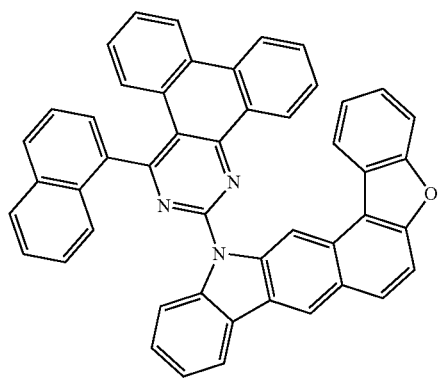
2-2-21
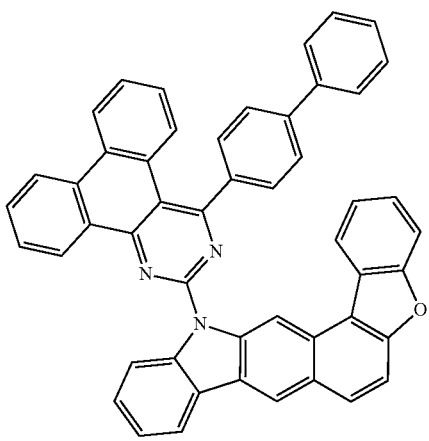
2-2-22
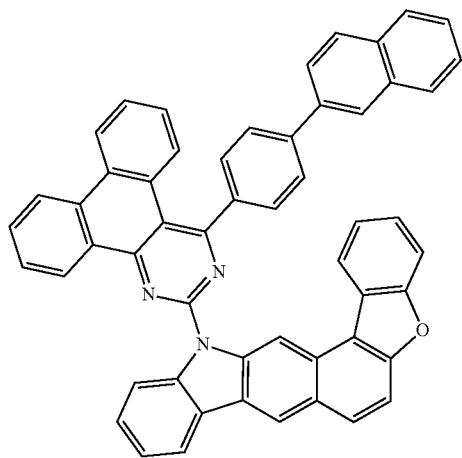
2-2-23
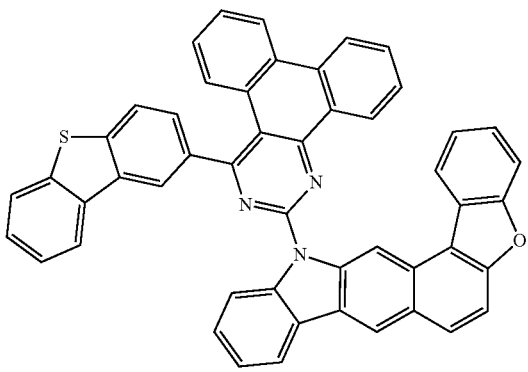

-continued
2-2-24
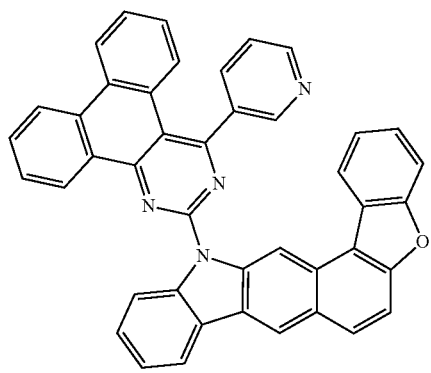
2-2-25
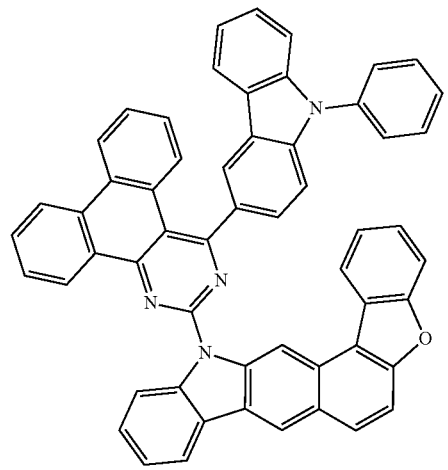
2-2-37
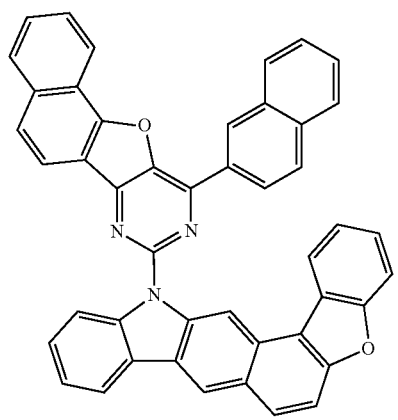
2-2-38
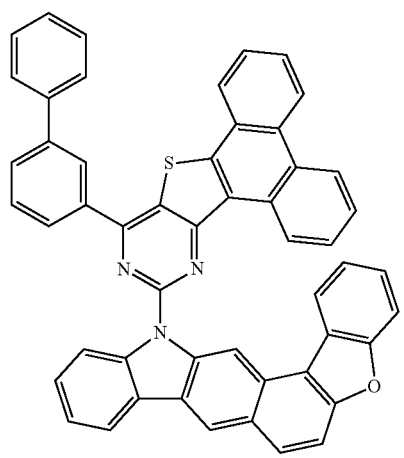
2-2-40
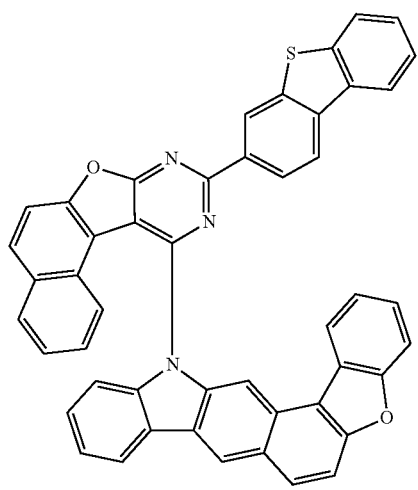
2-2-42
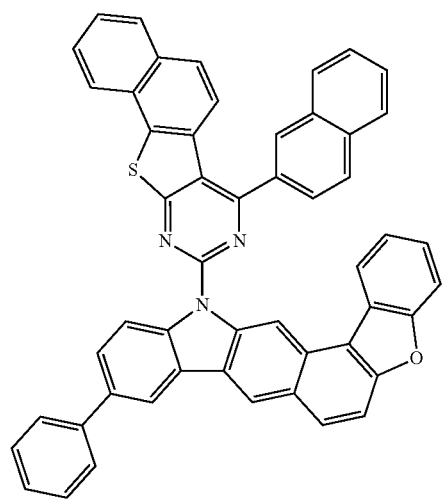

2-2-46
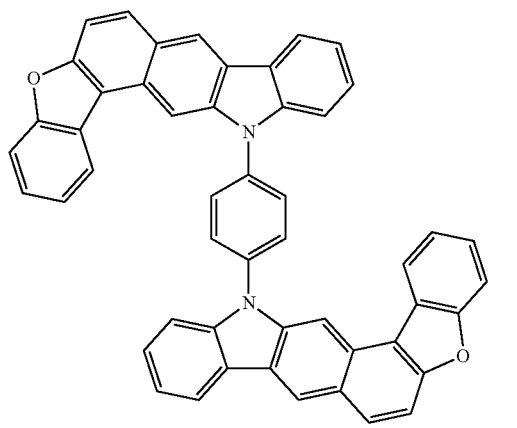
2-2-47
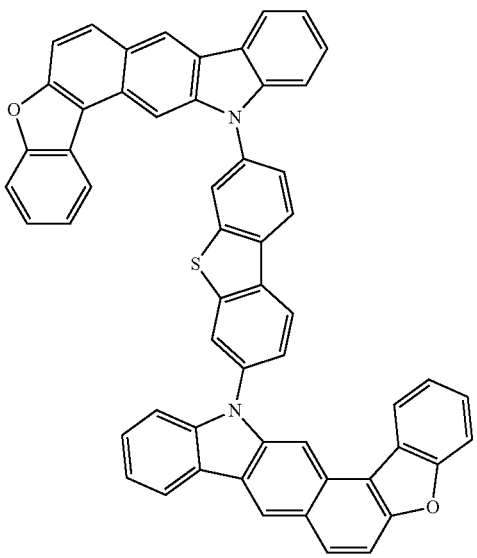
2-2-48
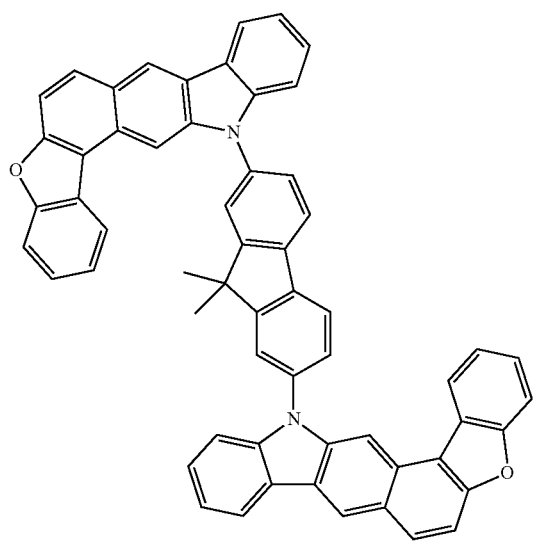
2-2-49
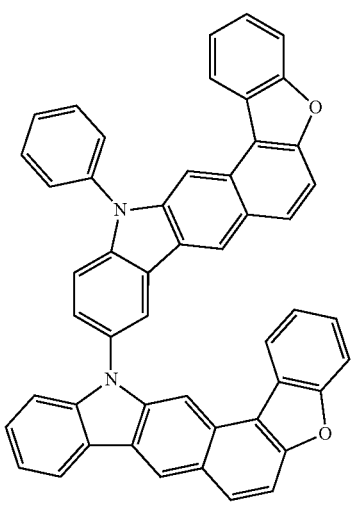
2-2-50
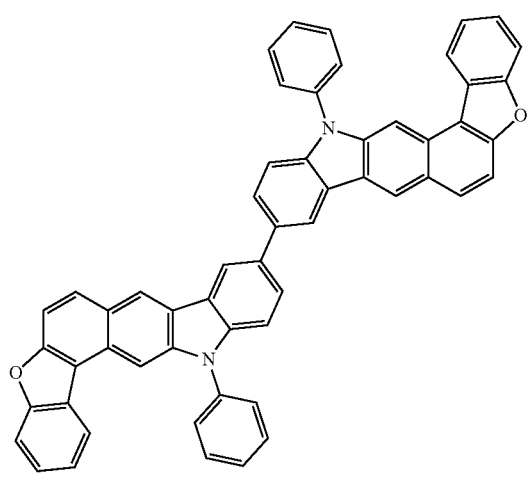
3-1-7
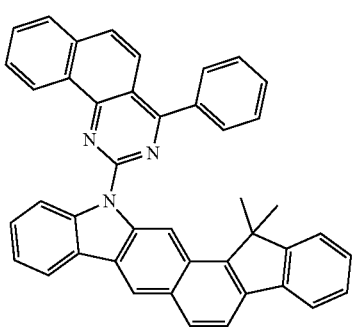

-continued
3-1-8
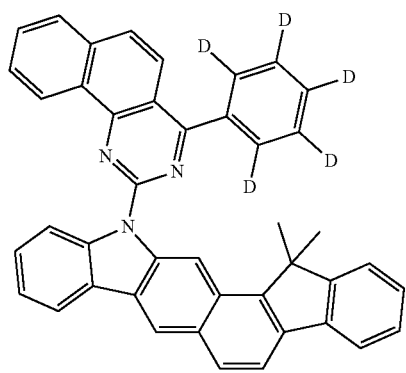
3-1-9
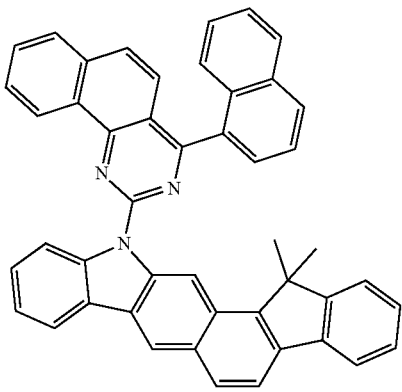
3-1-10
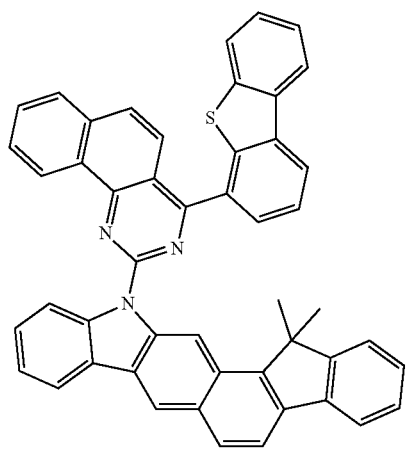
3-1-11
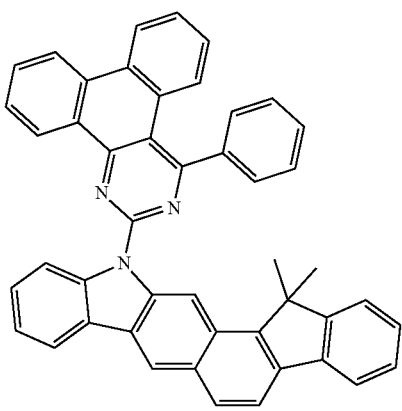
3-1-12
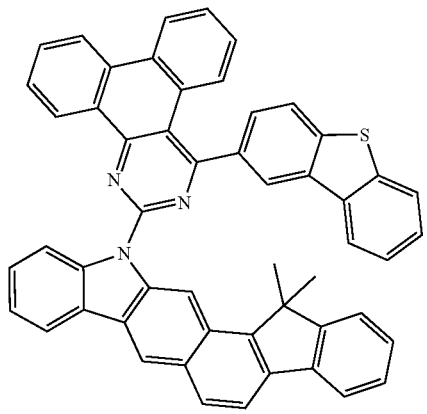
3-1-13
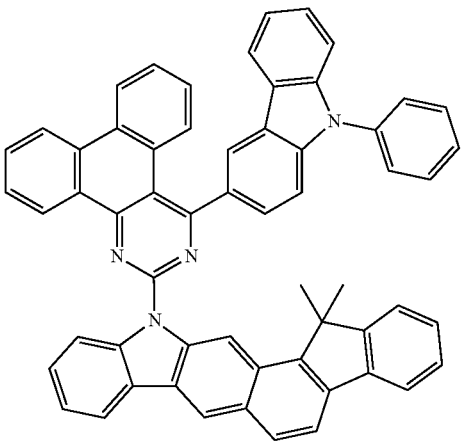

3-1-18
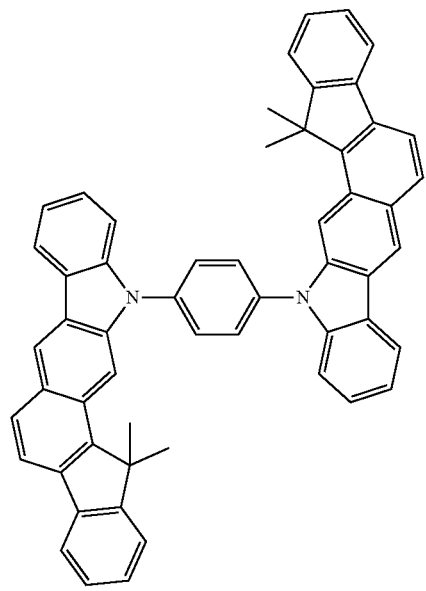
3-1-19
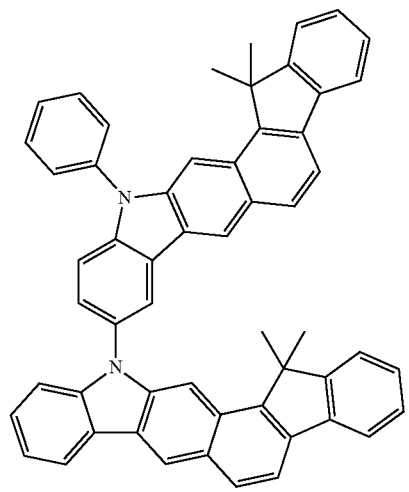
3-1-20
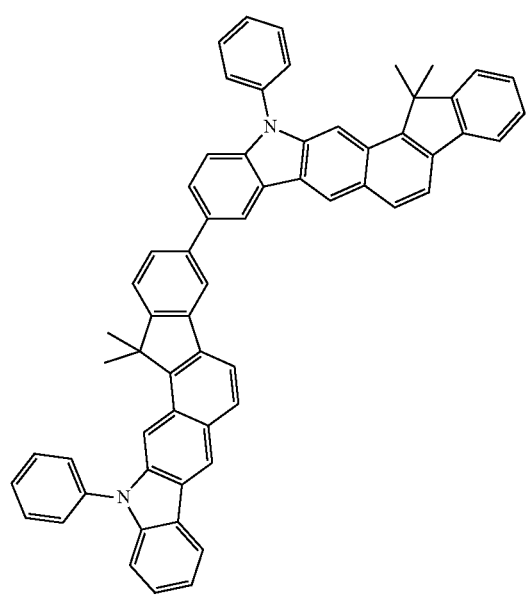
3-2-14
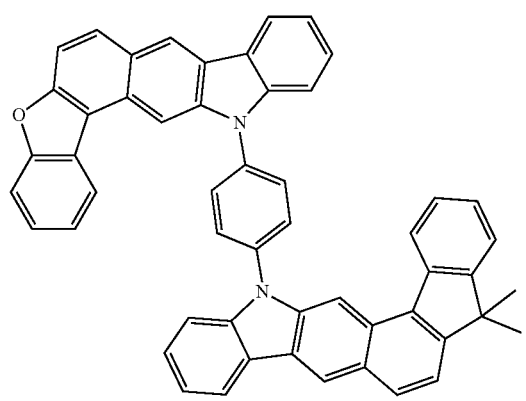
3-2-15
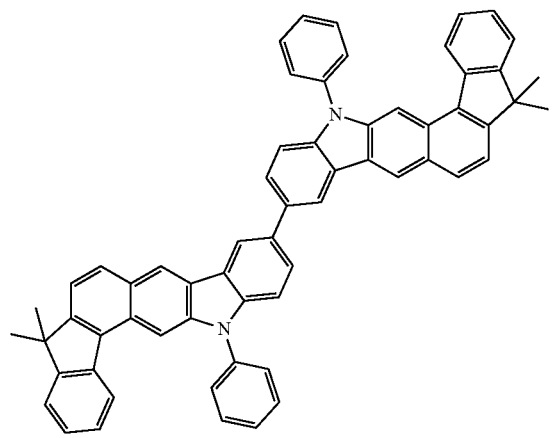
4-1-2
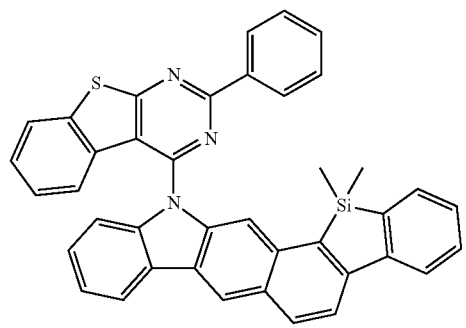

-continued
4-1-3
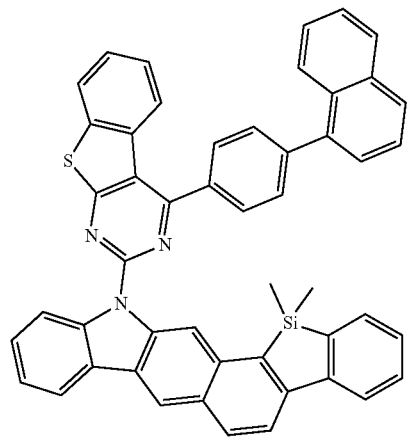
4-1-4
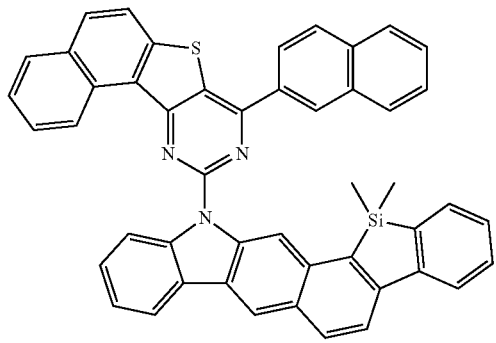
4-2-1
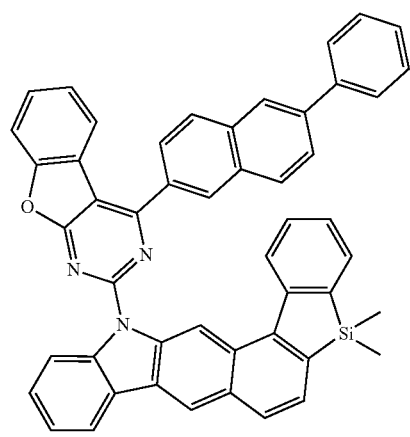
4-2-2
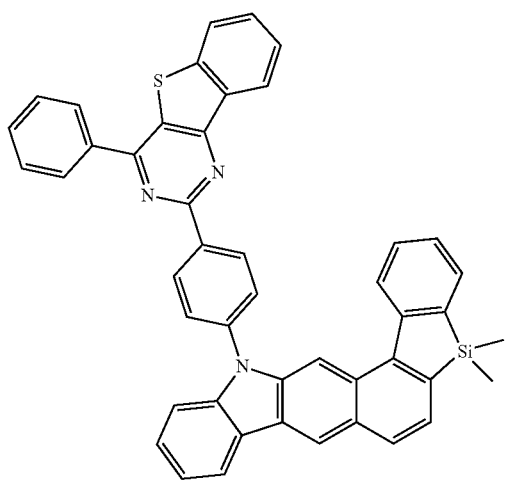
4-2-3
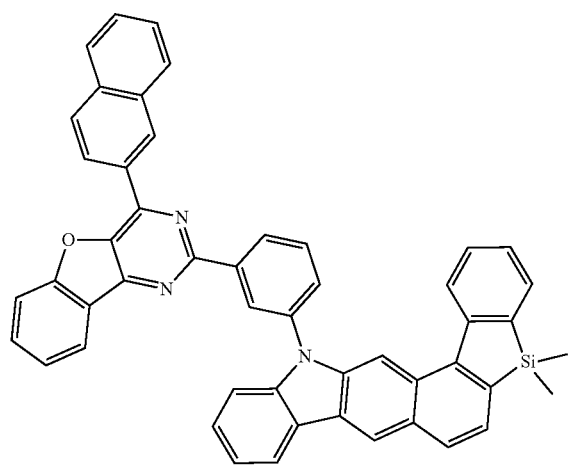
4-2-4
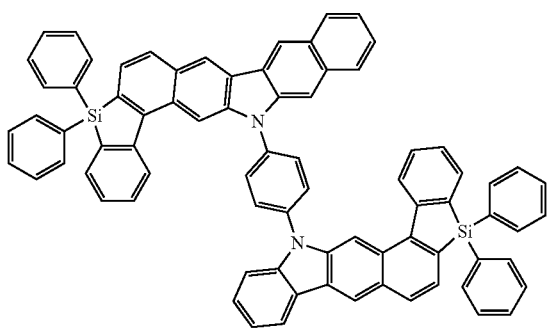

-continued
A 1-1-1
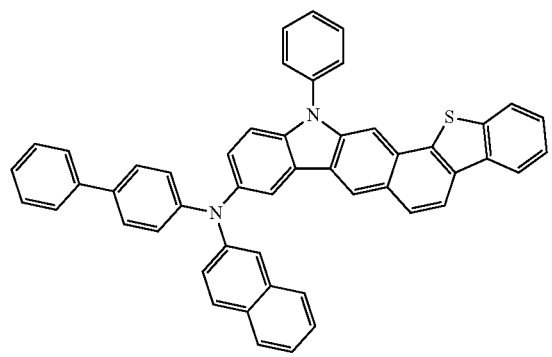
A 1-1-2
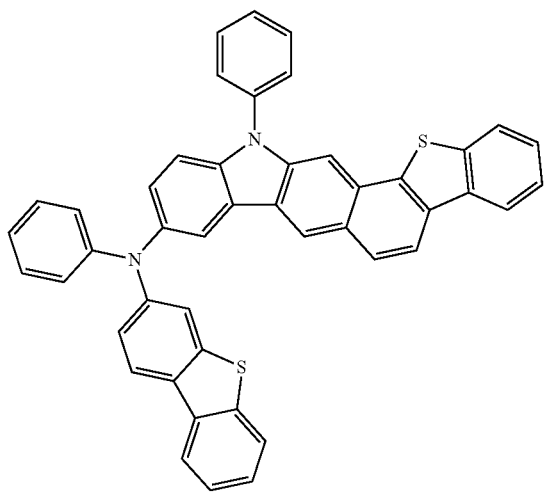
A 1-1-3
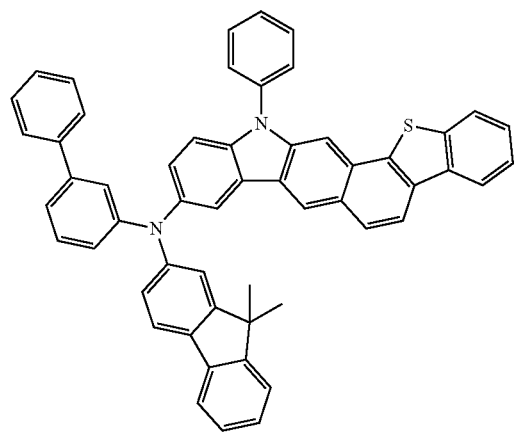
A 1-1-4
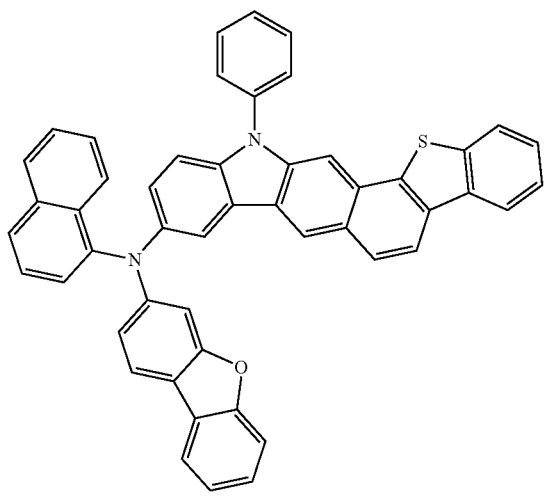
A 1-1-5
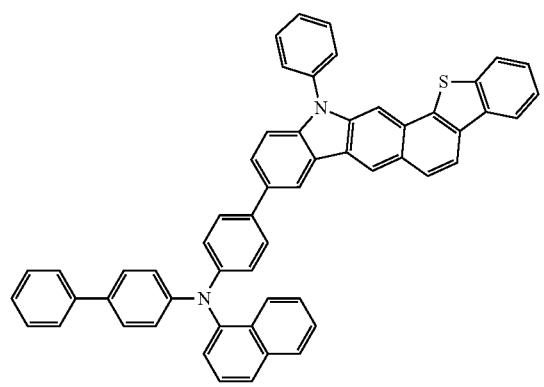
A 1-1-6
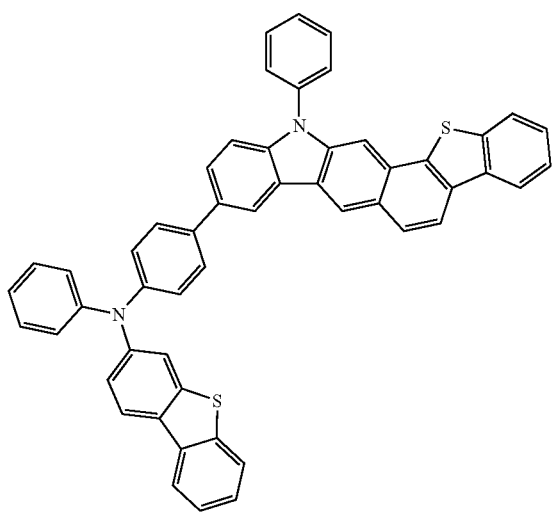

-continued
A 1-1-7
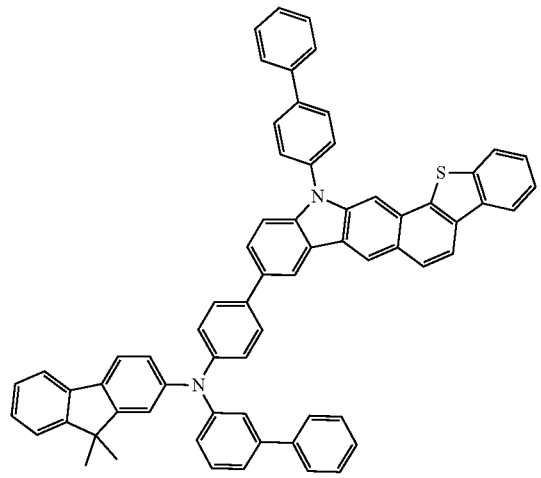
A 1-1-8
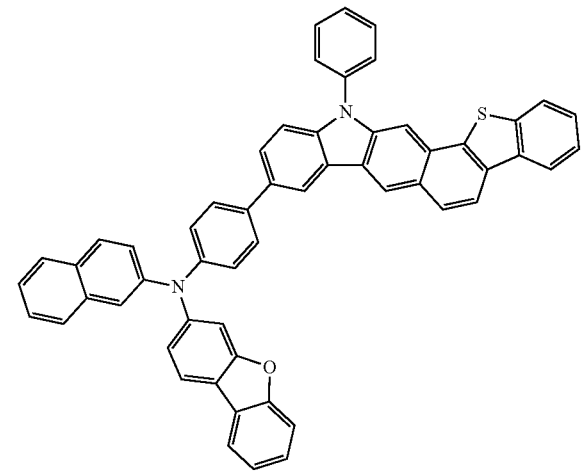
A 1-1-9
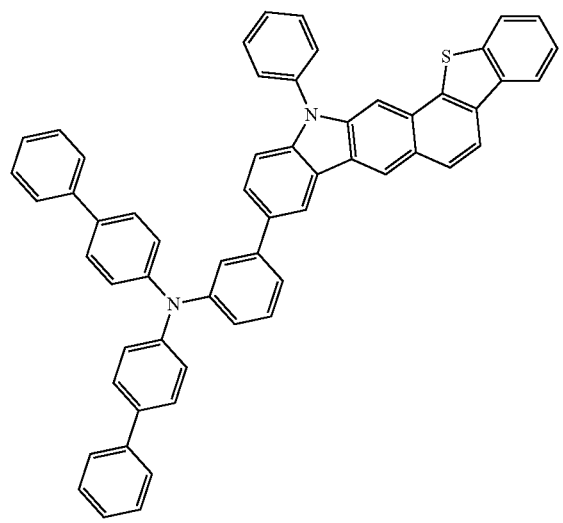
A 1-1-10
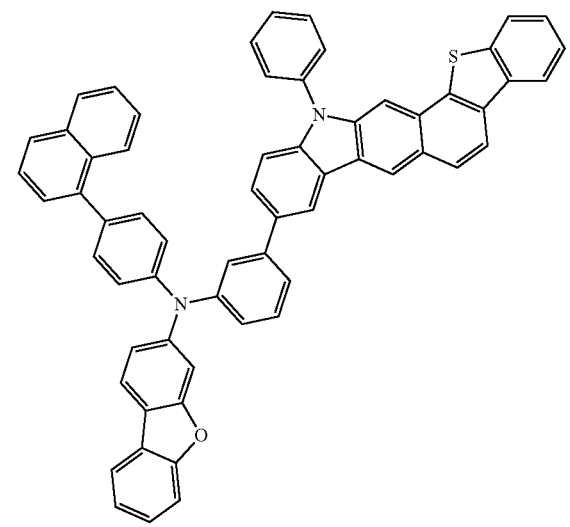
A 1-1-11
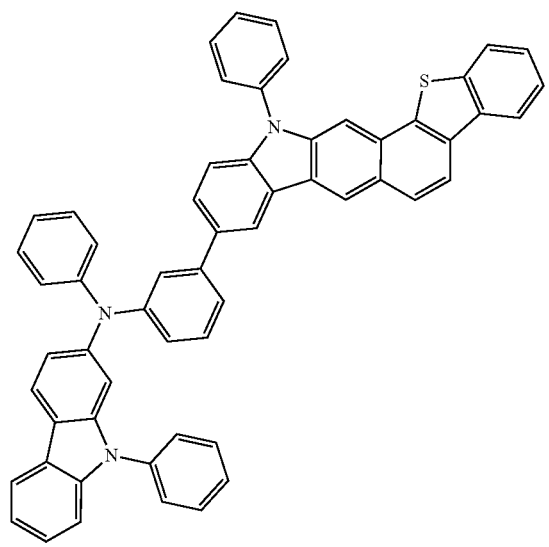
A 1-1-12
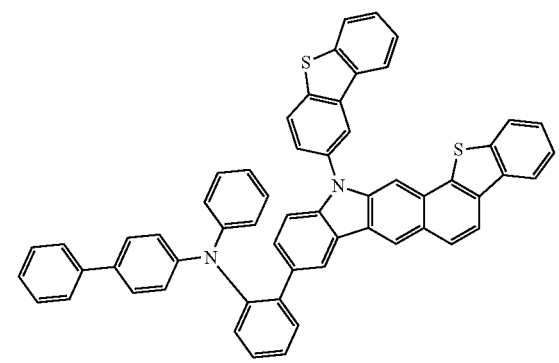

-continued
A 1-1-13
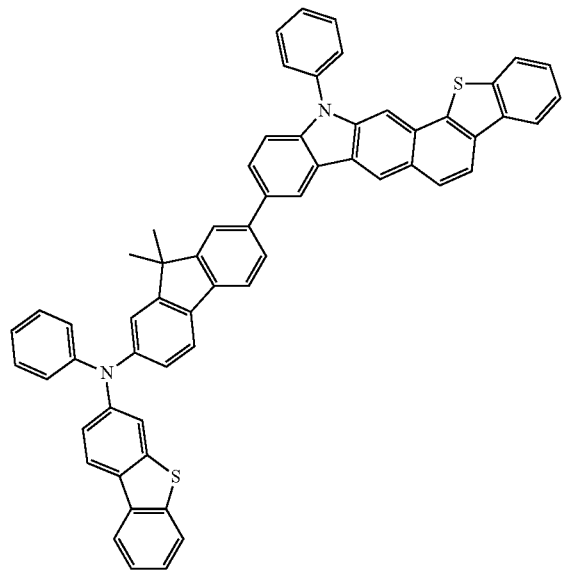
A 1-1-14
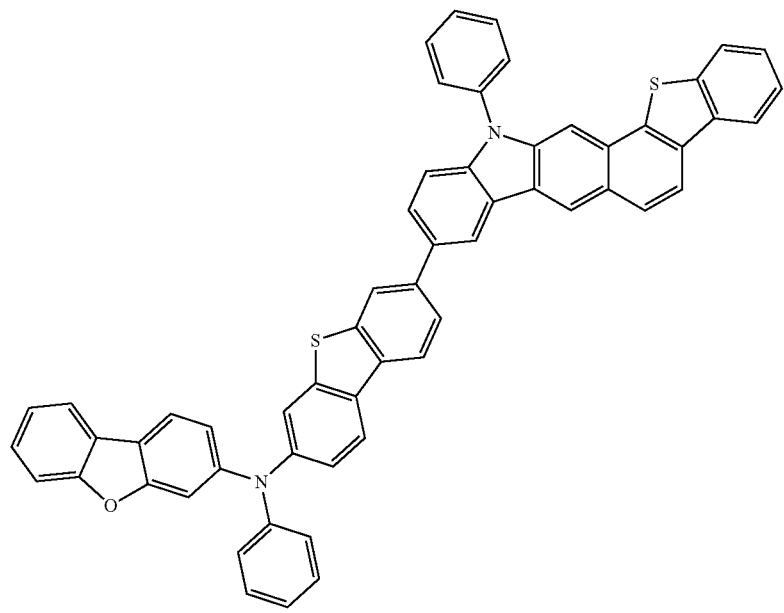
A 1-1-15
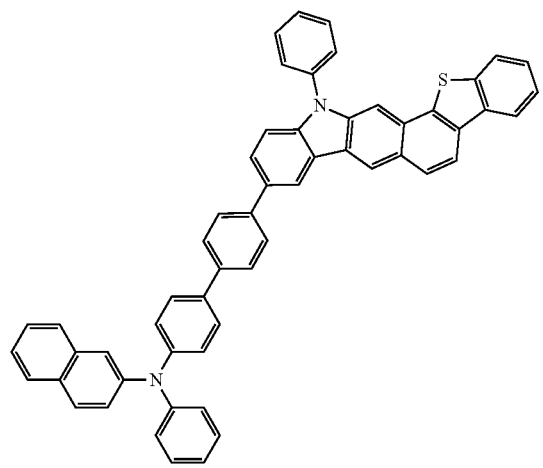
A 1-1-16
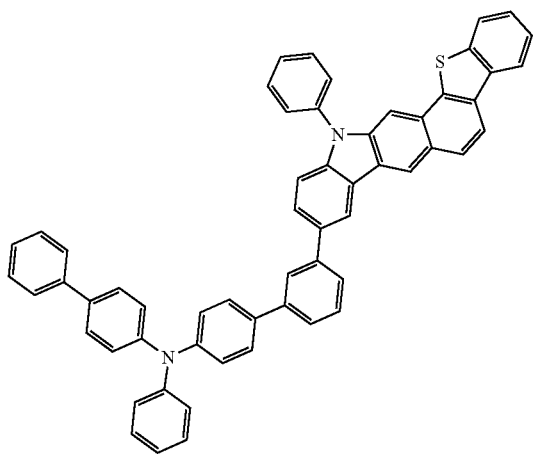

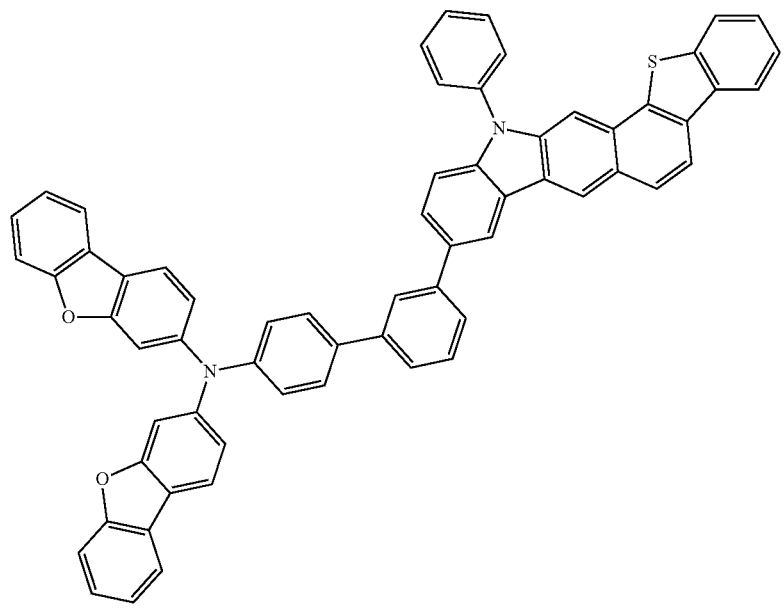
A 1-1-17
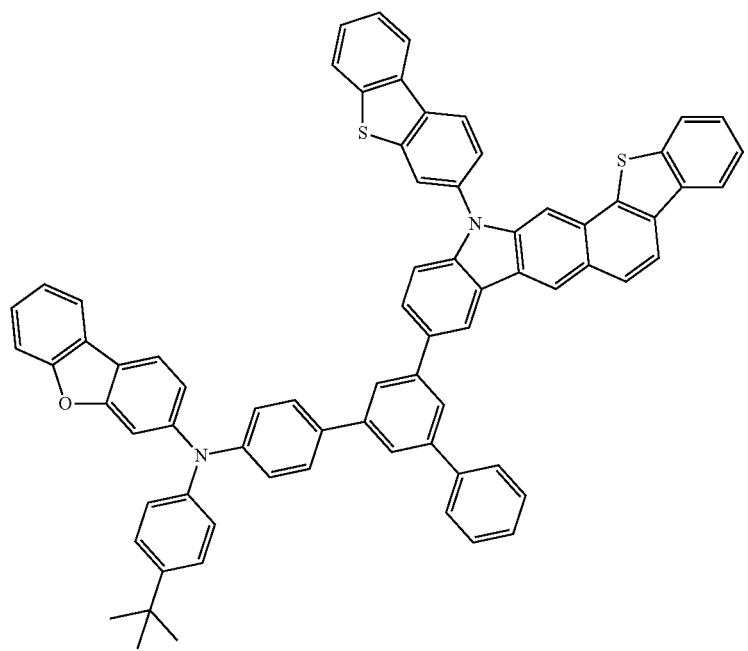
A 1-1-18

A 1-1-19
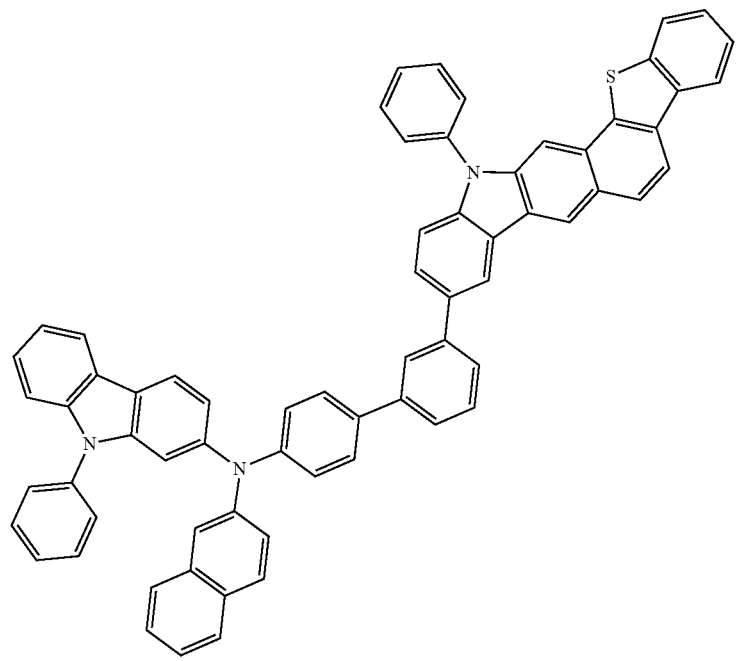
A 1-1-20
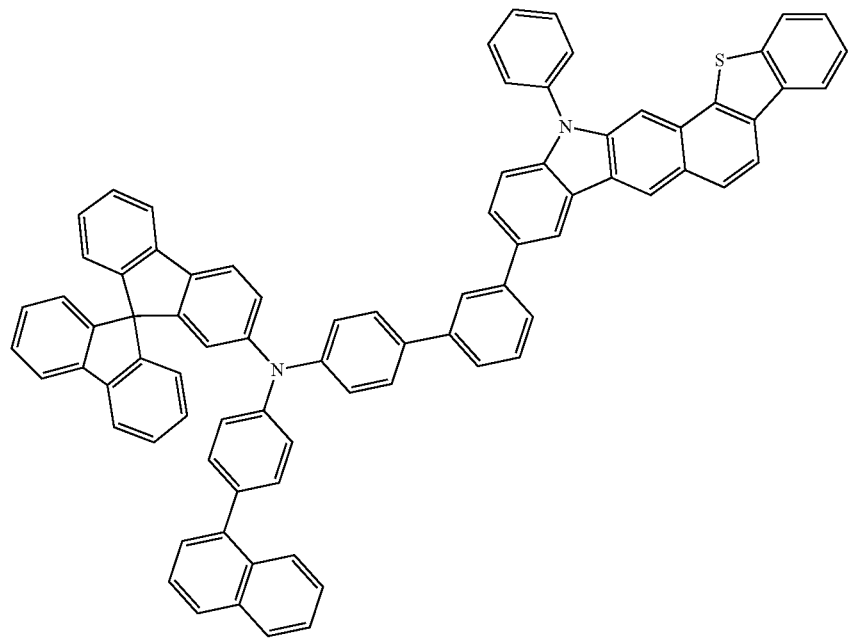

-continued
A 1-1-21
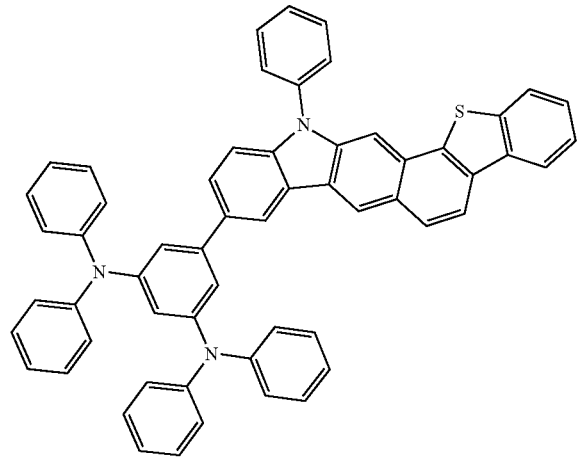
A 1-1-22
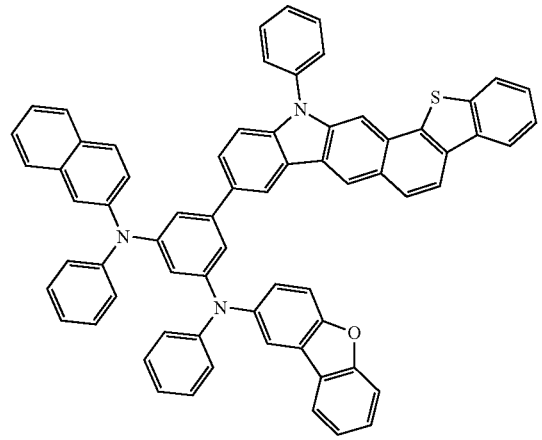
A 1-1-23
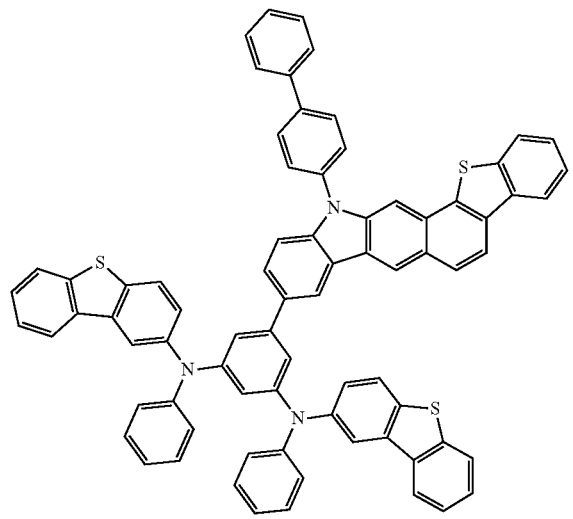
A 1-1-24
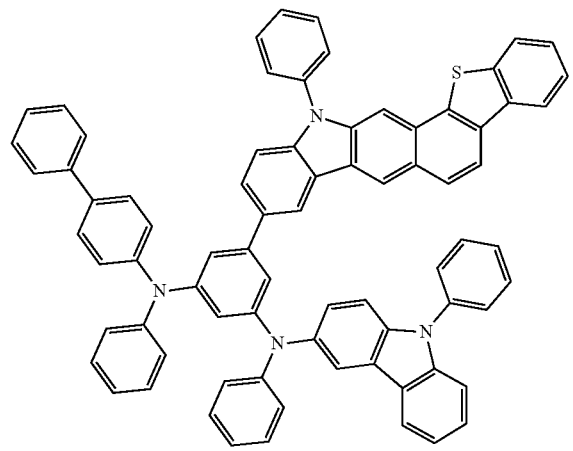
A 1-1-25
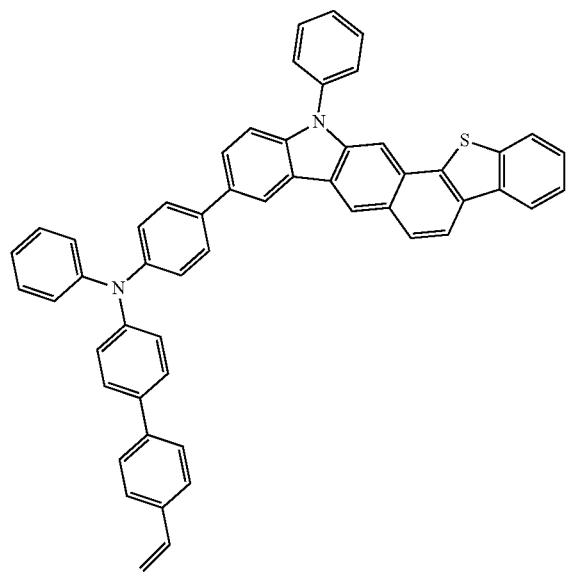
A 1-1-26
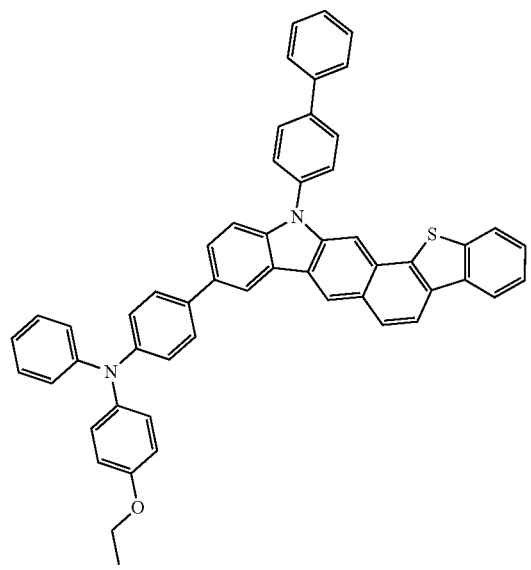

-continued
A 1-1-27
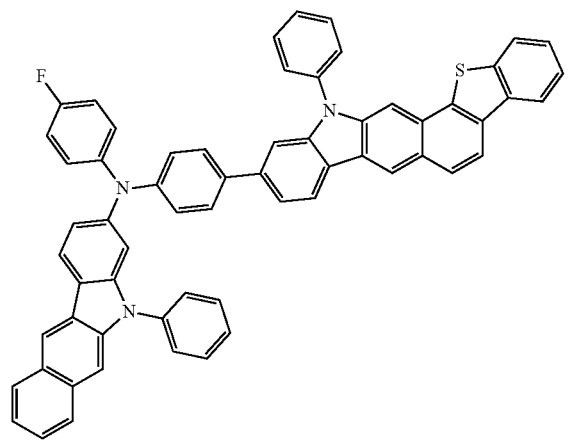
A 1-1-28
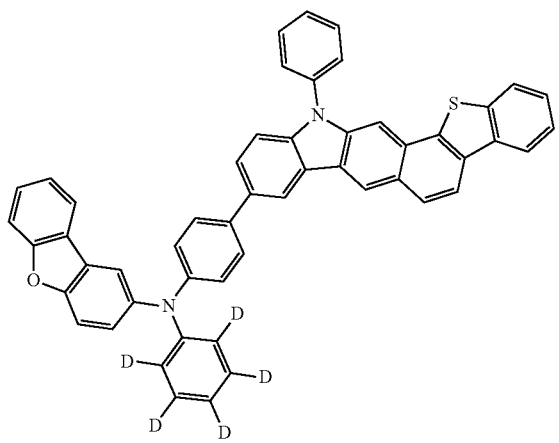
A 1-1-29
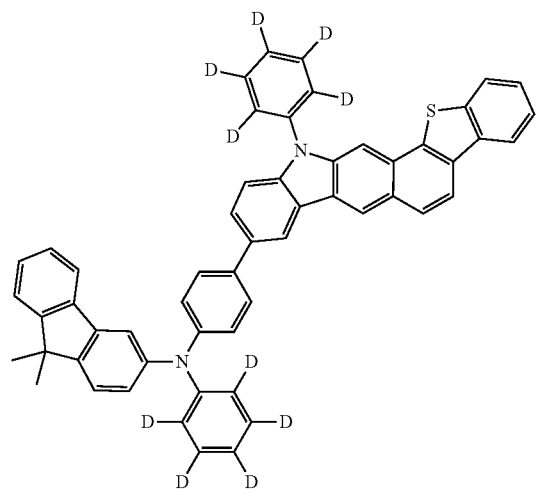
A 1-1-30
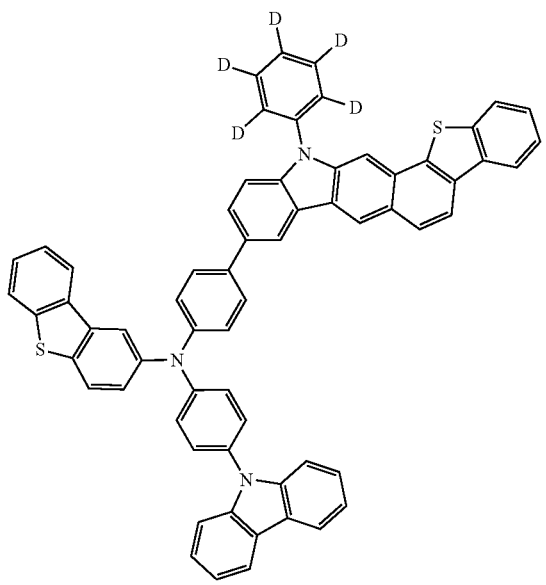
A 1-1-31
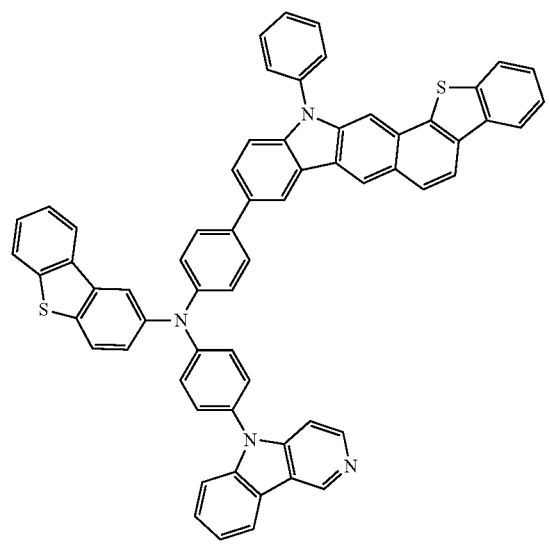
A 1-1-32
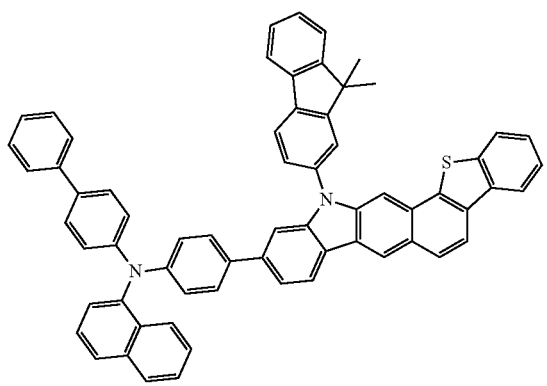

-continued
A 1-1-33
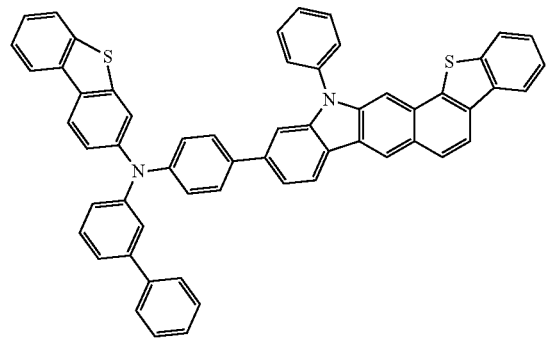
A 1-1-34
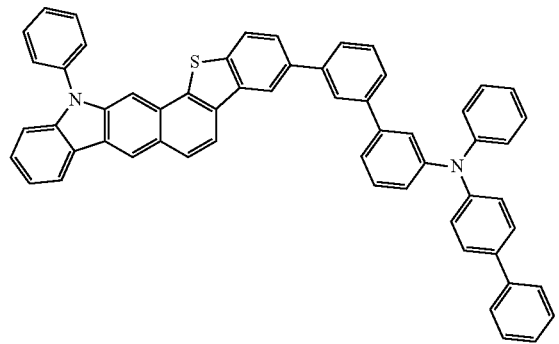
A 1-2-1
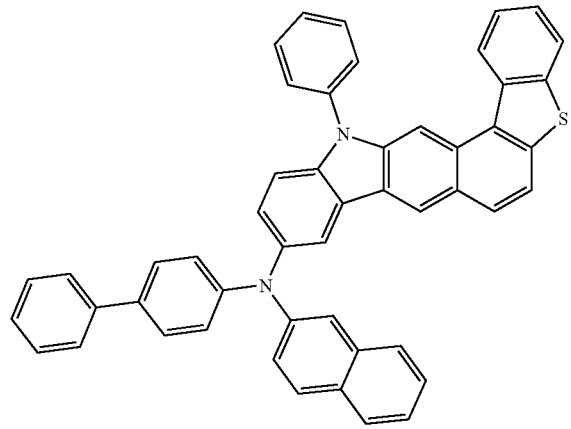
A 1-2-2
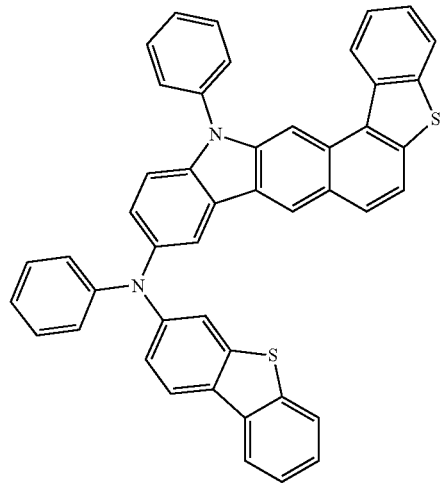
A 1-2-3
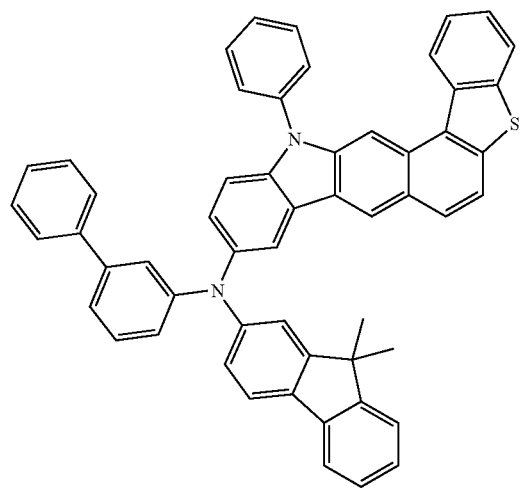
A 1-2-4
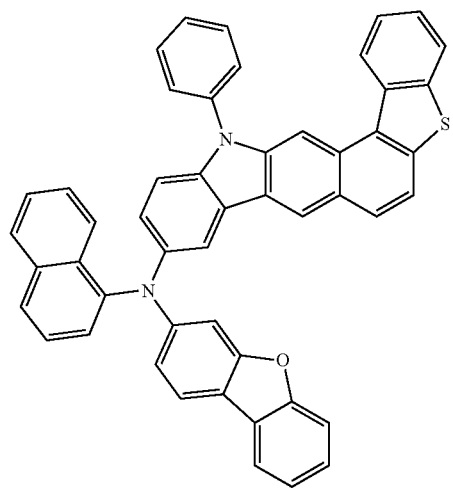

-continued
A 1-2-5
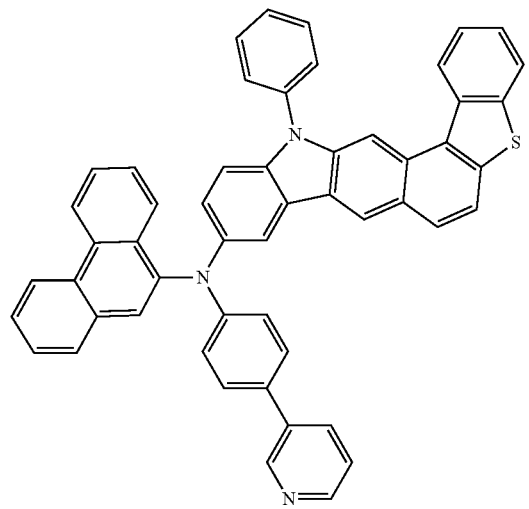
A 1-2-6
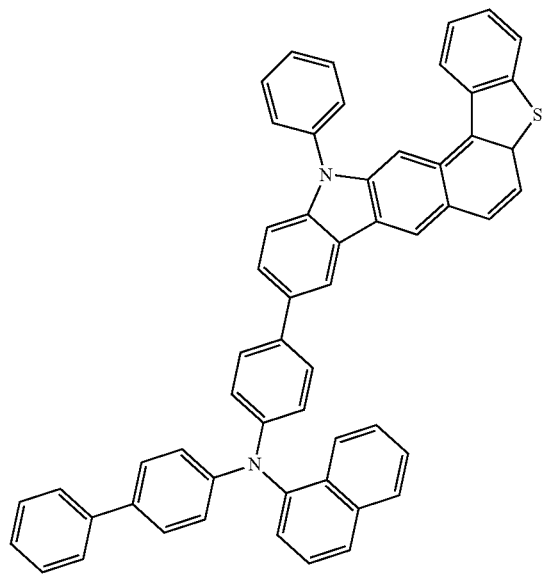
A 1-2-7
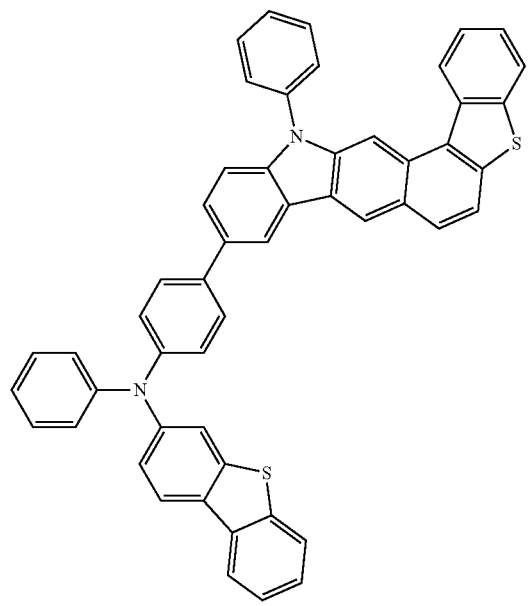
A 1-2-8
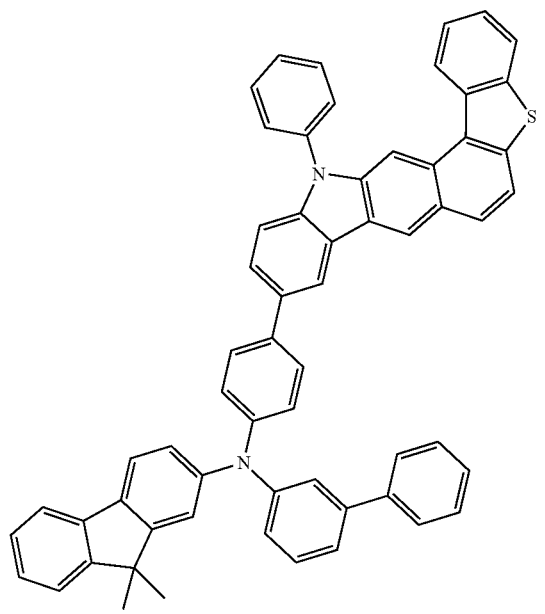

-continued
A 1-2-9
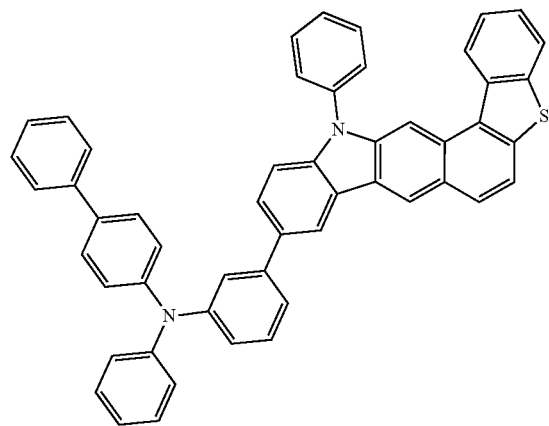
A 1-2-10
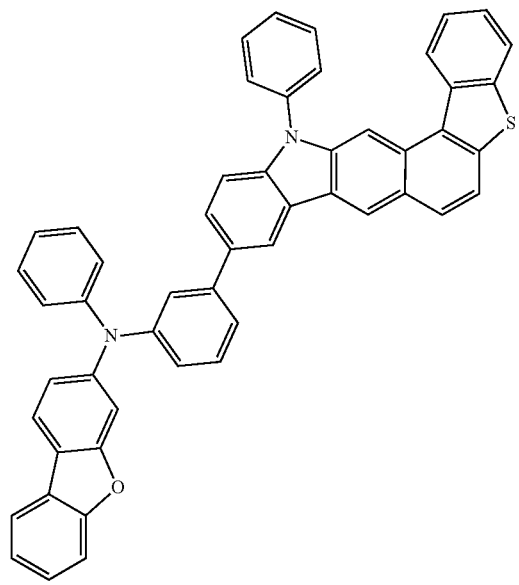
A 1-2-11
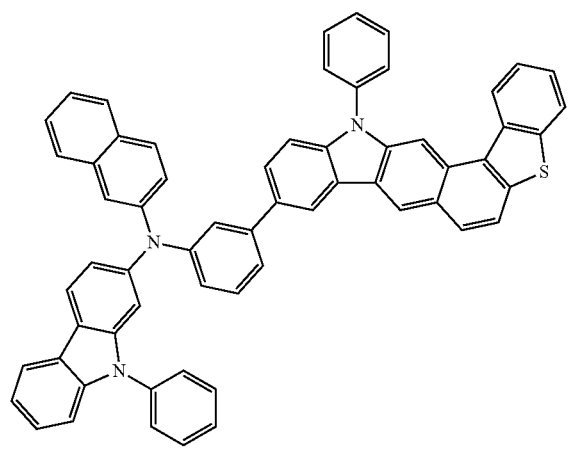
A 1-2-12
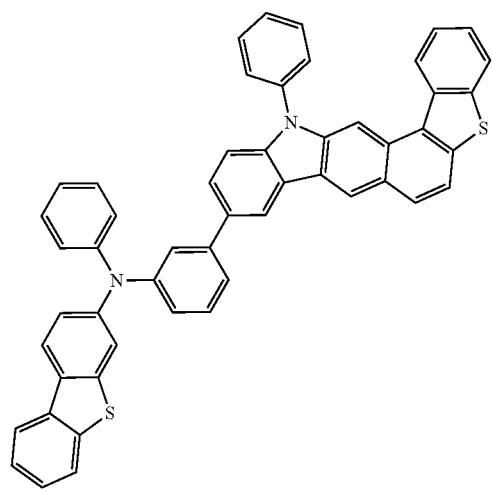
A 1-2-13
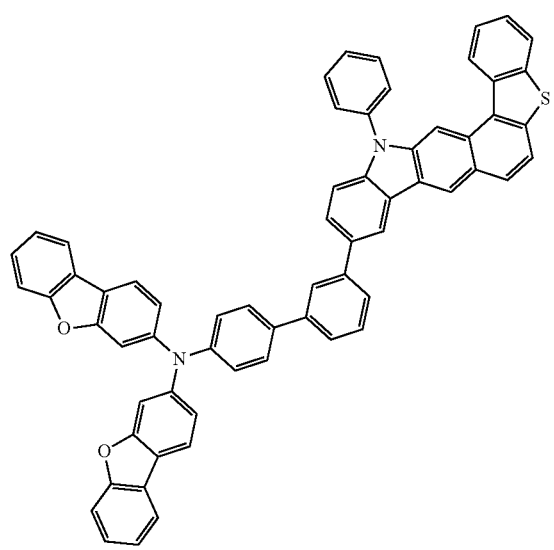
A 1-2-14
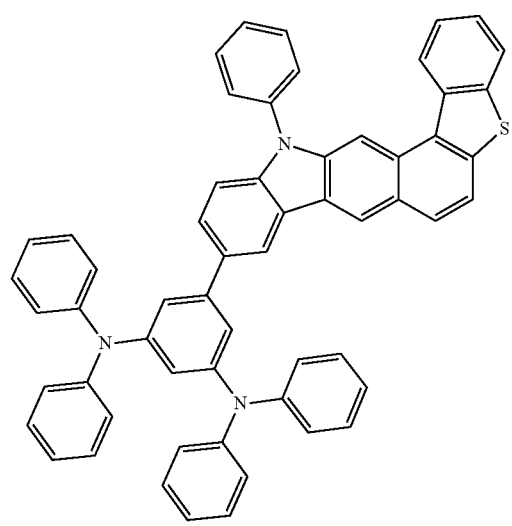

A 1-2-15    A 1-2-16
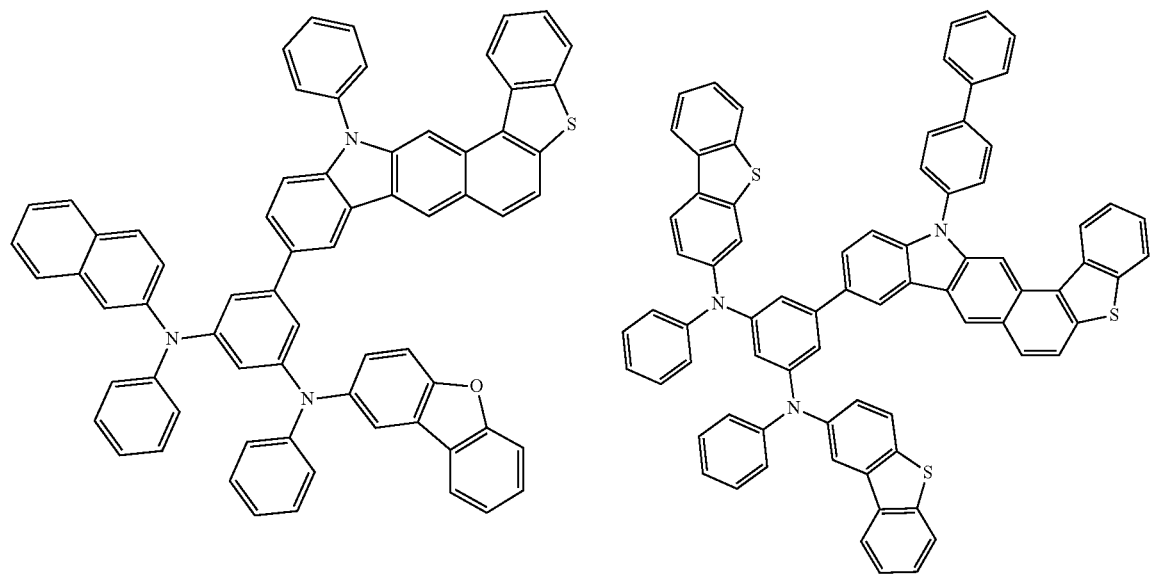
A 1-2-17    A 1-2-18
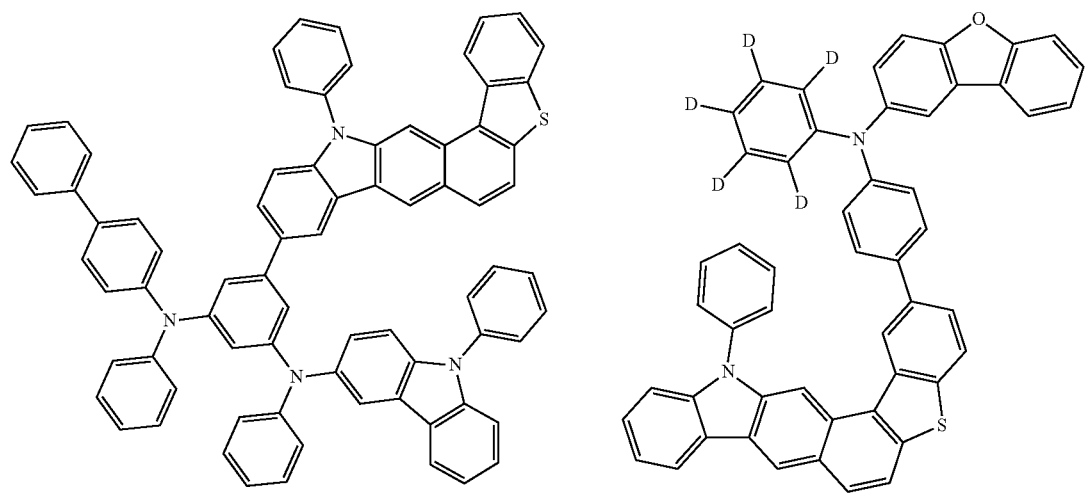
A 2-1-1    A 2-1-2
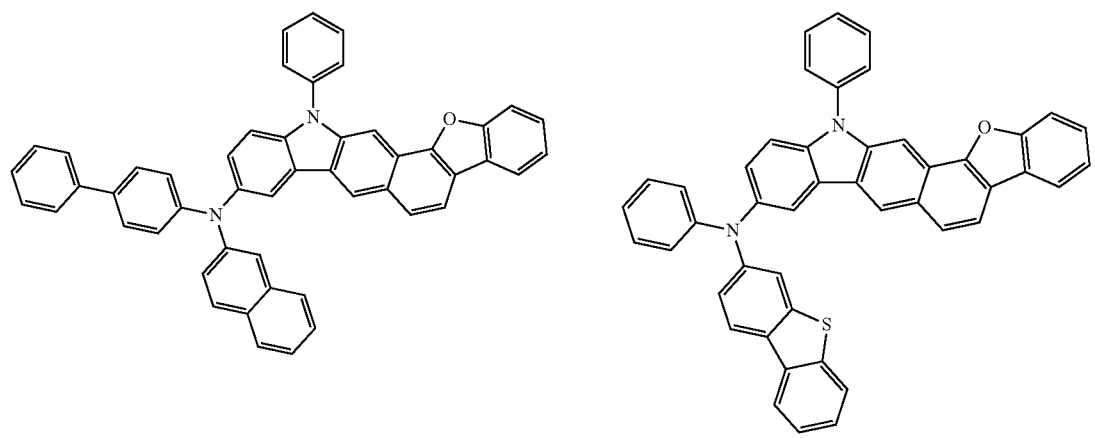

A 2-1-3
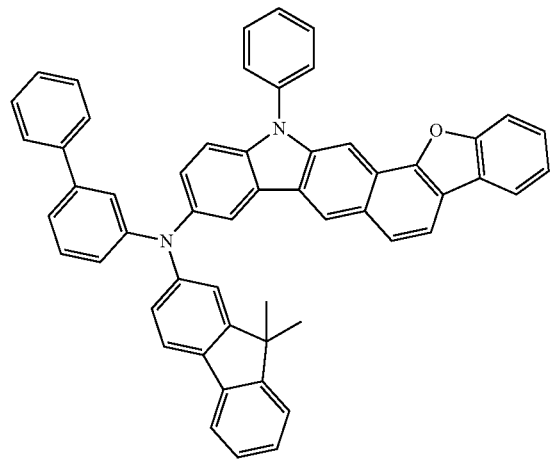
A 2-1-4
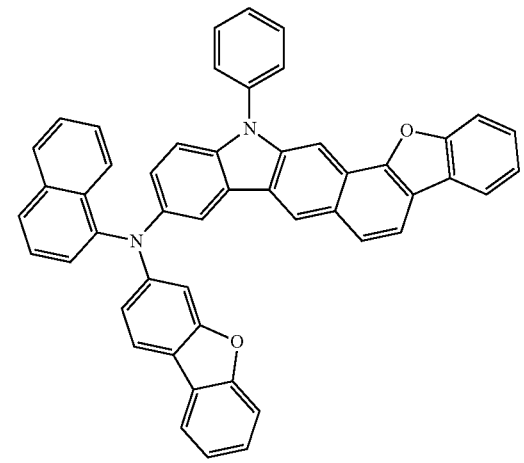
A 2-1-5
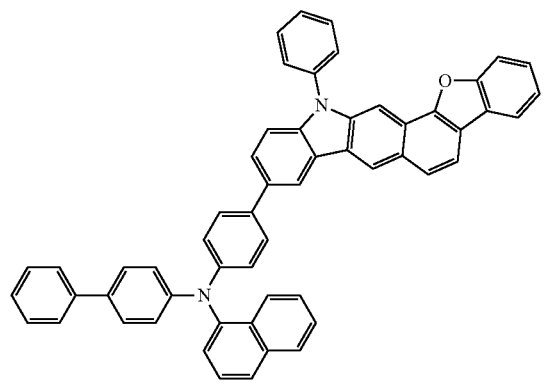
A 2-1-6
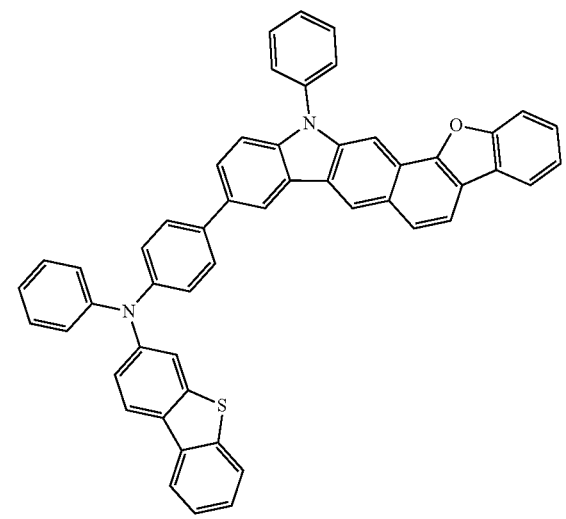
A 2-1-7
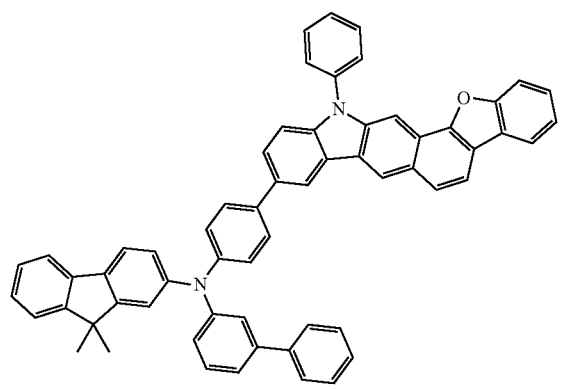
A 2-1-8
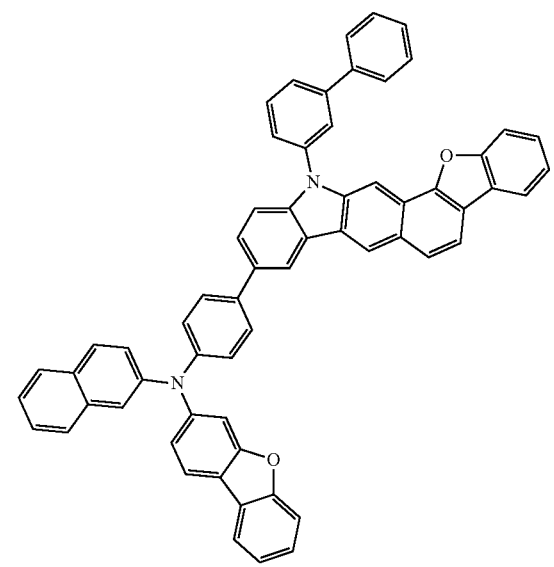

-continued
A 2-1-9
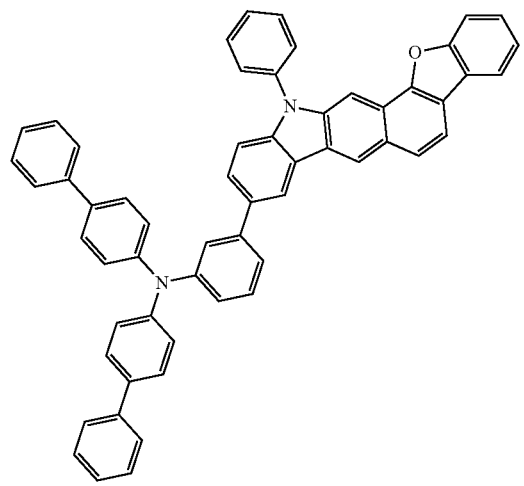
A 2-1-10
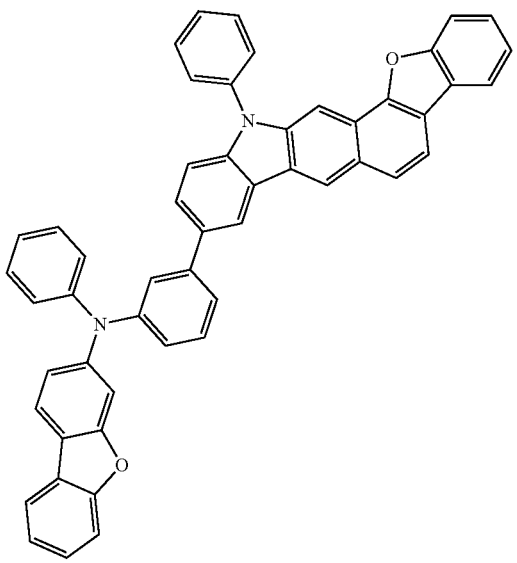
A 2-1-11
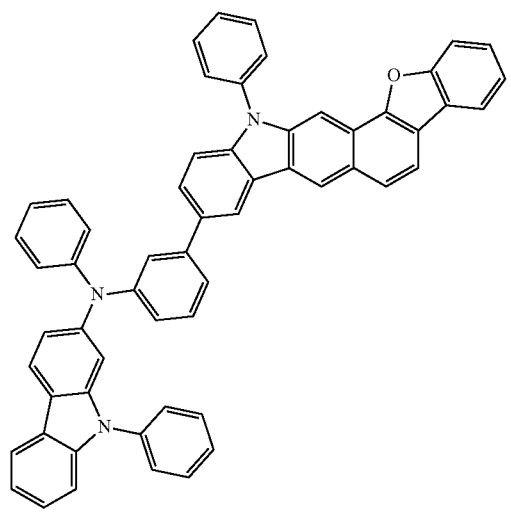
A 2-1-12
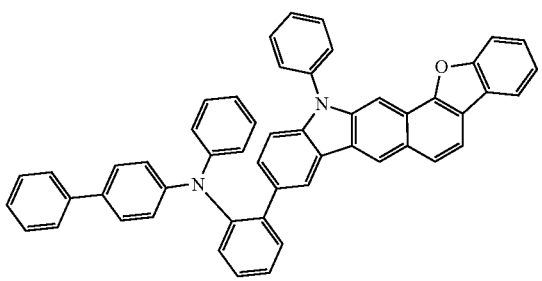

-continued
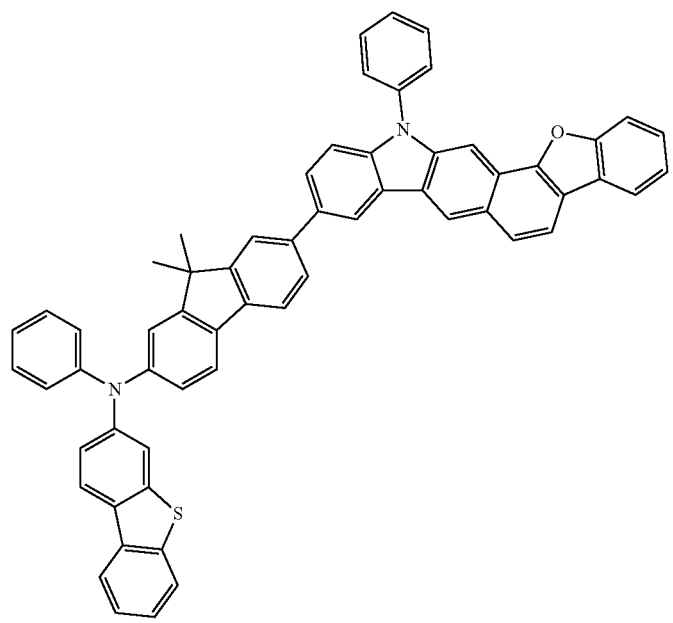
A 2-1-13
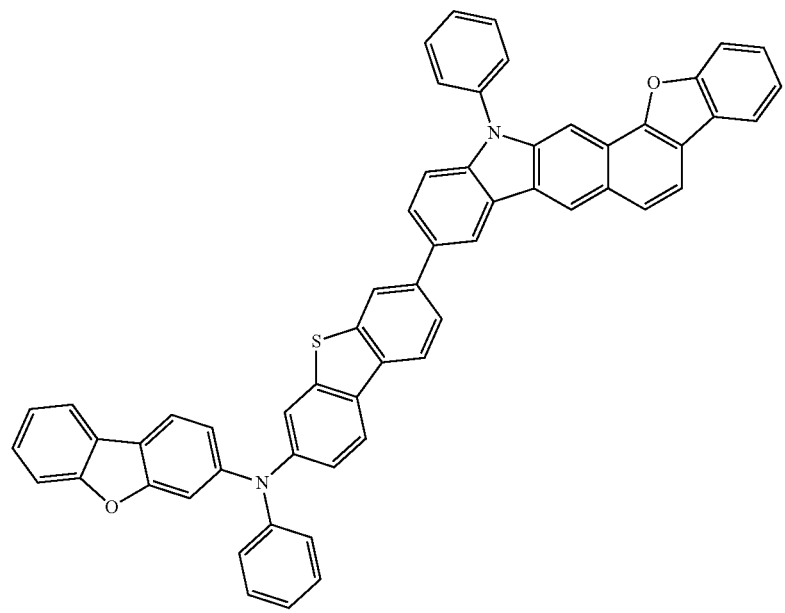
A 2-1-14

-continued
A 2-1-15
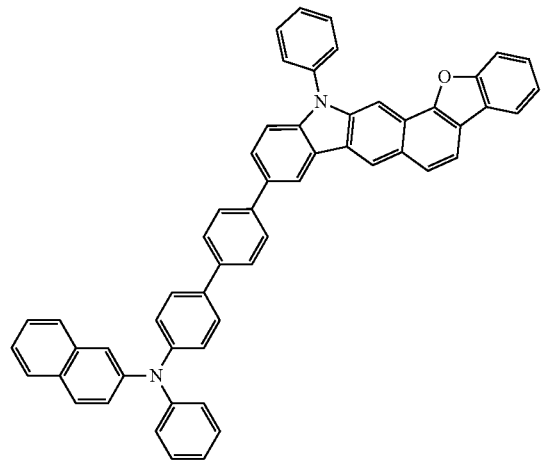
A 2-1-16
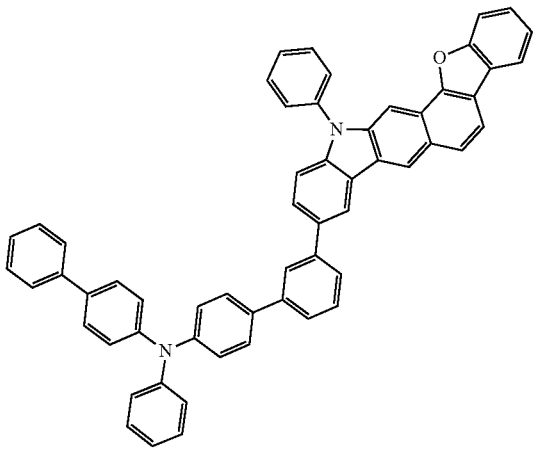
A 2-1-17
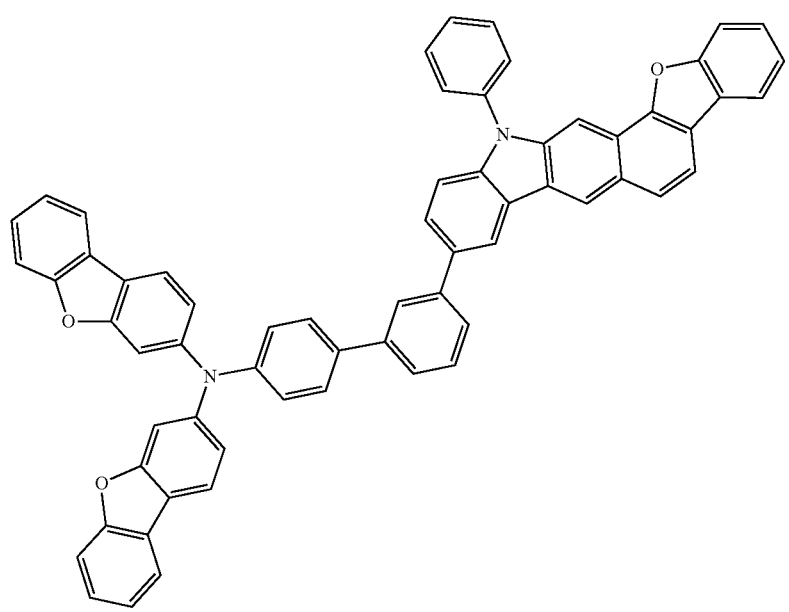

A 2-1-18
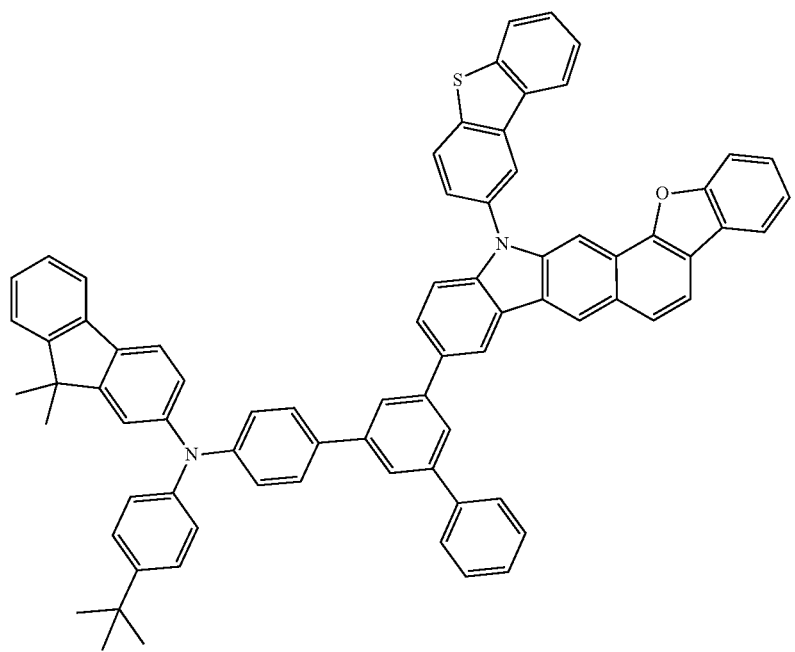
A 2-1-19 A 2-1-20
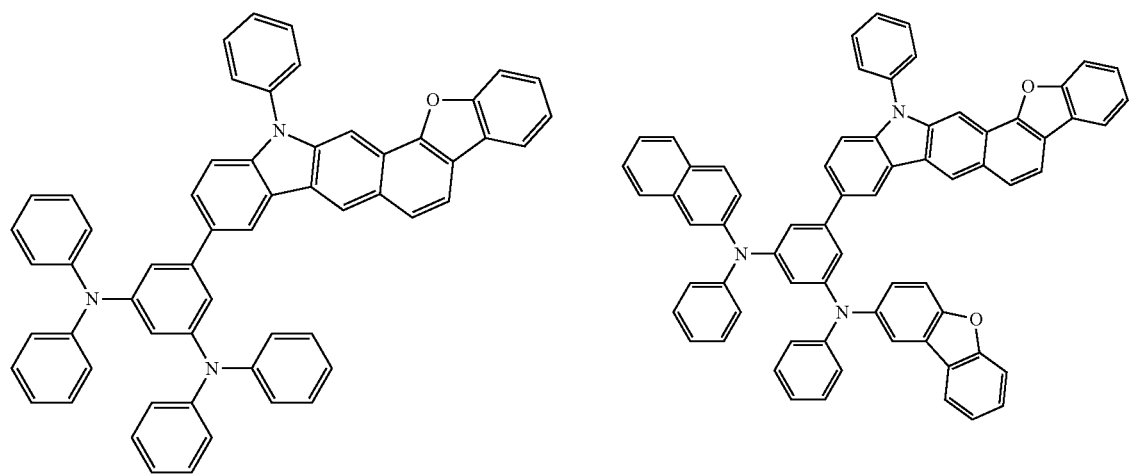

331
A 2-1-21
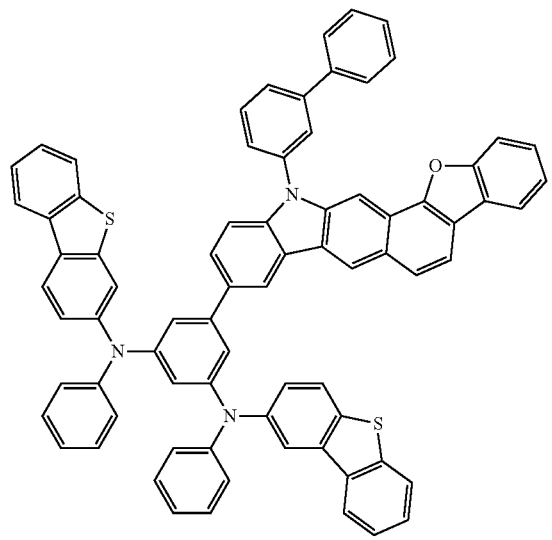
332
A 2-1-22
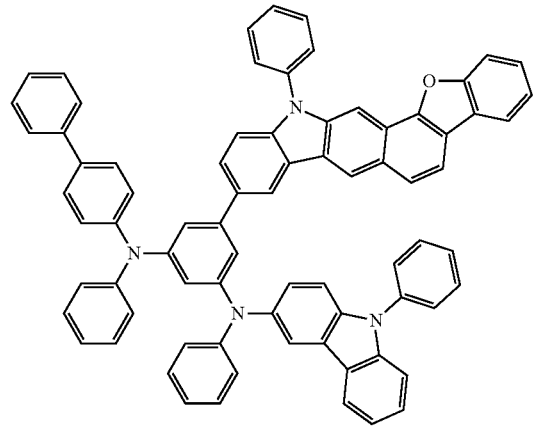
A 2-1-23
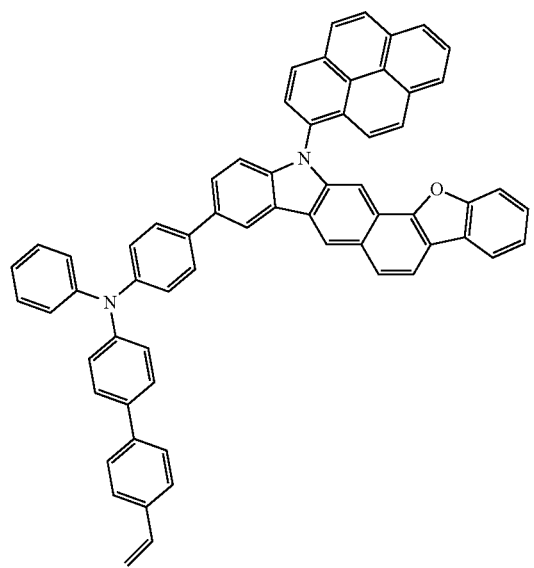
A 2-1-24
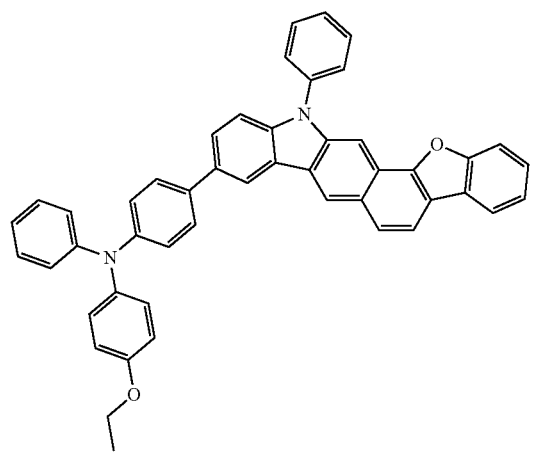

-continued
A 2-1-25
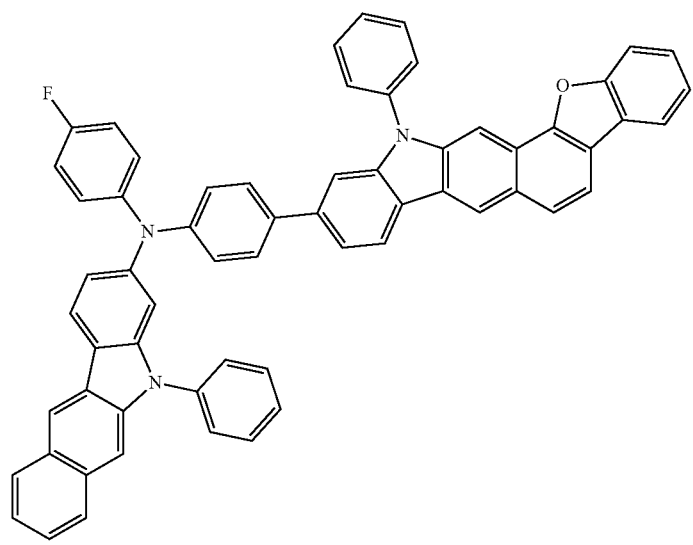
A 2-1-26
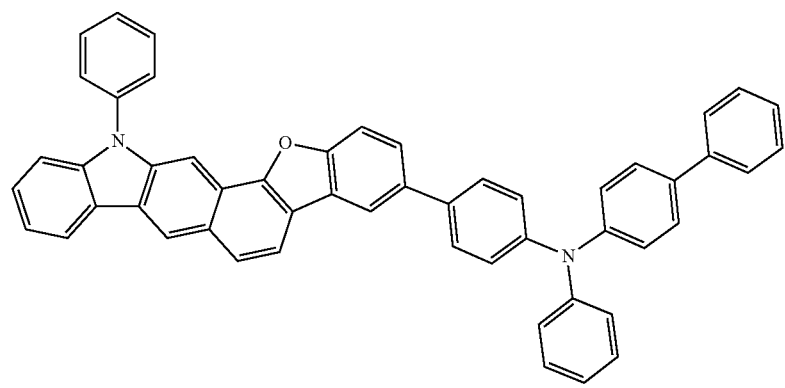
A 2-1-27
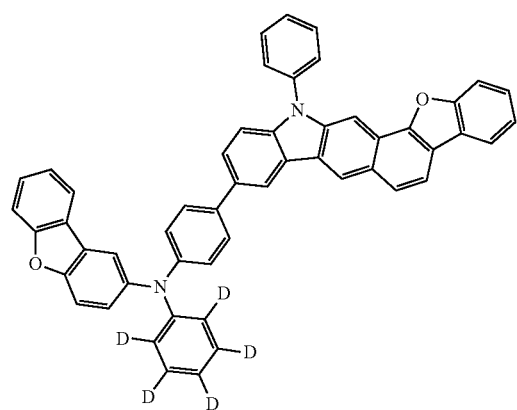
A 2-1-28
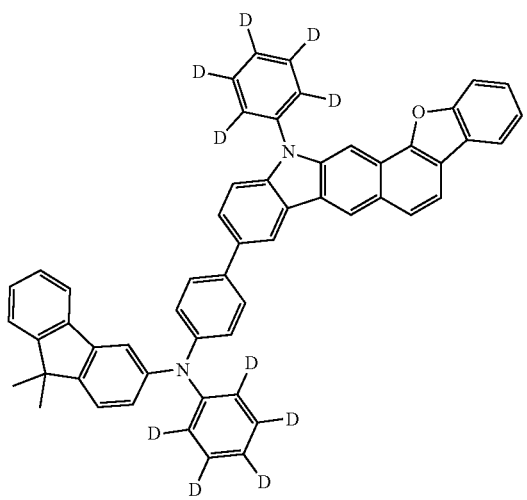

-continued
A 2-1-29
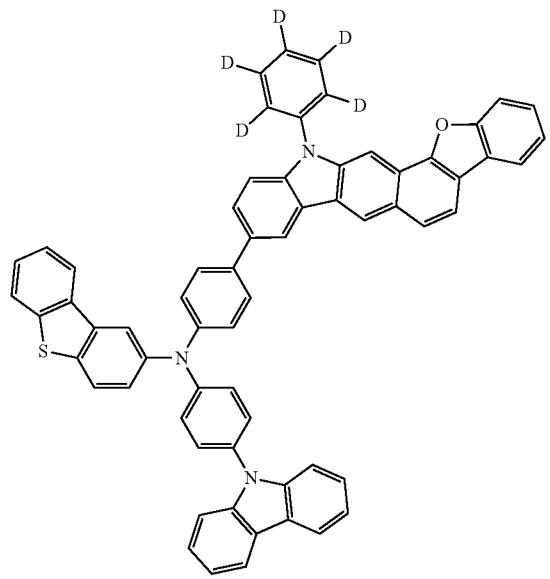
A 2-1-30
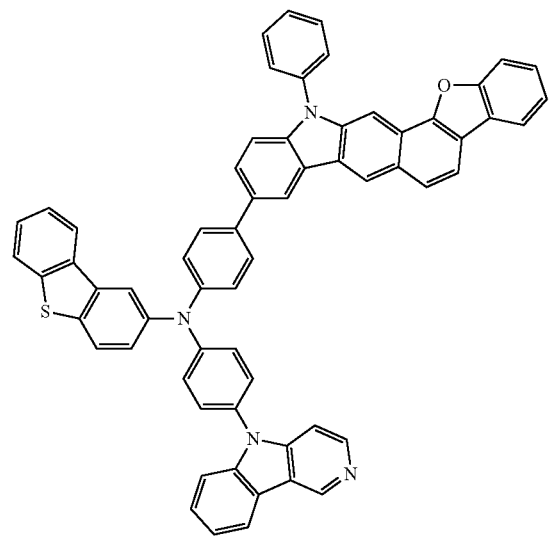
A 2-2-1
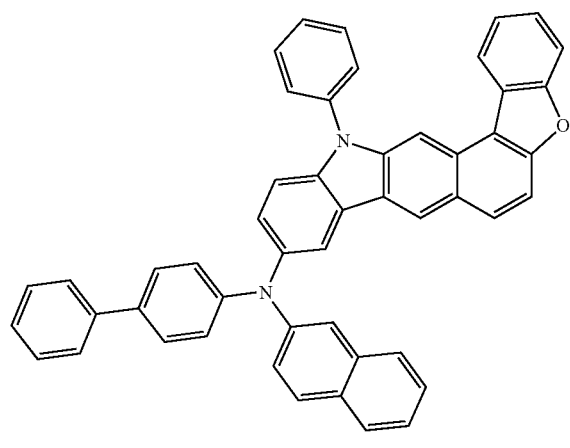
A 2-2-2
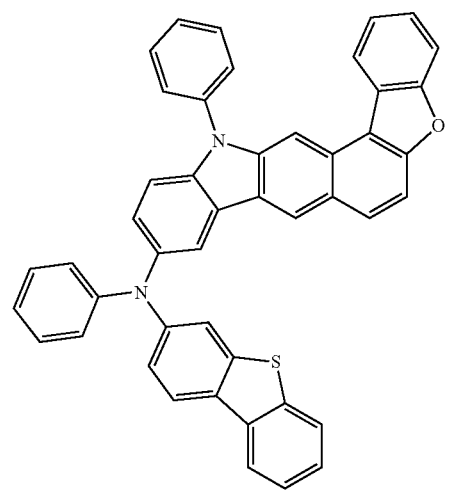
A 2-2-3
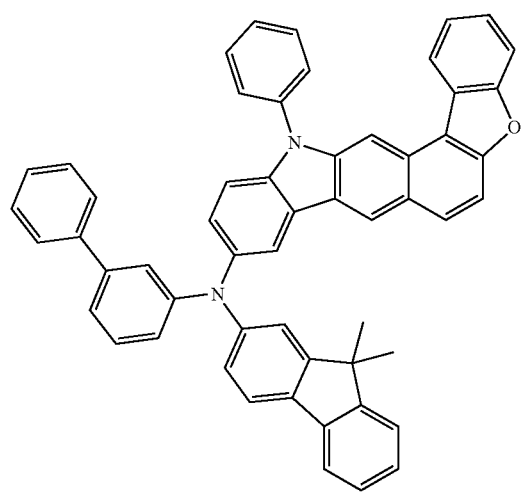
A 2-2-4
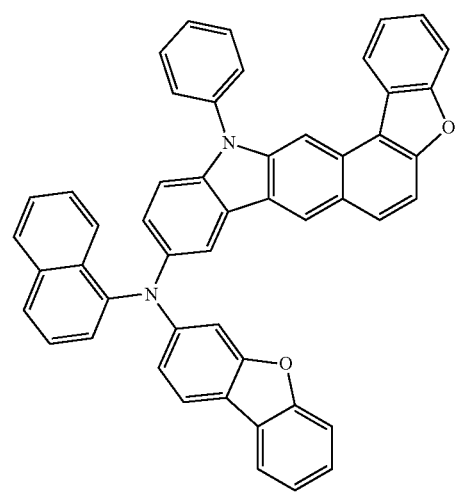

-continued
A 2-2-5
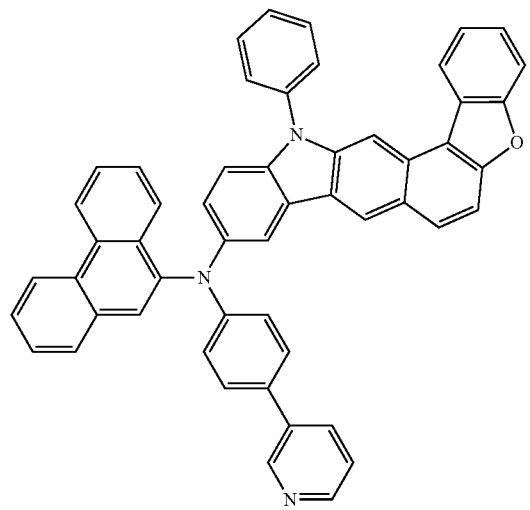
A 2-2-6
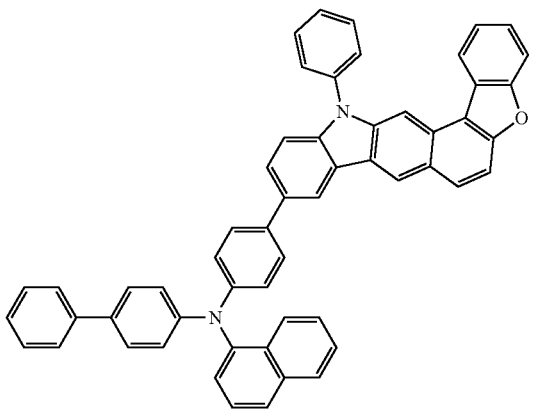
A 2-2-7
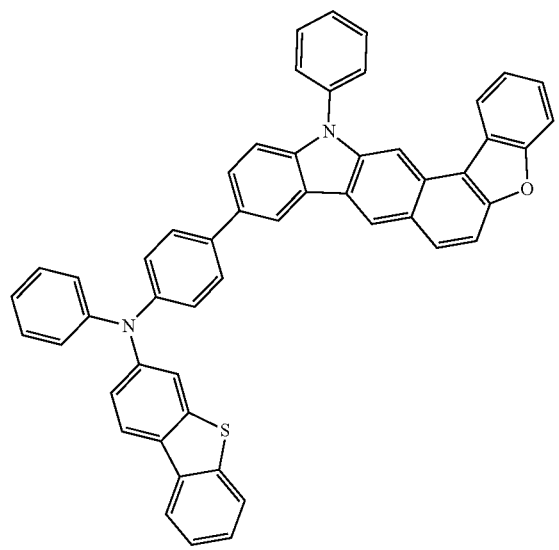
A 2-2-8
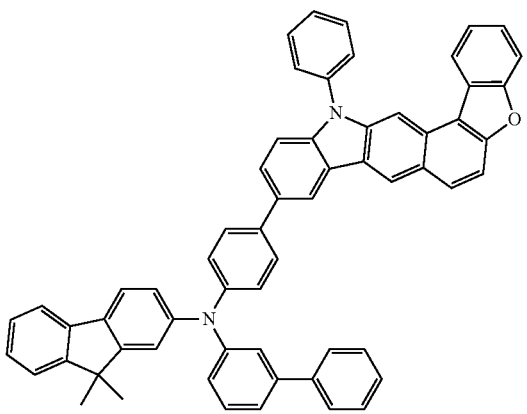
A 2-2-9
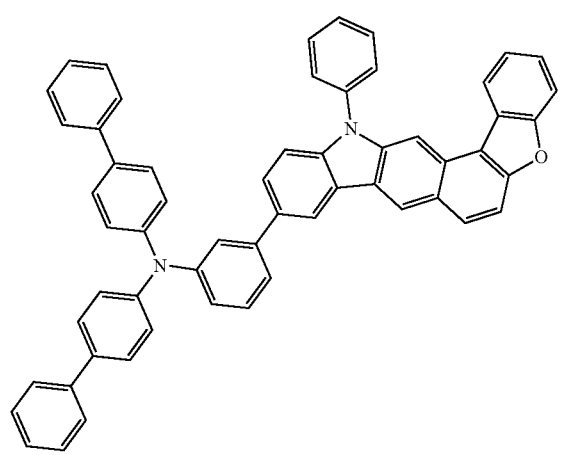
A 2-2-10
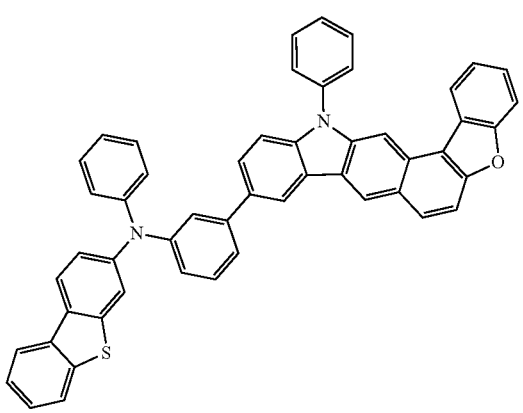

A 2-2-11
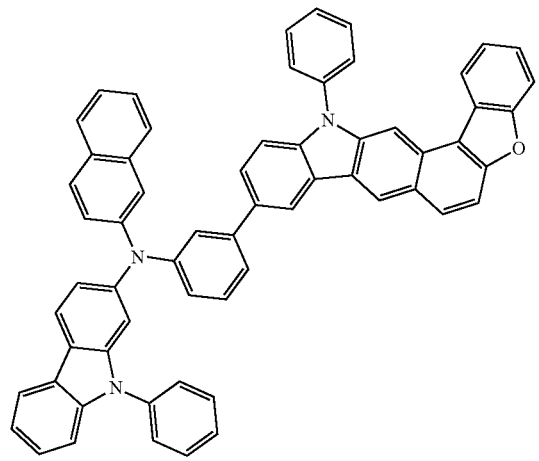
A 2-2-12
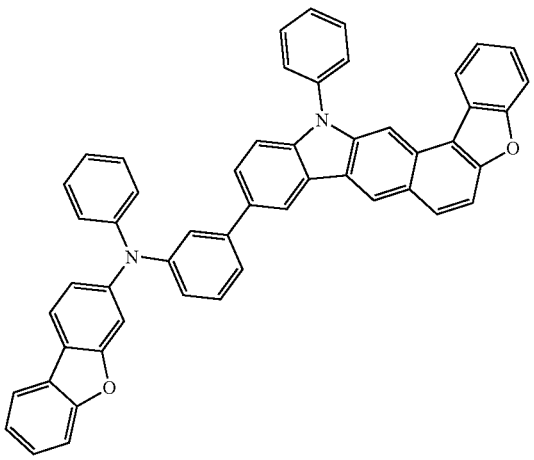
A 2-2-13
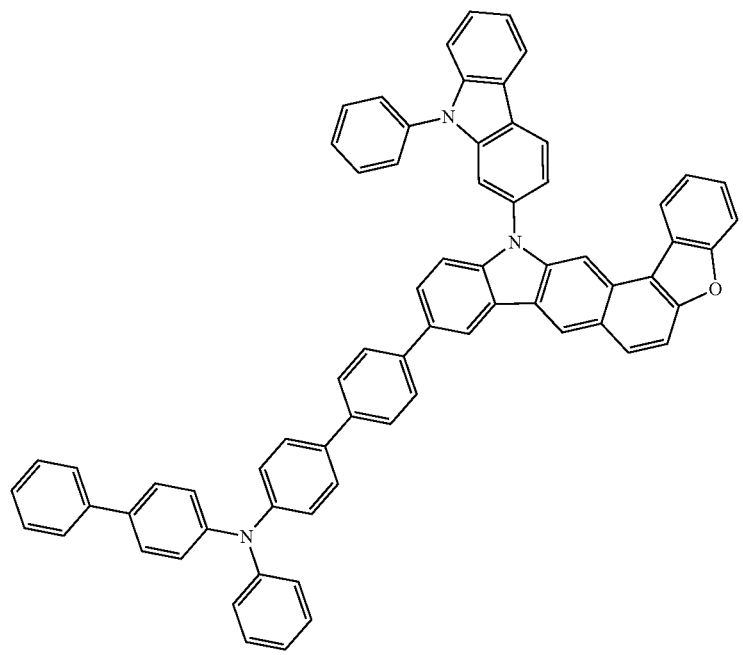
A 2-2-14
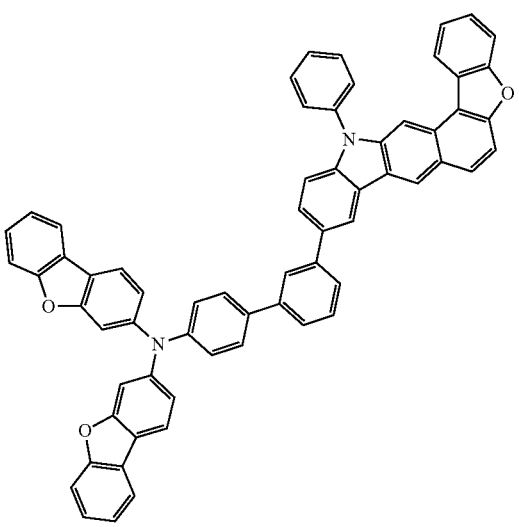
A 2-2-15

-continued
A 2-2-16
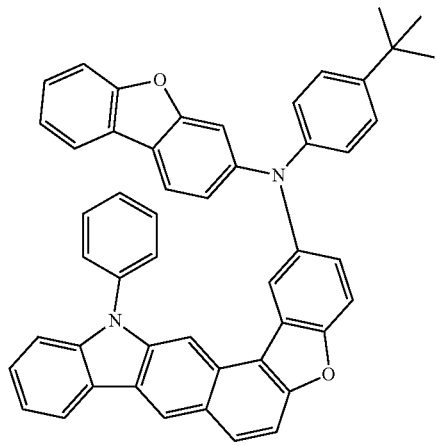
A 2-2-17
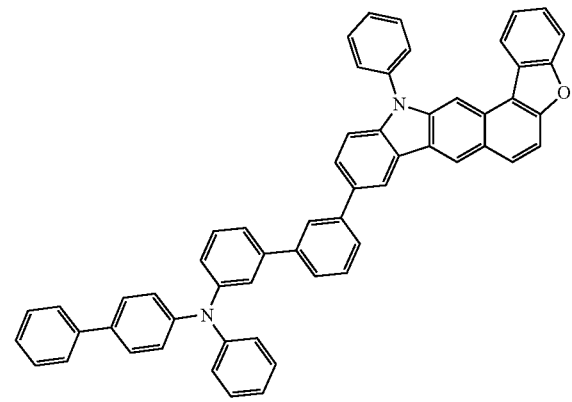
A 2-2-18
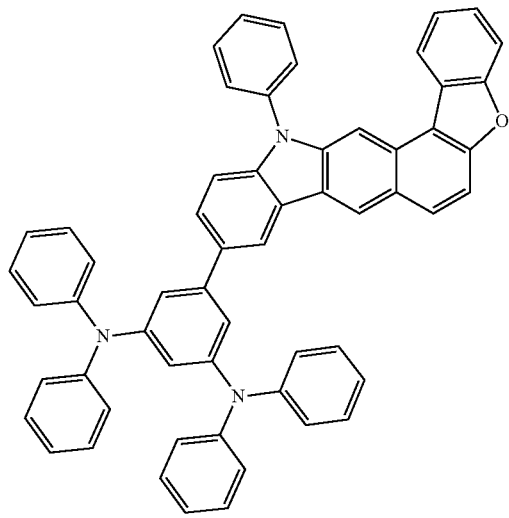
A 2-2-19
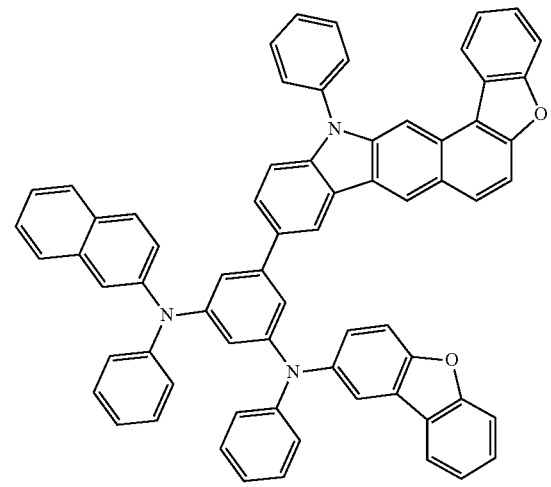
A 2-2-20
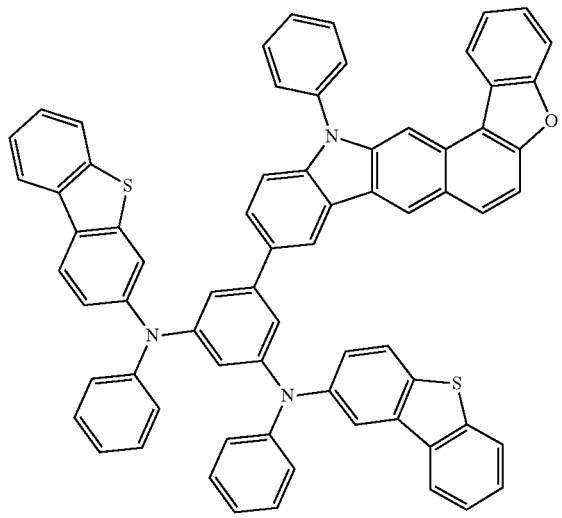
A 2-2-21
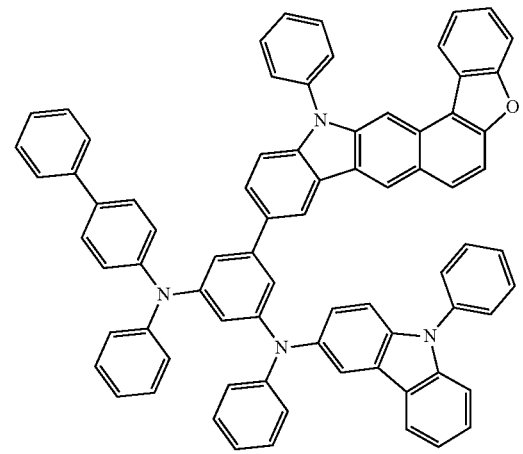

-continued
A 2-2-22
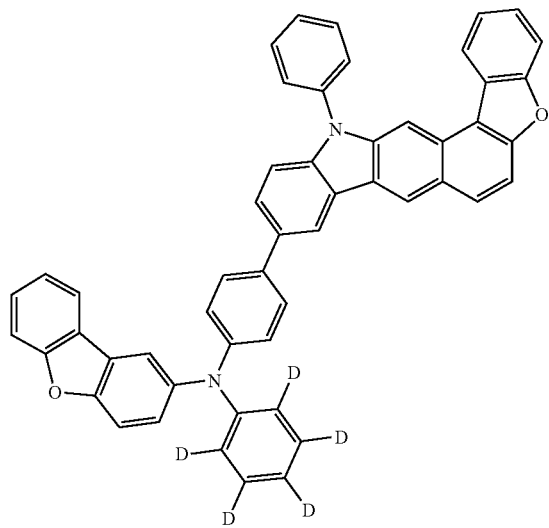
A 2-2-23
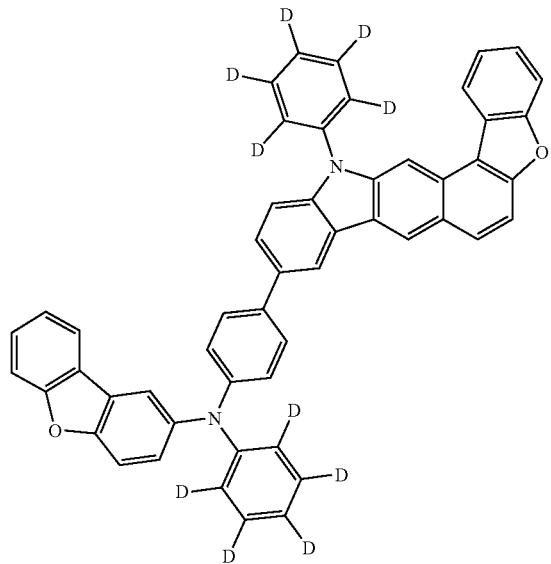
A 2-2-24
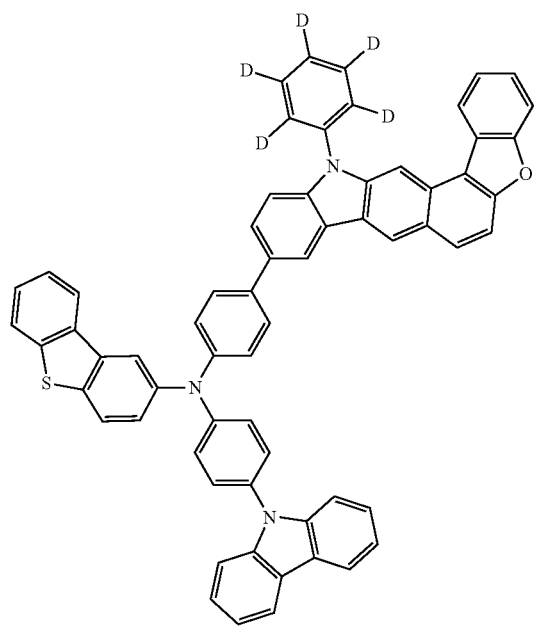
A 2-2-26
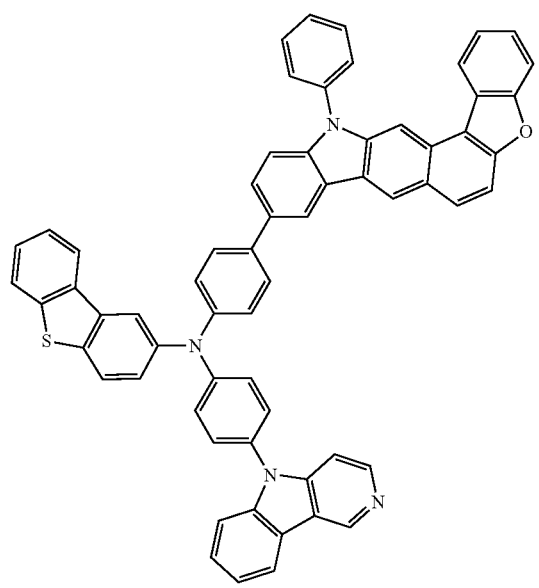

-continued
A 3-1-1
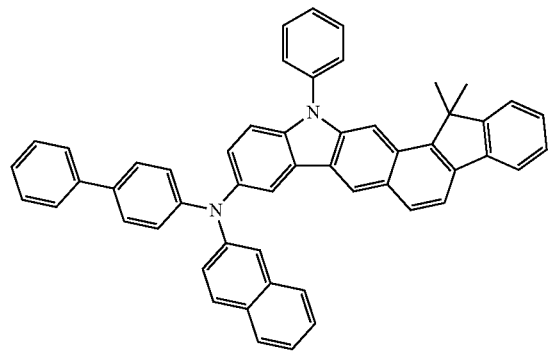
A 3-1-2
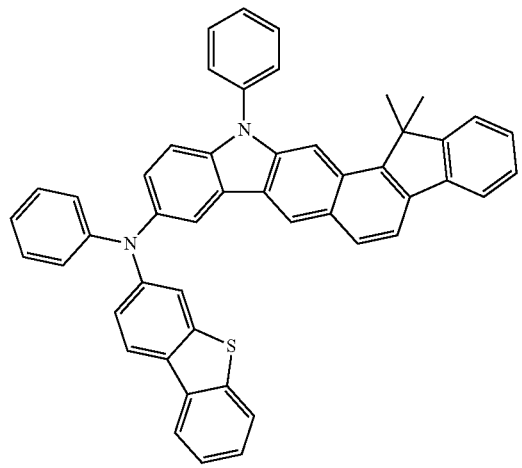
A 3-1-3
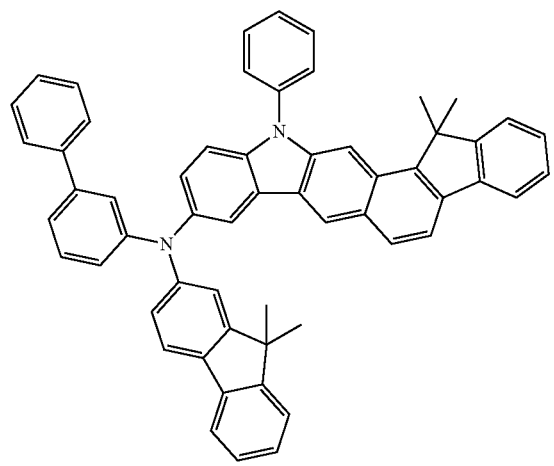
A 3-1-4
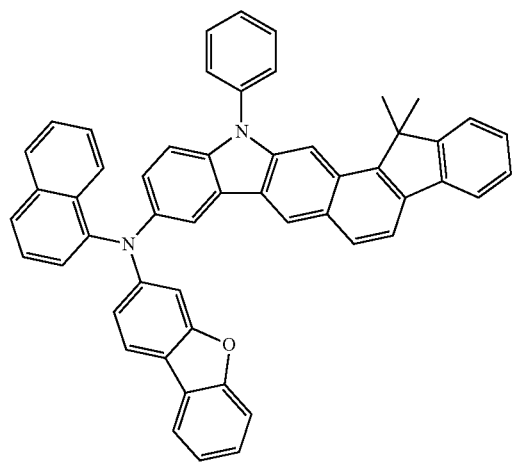
A 3-1-5
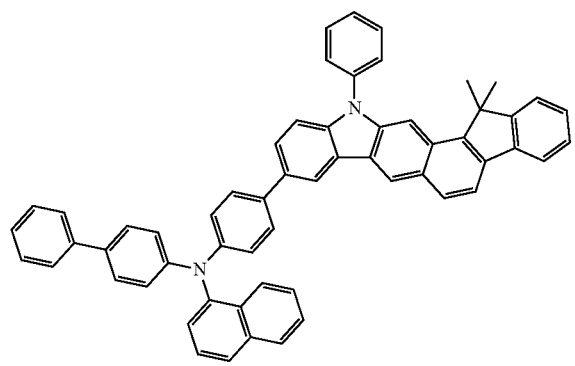
A 3-1-6
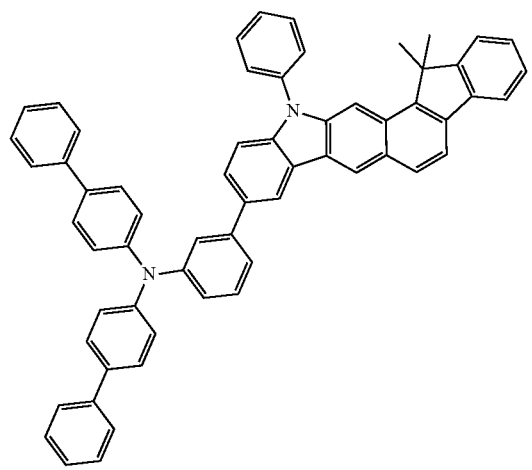

-continued
A 3-1-7
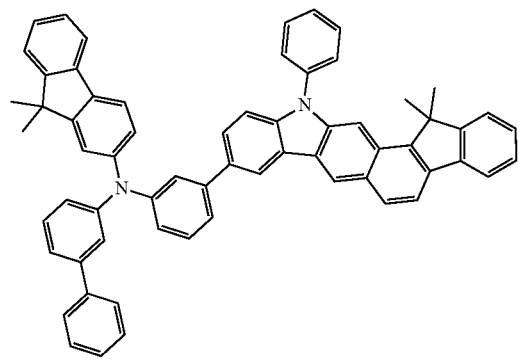
A 3-1-8
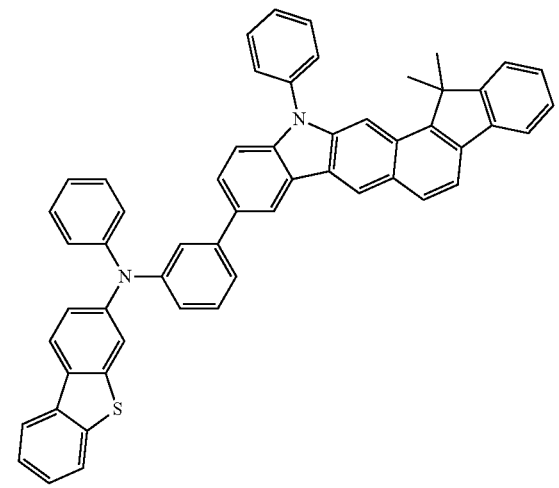
A 3-1-9
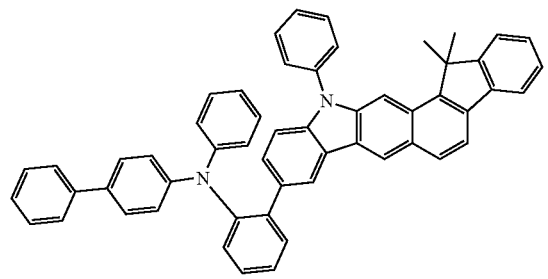
A 3-1-10
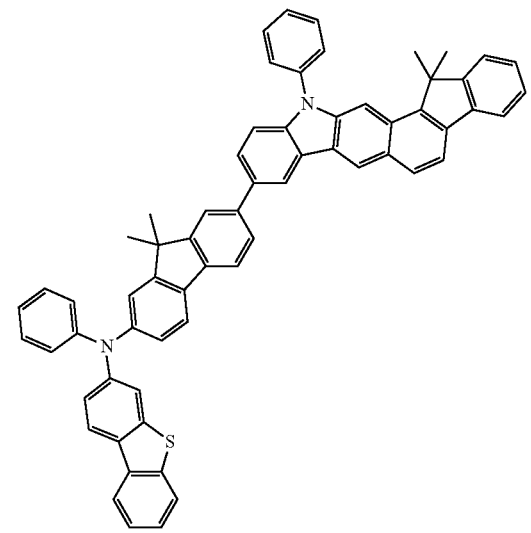
A 3-1-11
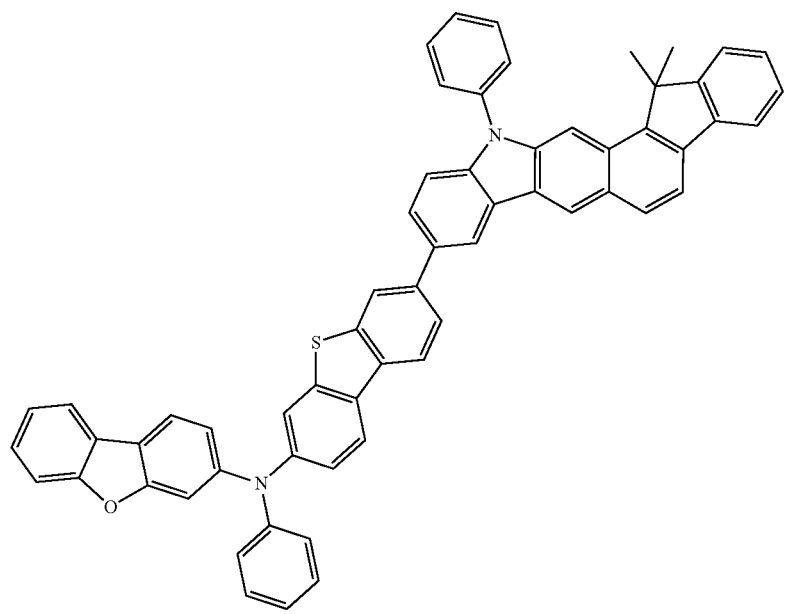

-continued
A 3-1-12
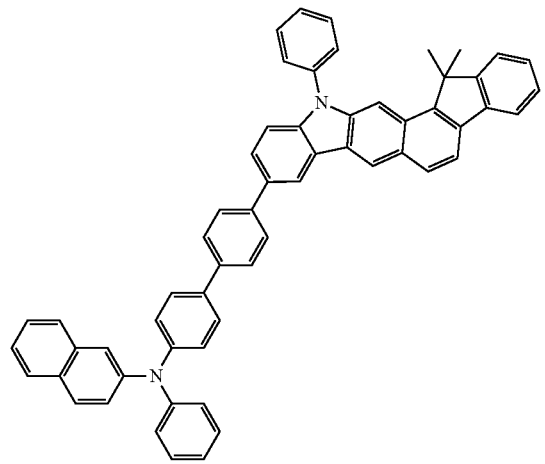
A 3-1-13
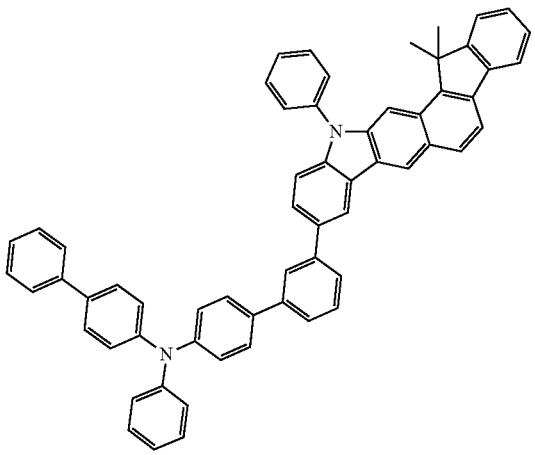
A 3-1-14
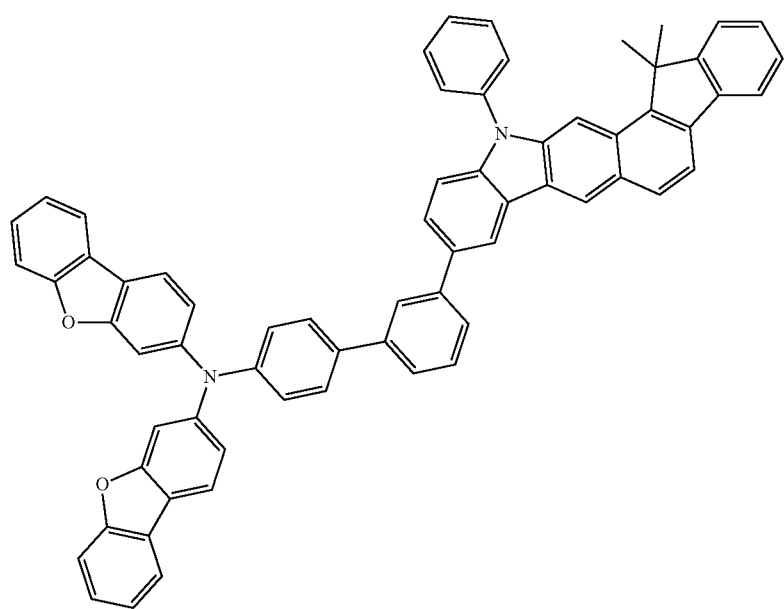
A 3-1-15
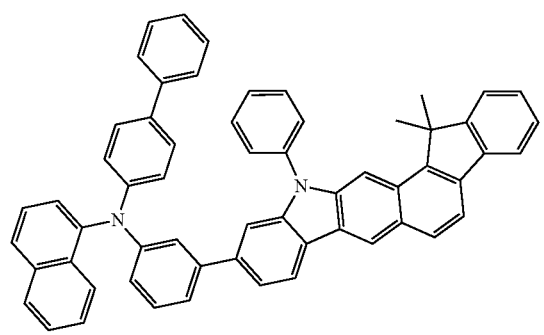
A 3-2-1
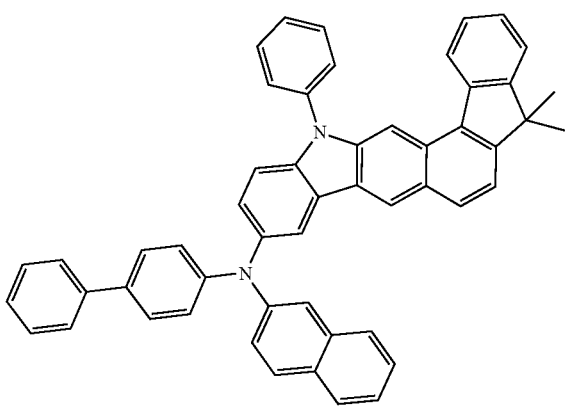

-continued
A 3-2-2
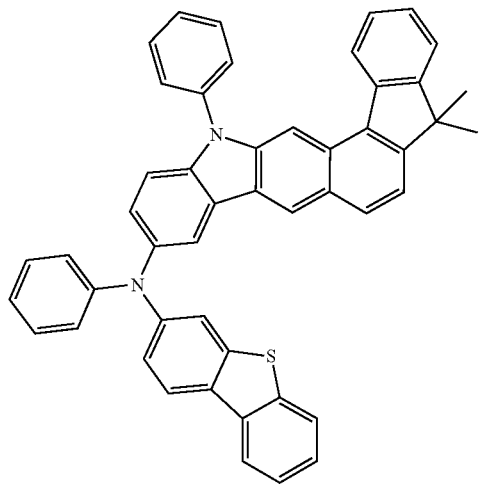
A 3-2-3
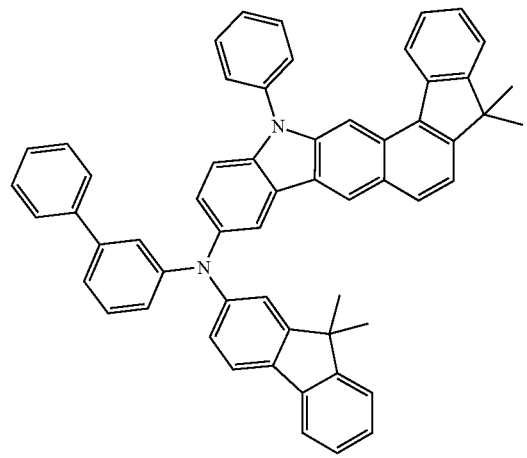
A 3-2-4
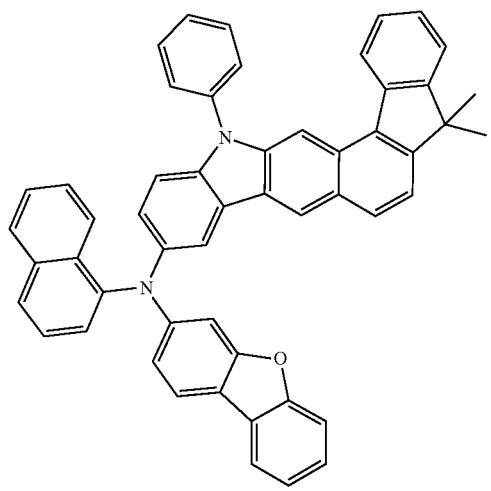
A 3-2-5
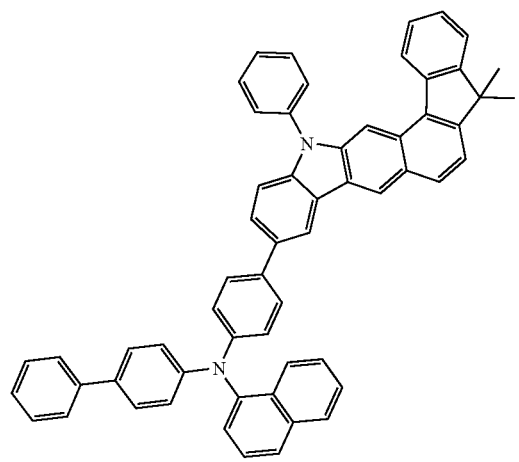
A 3-2-6
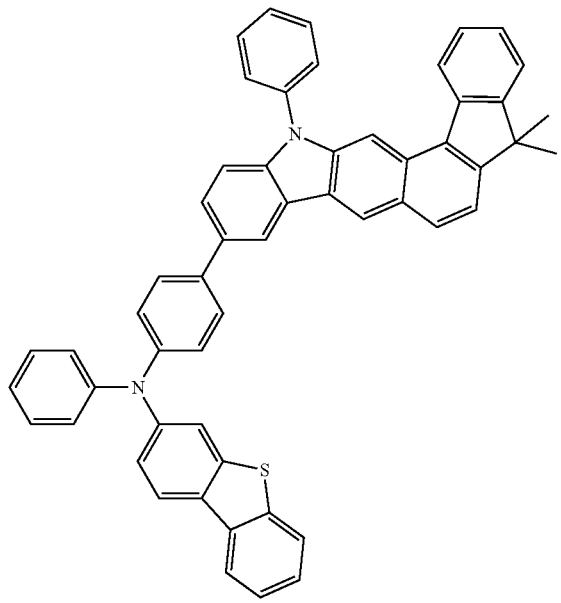
A 3-2-7
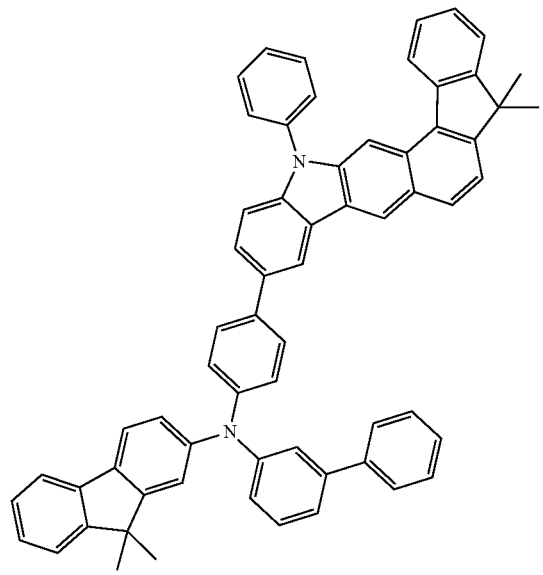

-continued
A 3-2-8
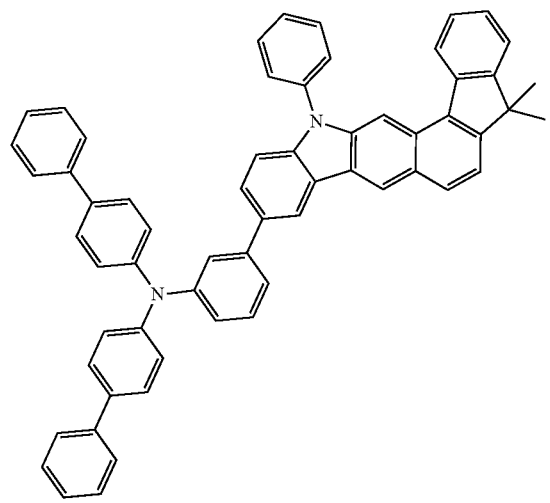
A 3-2-9
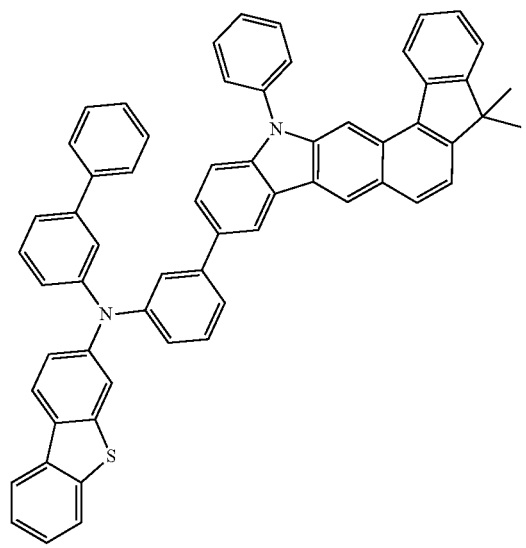
A 3-2-10
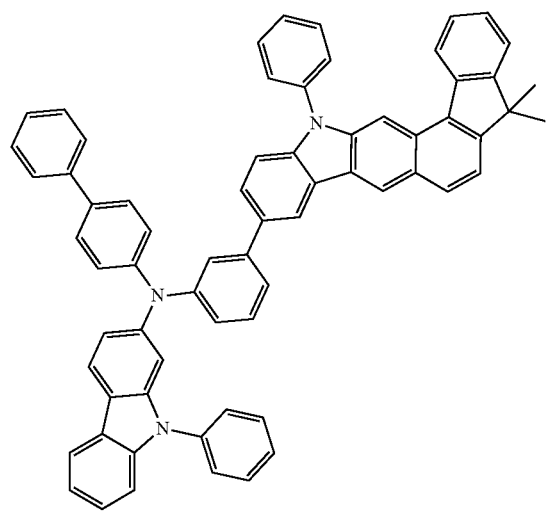
A 3-2-11
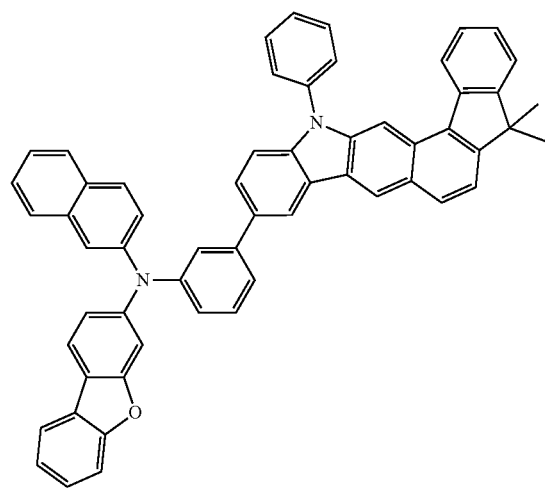
A 3-2-12
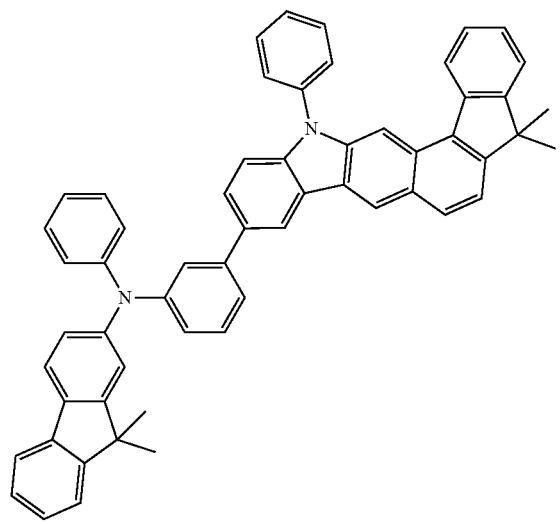
A 3-2-13
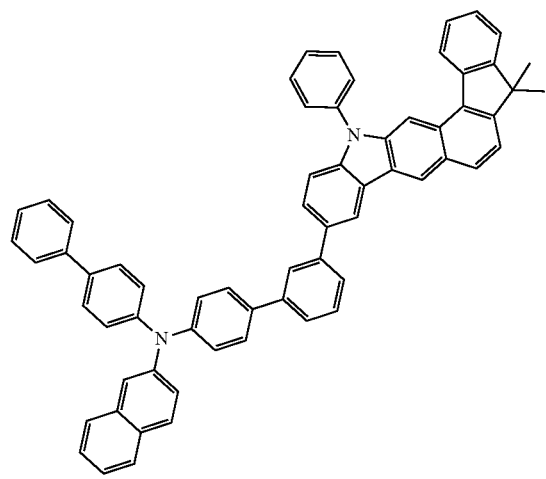

-continued
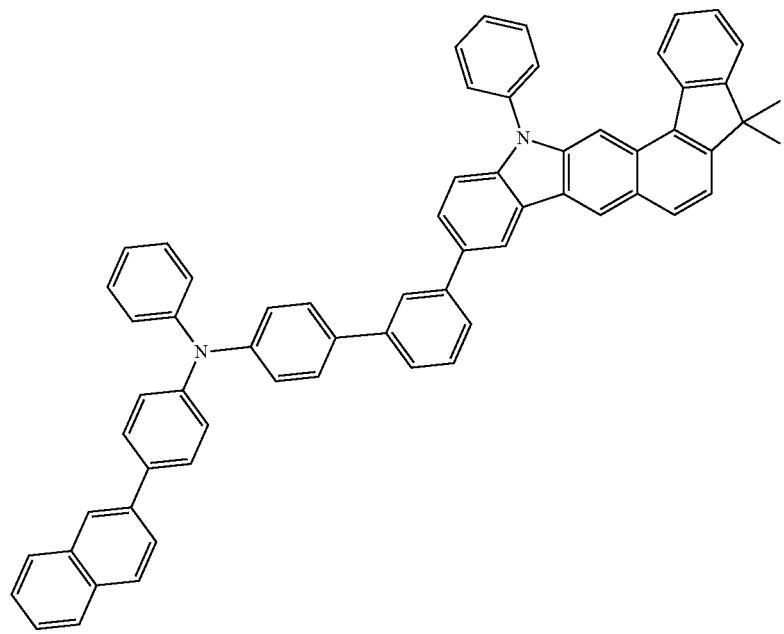
A 3-2-14
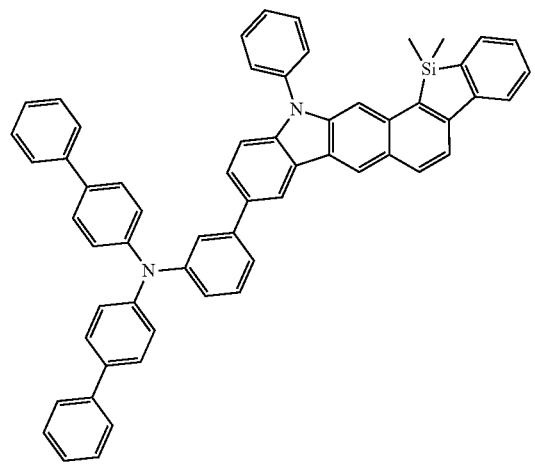
A 4-1-1
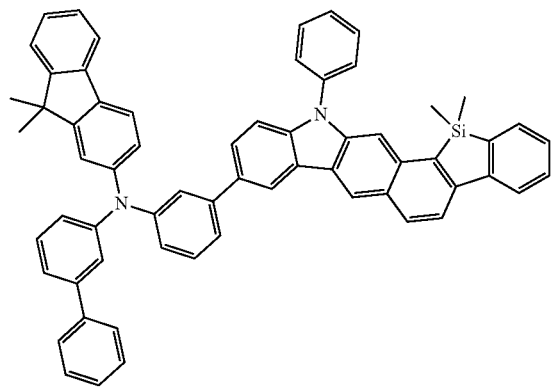
A 4-1-2
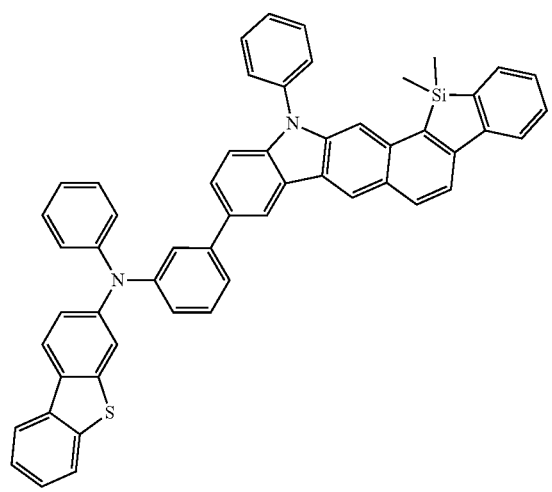
A 4-1-3
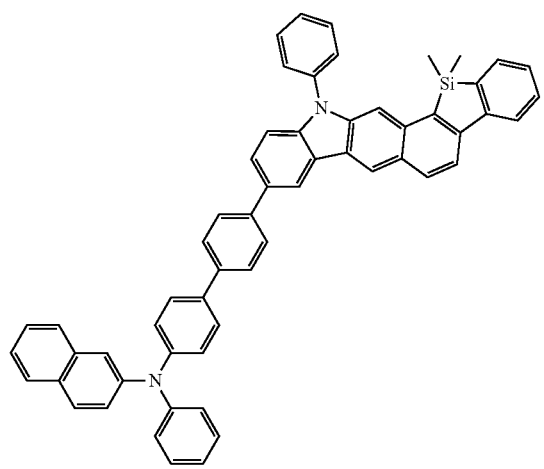
A 4-1-4

-continued
A 4-2-1
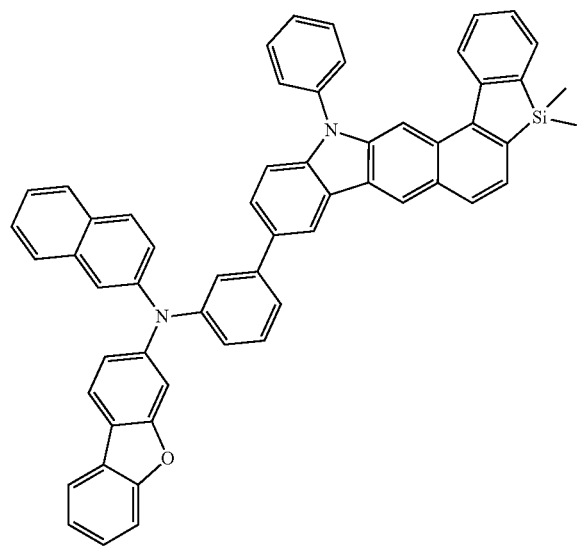
A 4-2-2
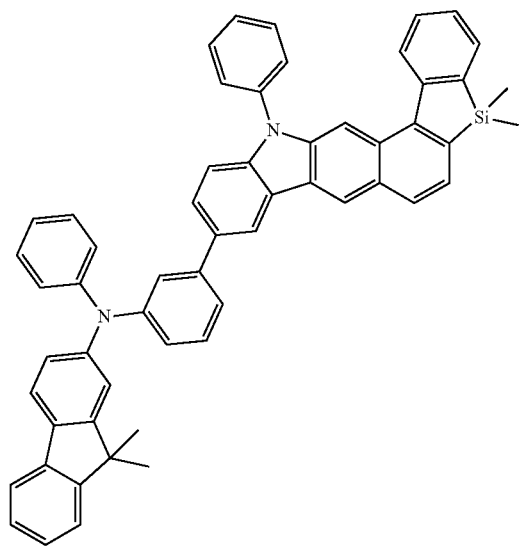
A 4-2-3
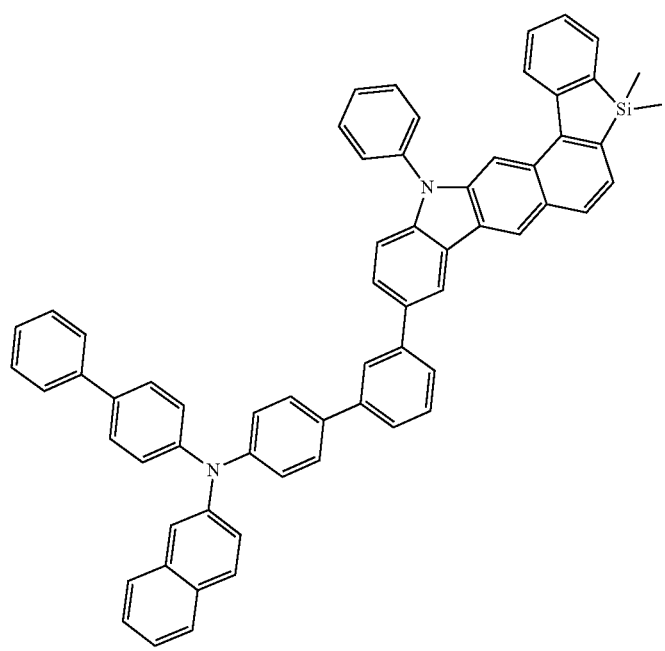

-continued

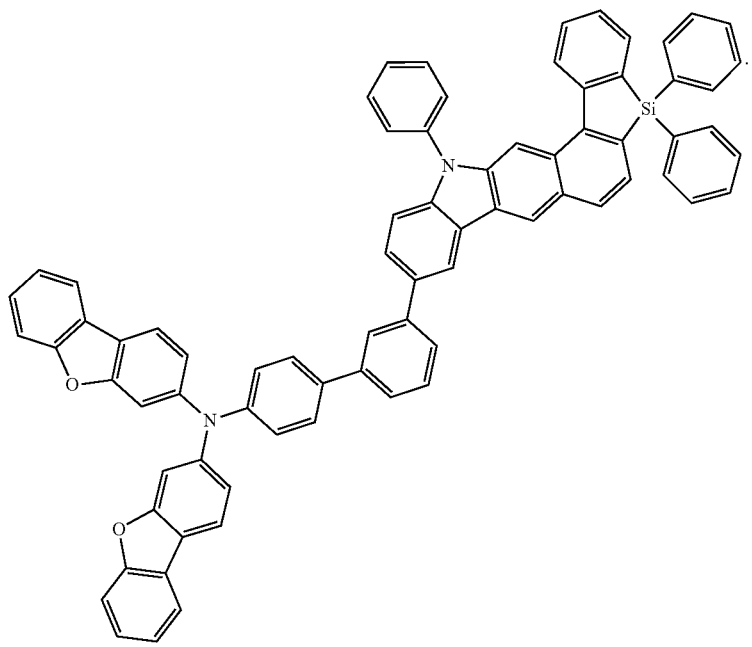

A 4-2-4

15. An organic electric element comprising a first electrode, a second electrode, and an organic material layer formed between the first electrode and the second electrode, wherein the organic material layer comprises the compound of claim 14.

16. An electronic device comprising a display device and a control unit for driving the display device, wherein the display device comprises the organic electric element of claim 15.

* * * * *

UNITED STATES PATENT AND TRADEMARK OFFICE
CERTIFICATE OF CORRECTION

PATENT NO. : 11,299,459 B2
APPLICATION NO. : 15/753803
DATED : April 12, 2022
INVENTOR(S) : Mun et al.

Page 1 of 2

It is certified that error appears in the above-identified patent and that said Letters Patent is hereby corrected as shown below:

In the Claims

Column 249, Claim 1, Line 35:
Please delete "$C_1$-$C_{60}$"
And replace with -- $C_6$-$C_{60}$ --

Column 252, Claim 1, Line 67:
Please delete "$C_1$-$C_{50}$)"
And replace with -- $C_1$-$C_{50}$ --

Column 255, Claim 11, Line 36:
Please delete "O, S, $C(R^{13})(R^{14})$,"
And replace with -- O, S, $C(R^{13})(R^{14})$, $Si(R^{13})(R^{14})$, --

Column 282, Claim 14, formula 2-1-57:

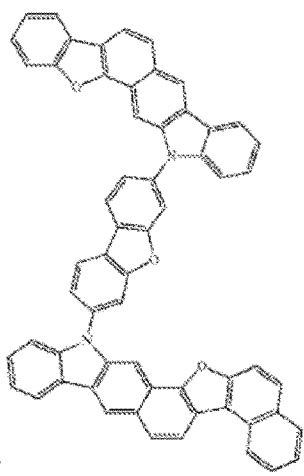

Please delete "                    "

Signed and Sealed this
Twenty-first Day of February, 2023

Katherine Kelly Vidal
*Director of the United States Patent and Trademark Office*

CERTIFICATE OF CORRECTION (continued)
U.S. Pat. No. 11,299,459 B2

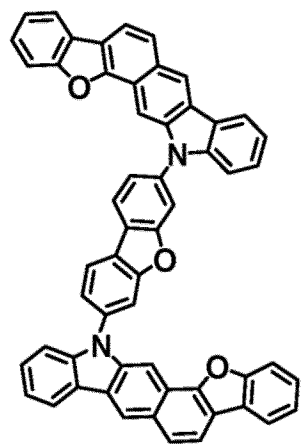

And replace with -- 2-1-57 --

Column 283, Claim 14, formula 2-1-58:

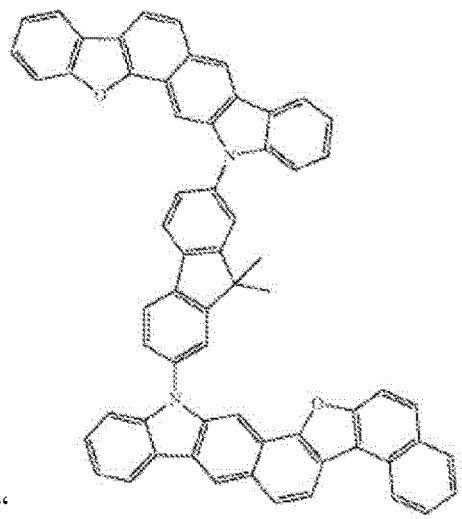

Please delete " "

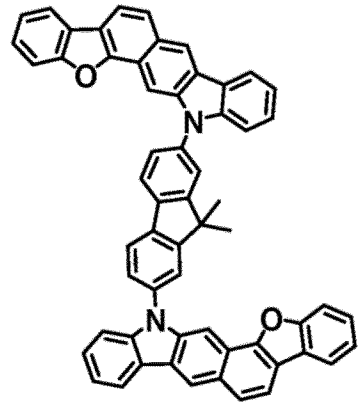

And replace with -- 2-1-58 --